US007576080B2

(12) United States Patent
Liu et al.

(10) Patent No.: US 7,576,080 B2
(45) Date of Patent: Aug. 18, 2009

(54) CERTAIN THIENOPYRIMIDINE DERIVATIVES AS PHOSPHODIESTERASE 10 INHIBITORS

(75) Inventors: Ruiping Liu, Huntington, NY (US); Mark Phillip Arrington, Westwood, NJ (US); Allen Hopper, Glen Rock, NJ (US); Ashok Tehim, Ridgewood, NJ (US)

(73) Assignee: Memory Pharmaceuticals Corporation, Montvale, NJ (US)

( * ) Notice: Subject to any disclaimer, the term of this patent is extended or adjusted under 35 U.S.C. 154(b) by 224 days.

(21) Appl. No.: 11/317,907

(22) Filed: Dec. 22, 2005

(65) Prior Publication Data

US 2007/0259896 A1 Nov. 8, 2007

Related U.S. Application Data

(60) Provisional application No. 60/638,179, filed on Dec. 23, 2004.

(51) Int. Cl.
*C07D 413/12* (2006.01)
*C07D 495/04* (2006.01)
*A61K 31/519* (2006.01)
*A61K 31/5355* (2006.01)
*A61P 25/18* (2006.01)
*A61P 25/28* (2006.01)

(52) U.S. Cl. .................... 514/234.2; 544/278; 544/118; 514/260.1

(58) Field of Classification Search ................ 544/278, 544/117; 540/600; 514/217.06, 260.1, 234.2, 514/252.16
See application file for complete search history.

(56) References Cited

U.S. PATENT DOCUMENTS

| 4,146,716 | A | 3/1979 | Cox et al. |
| 4,845,097 | A | 7/1989 | Matsumoto et al. |
| 5,227,387 | A | 7/1993 | Dreikorn et al. |
| 6,169,091 | B1 * | 1/2001 | Cockerill et al. ......... 514/228.2 |
| 6,492,383 | B1 | 12/2002 | Munchhof et al. |
| 6,703,421 | B1 | 3/2004 | Nunokawa et al. |
| 6,734,180 | B1 | 5/2004 | Nunokawa et al. |
| 6,946,478 | B2 | 9/2005 | Baxter et al. |
| 2003/0162795 | A1 | 8/2003 | Munchhof et al. |
| 2004/0014755 | A1 | 1/2004 | Nagarathnam et al. |
| 2004/0138238 | A1 | 7/2004 | Dhanoa et al. |
| 2005/0026935 | A1 * | 2/2005 | Ford et al. ............... 514/260.1 |
| 2005/0222175 | A1 | 10/2005 | Dhanoa et al. |
| 2005/0222176 | A1 | 10/2005 | Dhanoa et al. |

FOREIGN PATENT DOCUMENTS

| EP | 452002 | A2 | 10/1991 |
| EP | 1 250 923 | A2 | 10/2002 |
| JP | 02/105081 | A | 4/1990 |
| WO | WO 97/09316 | A1 | 3/1997 |
| WO | WO 97/13771 | A1 | 4/1997 |
| WO | WO 97/17843 | A1 | 5/1997 |
| WO | WO 99/24440 | A1 | 5/1999 |
| WO | WO 00/05234 | A1 | 2/2000 |
| WO | WO 01/21206 | A1 | 3/2001 |
| WO | WO 03/059913 | A1 | 7/2003 |
| WO | WO 03/093499 | A2 | 11/2003 |
| WO | WO 2004/014850 | A2 | 2/2004 |
| WO | WO 2004/092123 | A2 | 10/2004 |
| WO | WO 2004092123 | A2 * | 10/2004 |
| WO | WO 2004/111057 | A1 | 12/2004 |
| WO | WO 2006093518 | A2 * | 9/2006 |

OTHER PUBLICATIONS

International Search Report and Written opinion mailed May 9, 2006, for International Application No. PCT/US2005/047439, filed Dec. 27, 2005 (14 pages).
Yoon et al., 2004, "Efficient Synthesis of 4-Aminoquinazoline and Thieno[3,2-*d*]pyrimidin-4-ylamine Derivatives by Microwave Irradiation," Organic Letters, 6(25): 4775-4778.
M. Fujita et al., "Design, Synthesis and Bioactivities of Novel Diarylthiophenes: Inhibitors of Tumor Necrosis Factor-α (TNF-α) Production," Bioorganic & Medicinal Chemistry (2002), 10(10): 3113-3122.
A. A. Geies, "Synthesis of Thieno[2',3':4,5]pyrimido[2,1-*c*][1,2,4]triazoles and Pyrazolylthieno[2,3-*d*']dipyrimidines," Journal of Chemical Research (S), (1998), 6: 290-291.
H. M. Hosni et al., "Thienopyrimidines II: synthesis of newer thieno[2,3-d]pyrimidines and their quaternized derivatives with molluscicidal activity," Acta Poloniae Pharmaceutica (1999), 56(1): 49-56.
Z. A. Hozien et al., "Synthesis and application of some new thienopyrimidine derivatives as antimicrobial agents," Synthetic Communications (1996), 26(20): 3733-3755.
Webster's Third New International Dictionary, 1986, p. 2171, Merrian-Webster Inc., Springfield, MA, USA.
Dorland's Illustrated Medical Dictionary, 29th Edition, 2000, p. 1663, W.B. Saunders Company, Philadelphia, PA, USA.
Academic Press Dictionary of Science and Technology, 1992, p. 2033, Academic Press, Inc., San Diego, CA, USA.
Hackh's Chemical Dictionary, 4th Edition, 1969, p. 624, McGraw-Hill Book Co., New York, NY, 1969.
Stedman's Medical Dictionary, 27th Edition, p. 1654, Williams & Wilkins, Baltimore MD, 2000.
IUPAC, "Glossary of Class Names of Organic Compounds and Reactive Intermediates Based on Stucture," Pure and Applied Chemistry, vol. 67, Nos. 8/9, pp. 1307-1375, 1995.

* cited by examiner

*Primary Examiner*—Brenda L Coleman
*Assistant Examiner*—Susanna Moore
(74) *Attorney, Agent, or Firm*—Darby & Darby P.C.

(57) ABSTRACT

Certain thienopyrimidine derivatives are useful for the inhibition of PDE10 enzymes, and thus are useful for treating psychiatric or neurological syndromes, e.g., pyschoses, obsessive-compulsive disorder and/or Parkinson's disease, as well as, for example, treating a disease state modulated by PDE10 activity.

43 Claims, No Drawings

CERTAIN THIENOPYRIMIDINE DERIVATIVES AS PHOSPHODIESTERASE 10 INHIBITORS

This application claims priority to U.S. provisional application No. 60/638,179, filed on Dec. 23, 2004.

Provided are certain thienopyrimidines, methods of preparing such compounds, compositions containing such compounds, and methods of use thereof.

Neurotransmitters and hormones, as well as other types of extracellular signals such as light and odors, create intracellular signals by altering the amounts of cyclic nucleotide monophosphates (cAMP and cGMP) within cells. These intracellular messengers alter the functions of many intracellular proteins. Cyclic AMP regulates the activity of cAMP-dependent protein kinase (PKA). PKA phosphorylates and regulates the function of many types of proteins, including ion channels, enzymes, and transcription factors. Downstream mediators of cGMP signaling also include kinases and ion channels. In addition to actions mediated by kinases, cAMP and cGMP bind directly to some cellular proteins and directly regulate their activity.

Cyclic nucleotides are produced from the actions of adenylyl cyclase and guanylyl cyclase which convert ATP to cAMP and GTP to cGMP, respectively. Extracellular signals, often through the actions of G protein-coupled receptors, regulate the activity of the cyclases. Alternatively, the amount of cAMP and cGMP may be altered by regulating the activity of the enzymes that degrade cyclic nucleotides. Cell homeostasis is maintained by the rapid degradation of cyclic nucleotides after stimulus-induced increases. The enzymes that degrade cyclic nucleotides are called 3',5'-cyclic nucleotide-specific phosphodiesterases (PDEs).

Eleven PDE gene families (PDE1-PDE11) have been identified so far, based on their distinct amino acid sequences, catalytic and regulatory characteristics, and sensitivity to small molecule inhibitors. These PDE families are coded for by 21 genes; and further multiple splice variants are transcribed from many of these genes. Expression patterns of each of the gene families are distinct. PDEs differ with respect to their affinity for cAMP and cGMP. Activities of different PDEs are regulated by different signals. For example, PDE1 is stimulated by $Ca^{2+}$/calmodulin, PDE2 activity is stimulated by cGMP, PDE3 is inhibited by cGMP, PDE4 is cAMP specific and is specifically inhibited by rolipram, PDE5 is cGMP-specific and PDE6 is expressed in retina. Less is known about the expression patterns and functional attributes of the higher number PDEs (7 through 11).

PDE10 sequences were first identified by using bioinformatics and sequence information from other PDE gene families (Fujishige et al., J. Biol. Chem. 274:18438-18445, 1999; Loughney, K. et al., Gene 234:109-117, 1999; Soderling, S. et al., Proc. Natl. Acad. Sci. USA 96:7071-7076, 1999). PDE10 is defined as a unique gene family based on its amino acid sequence, functional properties and tissue distribution. The human PDE10 gene is large, over 200 kb, with up to 24 exons coding for each of the splice variants. The amino acid sequence is characterized by two GAF domains (which bind cGMP), a catalytic region, and alternatively spliced N and C termini. Numerous splice variants are possible because of at least 3 alternative exons encoding the N and 2 for the C-termini. PDE10A1, a splice variant of PDE10, is a 779 amino acid protein that hydrolyzes both cAMP and cGMP. The $K_m$ values for cAMP and cGMP are 0.05 and 3.0 micromolar, respectively. In addition to human variants, several variants with high homology have been isolated from both rat and mouse tissues and sequence banks.

PDE10 transcripts were initially detected in RNA from human testis and brain. Immunohistochemical analysis identified specific brain regions enriched in PDE10. The basal ganglia express the highest amounts of PDE10, Specifically, striatal neurons in the olfactory tubercle, caudate nucleus and nucleus accumbens are enriched in PDE10 (Seeger, T. F. et al., Brain Res. 2003, Sep. 26, 985(2):113-26). Western blots did not reveal the expression of PDE10 in other brain tissues, although immunoprecipitation of the PDE10 complex was possible in hippocampal and cortical tissues. This suggests that the expression level of PDE10 in these other tissues is 100-fold less than in striatal neurons. Expression in hippocampus is limited to the cell bodies, whereas PDE10 is expressed in terminals, dendrites and axons of striatal neurons.

The tissue distribution of PDE10 indicates that PDE10 inhibitors may play an important role in the basal ganglia. PDE10 selective inhibitors could be used to raise levels of cAMP and/or cGMP within cells that express the PDE10 enzyme, especially neurons that comprise the basal ganglia. Selective PDE10 inhibition could lead to altered basal ganglia function and may be effective in treating a variety of neuropsychiatric conditions involving the basal ganglia.

Provided is at least one chemical entity chosen from compounds of Formula I:

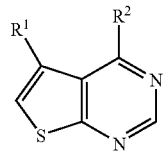

(Formula I)

and pharmaceutically acceptable salts, solvates, chelates, non-covalent complexes, prodrugs, and mixtures thereof, wherein $R^1$ is chosen from:
- (i) $C_{6-10}$ aryl;
- (ii) substituted $C_{6-10}$ aryl chosen from mono-, di-, and tri-substituted aryl wherein the substituents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —$COR^9$, —$CSR^9$, —$SR^9$, cyano, hydroxyl, nitro, and thio;
- (iii) heterocyclyl;
- (iv) substituted heterocyclyl chosen from mono-, di-, and tri-substituted heterocyclyl wherein the substitutents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —$COR^9$, —$CSR^9$, —$SR^9$, cyano, hydroxyl, nitro, oxo, and thio;
- (v) heteroaryl; and
- (vi) substituted heteroaryl chosen from mono-, di-, and tri-substituted heteroaryl wherein the substitutents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —$COR^9$, —$CSR^9$, —$SR^9$, cyano, hydroxyl, nitro, oxo, and thio;

$R^2$ is chosen from $C_{2-4}$ hydroxyalkyl, $C_{2-4}$ alkenyl, $C_{2-4}$ alkenylene-$R^5$, $C_{2-4}$ alkynyl, $C_{2-4}$ alkynylene-$R^5$, —O-arylene-Y—$R^5$, —X(CR$^3$R$^4$)$_n$YR$^5$ and —(CR$^6$R$^7$)$_m$YR$^5$ where:

X is chosen from —O—, —S— and —NR$^9$— where R$^9$ is chosen from H, $C_{1-8}$ alkyl; and $C_{3-8}$ cycloalkyl, substituted $C_{1-8}$ alkyl; and substituted $C_{3-8}$ cycloalkyl, wherein the substituents on the alkyl and cycloalkyl groups are independently chosen from halo, $C_{1-4}$-alkyl, $C_{1-4}$-alkoxy, and oxo;

Y is chosen from a covalent bond, —O—, —S— and —NR$^9$—;

n is chosen from 2, 3, 4, and 5;

m is chosen from 2, 3, 4, and 5;

$R^3$ and $R^4$ are each independently chosen from:
  (i) H;
  (ii) halo;
  (iii) $C_{1-12}$ alkyl;
  (iv) $C_{2-12}$ alkenyl;
  (v) $C_{2-12}$ alkynyl;
  (vi) $C_{3-12}$ cycloalkyl;
  (vii) substituted $C_{1-12}$ alkyl chosen from mono-, di-, and tri-substituted $C_{1-12}$ alkyl and wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl;
  (viii) substituted $C_{2-12}$ alkenyl chosen from mono-, di-, and tri-substituted $C_{2-12}$ alkenyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl;
  (ix) substituted $C_{2-12}$ alkynyl chosen from mono-, di-, and tri-substituted $C_{2-12}$ alkynyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl; and
  (x) substituted $C_{3-12}$ cycloalkyl chosen from mono-, di-, and tri-substituted $C_{3-12}$ cycloalkyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl;

$R^6$ and $R^7$ are independently chosen from
  (i) H;
  (ii) halo;
  (iii) $C_{1-12}$ alkyl;
  (iv) $C_{2-12}$ alkenyl;
  (v) $C_{2-12}$ alkynyl;
  (vi) $C_{3-12}$ cycloalkyl;
  (vii) substituted $C_{1-12}$ alkyl chosen from mono-, di-, and tri-substituted $C_{1-12}$ alkyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl;
  (viii) substituted $C_{2-12}$ alkenyl chosen from mono-, di-, and tri-substituted $C_{2-12}$ alkenyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl;
  (ix) substituted $C_{2-12}$ alkynyl chosen from mono-, di-, and tri-substituted $C_{2-12}$ alkynyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl; and
  (x) substituted $C_{3-12}$ cycloalkyl chosen from mono-, di-, and tri-substituted $C_{3-12}$ cycloalkyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl; and $R^5$ is chosen from $C_{6-10}$ aryl, substituted $C_{6-10}$ aryl, Het, substituted Het, $C_{6-10}$ aryl-$C_{1-8}$ alkyl, substituted $C_{6-10}$ aryl-$C_{1-8}$ alkyl, Het-$C_{1-8}$ alkyl, and substituted Het-$C_{1-8}$ alkyl, wherein the alkyl portions of $C_{6-10}$ aryl-$C_{1-8}$ alkyl and Het-$C_{1-8}$ alkyl are optionally substituted by oxo and wherein:

substituted $C_{6-10}$ aryl is chosen from mono-, di-, and tri-substituted $C_{6-10}$ aryl wherein the substituents are independently chosen from
  (1) $C_{1-8}$ alkyl,
  (2) $C_{3-8}$ cycloalkyl,
  (3) $C_{4-8}$ cycloalkylalkyl,
  (4) $C_{1-8}$ alkoxy,
  (5) $C_{3-8}$ cycloalkoxy,
  (6) $C_{4-8}$ cycloalkylalkoxy,
  (7) halo (such as F or Cl),
  (8) amino,
  (9) cyano,
  (10) hydroxyl,
  (11) nitro,
  (12) $C_{1-8}$ halogenated alkyl,
  (13) $C_{1-8}$ halogenated alkoxy,
  (14) $C_{1-8}$ hydroxyalkyl,
  (15) $C_{2-8}$ hydroxyalkoxy,
  (16) $C_{3-8}$ alkenyloxy,
  (17) $C_{1-8}$ alkylamino,
  (18) di-$C_{1-8}$ alkylamino,
  (19) carboxy,
  (20) alkoxycarbonyl,
  (21) carboxamido,
  (22) aminocarbonyl,
  (23) hydroxyaminocarbonyl,
  (24) alkylaminocarbonyl,
  (25) dialkylaminocarbonyl,
  (26) urea,
  (27) hydroxyurea,
  (28) alkylurea,
  (29) dialkylaminoalkylcarbonyl,
  (30) aminocarbonylalkylaminocarbonyl,
  (31) acylamido,
  (32) HCO—NH—NH—CO—,
  (33) NH$_2$NHCO—,
  (34) NH$_2$NHCONH—,

(35) acyloxy,
(36) $C_{1-8}$ alkylthio,
(37) $C_{1-8}$ alkylsulphinyl,
(38) $C_{1-8}$ alkylsulphonyl,
(39) $C_{1-8}$ alkylsulphonamido,
(40) (alkylsuphonyl)$_2$amino-,
(41) thiol,
(42) aminosulfonyl,
(43) alkylaminosulfonyl,
(44) $C_{6-10}$ aryl,
(45) substituted $C_{6-10}$ aryl chosen from mono-, di-, and trisubstituted $C_{6-10}$ aryl wherein the substituents are independently chosen from $C_{1-8}$ alkyl, halogenated $C_{1-8}$ alkyl, $C_{1-4}$ alkoxy, halogenated $C_{1-4}$ alkoxy, $C_{1-8}$ hydroxyalkyl, $C_{2-8}$ hydroxyalkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —COR$^9$, —CSR$^9$, —SR$^9$, cyano, hydroxyl, nitro, and thio;
(46) heterocyclyl;
(47) substituted heterocyclyl chosen from mono-, di-, and trisubstituted heterocyclyl wherein the substitutents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —COR$^9$, —CSR$^9$, —SR$^9$, cyano, hydroxyl, nitro, oxo, and thio;
(48) heterocyclyl-carbonyl; and
(49) heterocyclyl-carbonyl chosen from mono-, di-, and trisubstituted heterocyclyl-carbonyl wherein the substituents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —COR$^9$, —CSR$^9$, —SR$^9$, cyano, hydroxyl, nitro, oxo, and thio; and Het is chosen from heterocyclyl, substituted heterocyclyl chosen from mono-, di-, and tri-substituted heterocyclyl, heteroaryl, and substituted heteroaryl chosen from mono-, di-, and tri-substituted heteroaryl, wherein the substituents are independently chosen from
(1) $C_{1-8}$ alkyl,
(2) $C_{3-8}$ cycloalkyl,
(3) $C_{4-8}$ cycloalkylalkyl,
(4) $C_{1-8}$ alkoxy,
(5) $C_{3-8}$ cycloalkoxy,
(6) $C_{4-8}$ cycloalkylalkoxy,
(7) halo,
(8) amino,
(9) cyano,
(10) hydroxyl,
(11) nitro,
(12) $C_{1-8}$ halogenated alkyl,
(13) $C_{1-8}$ halogenated alkoxy,
(14) $C_{1-8}$ hydroxyalkyl,
(15) $C_{2-8}$ hydroxyalkoxy,
(16) $C_{3-8}$ alkenyloxy,
(17) $C_{1-8}$ alkylamino,
(18) di-$C_{1-8}$ alkylamino,
(19) carboxy,
(20) alkoxycarbonyl,
(21) carboxamido,
(22) aminocarbonyl,
(23) hydroxyaminocarbonyl,
(24) alkylaminocarbonyl,
(25) dialkylaminocarbonyl,
(26) urea,
(27) hydroxyurea,
(28) alkylurea,
(29) dialkylaminoalkylcarbonyl,
(30) aminocarbonylalkylaminocarbonyl,
(31) acylamido,
(32) HCO—NH—NH—CO—,
(33) NH$_2$NHCO—,
(34) NH$_2$NHCONH—,
(35) acyloxy,
(36) $C_{1-8}$ alkylthio,
(37) $C_{1-8}$ alkylsulphinyl,
(38) $C_{1-8}$ alkylsulphonyl,
(39) $C_{1-8}$ alkylsulphonamido,
(40) (alkylsuphonyl)$_2$amino-,
(41) thiol,
(42) aminosulfonyl,
(43) alkylaminosulfonyl,
(44) oxo,
(45) $C_{6-20}$ aryl,
(46) substituted $C_{6-20}$ aryl chosen from mono-, di-, and tri-substituted $C_{6-20}$ aryl wherein the substituents are independently chosen from halo, $C_{1-8}$ alkyl, halogenated $C_{1-8}$ alkyl, $C_{1-4}$ alkoxy, halogenated $C_{1-4}$ alkoxy, $C_{1-8}$ hydroxyalkyl, $C_{2-8}$ hydroxyalkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —COR$^9$, —CSR$^9$, —SR$^9$, cyano, hydroxyl, nitro, and thio,
(47) heterocyclyl,
(48) substituted heterocyclyl chosen from mono-, di-, and trisubstituted heterocyclyl wherein the substituents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —COR$^9$, —CSR$^9$, —SR$^9$, cyano, hydroxyl, nitro, oxo, and thio,
(49) heteroaryl,
(50) substituted heteroaryl chosen from mono-, di-, and trisubstituted heteroaryl wherein the substituents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —COR$^9$, —CSR$^9$, —SR$^9$, cyano, hydroxyl, nitro, oxo, and thio,
(51) heterocyclyl-carbonyl,
(52) substituted heterocyclyl-carbonyl chosen from mono-, di-, and trisubstituted heterocyclyl-carbonyl wherein the substituents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —COR$^9$, —CSR$^9$, —SR$^9$, cyano, hydroxyl, nitro, oxo, and thio,
(53) heteroaryl-carbonyl, and
(54) substituted heteroaryl-carbonyl chosen from mono-, di-, and trisubstituted heteroaryl-carbonyl wherein the substituents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-}$ salkylamino, $C_{1-8}$ alkylsulphinyl, $C_{1-8}$ alkylsulphonyl, $C_{1-8}$ alkylsulphonamido, —COR$^9$, —CSR$^9$, —SR$^9$, cyano, hydroxyl, nitro, oxo, and thio, and R$^9$ is chosen from H, $C_{1-8}$ alkyl, $C_{3-8}$ cycloalkyl, substituted $C_{1-8}$ alkyl chosen from mono-, di-, and trisubstituted $C_{1-8}$ alkyl, and substituted $C_{3-8}$ cycloalkyl chosen from mono-, di-, and trisubstituted $C_{3-8}$ cycloalkyl wherein the substituents are independently chosen from halo, $C_{1-4}$-alkyl, $C_{1-4}$-alkoxy, and oxo; and provided that the compound of Formula I is not chosen from:

(i) when R$^1$ is 4-methylphenyl, then R$^2$ is not —O-p-phenylene-O—(CH$_2$)phenyl, —O-p-phenylene-NH—C(O)-thiophen-2-yl, —O—(CH$_2$)$_2$—O-(phenyl), —NH(CH$_2$)$_2$-(4-hydroxyphenyl), —O—(CH$_2$)$_2$-(1,3-dioxoisoindolin-1-yl), —NH(CH$_2$)$_2$-(2-oxo-imidaziolidin-1-yl), —NH(CH$_2$)$_2$-(3,4,-dimethoxyphenyl), —S(CH$_2$)$_2$-phenyl, —NH(CH$_2$)$_2$-phenyl, —NH(CH$_2$)$_2$-morpholin-4-yl, —NH(CH$_2$)$_2$-thiophen-2-yl, —NH(CH$_2$)$_2$-(3,4-methylenedioxyphenyl), —NH(CH$_2$)$_3$-morpholin-4-yl, or —S(CH$_2$)$_3$-phenyl;

(ii) 2-methoxy-4-[[[2-[(5-phenylthieno[2,3-d]pyimidin-4-yl)amino]ethyl]imino]-methyl]-phenol;

(iii) 4,4'-[1,3-phenylenebis(oxy)bis[5-(4-chlorophenyl)-thieno[2,3-d]pyrimidine;

(iv) when R$^1$ is phenyl, then R$^2$ is not —O-p-phenylene-NH—C(O)-3,-4-dimethoxyphenyl, —O—(CH$_2$)$_2$—O-(4-methylphenyl), —O—(CH$_2$)$_2$-Ophenyl, —O—(CH$_2$)$_2$—O—(3-bromophenyl), —NH—(CH$_2$)$_2$—NH(3-CF$_3$-pyridin-2-yl), —S—(CH$_2$)$_2$—O-(3-methylphenyl), —S—(CH$_2$)$_2$—O-(4-Fphenyl), —S—(CH$_2$)$_2$—O-(2,4-dichlorophenyl), —NH—(CH$_2$)$_2$—NH(4-CF$_3$-pyrimidin-2-yl), —NH—(CH$_2$)$_2$—O-(3-acetylaminophenyl), —S—(CH$_2$)$_3$-phenyl, —S—(CH$_2$)$_4$-(1,3-dioxoisoindolin-1-yl), —NH—(CH$_2$)$_3$-morpholin-4-yl, —NH—(CH$_2$)$_3$-imidazol-1-yl, —NH—(CH$_2$)$_3$-(2-oxo-pyrrolidin-1-yl), —N(CH$_3$)—(CH$_2$)$_2$-pyridin-2-yl, —NH—(CH$_2$)$_2$-pyridin-2-yl, —S—(CH$_2$)$_2$-(1,3-dioxoisoindolin-1-yl, —S—(CH$_2$)$_2$-phenyl, —NH—(CH$_2$)$_2$-(2-chlorophenyl), —NH—(CH$_2$)$_2$-morpholin-4-yl, —NH—(CH$_2$)$_2$-(3,4-dimethoxyphenyl), —NH—(CH$_2$)$_2$-thiophen-2-yl, or —NH—(CH$_2$)$_2$-phenyl;

(v) when R$^1$ is 4-fluorophenyl, then R$^2$ is not chosen from —O—(CH$_2$)$_2$—O-(2-chlorophenyl), —O—(CH$_2$)$_2$—O-(4-fluorophenyl), —S—(CH$_2$)$_3$-phenyl, —NH—(CH$_2$)$_3$-phenyl, —NH—(CH$_2$)$_2$-phenyl, —NH—(CH$_2$)$_3$-morpholin-4-yl, —NH—(CH$_2$)$_3$-(2-oxo-pyrrolidin-1-yl), —NH—(CH$_2$)$_2$-morpholin-4-yl, —S—(CH$_2$)$_2$-phenyl, —NH—(CH$_2$)$_2$-azepan-1-yl, —S—(CH$_2$)$_2$-morpholin-4-yl, —NH—(CH$_2$)$_2$-(3,4-methylenedioxyphenyl), —NH—(CH$_2$)$_2$-thiophen-2-yl, and —NH—(CH$_2$)$_2$-(3,4-ethylenedioxyphenyl);

(vi) when R$^1$ is 4-chlorophenyl, then R$^2$ is not chosen from —O-p-phenylene-O—CH$_2$-phenyl, —O—(CH$_2$)$_2$—O-(4-methylphenyl), —S—(CH$_2$)$_4$-(1,3-dioxoisoindolin-1-yl), —S—(CH$_2$)$_3$-phenyl, —S—(CH$_2$)$_2$-phenyl, —NH—(CH$_2$)$_3$-imidazol-1-yl, —NH—(CH$_2$)$_3$-morpholin-4-yl, —NH—(CH$_2$)$_2$-morpholin-4-yl, —NH—(CH$_2$)$_2$-azepan-1-yl, —S—(CH$_2$)$_2$-(1,3-dioxoisoindolin-1-yl), —NH—(CH$_2$)$_2$-(3,4-methylenedioxyphenyl), —NH—(CH$_2$)$_2$-phenyl, —NH—(CH$_2$)$_2$-thiophen-2-yl, —NH—(CH$_2$)$_2$-(3,4-ethylenedioxyphenyl), —S—(CH$_2$)$_4$-(1,3-dioxoisoindolin-1-yl), —NH(CH$_2$)$_3$-(2-oxo-pyrrolidin-1-yl), and —NH(CH$_2$)$_2$-(3,4,-dimethoxyphenyl);

(vii) when R$^1$ is 3-methylphenyl, then R$^2$ is not —O—(CH$_2$)$_2$—O-(phenyl);

(viii) when R$^1$ is 3-thiophen-2-yl, then R$^2$ is not chosen from —NH—(CH$_2$)$_2$-morpholin-4-yl, —NH—(CH$_2$)$_3$-morpholin-4-yl, —NH—(CH$_2$)$_2$-phenyl, and —NH—(CH$_2$)$_2$-(3,4-dimethoxyphenyl);

(ix) when R$^1$ is 4-methoxyphenyl, then R$^2$ is not chosen from —S—(CH$_2$)$_3$-phenyl, —NH—(CH$_2$)$_2$-morpholin-4-yl, —NH—(CH$_2$)$_2$—C(CH$_3$)$_2$-morpholin-4-yl, —NHCH$_2$C(CH$_3$)$_2$-morpholin-4-yl, —N(CH$_3$)—(CH$_2$)$_2$-(3,4-dimethoxyphenyl), —S—(CH$_2$)$_2$-phenyl, and —NH—(CH$_2$)$_2$-(3,4-methylenedioxyphenyl);

(x) when R$^1$ is 3,4-dimethylphenyl, then R$^2$ is not chosen from —O-p-phenylene-O—CH$_2$-phenyl, —S—(CH$_2$)$_3$-phenyl, —S—(CH$_2$)$_3$-morpholin-4-yl, —S—(CH$_2$)$_2$-phenyl, —NH—(CH$_2$)$_3$-(4-hydroxyphenyl), —O—(CH$_2$)$_2$-(1,3-dioxoisoindolin-1-yl), —NH—(CH$_2$)$_2$-morpholin-4-yl, —NH—(CH$_2$)$_3$-morpholin-4-yl, —NH—(CH$_2$)$_2$-(3,4-methylenedioxyphenyl), —S—(CH$_2$)$_2$-phenyl, —NH—(CH$_2$)$_2$-phenyl, —NH—(CH$_2$)$_2$-thiophen-2-yl, and —NH—(CH$_2$)$_2$-(3,4-methylenedioxyphenyl);

(xi) when R$^1$ is 4-bromophenyl, then R$^2$ is not chosen from —(CH$_2$)$_3$-phenyl, —S—(CH$_2$)$_3$-morpholin-4-yl, —S—(CH$_2$)$_2$-phenyl, —S—(CH$_2$)$_3$-phenyl, —NH—(CH$_2$)$_3$-morpholin-4-yl, —NH—(CH$_2$)$_3$-(2-oxo-pyrrolidin-1-yl), and —NH—(CH$_2$)$_2$-(3,4-ethylenedioxyphenyl); and (xii) when R$^1$ is 4-biphenyl, then R$^2$ is not —NH—(CH$_2$)$_2$-(3,4-ethylenedioxyphenyl);

(xiii) when R$^1$ is 2,3-dihydro-1,4-benzodioxin-2-yl, then R$^2$ is not NH(CH$_2$)$_2$-phenyl, and (xiv) 5-(2-chlorophenyl)-4-[4-(phenylmethoxy)phenoxy]-thieno[2,3-d]pyrimidine.

Provided is at least one chemical entity chosen from compounds of Formula I

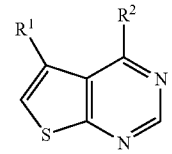

(Formula I)

and pharmaceutically acceptable salts, solvates, chelates, non-covalent complexes, prodrugs, and mixtures thereof, wherein R$^1$ is chosen from:
(i) $C_{6-10}$ aryl;
(ii) substituted $C_{6-10}$ aryl chosen from mono-, di-, and tri-substituted aryl wherein the substituents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —COR$^9$, —CSR$^9$, —SR$^9$, cyano, hydroxyl, nitro, and thio;
(iii) heterocyclyl;
(iv) substituted heterocyclyl chosen from mono-, di-, and tri-substituted heterocyclyl wherein the substitutents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —$COR^9$, —$CSR^9$, —$SR^9$, cyano, hydroxyl, nitro, oxo, and thio;
(v) heteroaryl; and
(vi) substituted heteroaryl chosen from mono-, di-, and tri-substituted heteroaryl wherein the substituents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —$COR^9$, —$CSR^9$, —$SR^9$, cyano, hydroxyl, nitro, oxo, and thio;

$R^2$ is chosen from $C_{2-4}$ hydroxyalkyl, $C_{2-4}$ alkenyl, $C_{2-4}$ alkenylene-$R^5$, $C_{2-4}$ alkynyl, $C_{2-4}$ alkynylene-$R^5$, —O-arylene-Y—$R^5$, —$X(CR^3R^4)_n YR^5$ and —$(CR^6R^7)_m YR^5$ where:

X is chosen from —O—, —S— and —$NR^9$—;
Y is chosen from a covalent bond, —O—, —S— and —$NR^9$—;
n is chosen from 2, 3, 4, and 5;
m is chosen from 2, 3, 4, and 5;
$R^3$ and $R^4$ are each independently chosen from:
  (i) H;
  (ii) halo;
  (iii) $C_{1-2}$ alkyl;
  (iv) $C_{2-12}$ alkenyl;
  (v) $C_{2-12}$ alkynyl;
  (vi) $C_{3-12}$ cycloalkyl;
  (vii) substituted $C_{1-12}$ alkyl chosen from mono-, di-, and tri-substituted $C_{1-12}$ alkyl and wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl;
  (viii) substituted $C_{2-12}$ alkenyl chosen from mono-, di-, and tri-substituted $C_{2-12}$ alkenyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl;
  (ix) substituted $C_{2-12}$ alkynyl chosen from mono-, di-, and tri-substituted $C_{2-12}$ alkynyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl; and
  (x) substituted $C_{3-12}$ cycloalkyl chosen from mono-, di-, and tri-substituted $C_{3-12}$ cycloalkyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl;

$R^6$ and $R^7$ are independently chosen from
  (i) H;
  (ii) halo;
  (iii) $C_{1-12}$ alkyl;
  (iv) $C_{2-12}$ alkenyl;
  (v) $C_{2-12}$ alkynyl;
  (vi) $C_{3-12}$ cycloalkyl;
  (vii) substituted $C_{1-12}$ alkyl chosen from mono-, di-, and tri-substituted $C_{1-12}$ alkyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl;
  (viii) substituted $C_{2-12}$ alkenyl chosen from mono-, di-, and tri-substituted $C_{2-12}$ alkenyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl;
  (ix) substituted $C_{2-12}$ alkynyl chosen from mono-, di-, and tri-substituted $C_{2-12}$ alkynyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl; and
  (x) substituted $C_{3-12}$ cycloalkyl chosen from mono-, di-, and tri-substituted $C_{3-12}$ cycloalkyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl;

$R^9$ is chosen from H, $C_{1-8}$ alkyl, $C_{3-8}$ cycloalkyl, substituted $C_{1-8}$ alkyl chosen from mono-, di-, and trisubstituted $C_{1-8}$ alkyl, and substituted $C_{3-8}$ cycloalkyl chosen from mono-, di-, and trisubstituted $C_{3-8}$ cycloalkyl wherein the substituents are independently chosen from halo, $C_{1-4}$-alkyl, $C_{1-4}$-alkoxy, and oxo; and $R^5$ is chosen from pyridin-3-yl and pyridin-4-yl, each of which is optionally substituted with one or two groups chosen from
(1) $C_{1-8}$ alkyl,
(2) $C_{3-8}$ cycloalkyl,
(3) $C_{4-8}$ cycloalkylalkyl,
(4) $C_{1-8}$ alkoxy,
(5) $C_{3-8}$ cycloalkoxy,
(6) $C_{4-8}$ cycloalkylalkoxy,
(7) halo,
(8) amino,
(9) cyano,
(10) hydroxyl,
(11) nitro,
(12) $C_{1-8}$ halogenated alkyl,
(13) $C_{1-8}$ halogenated alkoxy,
(14) $C_{1-8}$ hydroxyalkyl,
(15) $C_{2-8}$ hydroxyalkoxy,
(16) $C_{3-8}$ alkenyloxy,
(17) $C_{1-8}$ alkylamino,
(18) di-$C_{1-8}$ alkylamino,
(19) carboxy,
(20) alkoxycarbonyl,
(21) carboxamido,
(22) aminocarbonyl,
(23) hydroxyaminocarbonyl,
(24) alkylaminocarbonyl,
(25) dialkylaminocarbonyl,
(26) urea,
(27) hydroxyurea,

(28) alkylurea,
(29) dialkylaminoalkylcarbonyl,
(30) aminocarbonylalkylaminocarbonyl,
(31) acylamido,
(32) HCO—NH—NH—CO—,
(33) NH$_2$NHCO—,
(34) NH$_2$NHCONH—,
(35) acyloxy,
(36) C$_{1-8}$ alkylthio,
(37) C$_{1-8}$ alkylsulphinyl,
(38) C$_{1-8}$ alkylsulphonyl,
(39) C$_{1-8}$ alkylsulphonamido,
(40) (alkylsuphonyl)$_2$amino-,
(41) thiol,
(42) aminosulfonyl,
(43) alkylaminosulfonyl,
(44) oxo,
(45) C$_{6-20}$ aryl,
(46) substituted C$_{6-20}$ aryl chosen from mono-, di-, and tri-substituted C$_{6-20}$ aryl wherein the substituents are independently chosen from halo, C$_{1-8}$ alkyl, halogenated C$_{1-8}$ alkyl, C$_{1-4}$ alkoxy, halogenated C$_{1-4}$ alkoxy, C$_{1-8}$ hydroxyalkyl, C$_{2-8}$ hydroxyalkoxy, amino, C$_{1-8}$ alkylamino, di-C$_{1-8}$ alkylamino, C$_{1-8}$ alkylsulphinyl, C$_{1-8}$ alkylsulphonyl, C$_{1-8}$ alkylsulphonamido, —COR$^9$, —CSR$^9$, —SR$^9$, cyano, hydroxyl, nitro, and thio,
(47) heterocyclyl,
(48) substituted heterocyclyl chosen from mono-, di-, and trisubstituted heterocyclyl wherein the substituents are independently chosen from halo, C$_{1-8}$ alkyl, halogenated C$_{1-8}$ alkyl, C$_{1-4}$ alkoxy, halogenated C$_{1-4}$ alkoxy, hydroxy C$_{1-8}$ alkyl, hydroxy C$_{2-8}$ alkoxy, amino, C$_{1-8}$ alkylamino, di-C$_{1-8}$ alkylamino, C$_{1-8}$ alkylsulphinyl, C$_{1-8}$ alkylsulphonyl, C$_{1-8}$ alkylsulphonamido, —COR$^9$, —CSR$^9$, —SR$^9$, cyano, hydroxyl, nitro, oxo, and thio,
(49) heteroaryl,
(50) substituted heteroaryl chosen from mono-, di-, and trisubstituted heteroaryl wherein the substituents are independently chosen from halo, C$_{1-8}$ alkyl, halogenated C$_{1-8}$ alkyl, C$_{1-4}$ alkoxy, halogenated C$_{1-4}$ alkoxy, hydroxy C$_{1-8}$ alkyl, hydroxy C$_{2-8}$ alkoxy, amino, C$_{1-8}$ alkylamino, di-C$_{1-8}$ alkylamino, C$_{1-8}$ alkylsulphinyl, C$_{1-8}$ alkylsulphonyl, C$_{1-8}$ alkylsulphonamido, —COR$^9$, —CSR$^9$, —SR$^9$, cyano, hydroxyl, nitro, oxo, and thio,
(51) heterocyclyl-carbonyl,
(52) substituted heterocyclyl-carbonyl chosen from mono-, di-, and trisubstituted heterocyclyl-carbonyl wherein the substituents are independently chosen from halo, C$_{1-8}$ alkyl, halogenated C$_{1-8}$ alkyl, C$_{1-4}$ alkoxy, halogenated C$_{1-4}$ alkoxy, hydroxy C$_{1-8}$ alkyl, hydroxy C$_{2-8}$ alkoxy, amino, C$_{1-8}$ alkylamino, di-C$_{1-8}$ alkylamino, C$_{1-8}$ alkylsulphinyl, C$_{1-8}$ alkylsulphonyl, C$_{1-8}$ alkylsulphonamido, —COR$^9$, —CSR$^9$, —SR$^9$, cyano, hydroxyl, nitro, oxo, and thio,
(53) heteroaryl-carbonyl, and
(54) substituted heteroaryl-carbonyl chosen from mono-, di-, and trisubstituted heteroaryl-carbonyl wherein the substituents are independently chosen from halo, C$_{1-8}$ alkyl, halogenated C$_{1-8}$ alkyl, C$_{1-4}$ alkoxy, halogenated C$_{1-4}$ alkoxy, hydroxy C$_{1-8}$ alkyl, hydroxy C$_{2-8}$ alkoxy, amino, C$_{1-8}$ alkylamino, di-C$_{1-8}$ alkylamino, C$_{1-8}$ alkylsulphinyl, C$_{1-8}$ alkylsulphonyl, C$_{1-8}$ alkylsulphonamido, —COR$^9$, —CSR$^9$, —SR$^9$, cyano, hydroxyl, nitro, oxo, and thio.

Provided is at least one chemical entity chosen from compounds of Formula I:

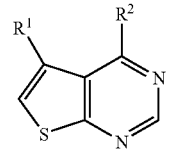

(Formula I)

and pharmaceutically acceptable salts, solvates, chelates, non-covalent complexes, prodrugs, and mixtures thereof, wherein
R$^1$ is chosen from:
(i) C$_{6-10}$ aryl;
(ii) substituted C$_{6-10}$ aryl chosen from mono-, di-, and tri-substituted aryl wherein the substituents are independently chosen from halo, C$_{1-8}$ alkyl, halogenated C$_{1-8}$ alkyl, C$_{1-4}$ alkoxy, halogenated C$_{1-4}$ alkoxy, hydroxy C$_{1-8}$ alkyl, hydroxy C$_{2-8}$ alkoxy, amino, C$_{1-8}$ alkylamino, di-C$_{1-8}$ alkylamino, C$_{1-8}$ alkylsulphinyl, C$_{1-8}$ alkylsulphonyl, C$_{1-8}$ alkylsulphonamido, —COR$^9$, —CSR$^9$, —SR$^9$, cyano, hydroxyl, nitro, and thio;
(iii) heterocyclyl;
(iv) substituted heterocyclyl chosen from mono-, di-, and tri-substituted heterocyclyl wherein the substitutents are independently chosen from halo, C$_{1-8}$ alkyl, halogenated C$_{1-8}$ alkyl, C$_{1-4}$ alkoxy, halogenated C$_{1-4}$ alkoxy, hydroxy C$_{1-8}$ alkyl, hydroxy C$_{2-8}$ alkoxy, amino, C$_{1-8}$ alkylamino, di-C$_{1-8}$ alkylamino, C$_{1-8}$ alkylsulphinyl, C$_{1-8}$ alkylsulphonyl, C$_{1-8}$ alkylsulphonamido, —COR$^9$, —CSR$^9$, —SR$^9$, cyano, hydroxyl, nitro, oxo, and thio;
(v) heteroaryl; and
(vi) substituted heteroaryl chosen from mono-, di-, and tri-substituted heteroaryl wherein the substitutents are independently chosen from halo, C$_{1-8}$ alkyl, halogenated C$_{1-8}$ alkyl, C$_{1-4}$ alkoxy, halogenated C$_{1-4}$ alkoxy, hydroxy C$_{1-8}$ alkyl, hydroxy C$_{2-8}$ alkoxy, amino, C$_{1-8}$ alkylamino, di-C$_{1-8}$ alkylamino, C$_{1-8}$ alkylsulphinyl, C$_{1-8}$ alkylsulphonyl, C$_{1-8}$ alkylsulphonamido, —COR$^9$, —CSR$^9$, —SR$^9$, cyano, hydroxyl, nitro, oxo, and thio;
R$^2$ is chosen from C$_{2-4}$ hydroxyalkyl, C$_{2-4}$ alkenyl, C$_{2-4}$ alkenylene-R$^5$, C$_{2-4}$ alkynyl, C$_{2-4}$ alkynylene-R$^5$, —O-arylene-Y—R$^5$, —X(CR$^3$R$^4$)$_n$YR$^5$ and —(CR$^6$R$^7$)$_m$YR$^5$ where:
X is chosen from —O—, —S— and —NR$^9$— where R$^9$ is chosen from H, C$_{1-8}$ alkyl; and C$_{3-8}$ cycloalkyl, substituted C$_{1-8}$ alkyl; and substituted C$_{3-8}$ cycloalkyl, wherein the substituents on the alkyl and cycloalkyl groups are independently chosen from halo, C$_{1-4}$-alkyl, C$_{1-4}$-alkoxy, and oxo;
Y is chosen from a covalent bond, —O—, —S— and —NR$^9$—;
n is chosen from 2, 3, 4, and 5;
m is chosen from 2, 3, 4, and 5;
R$^3$ and R$^4$ are each independently chosen from:
(i) H;
(ii) halo;
(iii) C$_{1-12}$ alkyl;
(iv) C$_{2-12}$ alkenyl;
(v) C$_{2-12}$ alkynyl;
(vi) C$_{3-12}$ cycloalkyl;
(vii) substituted C$_{1-12}$ alkyl chosen from mono-, di-, and tri-substituted C$_{1-2}$ alkyl and wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl;

(viii) substituted $C_{2-12}$ alkenyl chosen from mono-, di-, and tri-substituted $C_{2-12}$ alkenyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl;

(ix) substituted $C_{2-12}$ alkynyl chosen from mono-, di-, and tri-substituted $C_{2-12}$ alkynyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl; and (x) substituted $C_{3-12}$ cycloalkyl chosen from mono-, di-, and tri-substituted $C_{3-12}$ cycloalkyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl;

$R^6$ and $R^7$ are independently chosen from
(i) H;
(ii) halo;
(iii) $C_{1-12}$ alkyl;
(iv) $C_{2-12}$ alkenyl;
(v) $C_{2-12}$ alkynyl;
(vi) $C_{3-12}$ cycloalkyl;
(vii) substituted $C_{1-12}$ alkyl chosen from mono-, di-, and tri-substituted $C_{1-12}$ alkyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl;
(viii) substituted $C_{2-12}$ alkenyl chosen from mono-, di-, and tri-substituted $C_{2-12}$ alkenyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl; and
(ix) substituted $C_{2-12}$ alkynyl chosen from mono-, di-, and tri-substituted $C_{2-12}$ alkynyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl; and
(x) substituted $C_{3-12}$ cycloalkyl chosen from mono-, di-, and tri-substituted $C_{3-12}$ cycloalkyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl;

$R^9$ is chosen from H, $C_{1-8}$ alkyl, $C_{3-8}$ cycloalkyl, substituted $C_{1-8}$ alkyl chosen from mono-, di-, and trisubstituted $C_{1-8}$ alkyl, and substituted $C_{3-8}$ cycloalkyl chosen from mono-, di-, and trisubstituted $C_{3-8}$ cycloalkyl wherein the substituents are independently chosen from halo, $C_{1-4}$-alkyl, $C_{1-4}$-alkoxy, and oxo; and $R^5$ is chosen from pyridin-2-yl and pyridin-4-yl, each of which is substituted with one or two groups chosen from
(1) $C_{1-8}$ alkyl,
(2) $C_{3-8}$ cycloalkyl,
(3) $C_{4-8}$ cycloalkylalkyl,
(4) $C_{1-8}$ alkoxy,
(5) $C_{3-8}$ cycloalkoxy,
(6) $C_{4-8}$ cycloalkylalkoxy,
(7) halo,
(8) amino,
(9) cyano,
(10) hydroxyl,
(11) nitro,
(12) $C_{2-8}$ halogenated alkyl,
(13) $C_{1-8}$ halogenated alkoxy,
(14) $C_{1-8}$ hydroxyalkyl,
(15) $C_{2-8}$ hydroxyalkoxy,
(16) $C_{3-8}$ alkenyloxy,
(17) $C_{1-8}$ alkylamino,
(18) di-$C_{1-8}$ alkylamino,
(19) carboxy,
(20) alkoxycarbonyl,
(21) carboxamido,
(22) aminocarbonyl,
(23) hydroxyaminocarbonyl,
(24) alkylaminocarbonyl,
(25) dialkylaminocarbonyl,
(26) urea,
(27) hydroxyurea,
(28) alkylurea,
(29) dialkylaminoalkylcarbonyl,
(30) aminocarbonylalkylaminocarbonyl,
(31) acylamido,
(32) HCO—NH—NH—CO—,
(33) $NH_2NHCO$—,
(34) $NH_2NHCONH$—,
(35) acyloxy,
(36) $C_{1-8}$ alkylthio,
(37) $C_{1-8}$ alkylsulphinyl,
(38) $C_{1-8}$ alkylsulphonyl,
(39) $C_{1-8}$ alkylsulphonamido,
(40) (alkylsuphonyl)$_2$amino-,
(41) thiol,
(42) aminosulfonyl,
(43) alkylaminosulfonyl,
(44) oxo,
(45) $C_{6-20}$ aryl,
(46) substituted $C_{6-20}$ aryl chosen from mono-, di-, and tri-substituted $C_{6-20}$ aryl wherein the substituents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —$COR^9$, —$CSR^9$, —$SR^9$, cyano, hydroxyl, nitro, and thio,
(47) heterocyclyl,
(48) substituted heterocyclyl chosen from mono-, di-, and trisubstituted heterocyclyl wherein the substituents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —COR$^9$, —CSR$^9$, —SR$^9$, cyano, hydroxyl, nitro, oxo, and thio,

(49) heteroaryl,

(50) substituted heteroaryl chosen from mono-, di-, and trisubstituted heteroaryl wherein the substituents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —COR$^9$, —CSR$^9$, —SR$^9$, cyano, hydroxyl, nitro, oxo, and thio,

(51) heterocyclyl-carbonyl,

(52) substituted heterocyclyl-carbonyl chosen from mono-, di-, and trisubstituted heterocyclyl-carbonyl wherein the substituents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —COR$^9$, —CSR$^9$, —SR$^9$, cyano, hydroxyl, nitro, oxo, and thio,

(53) heteroaryl-carbonyl, and

(54) substituted heteroaryl-carbonyl chosen from mono-, di-, and trisubstituted heteroaryl-carbonyl wherein the substituents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —COR$^9$, —CSR$^9$, —SR$^9$, cyano, hydroxyl, nitro, oxo, and thio.

Provided is at least one chemical entity chosen from compounds of Formula II:

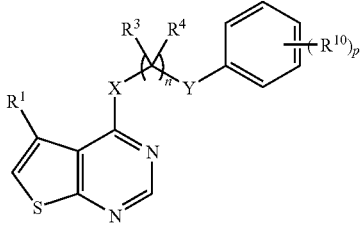

(Formula II)

and pharmaceutically acceptable salts, solvates, chelates, non-covalent complexes, prodrugs, and mixtures thereof, wherein $R^1$ is chosen from:
  (i) $C_{6-10}$ aryl;
  (ii) substituted $C_{6-10}$ aryl chosen from mono-, di-, and tri-substituted aryl wherein the substituents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —COR$^9$, —CSR$^9$, —SR$^9$, cyano, hydroxyl, nitro, and thio;
  (iii) heterocyclyl;
  (iv) substituted heterocyclyl chosen from mono-, di-, and tri-substituted heterocyclyl wherein the substituents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —COR$^9$, —CSR$^9$, —SR$^9$, cyano, hydroxyl, nitro, oxo, and thio;
  (v) heteroaryl; and
  (vi) substituted heteroaryl chosen from mono-, di-, and tri-substituted heteroaryl wherein the substituents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —COR$^9$, —CSR$^9$, —SR$^9$, cyano, hydroxyl, nitro, oxo, and thio;

$R^2$ is chosen from $C_{2-4}$ hydroxyalkyl, $C_{2-4}$ alkenyl, $C_{2-4}$ alkenylene-R$^5$, $C_{2-4}$ alkynyl, $C_{2-4}$ alkynylene-R$^5$, —O-arylene-Y—R$^5$, —X(CR$^3$R$^4$)$_n$YR$^5$ and —(CR$^6$R$^7$)$_m$YR$^5$ where:

X is chosen from —O—, —S— and —NR$^9$— where R$^9$ is chosen from H, $C_{1-8}$ alkyl; and $C_{3-8}$ cycloalkyl, substituted $C_{1-8}$ alkyl; and substituted $C_{3-8}$ cycloalkyl, wherein the substituents on the alkyl and cycloalkyl groups are independently chosen from halo, $C_{1-4}$-alkyl, $C_{1-4}$-alkoxy, and oxo;

Y is chosen from a covalent bond, —O—, —S— and —NR$^9$—;

n is chosen from 2, 3, 4, and 5;

m is chosen from 2, 3, 4, and 5;

$R^3$ and $R^4$ are each independently chosen from:
  (i) H;
  (ii) halo;
  (iii) $C_{1-12}$ alkyl;
  (iv) $C_{2-12}$ alkenyl;
  (v) $C_{2-12}$ alkynyl;
  (vi) $C_{3-12}$ cycloalkyl;
  (vii) substituted $C_{1-12}$ alkyl chosen from mono-, di-, and tri-substituted $C_{1-12}$ alkyl and wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl;
  (viii) substituted $C_{2-12}$ alkenyl chosen from mono-, di-, and tri-substituted $C_{2-12}$ alkenyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl;
  (ix) substituted $C_{2-12}$ alkynyl chosen from mono-, di-, and tri-substituted $C_{2-12}$ alkynyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl; and
  (x) substituted $C_{3-12}$ cycloalkyl chosen from mono-, di-, and tri-substituted $C_{3-12}$ cycloalkyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$- alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl;

$R^6$ and $R^7$ are independently chosen from
- (i) H;
- (ii) halo;
- (iii) $C_{1-12}$ alkyl;
- (iv) $C_{2-12}$ alkenyl;
- (v) $C_{2-12}$ alkynyl;
- (vi) $C_{3-12}$ cycloalkyl;
- (vii) substituted $C_{1-12}$ alkyl chosen from mono-, di-, and tri-substituted $C_{1-12}$ alkyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl;
- (viii) substituted $C_{2-12}$ alkenyl chosen from mono-, di-, and tri-substituted $C_{2-12}$ alkenyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl;
- (ix) substituted $C_{2-12}$ alkynyl chosen from mono-, di-, and tri-substituted $C_{2-12}$ alkynyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl; and
- (x) substituted $C_{3-12}$ cycloalkyl chosen from mono-, di-, and tri-substituted $C_{3-12}$ cycloalkyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl;

$R^9$ is chosen from H, $C_{1-8}$ alkyl, $C_{3-8}$ cycloalkyl, substituted $C_{1-8}$ alkyl chosen from mono-, di-, and trisubstituted $C_{1-8}$ alkyl, and substituted $C_{3-8}$ cycloalkyl chosen from mono-, di-, and trisubstituted $C_{3-8}$ cycloalkyl wherein the substituents are independently chosen from halo, $C_{1-4}$-alkyl, $C_{1-4}$-alkoxy, and oxo;

p is chosen from 1, 2, 3, and 4; and for each occurrence, $R^{10}$ is independently chosen from
- (1) $C_{2-8}$ alkyl,
- (2) $C_{3-8}$ cycloalkyl,
- (3) $C_{4-8}$ cycloalkylalkyl,
- (4) $C_{3-8}$ cycloalkoxy,
- (5) $C_{4-8}$ cycloalkylalkoxy,
- (6) amino,
- (7) cyano,
- (8) nitro,
- (9) $C_{1-8}$ halogenated alkyl,
- (10) $C_{1-8}$ halogenated alkoxy,
- (11) $C_{1-8}$ hydroxyalkyl,
- (12) $C_{2-8}$ hydroxyalkoxy,
- (13) $C_{1-8}$ alkylamino,
- (14) di-$C_{1-8}$alkylamino,
- (15) carboxy,
- (16) alkoxycarbonyl,
- (17) aminocarbonyl,
- (18) hydroxyaminocarbonyl,
- (19) alkylaminocarbonyl,
- (20) dialkylaminocarbonyl,
- (21) urea,
- (22) hydroxyurea,
- (23) alkylurea,
- (24) dialkylaminoalkylcarbonyl,
- (25) aminocarbonylalkylaminocarbonyl,
- (26) acylamido,
- (27) HCO—NH—NH—CO—,
- (28) $NH_2NHCO$—,
- (29) $NH_2NHCONH$—,
- (30) acyloxy,
- (31) $C_{1-8}$ alkylthio,
- (32) $C_{1-8}$ alkylsulphinyl,
- (33) $C_{1-8}$ alkylsulphonyl,
- (34) $C_{1-8}$ alkylsulphonamido,
- (35) (alkylsuphonyl)$_2$amino-,
- (36) thiol,
- (37) aminosulfonyl,
- (38) alkylaminosulfonyl,
- (39) $C_{6-20}$ aryl,
- (40) substituted $C_{6-20}$ aryl chosen from mono-, di-, and tri-substituted $C_{6-20}$ aryl wherein the substituents are independently chosen from halo, $C_{1-8}$ alkyl, halogenated $C_{1-8}$ alkyl, $C_{1-4}$ alkoxy, halogenated $C_{1-4}$ alkoxy, $C_{1-8}$ hydroxyalkyl, $C_{2-8}$ hydroxyalkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —$COR^9$, —$CSR^9$, —$SR^9$, cyano, hydroxyl, nitro, and thio,
- (41) heterocyclyl-carbonyl,
- (42) substituted heterocyclyl-carbonyl chosen from mono-, di-, and trisubstituted heterocyclyl-carbonyl wherein the substituents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —$COR^9$, —$CSR^9$, —$SR^9$, cyano, hydroxyl, nitro, oxo, and thio,
- (43) heteroaryl-carbonyl, and
- (44) substituted heteroaryl-carbonyl chosen from mono-, di-, and trisubstituted heteroaryl-carbonyl wherein the substituents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$alkylamino, $C_{1-8}$ alkylsulphinyl, $C_{1-8}$ alkylsulphonyl, $C_{1-8}$ alkylsulphonamido, —$COR^9$, —$CSR^9$, —$SR^9$, cyano, hydroxyl, nitro, oxo, and thio.

Also provided is a pharmaceutical composition comprising at least one chemical entity described herein and a pharmaceutically acceptable carrier.

Also provided is a method of selectively inhibiting PDE10 enzyme in a patient in need thereof comprising administering to said patient an effective amount of at least one chemical entity described herein.

Unless otherwise specified the following terms in the specification and the claims in this Application have the meanings given below.

Halo herein refers to F, Cl, Br, and I, such as F and Cl.

Alkyl means a straight-chain or branched-chain aliphatic hydrocarbon radical. Suitable alkyl groups include, but are not limited to, methyl, ethyl, propyl, isopropyl, butyl, sec-butyl, tert-butyl, pentyl, hexyl, heptyl, octyl, nonyl, decyl, undecyl, and dodecyl. Other examples of suitable alkyl groups include 1-, 2- or 3-methylbutyl, 1,1-, 1,2- or 2,2- dimethylpropyl, 1-ethylpropyl, 1-, 2-, 3- or 4-methylpentyl, 1,1-, 1,2-, 1,3-, 2,2-, 2,3- or 3,3-dimethylbutyl, 1- or 2-ethylbutyl, ethylmethylpropyl, trimethylpropyl, methylhexyl, dimethylpentyl, ethylpentyl, ethylmethylbutyl, dimethylbutyl, and the like.

Alkenyl refers to an unsaturated branched or straight-chain alkyl group having at least one carbon-carbon double bond derived by the removal of one hydrogen atom from a single carbon atom of a parent alkene. The group may be in either the cis or trans configuration about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl; and the like. In certain embodiments, an alkenyl group has from 2 to 20 carbon atoms and in other embodiments, from 2 to 6 carbon atoms. Alkenylene refers to a divalent alkenyl group.

Alkynyl refers to an unsaturated branched or straight-chain alkyl group having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl; butynyls such as but-1-yn-1-yl, but-1-yn-3-yl, but-3-yn-1-yl; and the like. In certain embodiments, an alkynyl group has from 2 to 20 carbon atoms and in other embodiments, from 3 to 6 carbon atoms. Alkynylene refers to a divalent alkynyl group.

Cycloalkyl herein refers to a non-aromatic monocyclic, bicyclic, or tricyclic carbocyclic ring, usually having from 3 to 8 ring carbon atoms, for example 4 to 6 ring carbon atoms. The ring may be saturated or have one or more carbon-carbon double bonds. Examples of cycloalkyl groups include cyclopropyl, cyclobutyl, cyclopentyl, cyclopentenyl, cyclohexyl, cyclohexenyl, cycloheptyl, and cyclooctyl, as well as bridged and caged saturated ring groups such as norbornane. Other suitable cycloalkyl groups include spiropentyl, bicyclo[2.1.0]pentyl, bicyclo[3.1.0]hexyl, spiro[2,4]heptyl, spiro[2,5]octyl, bicyclo[5.1.0]octyl, spiro[2,6]nonyl, bicyclo[2.2.0]hexyl, spiro[3,3]heptyl, and bicyclo[4.2.0]octyl.

In the arylalkyl groups and heteroarylalkyl groups, "alkyl" refers to a divalent alkylene group having, in certain embodiments, 1 to 4 carbon atoms.

In the cases where alkyl is a substituent (e.g., alkyl substituents on aryl and heteroaryl groups) or is part of a substituent (e.g., in the alkylamino, dialkylamino, hydroxyalkyl, hydroxyalkoxy, alkylthio, alkylsulphinyl, and alkylsulphonyl substituents), the alkyl portion usually has 1 to 12 carbon atoms, for example 1 to 8 carbon atoms, such as 1 to 4 carbon atoms.

Aryl, as a group or substituent per se or as part of a group or substituent, refers to an aromatic, monocyclic or bicyclic carbocyclic radical containing 6 to 14 carbon atoms, such as 6 to 12 carbon atoms, for example 6 to 10 carbon atoms. Suitable aryl groups include phenyl, naphthyl and biphenyl. Unless otherwise specified, substituted aryl groups include the above-described aryl groups which are substituted by at least one time, for example, one, two, or three times, by a group chosen from halo, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, and acyloxy (e.g., acetoxy).

Arylalkyl refers to an aryl-alkyl-radical in which the aryl and alkyl portions are in accordance with the previous descriptions. Suitable examples include 1-phenethyl, 2-phenethyl, phenpropyl, phenbutyl, phenpentyl, and naphthylenemethyl.

Heteroaryl encompasses:

5- to 7-membered aromatic, monocyclic rings containing one or more, for example, from 1 to 4, or in certain embodiments, from 1 to 3, such as 1 or 2, heteroatoms chosen from N, O, and S, with the remaining ring atoms being carbon;

bicyclic heterocyclyl rings containing one or more, for example, from 1 to 4, or in certain embodiments, from 1 to 3, such as 1 or 2, heteroatoms chosen from N, O, and S, with the remaining ring atoms being carbon and wherein at least one heteroatom is present in an aromatic ring; and tricyclic heterocyclyl rings containing one or more, for example, from 1 to 5, or in certain embodiments, from 1 to 4, such as 1 or 2, heteroatoms chosen from N, O, and S, with the remaining ring atoms being carbon and wherein at least one heteroatom is present in an aromatic ring.

For example, heteroaryl includes a 5- to 7-membered heterocyclyl, aromatic ring fused to a 5- to 7-membered cycloalkyl or heterocyclyl ring. For such fused, bicyclic heteroaryl ring systems wherein only one of the rings contains one or more heteroatoms, the point of attachment may be at either ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Examples of heteroaryl groups include, but are not limited to, furyl, thienyl, pyrrolyl, pyrazolyl, imidazolyl, pyridyl, pyrimidinyl, indolyl, quinolinyl, naphthyridinyl, azaindolyl (e.g., 7-azaindolyl), 1,2,3,4,-tetrahydroisoquinolyl, and the like. In certain embodiments, examples of heteroaryl groups include, but are not limited to 2-thienyl, 3-thienyl, 2-, 3- or 4-pyridyl, 2-, 3-, 4-, 5-, 6-, 7- or 8-quinolinyl, 7-azaindolyl, and 1-, 3-, 4-, 5-, 6-, 7- or 8-isoquinolinyl. Unless otherwise specified, substituted heteroaryl groups refer to the heteroaryl groups described above which are substituted in one or more places by halo, aryl, alkyl, alkoxy, cyano, halogenated alkyl (e.g., trifluoromethyl), nitro, oxo, amino, alkylamino, and dialkylamino. Heteroaryl does not encompass or overlap with aryl, cycloalkyl, or heterocyclyl, as defined herein Substituted heteroaryl also includes ring systems substituted with one or more oxide ($-O^-$) substituents, such as pyridinyl N-oxides.

Heteroarylalkyl refers to a heteroaryl-alkyl-group wherein the heteroaryl and alkyl portions are in accordance with the previous discussions. Suitable examples are pyridylmethyl, thienylmethyl, pyrimidinylmethyl, pyrazinylmethyl, isoquinolinylmethyl, pyridylethyl and thienylethyl.

By heterocycloalkyl or heterocyclyl is meant a single, non-aromatic ring, usually with 3 to 7 ring atoms, containing at least 2 carbon atoms in addition to 1-3 heteroatoms independently selected from oxygen, sulfur, and nitrogen, as well as combinations comprising at least one of the foregoing heteroatoms. Heterocyclyl also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteratoms independently selected from oxygen, sulfur, and nitrogen and is not aromatic. The ring or rings may be saturated or have one or more carbon-carbon double bonds. Suitable heterocyclyl groups include, for example (as numbered from the linkage position assigned priority 1), 3-tetrahydrofuranyl, piperidinyl, imidazolinyl, imidazolidinyl, pyrrolinyl, pyrrolidinyl, morpholinyl, piperazinyl, oxazolidinyl, and indolinyl. Substituted heterocyclyl also includes ring systems substituted with one or more oxo (=O) or oxide (—O⁻) substituents, such as piperidinyl N-oxide, morpholinyl-N-oxide, 1-oxo-1-thiomorpholinyl and 1,1-dioxo-1-thiomorpholinyl.

Acyl refers to alkanoyl radicals having 2 to 4 carbon atoms, such as formyl, acetyl, propionyl, and butanoyl.

Substituted radicals usually have 1 to 3 substituents, for example, 1 or 2 substituent, such as 1 substituent.

Compounds of Formula I include, but are not limited to, optical isomers of compounds of Formula I, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. Substantially pure enantiomers contain no more than 5% w/w of the corresponding opposite enantiomer, such as no more than 2%, for example, no more than 1%. In addition, compounds of Formula I include Z- and E-forms (or cis- and trans-forms) of compounds with carbon-carbon double bonds. Where compounds of Formula I exists in various tautomeric forms, chemical entities of the present invention include all tautomeric forms of the compound.

Chemical entities of the present invention include compounds of Formula I and all pharmaceutically acceptable forms thereof. Pharmaceutically acceptable forms of the compounds recited herein include pharmaceutically acceptable salts, solvates, crystal forms (including polymorphs and clathrates), chelates, non-covalent complexes, prodrugs, and mixtures thereof. In certain embodiments, the compounds described herein are in the form of pharmaceutically acceptable salts. Hence, the terms "chemical entity" and "chemical entities" also encompass pharmaceutically acceptable salts, solvates, chelates, non-covalent complexes, prodrugs, and mixtures.

A polymorph is a solid crystalline phase of a compound with at least two different arrangements or polymorphic forms of that compound molecule in the solid state. Polymorphic forms of any given compound are defined by the same chemical formula or composition and are as distinct in chemical structure as crystalline structures of two different chemical compounds.

Pharmaceutically acceptable salts include those obtained by reacting the main compound, functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid and citric acid. Other examples of acid salts that can be obtained by reaction with inorganic or organic acids: acetates, adipates, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxy-ethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and undecanoates.

Pharmaceutically acceptable salts also include those in which the main compound functions as an acid and is reacted with an appropriate base to form, e.g., sodium, potassium, calcium, magnesium, ammonium, and choline salts.

Those skilled in the art will recognize various synthetic methodologies that may be used to prepare non-toxic pharmaceutically acceptable addition salts.

As noted above, prodrugs also fall within the scope of chemical entities, for example ester or amide derivatives of the compounds of Formula I. The term "prodrugs" includes any compounds that become compounds of Formula I when administered to a patient, e.g., upon metabolic processing of the prodrug. Examples of prodrugs include, but are not limited to, acetate, formate, and benzoate and like derivatives of functional groups (such as alcohol or amine groups) in the compounds of Formula I.

The term solvate refers to the chemical entity formed by the interaction of a solvent and a compound. Solvates may also form when solvent molecules are incorporated into the crystalline lattice structure of the compound molecule during the crystallization process. Suitable solvates are pharmaceutically acceptable solvates, such as hydrates, e.g., monohydrates, dihydrates, sesquihydrates, and hemihydrates.

One of ordinary skill in the art will further recognize that compounds of Formulas I and Ia can exist in different solvate forms.

The term chelate refers to the chemical entity formed by the coordination of a compound to a metal ion at two (or more) points.

The term non-covalent complex refers to the chemical entity formed by the interaction of a compound and another molecule wherein a covalent bond is not formed between the compound and the molecule. For example, complexation can occur through van der Waals interactions, hydrogen bonding, and electrostatic interactions (also called ionic bonding).

Provided is at least one chemical entity chosen from compounds of Formula I:

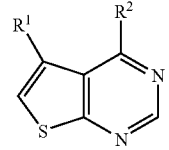

(Formula I)

and pharmaceutically acceptable salts, solvates, chelates, non-covalent complexes, prodrugs, and mixtures thereof, wherein $R^1$ is chosen from:
(i) $C_{6-10}$ aryl;
(ii) substituted $C_{6-10}$ aryl chosen from mono-, di-, and tri-substituted aryl wherein the substituents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —COR⁹, —CSR⁹, —SR⁹, cyano, hydroxyl, nitro, and thio;
(iii) heterocyclyl;
(iv) substituted heterocyclyl chosen from mono-, di-, and tri-substituted heterocyclyl wherein the substitutents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —COR$^9$, —CSR$^9$, —SR$^9$, cyano, hydroxyl, nitro, oxo, and thio;
(v) heteroaryl; and
(vi) substituted heteroaryl chosen from mono-, di-, and tri-substituted heteroaryl wherein the substituents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —COR$^9$, —CSR$^9$, —SR$^9$, cyano, hydroxyl, nitro, oxo, and thio;

$R^2$ is chosen from $C_{2-4}$ hydroxyalkyl, $C_{2-4}$ alkenyl, $C_{2-4}$ alkenylene-$R^5$, $C_{2-4}$ alkynyl, $C_{2-4}$ alkynylene-$R^5$, —O-arylene-Y—$R^5$, —X(CR$^3$R$^4$)$_n$YR$^5$ and —(CR$^6$R$^7$)$_m$YR$^5$ where:

X is chosen from —O—, —S— and —NR$^9$—;
Y is chosen from a covalent bond, —O—, —S— and —NR$^9$—;
n is chosen from 2, 3, 4, and 5;
m is chosen from 2, 3, 4, and 5;
$R^3$ and $R^4$ are each independently chosen from:
 (i) H;
 (ii) halo;
 (iii) $C_{1-12}$ alkyl;
 (iv) $C_{2-12}$ alkenyl;
 (V) $C_{2-12}$ alkynyl;
 (vi) $C_{3-12}$ cycloalkyl;
 (vii) substituted $C_{1-12}$ alkyl chosen from mono-, di-, and tri-substituted $C_{1-12}$ alkyl and wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl;
 (viii) substituted $C_{2-12}$ alkenyl chosen from mono-, di-, and tri-substituted $C_{2-12}$ alkenyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl;
 (ix) substituted $C_{2-12}$ alkynyl chosen from mono-, di-, and tri-substituted $C_{2-12}$ alkynyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl; and
 (x) substituted $C_{3-12}$ cycloalkyl chosen from mono-, di-, and tri-substituted $C_{3-12}$ cycloalkyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl;

$R^6$ and $R^7$ are independently chosen from
 (i) H;
 (ii) halo;
 (iii) $C_{1-12}$ alkyl;
 (iv) $C_{2-12}$ alkenyl;
 (v) $C_{2-12}$ alkynyl;
 (vi) $C_{3-12}$ cycloalkyl;
 (vii) substituted $C_{1-12}$ alkyl chosen from mono-, di-, and tri-substituted $C_{1-12}$ alkyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl;
 (viii) substituted $C_{2-12}$ alkenyl chosen from mono-, di-, and tri-substituted $C_{2-12}$ alkenyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl;
 (ix) substituted $C_{2-12}$ alkynyl chosen from mono-, di-, and tri-substituted $C_{2-12}$ alkynyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl; and
 (x) substituted $C_{3-12}$ cycloalkyl chosen from mono-, di-, and tri-substituted $C_{3-12}$ cycloalkyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl; and $R^5$ is chosen from $C_{6-10}$ aryl, substituted $C_{6-10}$ aryl, Het, substituted Het, $C_{6-10}$ aryl-$C_{1-8}$ alkyl, substituted $C_{6-10}$ aryl-$C_{1-8}$ alkyl, Het-$C_{1-8}$ alkyl, and substituted Het-$C_{1-8}$ alkyl, wherein the alkyl portions of $C_{6-10}$ aryl-$C_{1-8}$ alkyl and Het-$C_{1-8}$ alkyl are optionally substituted by oxo and wherein:
 substituted $C_{6-10}$ aryl is chosen from mono-, di-, and tri-substituted $C_{6-10}$ aryl wherein the substituents are independently chosen from
 (1) $C_{1-8}$ alkyl,
 (2) $C_{3-8}$ cycloalkyl,
 (3) $C_{4-8}$ cycloalkylalkyl,
 (4) $C_{1-8}$ alkoxy,
 (5) $C_{3-8}$ cycloalkoxy,
 (6) $C_{4-8}$ cycloalkylalkoxy,
 (7) halo (such as F or Cl),
 (8) amino,
 (9) cyano,
 (10) hydroxyl,
 (11) nitro,
 (12) $C_{1-8}$ halogenated alkyl,
 (13) $C_{1-8}$ halogenated alkoxy,
 (14) $C_{1-8}$ hydroxyalkyl,
 (15) $C_{2-8}$ hydroxyalkoxy,
 (16) $C_{3-8}$ alkenyloxy,
 (17) $C_{1-8}$ alkylamino,
 (18) di-$C_{1-8}$ alkylamino,
 (19) carboxy,
 (20) alkoxycarbonyl,
 (21) carboxamido,
 (22) aminocarbonyl,
 (23) hydroxyaminocarbonyl,
 (24) alkylaminocarbonyl,
 (25) dialkylaminocarbonyl,
 (26) urea,
 (27) hydroxyurea,

(28) alkylurea,
(29) dialkylaminoalkylcarbonyl,
(30) aminocarbonylalkylaminocarbonyl,
(31) acylamido,
(32) HCO—NH—NH—CO—,
(33) NH$_2$NHCO—,
(34) NH$_2$NHCONH—,
(35) acyloxy,
(36) C$_{1-8}$ alkylthio,
(37) C$_{1-8}$ alkylsulphinyl,
(38) C$_{1-8}$ alkylsulphonyl,
(39) C$_{1-8}$ alkylsulphonamido,
(40) (alkylsuphonyl)$_2$amino-,
(41) thiol,
(42) aminosulfonyl,
(43) alkylaminosulfonyl,
(44) C$_{6-10}$ aryl,
(45) substituted C$_{6-10}$ aryl chosen from mono-, di-, and trisubstituted C$_{6-10}$ aryl wherein the substituents are independently chosen from C$_{1-8}$ alkyl, halogenated C$_{1-8}$ alkyl, C$_{1-4}$ alkoxy, halogenated C$_{1-4}$ alkoxy, C$_{1-8}$ hydroxyalkyl, C$_{2-8}$ hydroxyalkoxy, amino, C$_{1-8}$ alkylamino, di-C$_{1-8}$ alkylamino, C$_{1-8}$ alkylsulphinyl, C$_{1-8}$ alkylsulphonyl, C$_{1-8}$ alkylsulphonamido, —COR$^9$, —CSR$^9$, —SR$^9$, cyano, hydroxyl, nitro, and thio;
(46) heterocyclyl;
(47) substituted heterocyclyl chosen from mono-, di-, and trisubstituted heterocyclyl wherein the substitutents are independently chosen from halo, C$_{1-8}$ alkyl, halogenated C$_{1-8}$ alkyl, C$_{1-4}$ alkoxy, halogenated C$_{1-4}$ alkoxy, hydroxy C$_{1-8}$ alkyl, hydroxy C$_{2-8}$ alkoxy, amino, C$_{1-8}$ alkylamino, di-C$_{1-8}$ alkylamino, C$_{1-8}$ alkylsulphinyl, C$_{1-8}$ alkylsulphonyl, C$_{1-8}$ alkylsulphonamido, —COR$^9$, —CSR$^9$, —SR$^9$, cyano, hydroxyl, nitro, oxo, and thio;
(48) heterocyclyl-carbonyl; and
(49) heterocyclyl-carbonyl chosen from mono-, di-, and trisubstituted heterocyclyl-carbonyl wherein the substituents are independently chosen from halo, C$_{1-8}$ alkyl, halogenated C$_{1-8}$ alkyl, C$_{1-4}$ alkoxy, halogenated C$_{1-4}$ alkoxy, hydroxy C$_{1-8}$ alkyl, hydroxy C$_{2-8}$ alkoxy, amino, C$_{1-8}$ alkylamino, di-C$_{1-8}$ alkylamino, C$_{1-8}$ alkylsulphinyl, C$_{1-8}$ alkylsulphonyl, C$_{1-8}$ alkylsulphonamido, —COR$^9$, —CSR$^9$, —SR$^9$, cyano, hydroxyl, nitro, oxo, and thio; and Het is chosen from heterocyclyl, substituted heterocyclyl chosen from mono-, di-, and tri-substituted heterocyclyl, heteroaryl, and substituted heteroaryl chosen from mono-, di-, and tri-substituted heteroaryl, wherein the substituents are independently chosen from
(1) C$_{1-8}$ alkyl,
(2) C$_{3-8}$ cycloalkyl,
(3) C$_{4-8}$ cycloalkylalkyl,
(4) C$_{1-8}$ alkoxy,
(5) C$_{3-8}$ cycloalkoxy,
(6) C$_{4-8}$ cycloalkylalkoxy,
(7) halo,
(8) amino,
(9) cyano,
(10) hydroxyl,
(11) nitro,
(12) C$_{1-8}$ halogenated alkyl,
(13) C$_{1-8}$ halogenated alkoxy,
(14) C$_{1-8}$ hydroxyalkyl,
(15) C$_{2-8}$ hydroxyalkoxy
(16) C$_{3-8}$ alkenyloxy,
(17) C$_{1-8}$ alkylamino,
(18) di-C$_{1-8}$ alkylamino,
(19) carboxy,
(20) alkoxycarbonyl,
(21) carboxamido,
(22) aminocarbonyl,
(23) hydroxyaminocarbonyl,
(24) alkylaminocarbonyl,
(25) dialkylaminocarbonyl,
(26) urea,
(27) hydroxyurea,
(28) alkylurea,
(29) dialkylaminoalkylcarbonyl,
(30) aminocarbonylalkylaminocarbonyl,
(31) acylamido,
(32) HCO—NH—NH—CO—,
(33) NH$_2$NHCO—,
(34) NH$_2$NHCONH—,
(35) acyloxy,
(36) C$_{1-8}$ alkylthio,
(37) C$_{1-8}$ alkylsulphinyl,
(38) C$_{1-8}$ alkylsulphonyl,
(39) C$_{1-8}$ alkylsulphonamido,
(40) (alkylsuphonyl)$_2$amino-,
(41) thiol,
(42) aminosulfonyl,
(43) alkylaminosulfonyl,
(44) oxo,
(45) C$_{6-20}$ aryl,
(46) substituted C$_{6-20}$ aryl chosen from mono-, di-, and tri-substituted C$_{6-20}$ aryl wherein the substituents are independently chosen from halo, C$_{1-8}$ alkyl, halogenated C$_{1-8}$ alkyl, C$_{1-4}$ alkoxy, halogenated C$_{1-4}$ alkoxy, C$_{1-8}$ hydroxyalkyl, C$_{2-8}$ hydroxyalkoxy, amino, C$_{1-8}$ alkylamino, di-C$_{1-8}$ alkylamino, C$_{1-8}$ alkylsulphinyl, C$_{1-8}$ alkylsulphonyl, C$_{1-8}$ alkylsulphonamido, —COR$^9$, —CSR$^9$, —SR$^9$, cyano, hydroxyl, nitro, and thio,
(47) heterocyclyl,
(48) substituted heterocyclyl chosen from mono-, di-, and trisubstituted heterocyclyl wherein the substituents are independently chosen from halo, C$_{1-8}$ alkyl, halogenated C$_{1-8}$ alkyl, C$_{1-4}$ alkoxy, halogenated C$_{1-4}$ alkoxy, hydroxy C$_{1-8}$ alkyl, hydroxy C$_{2-8}$ alkoxy, amino, C$_{1-8}$ alkylamino, di-C$_{1-8}$ alkylamino, C$_{1-8}$ alkylsulphinyl, C$_{1-8}$ alkylsulphonyl, C$_{1-8}$ alkylsulphonamido, —COR$^9$, —CSR$^9$, —SR$^9$, cyano, hydroxyl, nitro, oxo, and thio,
(49) heteroaryl,
(50) substituted heteroaryl chosen from mono-, di-, and trisubstituted heteroaryl wherein the substituents are independently chosen from halo, C$_{1-8}$ alkyl, halogenated C$_{1-8}$ alkyl, C$_{1-4}$ alkoxy, halogenated C$_{1-4}$ alkoxy, hydroxy C$_{1-8}$ alkyl, hydroxy C$_{2-8}$ alkoxy, amino, C$_{1-8}$ alkylamino, di-C$_{1-8}$ alkylamino, C$_{1-8}$ alkylsulphinyl, C$_{1-8}$ alkylsulphonyl, C$_{1-8}$ alkylsulphonamido, —COR$^9$, —CSR$^9$, —SR$^9$, cyano, hydroxyl, nitro, oxo, and thio,
(51) heterocyclyl-carbonyl,
(52) substituted heterocyclyl-carbonyl chosen from mono-, di-, and trisubstituted heterocyclyl-carbonyl wherein the substituents are independently chosen from halo, C$_{1-8}$ alkyl, halogenated C$_{1-8}$ alkyl, C$_{1-4}$ alkoxy, halogenated C$_{1-4}$ alkoxy, hydroxy C$_{1-8}$ alkyl, hydroxy C$_{2-8}$ alkoxy, amino, C$_{1-8}$ alkylamino, di-C$_{1-8}$ alkylamino, C$_{1-8}$ alkylsulphinyl, C$_{1-8}$ alkylsulphonyl, C$_{1-8}$ alkylsulphonamido, —COR$^9$, —CSR$^9$, —SR$^9$, cyano, hydroxyl, nitro, oxo, and thio,

(53) heteroaryl-carbonyl, and
(54) substituted heteroaryl-carbonyl chosen from mono-, di-, and trisubstituted heteroaryl-carbonyl wherein the substituents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$salkylamino, $C_{1-8}$ alkylsulphinyl, $C_{1-8}$ alkylsulphonyl, $C_{1-8}$ alkylsulphonamido, —$COR^9$, —$CSR^9$, —$SR^9$, cyano, hydroxyl, nitro, oxo, and thio, and $R^9$ is chosen from H, $C_{1-8}$ alkyl, $C_{3-8}$ cycloalkyl, substituted $C_{1-8}$ alkyl chosen from mono-, di-, and trisubstituted $C_{1-8}$ alkyl, and substituted $C_{3-8}$ cycloalkyl chosen from mono-, di-, and trisubstituted $C_{3-8}$ cycloalkyl wherein the substituents are independently chosen from halo, $C_{1-4}$-alkyl, $C_{1-4}$-alkoxy, and oxo; and provided that the compound of Formula I is not chosen from:

(i) when $R^1$ is 4-methylphenyl, then $R^2$ is not —O-p-phenylene-O—(CH$_2$)phenyl, —O-p-phenylene-NH—C(O)-thiophen-2-yl, —O—(CH$_2$)$_2$—O-(phenyl), —NH(CH$_2$)$_2$-(4-hydroxyphenyl), —O—(CH$_2$)$_2$-(1,3-dioxoisoindolin-1-yl), —NH(CH$_2$)$_2$-(2-oxo-imidaziolidin-1-yl), —NH(CH$_2$)$_2$-(3,4,-dimethoxyphenyl), —S(CH$_2$)$_2$-phenyl, —NH(CH$_2$)$_2$-phenyl, —NH(CH$_2$)$_2$-morpholin-4-yl, —NH(CH$_2$)$_2$-thiophen-2-yl, —NH(CH$_2$)$_2$-(3,4-methylenedioxyphenyl), —NH(CH$_2$)$_3$-morpholin-4-yl, or —S(CH$_2$)$_3$-phenyl;

(ii) 2-methoxy-4-[[[2-[(5-phenylthieno[2,3-d]pyrimidin-4-yl)amino]ethyl]imino]-methyl]-phenol;

(iii) 4,4'-[1,3-phenylenebis(oxy)bis[5-(4-chlorophenyl)-thieno[2,3-d]pyrimidine;

(iv) when $R^1$ is phenyl, then $R^2$ is not —O-p-phenylene-NH—C(O)-3,-dimethoxyphenyl, —O—(CH$_2$)$_2$—O-(4-methylphenyl), —O—(CH$_2$)$_2$-Ophenyl, —O—(CH$_2$)$_2$—O (3-bromophenyl), —NH—(CH$_2$)$_2$—NH(3-CF$_3$-pyridin-2-yl), —S—(CH$_2$)$_2$—O-(3-methylphenyl), —S—(CH$_2$)$_2$—O-(4-Fphenyl), —S—(CH$_2$)$_2$—O-(2,4-dichlorophenyl), —NH—(CH$_2$)$_2$—NH(4-CF$_3$-pyrimidin-2-yl), —NH—(CH$_2$)$_2$—O-(3-acetylaminophenyl), —S—(CH$_2$)$_3$-phenyl, —S—(CH$_2$)$_4$-(1,3-dioxoisoindolin-1-yl), —NH—(CH$_2$)$_3$-morpholin-4-yl, —NH—(CH$_2$)$_3$-imidazol-1-yl, —NH—(CH$_2$)$_3$-(2-oxo-pyrrolidin-1-yl), —N(CH$_3$)—(CH$_2$)$_2$-pyridin-2-yl, —NH—(CH$_2$)$_2$-pyridin-2-yl, —S—(CH$_2$)$_2$-(1,3-dioxoisoindolin-1-yl, —S—(CH$_2$)$_2$-phenyl, —NH—(CH$_2$)$_2$-(2-chlorophenyl), —NH—(CH$_2$)$_2$-morpholin-4-yl, —NH—(CH$_2$)$_2$-(3,4-dimethoxyphenyl), —NH—(CH$_2$)$_2$-thiophen-2-yl, or —NH—(CH$_2$)$_2$-phenyl;

(v) when $R^1$ is 4-fluorophenyl, then $R^2$ is not chosen from —O—(CH$_2$)$_2$—O-(2-chlorophenyl), —O—(CH$_2$)$_2$—O-(4-fluorophenyl), —S—(CH$_2$)$_3$-phenyl, —NH—(CH$_2$)$_3$-phenyl, —NH—(CH$_2$)$_2$-phenyl, —NH—(CH$_2$)$_3$-morpholin-4-yl, —NH—(CH$_2$)$_3$-(2-oxo-pyrrolidin-1-yl), —NH—(CH$_2$)$_2$-morpholin-4-yl, —S—(CH$_2$)$_2$-phenyl, —NH—(CH$_2$)$_2$-azepan-1-yl, —S—(CH$_2$)$_2$-morpholin-4-yl, —NH—(CH$_2$)$_2$-(3,4-methylenedioxyphenyl), —NH—(CH$_2$)$_2$-thiophen-2-yl, and —NH—(CH$_2$)$_2$-(3,4-ethylenedioxyphenyl);

(vi) when $R^1$ is 4-chlorophenyl, then $R^2$ is not chosen from —O-p-phenylene-O—CH$_2$-phenyl, —O—(CH$_2$)$_2$—O-(4-methylphenyl), —S—(CH$_2$)$_4$-(1,3-dioxoisoindolin-1-yl), —S—(CH$_2$)$_3$-phenyl, —S—(CH$_2$)$_2$-phenyl, —NH—(CH$_2$)$_3$-imidazol-1-yl, —NH—(CH$_2$)$_3$-morpholin-4-yl, —NH—(CH$_2$)$_2$-morpholin-4-yl, —NH—(CH$_2$)$_2$-azepan-1-yl, —S—(CH$_2$)$_2$-(1,3-dioxoisoindolin-1-yl), —NH—(CH$_2$)$_2$-(3,4-methylenedioxyphenyl), —NH—(CH$_2$)$_2$-phenyl, —NH—(CH$_2$)$_2$-thiophen-2-yl, —NH—(CH$_2$)$_2$-(3,4-ethylenedioxyphenyl), —S—(CH$_2$)$_4$-(1,3-dioxoisoindolin-1-yl), —NH(CH$_2$)$_3$-(2-oxo-pyrrolidin-1-yl), and —NH(CH$_2$)$_2$-(3,4,-dimethoxyphenyl);

(vii) when $R^1$ is 3-methylphenyl, then $R^2$ is not —O—(CH$_2$)$_2$—O-(phenyl);

(viii) when $R^1$ is 3-thiophen-2-yl, then $R^2$ is not chosen from —NH—(CH$_2$)$_2$-morpholin-4-yl, —NH—(CH$_2$)$_3$-morpholin-4-yl, —NH—(CH$_2$)$_2$-phenyl, and —NH—(CH$_2$)$_2$-(3,4-dimethoxyphenyl);

(ix) when $R^1$ is 4-methoxyphenyl, then $R^2$ is not chosen from —S—(CH$_2$)$_3$-phenyl, —NH—(CH$_2$)$_2$-morpholin-4-yl, —NH—(CH$_2$)$_2$—C(CH$_3$)$_2$-morpholin-4-yl, —NHCH$_2$C(CH$_3$)$_2$-morpholin-4-yl, —N(CH$_3$)—(CH$_2$)$_2$-(3,4-dimethoxyphenyl), —S—(CH$_2$)$_2$-phenyl, and —NH—(CH$_2$)$_2$-(3,4-methylenedioxyphenyl);

(x) when $R^1$ is 3,4-dimethylphenyl, then $R^2$ is not chosen from —O-p-phenylene-O—CH$_2$-phenyl, —S—(CH$_2$)$_3$-phenyl, —S—(CH$_2$)$_3$-morpholin-4-yl, —S—(CH$_2$)$_2$-phenyl, —NH—(CH$_2$)$_3$-(4-hydroxyphenyl), —O—(CH$_2$)$_2$-(1,3-dioxoisoindolin-1-yl), —NH—(CH$_2$)$_2$-morpholin-4-yl, —NH—(CH$_2$)$_3$— morpholin-4-yl, —NH—(CH$_2$)$_2$-(3,4-methylenedioxyphenyl), —S—(CH$_2$)$_2$-phenyl, —NH—(CH$_2$)$_2$-phenyl, —NH—(CH$_2$)$_2$-thiophen-2-yl, and —NH—(CH$_2$)$_2$-(3,4-methylenedioxyphenyl);

(xi) when $R^1$ is 4-bromophenyl, then $R^2$ is not chosen from —(CH$_2$)$_3$-phenyl, —S—(CH$_2$)$_3$-morpholin-4-yl, —S—(CH$_2$)$_2$-phenyl, —S—(CH$_2$)$_3$-phenyl, —NH—(CH$_2$)$_3$-morpholin-4-yl, —NH—(CH$_2$)$_3$-(2-oxo-pyrrolidin-1-yl), and —NH—(CH$_2$)$_2$-(3,4-ethylenedioxyphenyl); and (xii) when $R^1$ is 4-biphenyl, then $R^2$ is not —NH—(CH$_2$)$_2$-(3,4-ethylenedioxyphenyl);

(xiii) when $R^1$ is 2,3-dihydro-1,4-benzodioxin-2-yl, then $R^2$ is not NH(CH$_2$)$_2$-phenyl; and (xiv) 5-(2-chlorophenyl)-4-[4-(phenylmethoxy)phenoxy]-thieno[2,3-d]pyrimidine.

In certain embodiments, $R^1$ is chosen from aryl, substituted aryl, heterocyclyl, substituted heterocyclyl, heteroaryl, and substituted heteroaryl.

In certain embodiments, $R^1$ is chosen from aryl and substituted aryl wherein substituted aryl is chosen from mono-, di-, and tri-substituted aryl. In certain embodiments, $R^1$ is chosen from phenyl and substituted phenyl wherein substituted phenyl is chosen from mono-, di-, and tri-substituted phenyl. In certain embodiments, $R^1$ is chosen from phenyl and phenyl substituted with one or more (such as one, two, or three) halo (such as fluoro). In some embodiments, $R^1$ is chosen from phenyl and 4-F-phenyl.

In certain embodiments, $R^1$ is chosen from heterocyclyl, substituted heterocyclyl, heteroaryl, and substituted heteroaryl. In certain embodiments, $R^1$ is chosen from optionally substituted furanyl (e.g., optionally substituted furan-2-yl), optionally substituted pyridinyl (e.g., pyridin-4-yl, pyridin-3-yl, pyridin-2-yl, any of which is optionally substituted), optionally substituted pyrimidinyl (e.g., optionally substituted 5-pyrimidin-2-yl), optionally substituted pyrazinyl (e.g., optionally substituted 5-pyrazin-2-yl), and optionally substituted thiazolyl (e.g., optionally substituted 1,3-thiazol-2-yl).

In certain embodiments, $R^1$ is chosen from optionally substituted furanyl (e.g., optionally substituted furan-2-yl), optionally substituted pyridinyl (e.g., pyridin-4-yl, pyridin-3-yl, pyridin-2-yl, any of which is optionally substituted), and optionally substituted thiazolyl (e.g., optionally substituted 1,3-thiazol-2-yl).

In certain embodiments, $R^1$ is chosen from 5-chloro-furan-2-yl, furan-2-yl, pyridin-4-yl, pyridin-3-yl, pyridin-2-yl, 1,3-thiazol-2-yl, 5-pyrimidin-2-yl and 5-pyrazin-2-yl.

In certain embodiments, $R^1$ is chosen from furan-2-yl, pyridin-4-yl, pyridin-3-yl, 1,3-thiazol-2-yl, and 5-pyrimidin-2-yl.

In certain embodiments, $R^2$ is chosen from —O-arylene-Y—$R^5$, —X(CR$^3$R$^4$)$_n$Y$R^5$ and —(CR$^6$R$^7$)$_m$Y$R^5$.

In certain embodiments, $R^2$ is —O-arylene-Y—$R^5$. In certain embodiments, $R^2$ is —O-phenylene-Y—$R^5$. In certain embodiments, the —O and —Y$R^5$ substituents attached the phenylene group are meta-substituted.

In certain embodiments, $R^2$ is —X(CR$^3$R$^4$)$_n$Y—$R^5$.

In certain embodiments, $R^2$ is —(CR$^6$R$^7$)$_m$Y$R^5$.

In certain embodiments, X is —NH—. In certain embodiments, X is —O—.

In certain embodiments, Y is a bond. In certain embodiments, Y is —O—. In certain embodiments, Y is —NH—.

In certain embodiments, n is chosen from 3, 4, and 5. In certain embodiments, n is chosen from 2 and 3. In certain embodiments, n is 3. In certain embodiments, n is 2.

In certain embodiments, m is chosen from 3, 4, and 5.

In certain embodiments, $R^3$ and $R^4$ are independently chosen from H, CH$_3$, and F. In certain embodiments, $R^3$ and $R^4$ are H.

In certain embodiments, $R^6$ and $R^7$ are independently chosen from H, CH$_3$, and F. In certain embodiments, $R^6$ and $R^7$ are H;

In certain embodiments, —(CR$^6$R$^7$)$_m$Y—$R^5$ is —(CH$_2$)$_4$—O—$R^5$.

In certain embodiments, —X(CR$^3$R$^4$)$_n$Y—$R^5$ is chosen from —NH—(CH$_2$)$_3$—O—$R^5$, —NH—(CH$_2$)$_2$—NH—$R^5$, —O—(CH$_2$)$_2$—O—$R^5$, —O—(CH$_2$)$_3$—O—$R^5$, —O—CH$_2$—C(CH$_3$)$_2$—CH$_2$—O—$R^5$, and —NH—(CH$_2$)$_2$—O—$R^5$. In certain embodiments, —X(CR$^3$R$^4$)$_n$Y—$R^5$ is chosen from —NH—(CH$_2$)$_3$—O—$R^5$, —NH—(CH$_2$)$_2$—NH—$R^5$, —O—(CH$_2$)$_3$—O—$R^5$, and —NH—(CH$_2$)$_2$—O—$R^5$. In certain embodiments, —X(CR$^3$R$^4$)$_n$Y—$R^5$ is chosen from —NH—(CH$_2$)$_3$—O—$R^5$ and —O—(CH$_2$)$_3$—O—$R^5$.

In certain embodiments, —X(CR$^3$R$^4$)$_n$Y$R^5$ is —NH—(CH$_2$)$_3$—$R^5$ (i.e. Y is a covalent bond).

In certain embodiments, $R^9$ is chosen from H, C$_{1-4}$ alkyl; and C$_{3-8}$ cycloalkyl, substituted C$_{1-4}$ alkyl chosen from mono-, di-, and tri-substituted C$_{1-4}$ alkyl; and substituted C$_{3-8}$ cycloalkyl chosen from mono-, di-, and tri-substituted C$_{3-8}$ cycloalkyl, wherein the substituents on the alkyl and cycloalkyl groups are independently chosen from halo, C$_{1-4}$-alkyl, C$_{1-4}$-alkoxy, and oxo.

In certain embodiments, $R^5$ is chosen from pyridin-3-yl and pyridin-4-yl, each of which is optionally substituted with one or two groups chosen from (1) C$_{1-8}$ alkyl,
(2) C$_{3-8}$ cycloalkyl,
(3) C$_{4-8}$ cycloalkylalkyl,
(4) C$_{1-8}$ alkoxy,
(5) C$_{3-8}$ cycloalkoxy,
(6) C$_{4-8}$ cycloalkylalkoxy,
(7) halo,
(8) amino,
(9) cyano,
(10) hydroxyl,
(11) nitro,
(12) C$_{1-8}$ halogenated alkyl,
(13) C$_{1-8}$ halogenated alkoxy,
(14) C$_{1-8}$ hydroxyalkyl,
(15) C$_{2-8}$ hydroxyalkoxy,
(16) C$_{3-8}$ alkenyloxy,
(17) C$_{1-8}$ alkylamino,
(18) di-C$_{1-8}$alkylamino,
(19) carboxy,
(20) alkoxycarbonyl,
(21) carboxamido,
(22) aminocarbonyl,
(23) hydroxyaminocarbonyl,
(24) alkylaminocarbonyl,
(25) dialkylaminocarbonyl,
(26) urea,
(27) hydroxyurea,
(28) alkylurea,
(29) dialkylaminoalkylcarbonyl,
(30) aminocarbonylalkylaminocarbonyl,
(31) acylamido,
(32) HCO—NH—NH—CO—,
(33) NH$_2$NHCO—,
(34) NH$_2$NHCONH—,
(35) acyloxy,
(36) C$_{1-8}$ alkylthio,
(37) C$_{1-8}$ alkylsulphinyl,
(38) C$_{1-8}$ alkylsulphonyl,
(39) C$_{1-8}$ alkylsulphonamido,
(40) (alkylsuphonyl)$_2$amino-,
(41) thiol,
(42) aminosulfonyl,
(43) alkylaminosulfonyl,
(44) oxo,
(45) C$_{6-20}$ aryl,
(46) substituted C$_{6-20}$ aryl chosen from mono-, di-, and tri-substituted C$_{6-20}$ aryl wherein the substituents are independently chosen from halo, C$_{1-8}$ alkyl, halogenated C$_{1-8}$ alkyl, C$_{1-4}$ alkoxy, halogenated C$_{1-4}$ alkoxy, C$_{1-8}$ hydroxyalkyl, C$_{2-8}$ hydroxyalkoxy, amino, C$_{1-8}$ alkylamino, di-C$_{1-8}$ alkylamino, C$_{1-8}$ alkylsulphinyl, C$_{1-8}$ alkylsulphonyl, C$_{1-8}$ alkylsulphonamido, —COR$^9$, —CSR$^9$, —SR$^9$, cyano, hydroxyl, nitro, and thio,
(47) heterocyclyl,
(48) substituted heterocyclyl chosen from mono-, di-, and trisubstituted heterocyclyl wherein the substituents are independently chosen from halo, C$_{1-8}$ alkyl, halogenated C$_{1-8}$ alkyl, C$_{1-4}$ alkoxy, halogenated C$_{1-4}$ alkoxy, hydroxy C$_{1-8}$ alkyl, hydroxy C$_{2-8}$ alkoxy, amino, C$_{1-8}$ alkylamino, di-C$_{1-8}$ alkylamino, C$_{1-8}$ alkylsulphinyl, C$_{1-8}$ alkylsulphonyl, C$_{1-8}$ alkylsulphonamido, —COR$^9$, —CSR$^9$, —SR$^9$, cyano, hydroxyl, nitro, oxo, and thio,
(49) heteroaryl,
(50) substituted heteroaryl chosen from mono-, di-, and trisubstituted heteroaryl wherein the substituents are independently chosen from halo, C$_{1-8}$ alkyl, halogenated C$_{1-8}$ alkyl, C$_{1-4}$ alkoxy, halogenated C$_{1-4}$ alkoxy, hydroxy C$_{1-8}$ alkyl, hydroxy C$_{2-8}$ alkoxy, amino, C$_{1-8}$ alkylamino, di-C$_{1-8}$ alkylamino, C$_{1-8}$ alkylsulphinyl, C$_{1-8}$ alkylsulphonyl, C$_{1-8}$ alkylsulphonamido, —COR$^9$, —CSR$^9$, —SR$^9$, cyano, hydroxyl, nitro, oxo, and thio,
(51) heterocyclyl-carbonyl,
(52) substituted heterocyclyl-carbonyl chosen from mono-, di-, and trisubstituted heterocyclyl-carbonyl wherein the substituents are independently chosen from halo, C$_{1-8}$ alkyl, halogenated C$_{1-8}$ alkyl, C$_{1-4}$ alkoxy, halogenated C$_{1-4}$ alkoxy, hydroxy C$_{1-8}$ alkyl, hydroxy C$_{2-8}$ alkoxy, amino, C$_{1-8}$ alkylamino, di-C$_{1-8}$ alkylamino, C$_{1-8}$ alkylsulphinyl, C$_{1-8}$ alkylsulphonyl, C$_{1-8}$ alkylsulphonamido, —COR$^9$, —CSR$^9$, —SR$^9$, cyano, hydroxyl, nitro, oxo, and thio,
(53) heteroaryl-carbonyl, and
(54) substituted heteroaryl-carbonyl chosen from mono-, di-, and trisubstituted heteroaryl-carbonyl wherein the substituents are independently chosen from halo, C$_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —$COR^9$, —$CSR^9$, —$SR^9$, cyano, hydroxyl, nitro, oxo, and thio.

In certain embodiments, $R^5$ is chosen from pyridin-2-yl and pyridin-4-yl, each of which is substituted with one or two groups chosen from (1) $C_{1-8}$ alkyl,
(2) $C_{3-8}$ cycloalkyl,
(3) $C_{4-8}$ cycloalkylalkyl,
(4) $C_{1-8}$ alkoxy,
(5) $C_{3-8}$ cycloalkoxy,
(6) $C_{4-8}$ cycloalkylalkoxy,
(7) halo,
(8) amino,
(9) cyano,
(10) hydroxyl,
(11) nitro,
(12) $C_{2-8}$ halogenated alkyl,
(13) $C_{1-8}$ halogenated alkoxy,
(14) $C_{1-8}$ hydroxyalkyl,
(15) $C_{2-8}$ hydroxyalkoxy,
(16) $C_{3-8}$ alkenyloxy,
(17) $C_{1-8}$ alkylamino,
(18) di-$C_{1-8}$ alkylamino,
(19) carboxy,
(20) alkoxycarbonyl,
(21) carboxamido,
(22) aminocarbonyl,
(23) hydroxyaminocarbonyl,
(24) alkylaminocarbonyl,
(25) dialkylaminocarbonyl,
(26) urea,
(27) hydroxyurea,
(28) alkylurea,
(29) dialkylaminoalkylcarbonyl,
(30) aminocarbonylalkylaminocarbonyl,
(31) acylamido,
(32) HCO—NH—NH—CO—,
(33) $NH_2NHCO$—,
(34) $NH_2NHCONH$—,
(35) acyloxy,
(36) $C_{1-8}$ alkylthio,
(37) $C_{1-8}$ alkylsulphinyl,
(38) $C_{1-8}$ alkylsulphonyl,
(39) $C_{1-8}$ alkylsulphonamido,
(40) (alkylsuphonyl)$_2$amino-,
(41) thiol,
(42) aminosulfonyl,
(43) alkylaminosulfonyl,
(44) oxo,
(45) $C_{6-20}$ aryl,
(46) substituted $C_{6-20}$ aryl chosen from mono-, di-, and tri-substituted $C_{6-20}$ aryl wherein the substituents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —$COR^9$, —$CSR^9$, —$SR^9$, cyano, hydroxyl, nitro, and thio,
(47) heterocyclyl,
(48) substituted heterocyclyl chosen from mono-, di-, and trisubstituted heterocyclyl wherein the substituents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, —$C_{1-8}$ alkylsulphinyl, $C_{1-8}$ alkylsulphonyl, $C_{1-8}$ alkylsulphonamido, —$COR^9$, —$CSR^9$, —$SR^9$, cyano, hydroxyl, nitro, oxo, and thio,
(49) heteroaryl,
(50) substituted heteroaryl chosen from mono-, di-, and trisubstituted heteroaryl wherein the substituents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —$COR^9$, —$CSR^9$, —$SR^9$, cyano, hydroxyl, nitro, oxo, and thio,
(51) heterocyclyl-carbonyl,
(52) substituted heterocyclyl-carbonyl chosen from mono-, di-, and trisubstituted heterocyclyl-carbonyl wherein the substituents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —$COR^9$, —$CSR^9$, —$SR^9$, cyano, hydroxyl, nitro, oxo, and thio,
(53) heteroaryl-carbonyl, and
(54) substituted heteroaryl-carbonyl chosen from mono-, di-, and trisubstituted heteroaryl-carbonyl wherein the substituents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —$COR^9$, —$CSR^9$, —$SR^9$, cyano, hydroxyl, nitro, oxo, and thio.

Provided is at least one chemical entity chosen from compounds of Formula II:

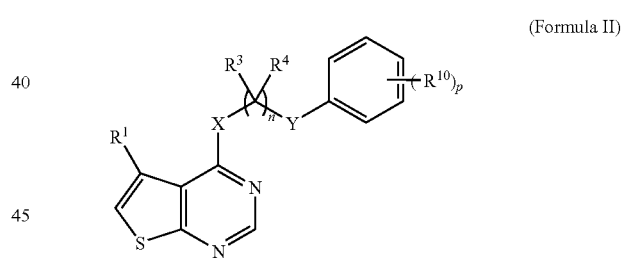

(Formula II)

and pharmaceutically acceptable salts, solvates, chelates, non-covalent complexes, prodrugs, and mixtures thereof, wherein $R^1$, X, Y, n, $R^3$, $R^4$, and $R^9$ are as described for compounds of Formula I and wherein p is chosen from 1, 2, 3, and 4;

for each occurrence, $R^{10}$ is independently chosen from
(1) $C_{2-8}$ alkyl,
(2) $C_{3-8}$ cycloalkyl,
(3) $C_{4-8}$ cycloalkylalkyl,
(4) $C_{3-8}$ cycloalkoxy,
(5) $C_{4-8}$ cycloalkylalkoxy,
(6) amino,
(7) cyano,
(8) nitro,
(9) $C_{1-8}$ halogenated alkyl,
(10) $C_{1-8}$ halogenated alkoxy,
(11) $C_{1-8}$ hydroxyalkyl,
(12) $C_{2-8}$ hydroxyalkoxy,

(13) $C_{1-8}$ alkylamino,
(14) di-$C_{1-8}$alkylamino,
(15) carboxy,
(16) alkoxycarbonyl,
(17) aminocarbonyl,
(18) hydroxyaminocarbonyl,
(19) alkylaminocarbonyl,
(20) dialkylaminocarbonyl,
(21) urea,
(22) hydroxyurea,
(23) alkylurea,
(24) dialkylaminoalkylcarbonyl,
(25) aminocarbonylalkylaminocarbonyl,
(26) acylamido,
(27) HCO—NH—NH—CO—,
(28) NH$_2$NHCO—,
(29) NH$_2$NHCONH—,
(30) acyloxy,
(31) $C_{1-8}$ alkylthio,
(32) $C_{1-8}$ alkylsulphinyl,
(33) $C_{1-8}$ alkylsulphonyl,
(34) $C_{1-8}$ alkylsulphonamido,
(35) (alkylsuphonyl)$_2$amino-,
(36) thiol,
(37) aminosulfonyl,
(38) alkylaminosulfonyl,
(39) $C_{6-20}$ aryl,
(40) substituted $C_{6-20}$ aryl chosen from mono-, di-, and tri-substituted $C_{6-20}$ aryl wherein the substituents are independently chosen from halo, $C_{1-8}$ alkyl, halogenated $C_{1-8}$ alkyl, $C_{1-4}$ alkoxy, halogenated $C_{1-4}$ alkoxy, $C_{1-8}$ hydroxyalkyl, $C_{2-8}$ hydroxyalkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —COR$^9$, —CSR$^9$, —SR$^9$, cyano, hydroxyl, nitro, and thio,
(41) heterocyclyl-carbonyl,
(42) substituted heterocyclyl-carbonyl chosen from mono-, di-, and trisubstituted heterocyclyl-carbonyl wherein the substituents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —COR$^9$, —CSR$^9$, —SR$^9$, cyano, hydroxyl, nitro, oxo, and thio,
(43) heteroaryl-carbonyl, and
(44) substituted heteroaryl-carbonyl chosen from mono-, di-, and trisubstituted heteroaryl-carbonyl wherein the substituents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$alkylamino, $C_{1-8}$ alkylsulphinyl, $C_{1-8}$ alkylsulphonyl, $C_{1-8}$ alkylsulphonamido, —COR$^9$, —CSR$^9$, —SR$^9$, cyano, hydroxyl, nitro, oxo, and thio.

In certain embodiments, $R^1$ is chosen from
aryl (such as phenyl),
substituted aryl chosen from mono-, di-, and trisubstituted aryl wherein the substitutent is halo (such as F, e.g., phenyl substituted by fluoro),
heterocyclyl, and
substituted heterocyclyl, such as optionally substituted heterocyclyl chosen from optionally substituted furanyl, optionally substituted pyridinyl, optionally substituted pyrimidinyl, optionally substituted pyrazinyl, and optionally substituted thiazolyl, such as heterocyclyl chosen from 5-chloro-furan-2-yl, furan-2-yl, pyridin-4-yl, pyridin-3-yl, pyridin-2-yl, 1,3-thiazol-2-yl, 5-pyrazin-2-yl, and 5-pyrimidin-2-yl;

$R^2$ is —X(CR$^3$R$^4$)$_n$Y—R$^5$;

—X(CR$^3$R$^4$)$_n$Y— is chosen from —NH—(CH$_2$)$_3$—O—, —NH—(CH$_2$)$_2$—NH—, —O—(CH$_2$)$_2$—O—, —O—(CH$_2$)$_3$—O—, —O—CH$_2$—C(CH$_3$)$_2$—CH$_2$—O—, and —NH—(CH$_2$)$_2$—O—, and in certain embodiments, —X(CR$^3$R$^4$)$_n$Y— is chosen from —NH—(CH$_2$)$_3$—O— and —O—(CH$_2$)$_3$—O—;

$R^3$, $R^4$, $R^6$, and $R^7$ are independently chosen from H, CH$_3$, and F, and in certain embodiments, $R^3$, $R^4$, $R^6$, and $R^7$ are H;

X is chosen from O and NR$^9$, and in certain embodiments, X is chosen from O and NH, Y is chosen from O and NR$^9$, and in certain embodiments, Y is chosen from O and NH, and in yet other certain embodiments, Y is O; and $R^5$ is chosen from
phenyl,
benzyl,
benzoyl,
benzothiadiazolyl,
pyrazolyl,
benzisothiazolyl,
dihydroindolyl,
pyridinyl,
substituted phenyl chosen from mono-, di-, and tri-substituted phenyl wherein the substituents are independently chosen from alkyl-CO—NH— (e.g., CH$_3$—CO—NH—, CH$_3$CH$_2$—CO—NH— and cyclopropyl-CO—NH—), NH$_2$—CO—NH—, alkyl-NH—CO—NH—, NH$_2$—NH—CO—NH—, OH—NH—CO—NH—, NH$_2$—CO—, NH$_2$—NH—CO—, HO—NH—CO—, alkyl-NH—CO—, (alkyl)$_2$N—CO—, NH$_2$-alkylene-NH—CO—, (alkyl)NH-alkylene-NH—CO—, (alkyl)$_2$N-alkylene-NH—CO—, NH$_2$-alkylene-NH—CO—, HCO—NH—NH—CO—, alkyl-SO$_2$—NH—, (alkyl-SO$_2$)$_2$N—, nitro, alkyl (e.g., ethyl), alkoxy (e.g., methoxy), halogenated alkoxy (e.g., trifluoromethoxy), cyano, alkoxycarbonyl (e.g., methoxycarbonyl), triazolyl, halo (e.g., F), amino, carboxy, methylpiperazinyloxycarbonyl, and morpholinylcarbonyl,
substituted benzyl chosen from mono-, di-, and tri-substituted benzyl wherein the substituents are independently chosen from alkyl-CO—NH— (e.g., CH$_3$—CO—NH—, CH$_3$CH$_2$—CO—NH— and cyclopropyl-CO—NH—), NH$_2$—CO—NH—, alkyl-NH—CO—NH—, NH$_2$—NH—CO—NH—, OH—NH—CO—NH—, NH$_2$—CO—, NH$_2$—NH—CO—, HO—NH—CO—, alkyl-NH—CO—, (alkyl)$_2$N—CO—, NH$_2$-alkylene-NH—CO—, (alkyl)NH-alkylene-NH—CO—, (alkyl)$_2$N-alkylene-NH—CO—, NH$_2$-alkylene-NH—CO—, HCO—NH—NH—CO—, alkyl-SO$_2$—NH—, (alkyl-SO$_2$)$_2$N—, nitro, alkyl (e.g., ethyl), alkoxy (e.g., methoxy), halogenated alkoxy (e.g., trifluoromethoxy), cyano, alkoxycarbonyl (e.g., methoxycarbonyl), triazolyl, halo (e.g., F), amino, carboxy, methylpiperazinyloxycarbonyl, and morpholinylcarbonyl,
substituted benzoyl chosen from mono-, di-, and tri-substituted benzoyl wherein the substituents are independently chosen from alkyl-CO—NH— (e.g., CH$_3$—CO—NH—, CH$_3$CH$_2$—CO—NH— and cyclopropyl-CO—NH—), NH$_2$—CO—NH—, alkyl-NH—CO—NH—, NH$_2$—NH—CO—NH—, OH—NH—CO—NH—, NH$_2$—CO—, NH$_2$—NH—CO—, HO—NH—CO—, alkyl-NH—CO—, (alkyl)$_2$N—CO—, NH$_2$-alkylene-NH—

CO—, (alkyl)NH-alkylene-NH—CO—, (alkyl)₂N-alkylene-NH—CO—, NH₂-alkylene-NH—CO—, HCO—NH—NH—CO—, alkyl-SO₂—NH—, (alkyl-SO₂)₂N—, nitro, alkyl (e.g., ethyl), alkoxy (e.g., methoxy), halogenated alkoxy (e.g., trifluoromethoxy), cyano, alkoxycarbonyl (e.g., methoxycarbonyl), triazolyl, halo (e.g., F), amino, carboxy, methylpiperazinyloxycarbonyl, and morpholinylcarbonyl, substituted benzothiadiazolyl chosen from mono-, di-, and tri-substituted benzothiadiazolyl wherein the substituents are independently chosen from alkyl-CO—NH— (e.g., CH₃—CO—NH—, CH₃CH₂—CO—NH— and cyclopropyl-CO—NH—), NH₂—CO—NH—, alkyl-NH—CO—NH—, NH₂—NH—CO—NH—, OH—NH—CO—NH—, NH₂—CO—, NH₂—NH—CO—, HO—NH—CO—, alkyl-NH—CO—, (alkyl)₂N—CO—, NH₂-alkylene-NH—CO—, (alkyl)NH-alkylene-NH—CO—, (alkyl)₂N-alkylene-NH—CO—, NH₂-alkylene-NH—CO—, HCO—NH—NH—CO—, alkyl-SO₂—NH—, (alkyl-SO₂)₂N—, nitro, alkyl (e.g., ethyl), alkoxy (e.g., methoxy), halogenated alkoxy (e.g., trifluoromethoxy), cyano, alkoxycarbonyl (e.g., methoxycarbonyl), triazolyl, halo (e.g., F), amino, carboxy, methylpiperazinyloxycarbonyl, and morpholinylcarbonyl, substituted pyrazolyl chosen from mono-, di-, and tri-substituted pyrazolyl wherein the substituents are independently chosen from alkyl-CO—NH— (e.g., CH₃—CO—NH—, CH₃CH₂—CO—NH— and cyclopropyl-CO—NH—), NH₂—CO—NH—, alkyl-NH—CO—NH—, NH₂—NH—CO—NH—, OH—NH—CO—NH—, NH₂—CO—, NH₂—NH—CO—, HO—NH—CO—, alkyl-NH—CO—, (alkyl)₂N—CO—, NH₂-alkylene-NH—CO—, (alkyl)NH-alkylene-NH—CO—, (alkyl)₂N-alkylene-NH—CO—, NH₂-alkylene-NH—CO—, HCO—NH—NH—CO—, alkyl-SO₂—NH—, (alkyl-SO₂)₂N—, nitro, alkyl (e.g., ethyl), alkoxy (e.g., methoxy), halogenated alkoxy (e.g., trifluoromethoxy), cyano, alkoxycarbonyl (e.g., methoxycarbonyl), triazolyl, halo (e.g., F), amino, carboxy, methylpiperazinyloxycarbonyl, and morpholinylcarbonyl, substituted benzisothiazolyl chosen from mono-, di-, and tri-substituted benzisothiazolyl wherein the substituents are independently chosen from alkyl-CO—NH— (e.g., CH₃—CO—NH—, CH₃CH₂—CO—NH— and cyclopropyl-CO—NH—), NH₂—CO—NH—, alkyl-NH—CO—NH—, NH₂—NH—CO—NH—, OH—NH—CO—NH—, NH₂—CO—, NH₂—NH—CO—, HO—NH—CO—, alkyl-NH—CO—, (alkyl)₂N—CO—, NH₂-alkylene-NH—CO—, (alkyl)NH-alkylene-NH—CO—, (alkyl)₂N-alkylene-NH—CO—, NH₂-alkylene-NH—CO—, HCO—NH—NH—CO—, alkyl-SO₂—NH—, (alkyl-SO₂)₂N—, nitro, alkyl (e.g., ethyl), alkoxy (e.g., methoxy), halogenated alkoxy (e.g., trifluoromethoxy), cyano, alkoxycarbonyl (e.g., methoxycarbonyl), triazolyl, halo (e.g., F), amino, carboxy, methylpiperazinyloxycarbonyl, and morpholinylcarbonyl, substituted dihydroindolyl chosen from mono-, di-, and tri-substituted dihydroindolyl wherein the substituents are independently chosen from alkyl-CO—NH— (e.g., CH₃—CO—NH—, CH₃CH₂—CO—NH— and cyclopropyl-CO—NH—), NH₂—CO—NH—, alkyl-NH—CO—NH—, NH₂—NH—CO—NH—, OH—NH—CO—NH—, NH₂—CO—, NH₂—NH—CO—, HO—NH—CO—, alkyl-NH—CO—, (alkyl)₂N—CO—, NH₂-alkylene-NH—CO—, (alkyl)NH-alkylene-NH—CO—, (alkyl)₂N-alkylene-NH—CO—, NH₂-alkylene-NH—CO—, HCO—NH—NH—CO—, alkyl-SO₂—NH—, (alkyl-SO₂)₂N—, nitro, alkyl (e.g., ethyl), alkoxy (e.g., methoxy), halogenated alkoxy (e.g., trifluoromethoxy), cyano, alkoxycarbonyl (e.g., methoxycarbonyl), triazolyl, halo (e.g., F), amino, carboxy, methylpiperazinyloxycarbonyl, and morpholinylcarbonyl, and substituted pyridinyl chosen from mono-, di-, and tri-substituted pyridinyl wherein the substituents are independently chosen from alkyl-CO—NH— (e.g., CH₃—CO—NH—, CH₃CH₂—CO—NH— and cyclopropyl-CO—NH—), NH₂—CO—NH—, alkyl-NH—CO—NH—, NH₂—NH—CO—NH—, OH—NH—CO—NH—, NH₂—CO—, NH₂—NH—CO—, HO—NH—CO—, alkyl-NH—CO—, (alkyl)₂N—CO—, NH₂-alkylene-NH—CO—, (alkyl)NH-alkylene-NH—CO—, (alkyl)₂N-alkylene-NH—CO—, NH₂-alkylene-NH—CO—, HCO—NH—NH—CO—, alkyl-SO₂—NH—, (alkyl-SO₂)₂N—, nitro, alkyl (e.g., ethyl), alkoxy (e.g., methoxy), halogenated alkoxy (e.g., trifluoromethoxy), cyano, alkoxycarbonyl (e.g., methoxycarbonyl), triazolyl, halo (e.g., F), amino, carboxy, methylpiperazinyloxycarbonyl, and morpholinylcarbonyl; and in certain embodiments, $R^5$ is chosen from phenyl and substituted phenyl wherein substituted phenyl is chosen from mono-, di-, and tri-substituted phenyl and wherein the substituents are independently chosen from alkyl-CO—NH— (e.g., CH₃—CO—NH—, CH₃CH₂—CO—NH— and cyclopropyl-CO—NH—), NH₂—CO—NH—, alkyl-NH—CO—NH—, NH₂—NH—CO—NH—, OH—NH—CO—NH—, NH₂—CO—, NH₂—NH—CO—, HO—NH—CO—, alkyl-NH—CO—, (alkyl)₂N—CO—, NH₂-alkylene-NH—CO—, (alkyl)NH-alkylene-NH—CO—, (alkyl)₂N-alkylene-NH—CO—, NH₂-alkylene-NH—CO—, HCO—NH—NH—CO—, alkyl-SO₂—NH—, (alkyl-SO₂)₂N—, nitro, alkyl (e.g., ethyl), alkoxy (e.g., methoxy), halogenated alkoxy (e.g., trifluoromethoxy), cyano, alkoxycarbonyl (e.g., methoxycarbonyl), triazolyl, halo (e.g., F), amino, carboxy, methylpiperazinyloxycarbonyl, and morpholinylcarbonyl.

In certain embodiments, $R^1$ is chosen from aryl (such as phenyl), aryl (such as phenyl) substituted by halo (such as F), and heterocyclyl, substituted heterocyclyl, such as optionally substituted heterocyclyl chosen from optionally substituted furanyl, optionally substituted pyridinyl, and optionally substituted thiazolyl, such as heterocyclyl chosen from furan-2-yl, pyridin-4-yl, pyridin-3-yl, pyridin-2-yl, and 1,3-thiazol-2-yl;

$R^2$ is —X(CR³R⁴)ₙY—R⁵;

—X(CR³R⁴)ₙY— is chosen from —NH—(CH₂)₃—O—, —NH—(CH₂)₂—NH—, —O—(CH₂)₃—O—, and —NH—(CH₂)₂—O—, and in certain embodiments, —X(CR³R⁴)ₙY— is chosen from —NH—(CH₂)₃—O— and —O—(CH₂)₃—O—;

$R^3$, $R^4$, $R^6$, and $R^7$ are independently chosen from H, CH₃, and F, and in certain embodiments, $R^3$, $R^4$, $R^6$, and $R^7$ are H;

X is chosen from O and NR⁹, and in certain embodiments, X is chosen from O and NH;

Y is chosen from O and NR⁹, and in certain embodiments, Y is chosen from O and NH, and in yet other certain embodiments, Y is O;

the subscript n is chosen from 2 and 3, and in certain embodiments, the subscript n is 3;

$R^5$ is chosen from
- phenyl,
- benzyl,
- benzoyl,
- benzothiadiazolyl,
- pyrazolyl,
- benzisothiazolyl,
- dihydroindolyl,
- pyridinyl,
- substituted phenyl chosen from mono-, di-, and tri-substituted phenyl wherein the substituents are independently chosen from alkyl-CO—NH— (e.g., CH$_3$—CO—NH—, CH$_3$CH$_2$—CO—NH— and cyclopropyl-CO—NH—), NH$_2$—CO—NH—, alkyl-NH—CO—NH—, NH$_2$—NH—CO—NH—, OH—NH—CO—NH—, NH$_2$—CO—, NH$_2$—NH—CO—, HO—NH—CO—, alkyl-NH—CO—, (alkyl)$_2$N—CO—, NH$_2$-alkylene-NH—CO—, (alkyl)NH-alkylene-NH—CO—, (alkyl)$_2$N-alkylene-NH—CO—, NH$_2$-alkylene-NH—CO—, HCO—NH—NH—CO—, alkyl-SO$_2$—NH—, (alkyl-SO$_2$)$_2$N—, nitro, alkyl (e.g., ethyl), alkoxy (e.g., methoxy), halogenated alkoxy (e.g., trifluoromethoxy), cyano, alkoxycarbonyl (e.g., methoxycarbonyl), triazolyl, halo (e.g., F), amino, carboxy, methylpiperazinyloxycarbonyl, and morpholinylcarbonyl,
- substituted benzyl chosen from mono-, di-, and tri-substituted benzyl wherein the substituents are independently chosen from alkyl-CO—NH— (e.g., CH$_3$—CO—NH—, CH$_3$CH$_2$—CO—NH— and cyclopropyl-CO—NH—), NH$_2$—CO—NH—, alkyl-NH—CO—NH—, NH$_2$—NH—CO—NH—, OH—NH—CO—NH—, NH$_2$—CO—, NH$_2$—NH—CO—, HO—NH—CO—, alkyl-NH—CO—, (alkyl)$_2$N—CO—, NH$_2$-alkylene-NH—CO—, (alkyl)NH-alkylene-NH—CO—, (alkyl)$_2$N-alkylene-NH—CO—, NH$_2$-alkylene-NH—CO—, HCO—NH—NH—CO—, alkyl-SO$_2$—NH—, (alkyl-SO$_2$)$_2$N—, nitro, alkyl (e.g., ethyl), alkoxy (e.g., methoxy), halogenated alkoxy (e.g., trifluoromethoxy), cyano, alkoxycarbonyl (e.g., methoxycarbonyl), triazolyl, halo (e.g., F), amino, carboxy, methylpiperazinyloxycarbonyl, and morpholinylcarbonyl,
- substituted benzoyl chosen from mono-, di-, and tri-substituted benzoyl wherein the substituents are independently chosen from alkyl-CO—NH— (e.g., CH$_3$—CO—NH—, CH$_3$CH$_2$—CO—NH— and cyclopropyl-CO—NH—), NH$_2$—CO—NH—, alkyl-NH—CO—NH—, NH$_2$—NH—CO—NH—, OH—NH—CO—NH—, NH$_2$—CO—, NH$_2$—NH—CO—, HO—NH—CO—, alkyl-NH—CO—, (alkyl)$_2$N—CO—, NH$_2$-alkylene-NH—CO—, (alkyl)NH-alkylene-NH—CO—, (alkyl)$_2$N-alkylene-NH—CO—, NH$_2$-alkylene-NH—CO—, HCO—NH—NH—CO—, alkyl-SO$_2$—NH—, (alkyl-SO$_2$)$_2$N—, nitro, alkyl (e.g., ethyl), alkoxy (e.g., methoxy), halogenated alkoxy (e.g., trifluoromethoxy), cyano, alkoxycarbonyl (e.g., methoxycarbonyl), triazolyl, halo (e.g., F), amino, carboxy, methylpiperazinyloxycarbonyl, and morpholinylcarbonyl,
- substituted benzothiadiazolyl chosen from mono-, di-, and tri-substituted benzothiadiazolyl wherein the substituents are independently chosen from alkyl-CO—NH— (e.g., CH$_3$—CO—NH—, CH$_3$CH$_2$—CO—NH— and cyclopropyl-CO—NH—), NH$_2$—CO—NH—, alkyl-NH—CO—NH—, NH$_2$—NH—CO—NH—, OH—NH—CO—NH—, NH$_2$—CO—, NH$_2$—NH—CO—, HO—NH—CO—, alkyl-NH—CO—, (alkyl)$_2$N—CO—, NH$_2$-alkylene-NH—CO—, (alkyl)NH-alkylene-NH—CO—, (alkyl)$_2$N-alkylene-NH—CO—, NH$_2$-alkylene-NH—CO—, HCO—NH—NH—CO—, alkyl-SO$_2$—NH—, (alkyl-SO$_2$)$_2$N—, nitro, alkyl (e.g., ethyl), alkoxy (e.g., methoxy), halogenated alkoxy (e.g., trifluoromethoxy), cyano, alkoxycarbonyl (e.g., methoxycarbonyl), triazolyl, halo (e.g., F), amino, carboxy, methylpiperazinyloxycarbonyl, and morpholinylcarbonyl,
- substituted pyrazolyl chosen from mono-, di-, and tri-substituted pyrazolyl wherein the substituents are independently chosen from alkyl-CO—NH— (e.g., CH$_3$—CO—NH—, CH$_3$CH$_2$—CO—NH— and cyclopropyl-CO—NH—), NH$_2$—CO—NH—, alkyl-NH—CO—NH—, NH$_2$—NH—CO—NH—, OH—NH—CO—NH—, NH$_2$—CO—, NH$_2$—NH—CO—, HO—NH—CO—, alkyl-NH—CO—, (alkyl)$_2$N—CO—, NH$_2$-alkylene-NH—CO—, (alkyl)NH-alkylene-NH—CO—, (alkyl)$_2$N-alkylene-NH—CO—, NH$_2$-alkylene-NH—CO—, HCO—NH—NH—CO—, alkyl-SO$_2$—NH—, (alkyl-SO$_2$)$_2$N—, nitro, alkyl (e.g., ethyl), alkoxy (e.g., methoxy), halogenated alkoxy (e.g., trifluoromethoxy), cyano, alkoxycarbonyl (e.g., methoxycarbonyl), triazolyl, halo (e.g., F), amino, carboxy, methylpiperazinyloxycarbonyl, and morpholinylcarbonyl,
- substituted benzisothiazolyl chosen from mono-, di-, and tri-substituted benzisothiazolyl wherein the substituents are independently chosen from alkyl-CO—NH— (e.g., CH$_3$—CO—NH—, CH$_3$CH$_2$—CO—NH— and cyclopropyl-CO—NH—), NH$_2$—CO—NH—, alkyl-NH—CO—NH—, NH$_2$—NH—CO—NH—, OH—NH—CO—NH—, NH$_2$—CO—, NH$_2$—NH—CO—, HO—NH—CO—, alkyl-NH—CO—, (alkyl)$_2$N—CO—, NH$_2$-alkylene-NH—CO—, (alkyl)NH-alkylene-NH—CO—, (alkyl)$_2$N-alkylene-NH—CO—, NH$_2$-alkylene-NH—CO—, HCO—NH—NH—CO—, alkyl-SO$_2$—NH—, (alkyl-SO$_2$)$_2$N—, nitro, alkyl (e.g., ethyl), alkoxy (e.g., methoxy), halogenated alkoxy (e.g., trifluoromethoxy), cyano, alkoxycarbonyl (e.g., methoxycarbonyl), triazolyl, halo (e.g., F), amino, carboxy, methylpiperazinyloxycarbonyl, and morpholinylcarbonyl,
- substituted dihydroindolyl chosen from mono-, di-, and tri-substituted dihydroindolyl wherein the substituents are independently chosen from alkyl-CO—NH— (e.g., CH$_3$—CO—NH—, CH$_3$CH$_2$—CO—NH— and cyclopropyl-CO—NH—), NH$_2$—CO—NH—, alkyl-NH—CO—NH—, NH$_2$—NH—CO—NH—, OH—NH—CO—NH—, NH$_2$—CO—, NH$_2$—NH—CO—, HO—NH—CO—, alkyl-NH—CO—, (alkyl)$_2$N—CO—, NH$_2$-alkylene-NH—CO—, (alkyl)NH-alkylene-NH—CO—, (alkyl)$_2$N-alkylene-NH—CO—, NH$_2$-alkylene-NH—CO—, HCO—NH—NH—CO—, alkyl-SO$_2$—NH—, (alkyl-SO$_2$)$_2$N—, nitro, alkyl (e.g., ethyl), alkoxy (e.g., methoxy), halogenated alkoxy (e.g., trifluoromethoxy), cyano, alkoxycarbonyl (e.g., methoxycarbonyl), triazolyl, halo (e.g., F), amino, carboxy, methylpiperazinyloxycarbonyl, and morpholinylcarbonyl, and
- substituted pyridinyl chosen from mono-, di-, and tri-substituted pyridinyl wherein the substituents are independently chosen from alkyl-CO—NH— (e.g., CH$_3$—CO—NH—, CH$_3$CH$_2$—CO—NH— and cyclopropyl-CO—NH—), NH$_2$—CO—NH—, alkyl-NH—CO—NH—, NH$_2$—NH—CO—NH—, OH—NH—CO—NH—, NH$_2$—CO—, NH$_2$—NH—CO—, HO—NH—CO—, alkyl-NH—CO—, (alkyl)$_2$N—CO—, NH$_2$-alkylene-NH—CO—, (alkyl)NH-alkylene-NH—CO—, (alkyl)$_2$N-alkylene-NH—CO—, NH$_2$-alkylene-NH—CO—, HCO—NH—NH—CO—, alkyl-SO$_2$—NH—, (alkyl-SO$_2$)$_2$N—, nitro, alkyl (e.g., ethyl), alkoxy (e.g., methoxy), halogenated alkoxy (e.g., trifluoromethoxy), cyano, alkoxycarbonyl (e.g., methoxycarbonyl), triazolyl, halo (e.g., F), amino, carboxy, methylpiperazinyloxycarbonyl, and morpholinylcarbonyl; and in certain embodiments, $R^5$ is chosen from phenyl and substituted phenyl wherein substituted phenyl is chosen from mono-, di-, and tri-substituted phenyl and wherein the substituents are independently chosen from alkyl-CO—NH— (e.g., $CH_3$—CO—NH—, $CH_3CH_2$—CO—NH— and cyclopropyl-CO—NH—), $NH_2$—CO—NH—, alkyl-NH—CO—NH—, $NH_2$—NH—CO—NH—, OH—NH—CO—NH—, $NH_2$—CO—, $NH_2$—NH—CO—, HO—NH—CO—, alkyl-NH—CO—, (alkyl)$_2$N—CO—, $NH_2$-alkylene-NH—CO—, (alkyl)NH-alkylene-NH—CO—, (alkyl)$_2$N-alkylene-NH—CO—, $NH_2$-alkylene-NH—CO—, HCO—NH—NH—CO—, alkyl-SO$_2$—NH—, (alkyl-SO$_2$)$_2$N—, nitro, alkyl (e.g., ethyl), alkoxy (e.g., methoxy), halogenated alkoxy (e.g., trifluoromethoxy), cyano, alkoxycarbonyl (e.g., methoxycarbonyl), triazolyl, halo (e.g., F), amino, carboxy, methylpiperazinyloxycarbonyl, and morpholinylcarbonyl.

In certain embodiments, $R^1$ is chosen from phenyl, furanyl, pyridinyl, pyrimidinyl, thiazolyl, substituted phenyl, substituted furanyl, substituted pyridinyl, substituted pyrimidinyl, and substituted thiazolyl, and $R^2$ is —X(CR$^3$R$^4$)$_n$YR$^5$.

In certain embodiments, $R^1$ is chosen from furanyl, pyridinyl, thiazolyl, phenyl, and phenyl substituted by halo, and $R^2$ is —X(CR$^3$R$^4$)$_n$YR$^5$.

In certain embodiments, $R^1$ is chosen from phenyl and phenyl substituted by halo, and $R^2$ is —X(CR$^3$R$^4$)$_n$YR$^5$.

In certain embodiments, $R^1$ is chosen from phenyl, furanyl, pyridinyl, thiazolyl, substituted phenyl, substituted furanyl, substituted pyridinyl, and substituted thiazolyl, and $R^2$ is chosen from —NH—(CH$_2$)$_3$—O—R$^5$, —NH—(CH$_2$)$_2$—NH—R$^5$, —O—(CH$_2$)$_3$—O—R$^5$, and —NH—(CH$_2$)$_2$—O—R$^5$.

In certain embodiments, $R^1$ is chosen from phenyl, phenyl substituted by halo, furanyl, pyridinyl, and thiazolyl, and $R^2$ is chosen from —NH—(CH$_2$)$_3$—O—R$^5$, —NH—(CH$_2$)$_2$—NH—R$^5$, —O—(CH$_2$)$_3$—O—R$^5$, and —NH—(CH$_2$)$_2$—O—R$^5$.

In certain embodiments, $R^1$ is chosen from phenyl and phenyl substituted by halo, and $R^2$ is chosen from —NH—(CH$_2$)$_3$—O—R$^5$, —NH—(CH$_2$)$_2$—NH—R$^5$, —O—(CH$_2$)$_3$—O—R$^5$, and —NH—(CH$_2$)$_2$—O—R$^5$.

In certain embodiments, $R^1$ is chosen from phenyl, furanyl, pyridinyl, or thiazolyl, substituted phenyl, substituted furanyl, substituted pyridinyl, and substituted thiazolyl, and $R^2$ is chosen from NH—(CH$_2$)$_3$—O—R$^5$ and —O—(CH$_2$)$_3$—O—R$^5$.

In certain embodiments, $R^1$ is chosen from phenyl, phenyl substituted by halo, furanyl, pyridinyl, and thiazolyl, and $R^2$ is chosen from NH—(CH$_2$)$_3$—O—R$^5$ and —O—(CH$_2$)$_3$—O—R$^5$.

In certain embodiments, $R^1$ is chosen from phenyl and phenyl substituted by halo, and $R^2$ is chosen from NH—(CH$_2$)$_3$—O—R$^5$ and —O—(CH$_2$)$_3$—O—R$^5$.

In certain embodiments, $R^1$ is chosen from phenyl, furanyl, pyridinyl, and thiazolyl, which in each case is unsubstituted or substituted, and $R^2$ is —O—(CH$_2$)$_3$—O—R$^5$.

In certain embodiments, $R^1$ is chosen from phenyl, phenyl substituted by halo, furanyl, pyridinyl, and thiazolyl, and $R^2$ is —O—(CH$_2$)$_3$—O—R$^5$.

In certain embodiments, $R^1$ is chosen from phenyl and phenyl substituted by halo, and $R^2$ is —O—(CH$_2$)$_3$—O—R$^5$.

In certain embodiments, $R^1$ is chosen from phenyl, furanyl, pyridinyl, and thiazolyl, substituted phenyl, substituted furanyl, substituted pyridinyl, and substituted thiazolyl; $R^2$ is chosen from NH—(CH$_2$)$_3$—O—R$^5$ and —O—(CH$_2$)$_3$—O—R$^5$; and $R^5$ is chosen from phenyl, benzyl, benzoyl), benzothiadiazolyl, pyridinyl, substituted phenyl, substituted benzyl, substituted benzoyl), substituted benzothiadiazolyl, and substituted pyridinyl.

In certain embodiments, $R^1$ is chosen from phenyl, phenyl substituted by halo, furanyl, pyridinyl, and thiazolyl; $R^2$ is chosen from NH—(CH$_2$)$_3$—O—R$^5$ and —O—(CH$_2$)$_3$—O—R$^5$, and $R^5$ is chosen from phenyl, benzyl, benzoyl), benzothiadiazolyl, and pyridinyl, substituted phenyl, substituted benzyl, substituted benzoyl), substituted benzothiadiazolyl, and substituted pyridinyl.

In certain embodiments, $R^1$ is chosen from phenyl and phenyl substituted by halo; $R^2$ is chosen from NH—(CH$_2$)$_3$—O—R$^5$ or —O—(CH$_2$)$_3$—O—R$^5$; and $R^5$ is chosen from phenyl, benzyl, benzoyl), benzothiadiazolyl, pyridinyl, substituted phenyl, substituted benzyl, substituted benzoyl), substituted benzothiadiazolyl, and substituted pyridinyl.

In certain embodiments, $R^1$ is chosen from phenyl, furanyl, pyridinyl, and thiazolyl, substituted phenyl, substituted furanyl, substituted pyridinyl, and substituted thiazolyl; $R^2$ is chosen from NH—(CH$_2$)$_3$—O—R$^5$ and —O—(CH$_2$)$_3$—O—R$^5$, and $R^5$ is chosen from phenyl and pyridinyl, which in each case is substituted by alkyl-CO—NH— (e.g., $CH_3$—CO—NH—, $CH_3CH_2$—CO—NH— or cyclopropyl-CO—NH—), $NH_2$—CO—NH—, alkyl-NH—CO—NH—, $NH_2$—NH—CO—NH—, OH—NH—CO—NH—, $NH_2$—CO—, $NH_2$—NH—CO—, HO—NH—CO—, alkyl-NH—CO—, (alkyl)$_2$N—CO—, $NH_2$-alkylene-NH—CO—, (alkyl)NH-alkylene-NH—CO—, (alkyl)$_2$N-alkylene-NH—CO—, $NH_2$-alkylene-NH—CO—, HCO—NH—NH—CO—, alkyl-SO$_2$—NH—, (alkyl-SO$_2$)$_2$N—, nitro, alkoxy (e.g., methoxy), halogenated alkoxy (e.g., trifluoromethoxy), cyano, alkoxycarbonyl (e.g., methoxycarbonyl), triazolyl, halo (e.g., F), amino, carboxy, methylpiperazinyloxycarbonyl, and morpholinylcarbonyl.

In certain embodiments, $R^1$ is chosen from phenyl, phenyl substituted by halo, furanyl, pyridinyl, and thiazolyl; $R^2$ is chosen from NH—(CH$_2$)$_3$—O—R$^5$ and —O—(CH$_2$)$_3$—O—R$^5$, and $R^5$ is chosen from phenyl and pyridinyl, which in each case is substituted by alkyl-CO—NH— (e.g., $CH_3$—CO—NH—, $CH_3CH_2$—CO—NH— or cyclopropyl-CO—NH—), $NH_2$—CO—NH—, alkyl-NH—CO—NH—, $NH_2$—NH—CO—NH—, OH—NH—CO—NH—, $NH_2$—CO—, $NH_2$—NH—CO—, HO—NH—CO—, alkyl-NH—CO—, (alkyl)$_2$N—CO—, $NH_2$-alkylene-NH—CO—, (alkyl)NH-alkylene-NH—CO—, (alkyl)$_2$N-alkylene-NH—CO—, $NH_2$-alkylene-NH—CO—, HCO—NH—NH—CO—, alkyl-SO$_2$—NH—, (alkyl-SO$_2$)$_2$N—, nitro, alkoxy (e.g., methoxy), halogenated alkoxy (e.g., trifluoromethoxy), cyano, alkoxycarbonyl (e.g., methoxycarbonyl), triazolyl, halo (e.g., F), amino, carboxy, methylpiperazinyl-oxycarbonyl, and morpholinylcarbonyl.

In certain embodiments, $R^1$ is chosen from phenyl and phenyl substituted by halo; $R^2$ is chosen from NH—(CH$_2$)$_3$—O—R$^5$ and —O—(CH$_2$)$_3$—O—R$^5$; and $R^5$ is chosen from phenyl and pyridinyl, which in each case is substituted by alkyl-CO—NH— (e.g., $CH_3$—CO—NH—, $CH_3CH_2$—CO—NH— or cyclopropyl-CO—NH—), $NH_2$—CO—NH—, alkyl-NH—CO—NH—, $NH_2$—NH—CO—NH—, OH—NH—CO—NH—, $NH_2$—CO—, $NH_2$—NH—CO—, HO—NH—CO—, alkyl-NH—CO—, (alkyl)$_2$N—CO—, $NH_2$-alkylene-NH—CO—, (alkyl)NH-alkylene-NH—CO—, (alkyl)$_2$N-alkylene-NH—CO—, $NH_2$-alkylene-NH—CO—, HCO—NH—NH—CO—, alkyl-SO$_2$—NH—, (alkyl-SO$_2$)$_2$N—, nitro, alkoxy (e.g., methoxy), halogenated alkoxy (e.g., trifluoromethoxy), cyano, alkoxycarbonyl (e.g., methoxycarbonyl), triazolyl, halo (e.g., F), amino, carboxy, methylpiperazinyloxy-carbonyl, and morpholinylcarbonyl.

In certain embodiments, $R^1$ is chosen from phenyl and phenyl substituted by halo; $R^2$ is NH—$(CH_2)_2$—O—$R^5$, and $R^5$ is chosen from phenyl and phenyl substituted by alkyl-CO—NH—.

In certain embodiments, $R^1$ is chosen from phenyl and phenyl substituted by halo; $R^2$ is NH—$(CH_2)_3$—O—$R^5$, and; $R^5$ is chosen from benzyl, benzoyl), and benzothiadiazolyl, substituted benzyl, substituted benzoyl), and substituted benzothiadiazolyl, which in each case the substituents are chosen from nitro, alkoxy (e.g., methoxy), cyano, halogenated alkoxy (e.g., $OCF_3$), alkoxycarbonyl (e.g., methoxycarbonyl), and alkyl-CO—NH— (e.g., acetamido).

In certain embodiments, $R^1$ is chosen from phenyl, furanyl, pyridinyl, thiazolyl, substituted phenyl, substituted furanyl, substituted pyridinyl, and substituted thiazolyl; $R^2$ is —O—$(CH_2)_3$—O—$R^5$, and $R^5$ is chosen from phenyl and pyridinyl, which in each case is substituted by alkyl-CO—NH— (e.g., $CH_3$—CO—NH—, $CH_3CH_2$—CO—NH— or cyclopropyl-CO—NH—), $NH_2$—CO—NH—, alkyl-NH—CO—NH—, $NH_2$—NH—CO—NH—, OH—NH—CO—NH—, $NH_2$—CO—, $NH_2$—NH—CO—, HO—NH—CO—, alkyl-NH—CO—, $(alkyl)_2$N—CO—, $NH_2$-alkylene-NH—CO—, (alkyl)NH-alkylene-NH—CO—, $(alkyl)_2$N-alkylene-NH—CO—, $NH_2$-alkylene-NH—CO—, HCO—NH—NH—CO—, alkyl-$SO_2$—NH—, $(alkyl-SO_2)_2$N—, nitro, alkoxy (e.g., methoxy), halogenated alkoxy (e.g., trifluoromethoxy), cyano, alkoxycarbonyl (e.g., methoxycarbonyl), triazolyl, halo (e.g., F), amino, carboxy, methylpiperazinyl-oxycarbonyl, and morpholinylcarbonyl.

In certain embodiments, $R^1$ is chosen from phenyl and halogenated phenyl; $R^2$ is —O—$(CH_2)_3$—O—$R^5$, and $R^5$ is chosen from phenyl and pyridinyl, which in each case is substituted by alkyl-CO—NH— (e.g., $CH_3$—CO—NH—, $CH_3CH_2$—CO—NH— or cyclopropyl-CO—NH—), $NH_2$—CO—NH—, alkyl-NH—CO—NH—, $NH_2$—NH—CO—NH—, OH—NH—CO—NH—, $NH_2$—CO—, $NH_2$—NH—CO—, HO—NH—CO—, alkyl-NH—CO—, $(alkyl)_2$N—CO—, $NH_2$-alkylene-NH—CO—, (alkyl)NH-alkylene-NH—CO—, $(alkyl)_2$N-alkylene-NH—CO—, $NH_2$-alkylene-NH—CO—, HCO—NH—NH—CO—, alkyl-$SO_2$—NH—, $(alkyl-SO_2)_2$N—, nitro, alkoxy (e.g., methoxy), halogenated alkoxy (e.g., trifluoromethoxy), cyano, alkoxycarbonyl (e.g., methoxycarbonyl), triazolyl, halo (e.g., F), amino, carboxy, methylpiperazinyl-oxycarbonyl, and morpholinylcarbonyl.

In certain embodiments, the compound of Formula I is chosen from:

N-[3-(3-{[5-(4-fluorophenyl)thieno[2,3-d]pyrimidin-4-yl]amino}propoxy)-phenyl]-acetamide, N-(3-nitrobenzyl)-N'-(5-phenylthieno[2,3-d]pyrimidin-4-yl)ethane-1,2-diamine, N-(3,4-dimethoxybenzyl)-N'-(5-phenylthieno[2,3-d]pyrimidin-4-yl)ethane-1,2-diamine, N-(2,1,3-benzothiadiazol-5-ylmethyl)-N'-(5-phenylthieno[2,3-d]pyrimidin-4-yl)ethane-1,2-diamine, N-{3-[({2-[(5-phenylthieno[2,3-d]pyrimidin-4-yl)amino]ethyl}amino)methyl]-phenyl}-acetamide, N-{4-[({2-[(5-phenylthieno[2,3-d]pyrimidin-4-yl)amino]ethyl}amino)methyl]-phenyl}-acetamide, 3-(acetylamino)-N-{2-[(5-phenylthieno[2,3-d]pyrimidin-4-yl)amino]-ethyl}benzamide, 3-[({2-[(5-phenylthieno[2,3-d]pyrimidin-4-yl)amino]ethyl}amino)methyl]-benzonitrile, Methyl 3-[({2-[(5-phenylthieno[2,3-d]pyrimidin-4-yl)amino]ethyl}amino)-methyl]-benzoate, N-(5-phenylthieno[2,3-d]pyrimidin-4-yl)-N'-[3-(trifluoromethoxy)benzyl]ethane-1,2-diamine, 5-(4-fluorophenyl)-4-[3-(3-nitrophenoxy)propoxy]thieno[2,3-d]pyrimidine, N-[4-(3-{[5-(4-fluorophenyl)thieno[2,3-d]pyrimidin-4-yl]amino}propoxy)-phenyl]-acetamide, N-[3-(3-{[5-(4-fluorophenyl)thieno[2,3-d]pyrimidin-4-yl]oxy}propoxy)phenyl]-acetamide, N-[4-(3-{[5-(4-fluorophenyl)thieno[2,3-d]pyrimidin-4-yl]oxy}propoxy)phenyl]-acetamide, 5-(4-fluorophenyl)-4-{3-[4-(1H-1,2,4-triazol-1-yl)phenoxy]propoxy}thieno[2,3-d]pyrimnidine, 4-[3-(4-fluorophenoxy)propoxy]-5-(4-fluorophenyl)thieno[2,3-d]pyrimidine, Methyl 3-(3-{[5-(4-fluorophenyl)thieno[2,3-d]pyrimidin-4-yl]oxy}propoxy)benzoate, 3-(3-{[5-(4-fluorophenyl)thieno[2,3-d]pyrimidin-4-yl]oxy}propoxy)aniline, 3-(3-{[5-(4-fluorophenyl)thieno[2,3-d]pyrimidin-4-yl]oxy}propoxy)benzoic acid, N-[3-(3-{[5-(4-fluorophenyl)thieno[2,3-d]pyrimidin-4-yl]oxy}propoxy)phenyl]-cyclopropanecarboxamide, 5-(4-fluorophenyl)-4-(3-{3-[(4-methylpiperazin-1-yl)carbonyl]phenoxy}-propoxy)-thieno[2,3-d]pyrimidine, 5-(4-fluorophenyl)-4-{3-[3-(morpholin-4-ylcarbonyl)phenoxy]propoxy}-thieno[2,3-d]pyrimidine, N-ethyl-3-(3-{[5-(4-fluorophenyl)thieno[2,3-d]pyrimidin-4-yl]oxy}propoxy)-benzamide, 3-(3-{[5-(4-fluorophenyl)thieno[2,3-d]pyrimidin-4-yl]oxy}propoxy)-N,N-dimethylbenzamide, N-[2-(dimethylamino)ethyl]-3-(3-{[5-(4-fluorophenyl)thieno[2,3-d]pyrimidin-4-yl]oxy}propoxy)benzamide, N-(2-amino-2-oxoethyl)-3-(3-{[5-(4-fluorophenyl)thieno[2,3-d]pyrimidin-4-yl]oxy}propoxy)benzamide, 3-(3-{[5-(4-fluorophenyl)thieno[2,3-d]pyrimidin-4-yl]oxy}propoxy)-N'-formylbenzohydrazide, 3-(3-{[5-(4-fluorophenyl)thieno[2,3-d]pyrimidin-4-yl]oxy}propoxy)-N-methylbenzamide, 3-(3-{[5-(4-fluorophenyl)thieno[2,3-d]pyrimidin-4-yl]oxy}propoxy)benzamide, 3-(2-{[5-(4-fluorophenyl)thieno[2,3-d]pyrimidin-4-yl]oxy}ethoxy)-N-methylbenzamide, N-[3-(2-{[5-(4-fluorophenyl)thieno[2,3-d]pyrimidin-4-yl]oxy}ethoxy)phenyl]-urea, N-[3-(3-{[5-(4-fluorophenyl)thieno[2,3-d]pyrimidin-4-yl]oxy}propoxy)-phenyl]urea, 3-(2-{[5-(4-fluorophenyl)thieno[2,3-d]pyrimidin-4-yl]oxy}ethoxy)benzamide, 3-(3-{[5-(4-fluorophenyl)thieno[2,3-d]pyrimidin-4-yl]oxy}propoxy)-benzohydrazide, 3-(3-{[5-(4-fluorophenyl)thieno[2,3-d]pyrimidin-4-yl]oxy}propoxy)-N-hydroxybenzamide, 4-(2-{[5-(4-fluorophenyl)thieno[2,3-d]pyrimidin-4-yl]oxy}ethoxy)benzamide N-ethyl-N'-[3-(3-{[5-(4-fluorophenyl)thieno[2,3-d]pyrimidin-4-yl]oxy}propoxy)phenyl]urea, N-[3-(3-{[5-(4-fluorophenyl)thieno[2,3-d]pyrimidin-4-yl]oxy}propoxy)phenyl]-methanesulfonamide, N-[4-(3-{[5-(4-fluorophenyl)thieno[2,3-d]pyrimidin-4-yl]oxy}propoxy)phenyl]-methanesulfonamide, N-[4-(3-{[5-(4-fluorophenyl)thieno[2,3-d]pyrimidin-4-yl]oxy}propoxy)phenyl]-N-(methylsulfonyl)methanesulfonamide, N-(ethylsulfonyl)-N-[4-(3-{[5-(4-fluorophenyl)thieno[2,3-d]pyrimidin-4-yl]oxy}-propoxy)phenyl]ethanesulfonamide,
N-[4-(3-{[5-(4-fluorophenyl)thieno[2,3-d]pyrimidin-4-yl]oxy}propoxy)phenyl]-ethanesulfonamide,
N-[4-(3-{[5-(4-fluorophenyl)thieno[2,3-d]pyrimidin-4-yl]oxy}propoxy)phenyl]-N'-methylurea,
N-ethyl-N'-[4-(3-{[5-(4-fluorophenyl)thieno[2,3-d]pyrimidin-4-yl]oxy}propoxy)-phenyl]-urea,
N-[3-(3-{[5-(4-fluorophenyl)thieno[2,3-d]pyrimidin-4-yl]oxy}propoxy)phenyl]-ethanesulfonamide,
N-[3-(3-{[5-(4-fluorophenyl)thieno[2,3-d]pyrimidin-4-yl]oxy}propoxy)phenyl]-N'-methylurea,
N-[3-(3-{[5-(4-fluorophenyl)thieno[2,3-d]pyrimidin-4-yl]oxy}propoxy)phenyl]-hydrazinecarboxamide,
N-[3-(3-{[5-(4-fluorophenyl)thieno[2,3-d]pyrimidin-4-yl]oxy}propoxy)phenyl]-N'-hydroxyurea,
4-{3-[5-(4-fluorophenyl)-thieno[2,3d]pyrimidin-4-yloxy]-propoxy}-benzamide,
5-{3-[5-(4-fluorophenyl)-thieno[2,3-d]pyrimidin-4-yloxy]-propoxy}-nicotinic acid, methyl ester, N-{3-[3-(5-furan-2-yl-thieno[2,3d]pyrimidin-4-yloxy)-propoxy]-phenyl}acetamide,
2-(3-{[5-(4-fluorophenyl)thieno[2,3-d]pyrimidin-4-yl]oxy}propoxy)benzamide,
5-{3-[5-(4-fluorophenyl)-thieno[2,3-d]pyrimidin-4-yloxy]-propoxy}-nicotinic acid,
N-(3-{3-[(5-phenylthieno[2,3-d]pyrimidin-4-yl)oxy]propoxy}phenyl)acetamide,
N-[4-(3-{[5-(4-fluorophenyl)thieno[2,3-d]pyrimidin-4-yl]oxy}propoxy)phenyl]-hydrazinecarboxamide,
5-{3-[(5-pyridin-4-ylthieno[2,3-d]pyrimidin-4-yl)oxy]propoxy}pyridine-2-carboxamide,
5-(3-{[5-(4-fluorophenyl)thieno[2,3-d]pyrimidin-4-yl]oxy}propoxy)pyridine-2-carboxamide,
5-(3-{[5-(1,3-thiazol-2-yl)thieno[2,3-d]pyrimidin-4-yl]oxy}propoxy)pyridine-2-carboxamide,
5-{3-[(5-pyridin-3-ylthieno[2,3-d]pyrimidin-4-yl)oxy]propoxy}pyridine-2-carboxamide
N-methyl-5-{3-[(5-pyridin-4-ylthieno[2,3-d]pyrimidin-4-yl)oxy]propoxy}-pyridine-2-carboxamide,
5-(3-{[5-(4-fluorophenyl)thieno[2,3-d]pyrimidin-4-yl]oxy}propoxy)-N-methylpyridine-2-carboxamide,
N-methyl-5-(3-{[5-(1,3-thiazol-2-yl)thieno[2,3-d]pyrimidin-4-yl]oxy}propoxy)-pyridine-2-carboxamide,
N-methyl-5-{3-[(5-pyridin-3-ylthieno[2,3-d]pyrimidin-4-yl)oxy]propoxy}-pyridine-2-carboxamide, In certain embodiments, the compound of Formula I is chosen from:

N-methyl-3-{3-[(5-pyridin-3-ylthieno[2,3-d]pyrimidin-4-yl)oxy]propoxy}benzamide,
N-methyl-5-(3-{[5-(1,3-thiazol-2-yl)-thieno[2,3-d]pyrimidin-4-yl]amino}-propoxy)pyridine-2-carboxamide,
5-(3-{[5-(5-chloro-2-furyl)thieno[2,3-d]pyrimidin-4-yl]amino}propoxy)-N-methylpyridine-2-carboxamide,
N-methyl-5-{3-[(5-pyridin-3-ylthieno[2,3-d]pyrimidin-4-yl)amino]propoxy}pyridine-2-carboxamide,
N-methyl-5-{3-[(5-pyridin-2-ylthieno[2,3-d]pyrimidin-4-yl)amino]propoxy}pyridine-2-carboxamide,
N-methyl-5-{3-[(5-pyridin-2-ylthieno[2,3-d]pyrimidin-4-yl)amino]propoxy}-nicotinamide,
5-{3-[(5-pyridin-3-ylthieno[2,3-d]-pyrimidin-4-yl)oxy]propoxy}pyridine-2-carboxamide hydroformate,
5-(4-fluorophenyl)-4-(3-{[1-methyl-5-(trifluoromethyl)-1H-pyrazol-3-yl]oxy}propoxy)thieno[2,3-d]pyrimidine,
4-[3-(4-chlorophenoxy)propoxy]-5-(4-fluorophenyl)thieno[2,3-d]pyrimidine,
4-[3-(3,5-difluorophenoxy)propoxy]-5-(4-fluorophenyl)thieno[2,3-d]pyrimidine,
4-[3-(3,4-dimethoxyphenoxy)propoxy]-5-(4-fluorophenyl)thieno[2,3-d]pyrimidine,
4-[3-(1,2-benzisothiazol-3-yloxy)propoxy]-5-(4-fluorophenyl)thieno[2,3-d]pyrimidine,
5-(4-fluorophenyl)-4-(3-phenoxypropoxy)-thieno[2,3-d]pyrimidine,
5-(4-fluorophenyl)-4-[3-(3-methoxy-phenoxy)propoxy]thieno[2,3-d]pyrimidine,
5-(4-fluorophenyl)-4-[3-(3-methyl-phenoxy)propoxy]thieno[2,3-d]pyrimidine,
5-(4-fluorophenyl)-4-{3-[3-(trifluoro-methoxy)phenoxy]propoxy}thieno[2,3-d]pyrimidine,
4-[3-(3-ethylphenoxy)propoxy]-5-(4-fluorophenyl)thieno[2,3-d]pyrimidine,
5-{3-[(5-pyrimidin-2-ylthieno[2,3-d]pyrimidin-4-yl)amino]propoxy}pyridine-2-carboxylic acid hydroformate,
5-(3-{[5-(1,3-thiazol-2-yl)thieno[2,3-d]pyrimidin-4-yl]amino}propoxy)pyridine-2-carboxylic acid hydroformate,
5-{3-[(5-pyrazin-2-ylthieno[2,3-d]pyrimidin-4-yl)amino]propoxy}pyridine-2-carboxylic acid hydroformate,
4-[5-(4-fluorophenyl)thieno[2,3-d]pyrimidin-4-yl]butan-1-ol,
4-but-3-en-1-yl-5-(4-fluorophenyl)-thieno[2,3-d]pyrimidine,
Methyl 5-{4-[5-(4-fluorophenyl)-thieno[2,3-d]pyrimidin-4-yl]butoxy}-nicotinate,
5-{4-[5-(4-fluorophenyl)thieno[2,3-d]pyrimidin-4-yl]butoxy}nicotinic acid hydroformate,
5-{4-[5-(4-fluorophenyl)thieno[2,3-d]pyrimidin-4-yl]butoxy}-N-methylnicotinamide hydroformate,
5-{4-[5-(4-fluorophenyl)thieno[2,3-d]pyrimidin-4-yl]butoxy}nicotinamide hydroformate,
N-[3-(3-{[5-(4-fluorophenyl)thieno[2,3-d]pyrimidin-4-yl]oxy}phenoxy)-phenyl]acetamide hydroformate,
N-[3-(2,2-dimethyl-3-{[5-(1,3-thiazol-2-yl)thieno[2,3-d]pyrimidin-4-yl]oxy}propoxy)phenyl]acetamide hydroformate,
N-[3-(3-{[5-(1,3-thiazol-2-yl)thieno[2,3-d]pyrimidin-4-yl]oxy}phenoxy)phenyl]-acetamide hydroformate,
N-[3-(3-{[5-(4-fluorophenyl)thieno[2,3-d]pyrimidin-4-yl]oxy}-2,2-dimethyl-propoxy)phenyl]acetamide hydroformate,
5-(3-{[5-(4-fluorophenyl)thieno[2,3-d]pyrimidin-4-yl]oxy}propoxy)-1,3-dihydro-2H-indol-2-one,
5-{3-[(5-pyridin-3-ylthieno[2,3-d]pyrimidin-4-yl)amino]propoxy}pyridine-2-carboxamide hydroformate,
5-(3-{[5-(1,3-thiazol-2-yl)thieno[2,3-d]pyrimidin-4-yl]amino}propoxy)pyridine-2-carboxamide hydroformate,
N-[4-(3-{[5-(4-fluorophenyl)thieno[2,3-d]pyrimidin-4-yl]amino}propyl)phenyl]-acetamide,
N-(3-{3-[(5-pyridin-3-ylthieno[2,3-d]pyrimidin-4-yl)amino]propoxy}phenyl)-acetamide,
N-[3-(3-{[5-(1,3-thiazol-2-yl)thieno[2,3-d]pyrimidin-4-yl]amino}propoxy)-phenyl]acetamide,
N-(3-{3-[(5-pyridin-2-ylthieno[2,3-d]pyrimidin-4-yl)amino]propoxy}phenyl)-acetamide,
N-[4-(3-{[5-(1,3-thiazol-2-yl)thieno[2,3-d]pyrimidin-4-yl]amino}propoxy)-phenyl]acetamide,
N-(4-{3-[(5-pyridin-3-ylthieno[2,3-d]pyrimidin-4-yl)amino]propoxy}phenyl)-acetamide,
N-[4-(3-{[5-(5-chloro-2-furyl)thieno[2,3-d]pyrimidin-4-yl]amino}propoxy)-phenyl]acetamide,
5-(4-fluorophenyl)-4-[3-(3-nitrophenoxy)propoxy]thieno[2,3-d]pyrimidine, N-methyl-4-{3-[(5-pyridin-3-ylthieno[2,3-d]pyrimidin-4-yl)oxy]propoxy}-benzamide,
N-methyl-5-(3-{[5-(1,3-thiazol-2-yl)thieno[2,3-d]pyrimidin-4-yl]oxy}propoxy)-nicotinamide,
N-methyl-5-{3-[(5-pyridin-3-ylthieno[2,3-d]pyrimidin-4-yl)oxy]propoxy}-nicotinamide,
N-methyl-3-(3-{[5-(1,3-thiazol-2-yl)thieno[2,3-d]pyrimidin-4-yl]oxy}propoxy)-benzamide,
N-[4-(3-{[5-(1,3-thiazol-2-yl)thieno[2,3-d]pyrimidin-4-yl]oxy}propoxy)phenyl]-acetamide, and
N-(4-{3-[(5-pyridin-3-ylthieno[2,3-d]pyrimidin-4-yl)oxy]propoxy}phenyl)-acetamide.

In certain embodiments, the compound of Formula I is chosen from those listed in Table I:

TABLE 1

| Cpd # | Structure | Name |
|---|---|---|
| 1 | 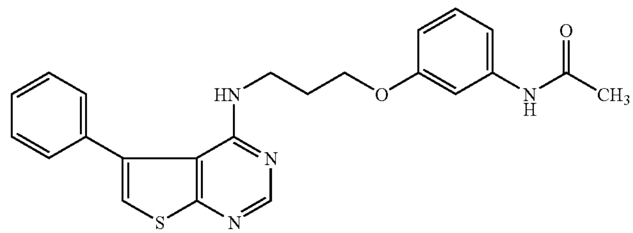 | N-(3-{3-[(5-phenylthieno[2,3-d]pyrimidin-4-yl)amino]-propoxy}phenyl)-acetamide |
| 2 | 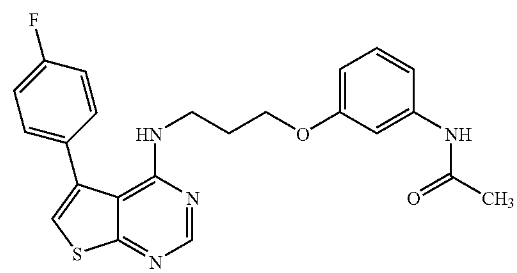 | N-[3-(3-{[5-(4-fluorophenyl)-thieno[2,3-d]pyrimidin-4-yl]amino}-propoxy)phenyl]-acetamide |
| 3 | 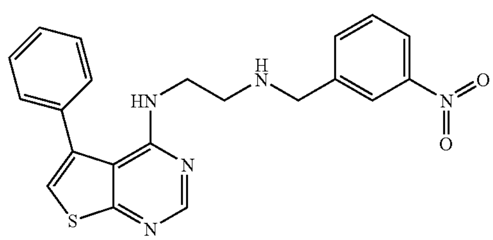 | N-(3-nitrobenzyl)-N'-(5-phenylthieno[2,3-d]pyrimidin-4-yl)ethane-1,2-diamine |
| 4 | 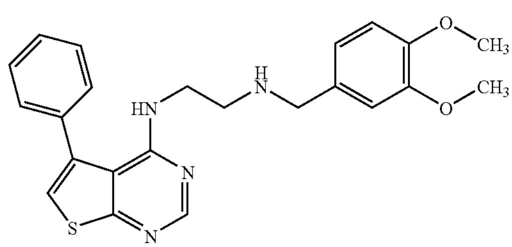 | N-(3,4-dimethoxybenzyl)-N'-(5-phenylthieno[2,3-d]pyrimidin-4-yl)ethane-1,2-diamine |
| 5 | 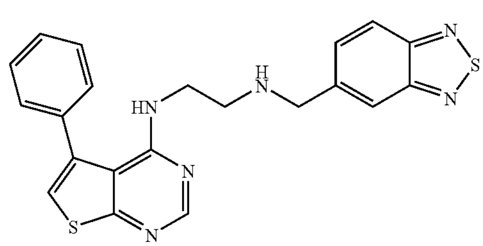 | N-(2,1,3-benzothiadiazol-5-ylmethyl)-N'-(5-phenylthieno[2,3-d]pyrimidin-4-yl)ethane-1,2-diamine |

TABLE 1-continued

| Cpd # | Structure | Name |
|---|---|---|
| 6 | 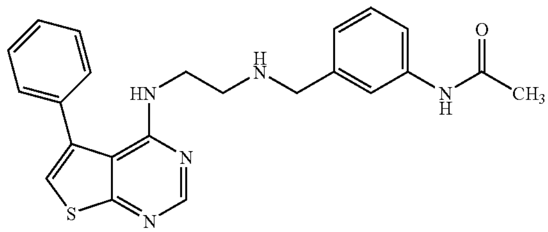 | N-{3-[({2-[(5-phenylthieno[2,3-d]pyrimidin-4-yl)amino]ethyl}-amino)methyl]phenyl}acetamide |
| 7 | 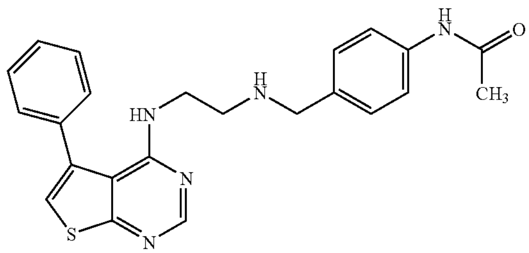 | N-{4-[({2-[(5-phenylthieno[2,3-d]pyrimidin-4-yl)amino]ethyl}amino)-methyl]phenyl}acetamide |
| 8 | 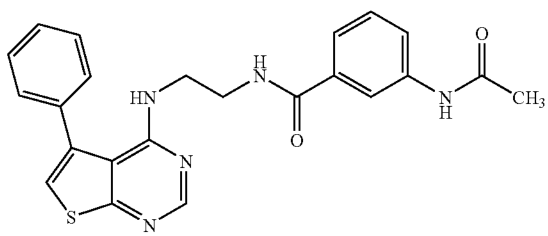 | 3-(acetylamino)-N-{2-[(5-phenylthieno[2,3-d]pyrimidin-4-yl)amino]ethyl}benzamide |
| 9 | 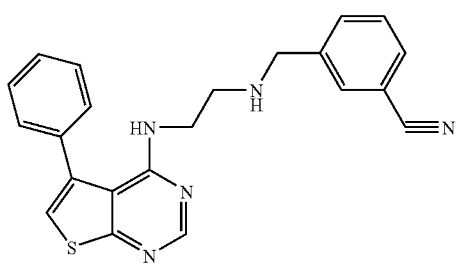 | 3-[({2-[(5-phenylthieno[2,3-d]pyrimidin-4-yl)amino]ethyl}-amino)-methyl]benzonitrile |
| 10 | 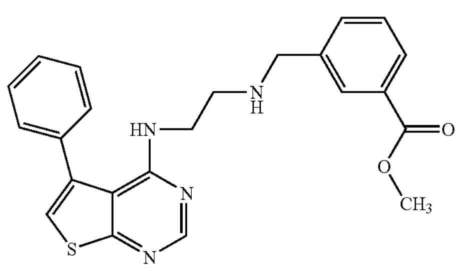 | methyl 3-[({2-[(5-phenylthieno[2,3-d]pyrimidin-4-yl)amino]ethyl}-amino)methyl]benzoate |
| 11 | 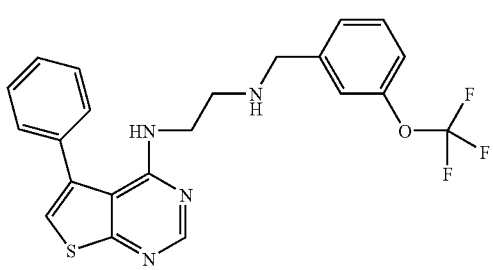 | N-(5-phenylthieno[2,3-d]pyrimidin-4-yl)-N'-[3-(trifluoromethoxy)-benzyl]-ethane-1,2-diamine |

TABLE 1-continued

| Cpd # | Structure | Name |
|---|---|---|
| 12 | 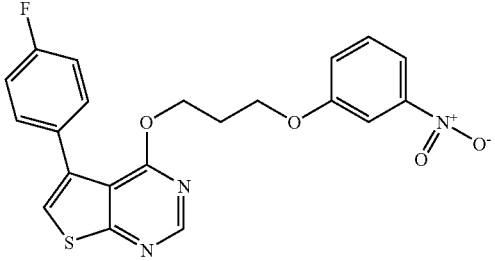 | 5-(4-fluorophenyl)-4-[3-(3-nitrophenoxy)propoxy]thieno[2,3-d]pyrimidine |
| 13 | 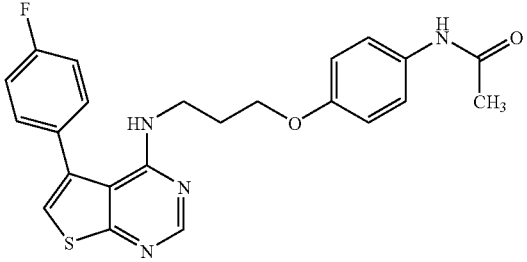 | N-[4-(3-{[5-(4-fluorophenyl)thieno[2,3-d]pyrimidin-4-yl]amino}-propoxy)phenyl]acetamide |
| 14 | 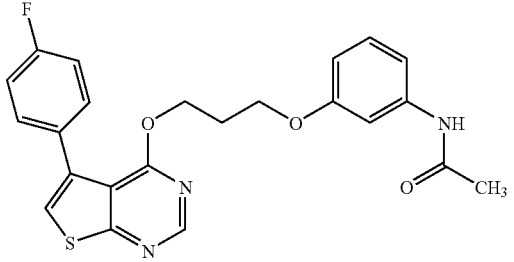 | N-[3-(3-{[5-(4-fluorophenyl)-thieno[2,3-d]pyrimidin-4-yl]oxy}propoxy)-phenyl]acetamide |
| 15 | 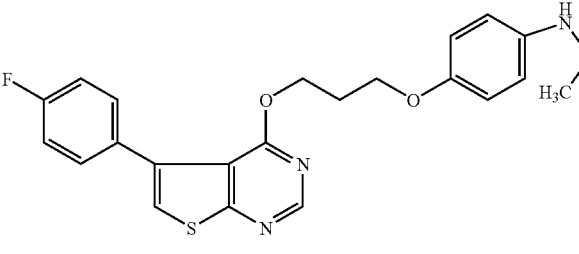 | N-[4-(3-{[5-(4-fluorophenyl)-thieno[2,3-d]pyrimidin-4-yl]oxy}propoxy)-phenyl]acetamide |
| 16 | 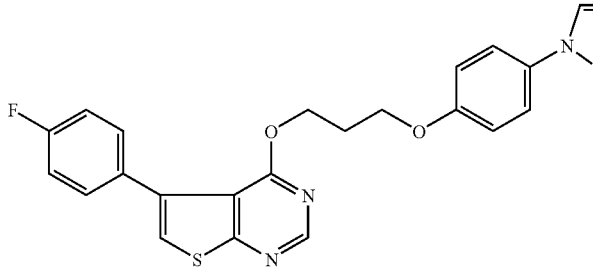 | 5-(4-fluorophenyl)-4-{3-[4-(1H-1,2,4-triazol-1-yl)phenoxy]-propoxy}-thieno[2,3-d]pyrimidine |

TABLE 1-continued

| Cpd # | Structure | Name |
|---|---|---|
| 17 | 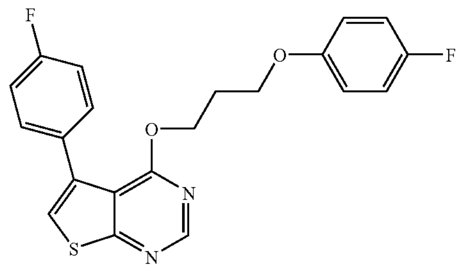 | 4-[3-(4-fluorophenoxy)propoxy]-5-(4-fluorophenyl)thieno[2,3-d]pyrimidine |
| 18 | 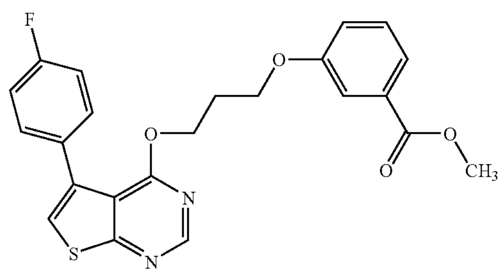 | methyl 3-(3-{[5-(4-fluorophenyl)-thieno[2,3-d]pyrimidin-4-yl]oxy}-propoxy)benzoate |
| 19 | 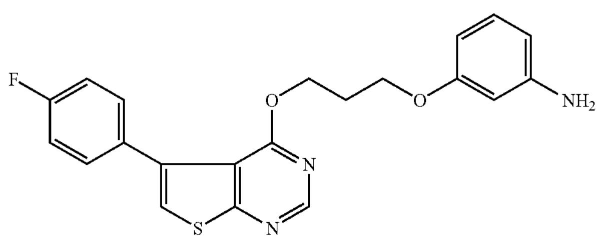 | 3-(3-{[5-(4-fluorophenyl)-thieno[2,3-d]pyrimidin-4-yl]oxy}propoxy)-aniline |
| 20 | 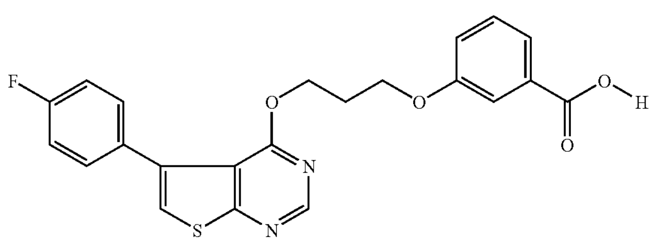 | 3-(3-{[5-(4-fluorophenyl)-thieno[2,3-d]pyrimidin-4-yl]oxy}propoxy)-benzoic acid |
| 21 | 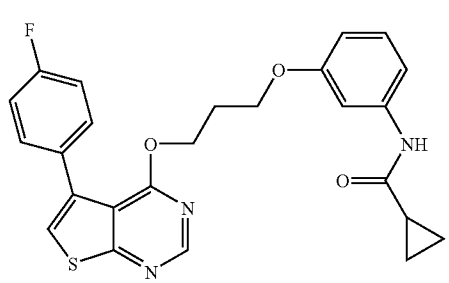 | N-[3-(3-{[5-(4-fluorophenyl)-thieno[2,3-d]pyrimidin-4-yl]oxy}propoxy)-phenyl]cyclo-propanecarboxamide |

TABLE 1-continued

| Cpd # | Structure | Name |
| --- | --- | --- |
| 22 | 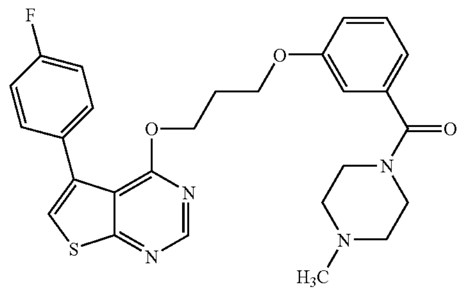 | 5-(4-fluorophenyl)-4-(3-{3-[(4-methylpiperazin-1-yl)carbonyl]-phenoxy}-propoxy)thieno[2,3-d]pyrimidine |
| 23 | 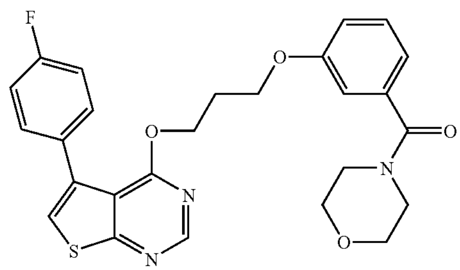 | 5-(4-fluorophenyl)-4-{3-[3-(morpholin-4-ylcarbonyl)-phenoxy]propoxy}-thieno[2,3-d]pyrimidine |
| 24 | 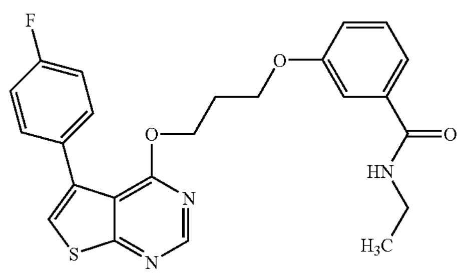 | N-ethyl-3-(3-{[5-(4-fluorophenyl)-thieno[2,3-d]pyrimidin-4-yl]oxy}-propoxy)benzamide |
| 25 | 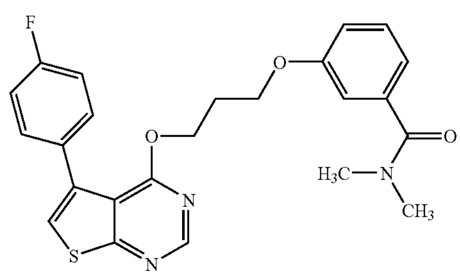 | 3-(3-{[5-(4-fluorophenyl)-thieno[2,3-d]pyrimidin-4-yl]oxy}propoxy)-N,N-dimethylbenzamide |
| 26 | 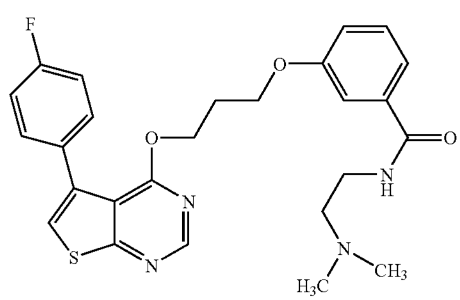 | N-[2-(dimethylamino)ethyl]-3-(3-{[5-(4-fluorophenyl)thieno[2,3-d]pyrimidin-4-yl]oxy}propoxy)-benzamide |

TABLE 1-continued

| Cpd # | Structure | Name |
|---|---|---|
| 27 | 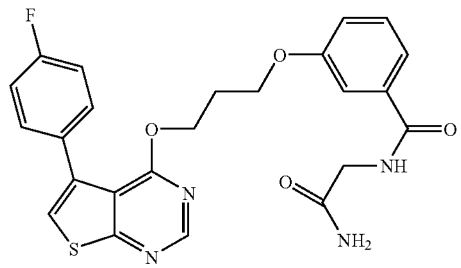 | N-(2-amino-2-oxoethyl)-3-(3-{[5-(4-fluorophenyl)thieno[2,3-d]pyrimidin-4-yl]oxy}propoxy)-benzamide |
| 28 | 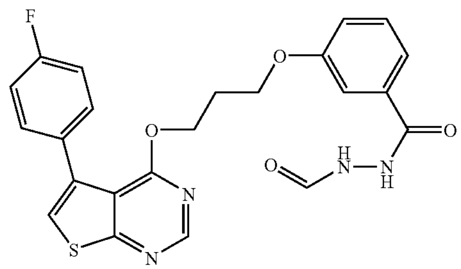 | 3-(3-{[5-(4-fluorophenyl)-thieno[2,3-d]pyrimidin-4-yl]oxy}propoxy)-N'-formylbenzohydrazide |
| 29 | 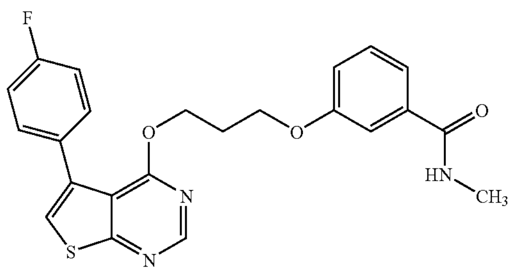 | 3-(3-{[5-(4-fluorophenyl)-thieno[2,3-d]pyrimidin-4-yl]oxy}propoxy)-N-methyl-benzamide |
| 30 | 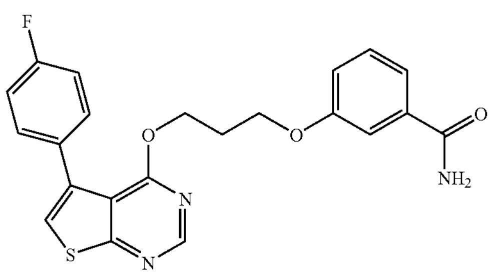 | 3-(3-{[5-(4-fluorophenyl-)thieno[2,3-d]pyrimidin-4-yl]oxy}propoxy)-benzamide |
| 31 | 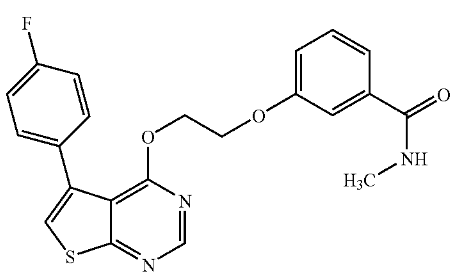 | 3-(2-{[5-(4-fluorophenyl)-thieno[2,3-d]pyrimidin-4-yl]oxy}ethoxy)-N-methylbenzamide |

TABLE 1-continued

| Cpd # | Structure | Name |
|---|---|---|
| 32 | 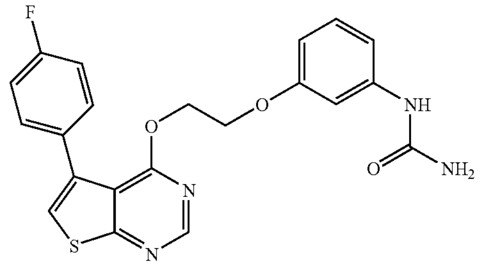 | N-[3-(2-{[5-(4-fluorophenyl)-thieno[2,3-d]pyrimidin-4-yl]oxy}ethoxy)phenyl]urea |
| 33 | 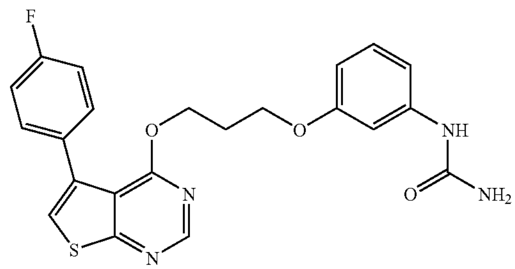 | N-[3-(3-{[5-(4-fluorophenyl)-thieno[2,3-d]pyrimidin-4-yl]oxy}propoxy)phenyl]urea |
| 34 | 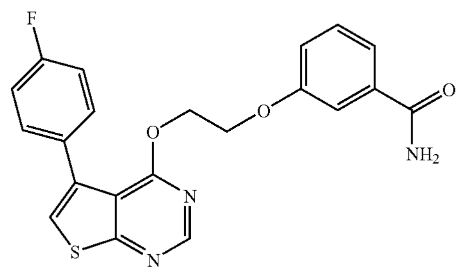 | 3-(2-{[5-(4-fluorophenyl)-thieno[2,3-d]pyrimidin-4-yl]oxy}ethoxy)-benzamide |
| 35 | 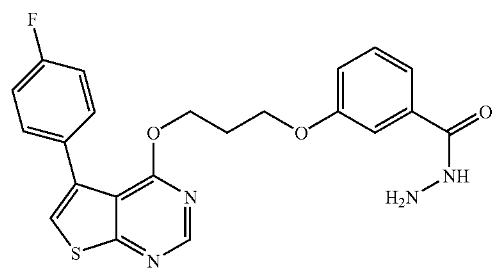 | 3-(3-{[5-(4-fluorophenyl)-thieno[2,3-d]pyrimidin-4-yl]oxy}propoxy)-benzohydrazide |
| 36 | 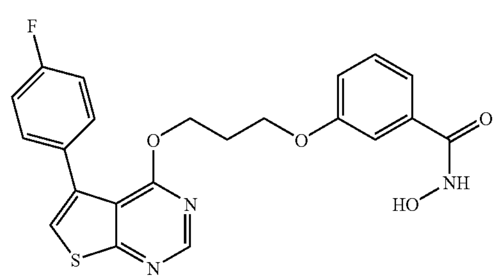 | 3-(3-{[5-(4-fluorophenyl)-thieno[2,3-d]pyrimidin-4-yl]oxy}propoxy)-N-hydroxy-benzamide |

TABLE 1-continued

| Cpd # | Structure | Name |
|---|---|---|
| 37 | 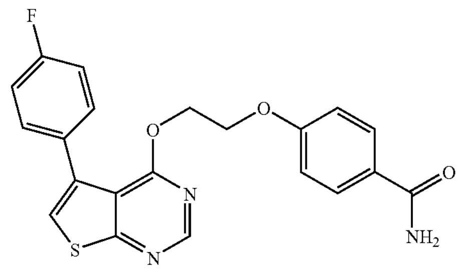 | 4-(2-{[5-(4-fluorophenyl)-thieno[2,3-d]pyrimidin-4-yl]oxy}ethoxy)-benzamide |
| 38 | 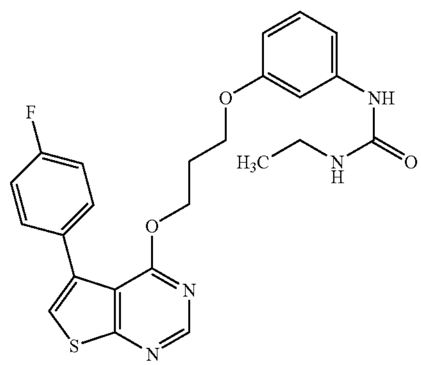 | N-ethyl-N'-[3-(3-{[5-(4-fluorophenyl)thieno[2,3-d]pyrimidin-4-yl]oxy}propoxy)-phenyl]urea |
| 39 | 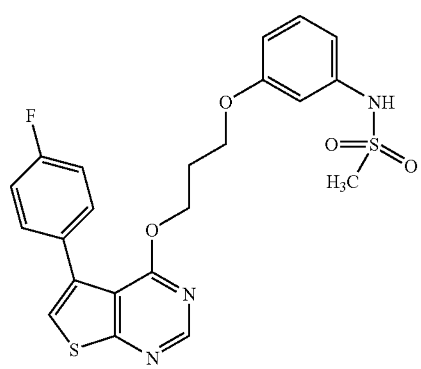 | N-[3-(3-{[5-(4-fluorophenyl)-thieno[2,3-d]pyrimidin-4-yl]oxy}propoxy)-phenyl]methane-sulfonamide |
| 40 | 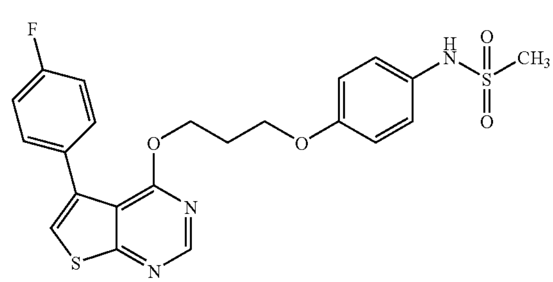 | N-[4-(3-{[5-(4-fluorophenyl)-thieno[2,3-d]pyrimidin-4-yl]oxy}-propoxy)phenyl]methansulfonamide |

TABLE 1-continued

| Cpd # | Structure | Name |
|---|---|---|
| 41 | 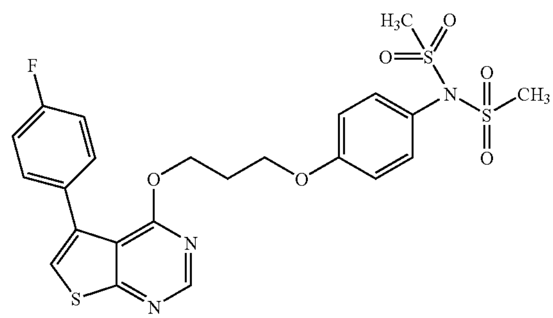 | N-[4-(3-{[5-(4-fluorophenyl)-thieno[2,3-d]pyrimidin-4-yl]oxy}propoxy)-phenyl]-N-(methylsulfonyl)methansulfonamide |
| 42 | 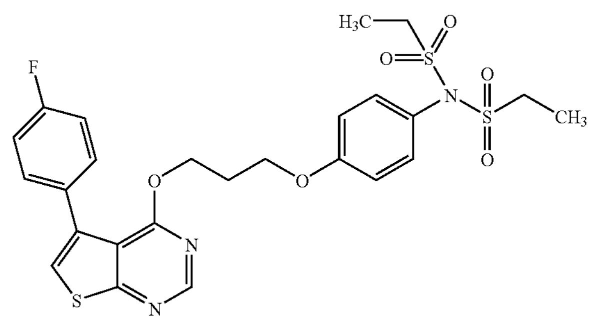 | N-(ethylsulfonyl)-N-[4-(3-{[5-(4-fluorophenyl)thieno[2,3-d]pyrimidin-4-yl]oxy}propoxy)phenyl]ethanesulfonamide |
| 43 | 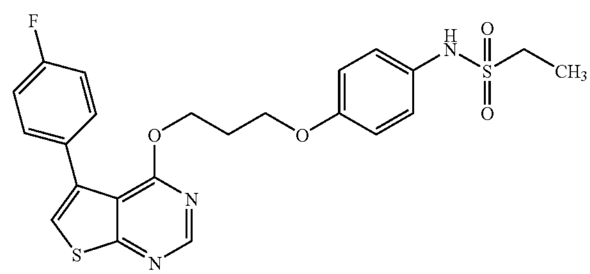 | N-[4-(3-{[5-(4-fluorophenyl)thieno[2,3-d]pyrimidin-4-yl]oxy}propoxy)-phenyl]ethanesulfonamide |
| 44 | 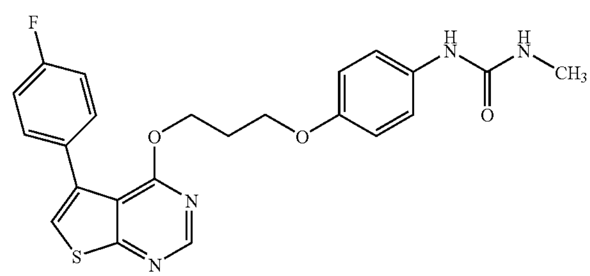 | N-[4-(3-{[5-(4-fluorophenyl)thieno[2,3-d]pyrimidin-4-yl]oxy}propoxy)-phenyl]-N'-methylurea |
| 45 | 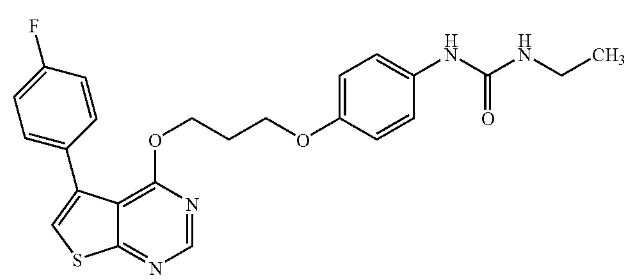 | N-ethyl-N'-[4-(3-{[5-(4-fluorophenyl)thieno[2,3-d]pyrimidin-4-yl]oxy}-propoxy)phenyl]urea |

TABLE 1-continued

| Cpd # | Structure | Name |
|---|---|---|
| 46 | 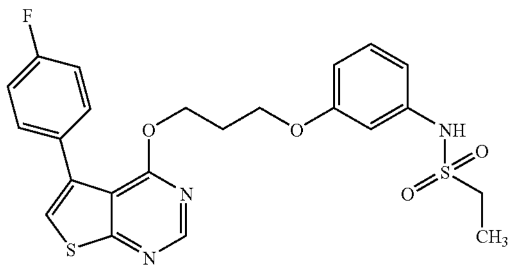 | N-[3-(3-{[5-(4-fluorophenyl)thieno[2,3-d]pyrimidin-4-yl]oxy}propoxy)-phenyl]ethanesulfonamide |
| 47 | 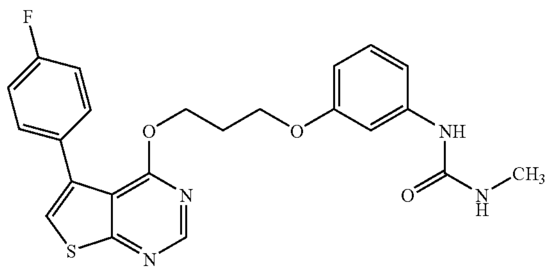 | N-[3-(3-{[5-(4-fluorophenyl)thieno[2,3-d]pyrimidin-4-yl]oxy}propoxy)-phenyl]-N'-methylurea |
| 48 | 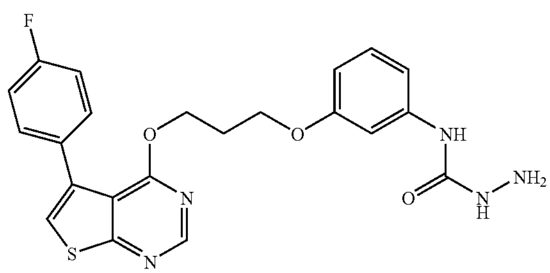 | N-[3-(3-{[5-(4-fluorophenyl)thieno[2,3-d]pyrimidin-4-yl]oxy}propoxy)-phenyl]hydrazinecarboxamide |
| 49 | 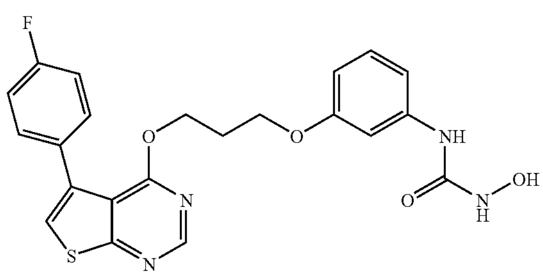 | N-[3-(3-{[5-(4-fluorophenyl)thieno[2,3-d]pyrimidin-4-yl]oxy}propoxy)-phenyl]-N'-hydroxyurea |
| 50 | 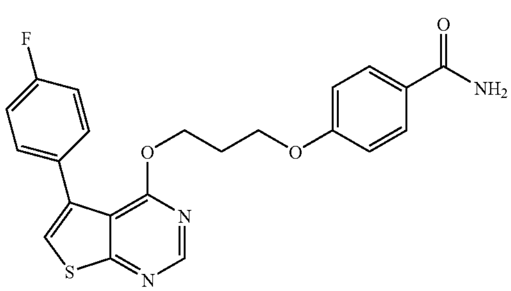 | 4-{3-[5-(4-fluorophenyl)-thieno[2,3d]-pyrimidin-4-yloxy]-propoxy}-benzamide |

TABLE 1-continued

| Cpd # | Structure | Name |
|---|---|---|
| 51 | 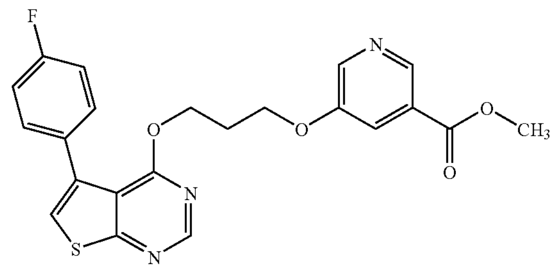 | 5-{3-[5-(4-fluorophenyl)-thieno[2,3-d]pyrimidin-4-yloxy]-propoxy}-nicotinic acid methyl ester |
| 52 | 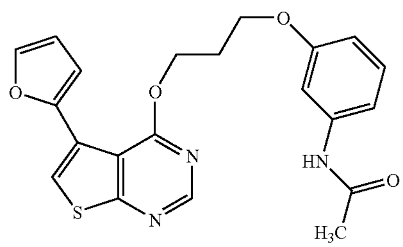 | N-{3-[3-(5-furan-2-yl-thieno[2,3d]-pyrimidin-4-yloxy)-propoxy]-phenyl}acetamide |
| 53 | 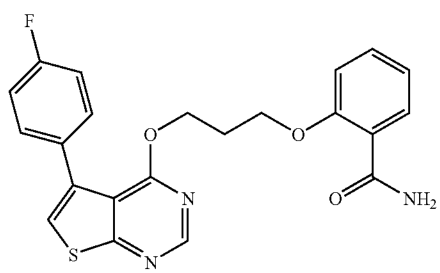 | 2-(3-{[5-(4-fluorophenyl)thieno[2,3-d]pyrimidin-4-yl]oxy}propoxy)-benzamide |
| 54 | 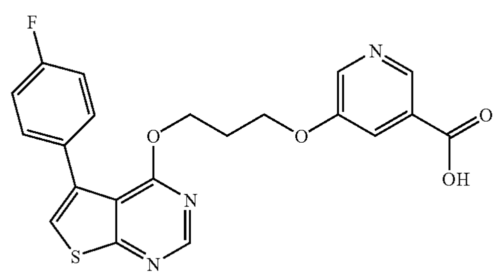 | 5-{3-[5-(4-fluorophenyl)-thieno[2,3-d]pyrimidin-4-yloxy]-propoxy}-nicotinic acid |
| 55 | 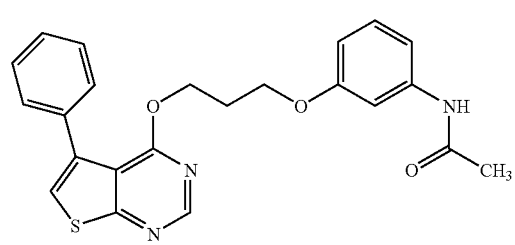 | N-(3-{3-[(5-phenylthieno[2,3-d]pyrimidin-4-yl)oxy]propoxy}phenyl)-acetamide |
| 56 | 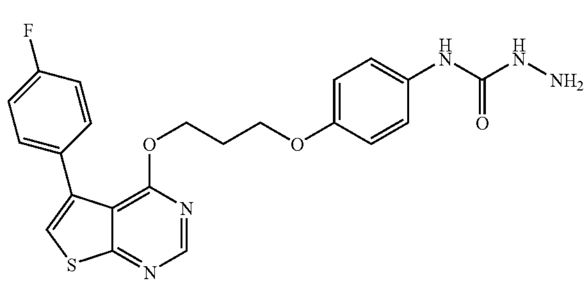 | N-[4-(3-{[5-(4-fluorophenyl)thieno[2,3-d]pyrimidin-4-yl]oxy}propoxy)-phenyl]hydrazinecarboxamide |

TABLE 1-continued

| Cpd # | Structure | Name |
|---|---|---|
| 57 | 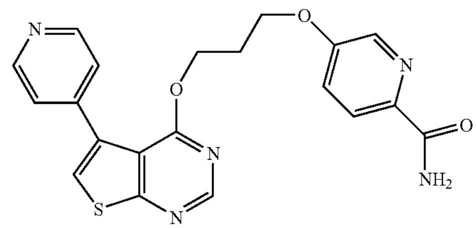 | 5-{3-[(5-pyridin-4-ylthieno[2,3-d]pyrimidin-4-yl)oxy]propoxy}pyridine-2-carboxamide |
| 58 | 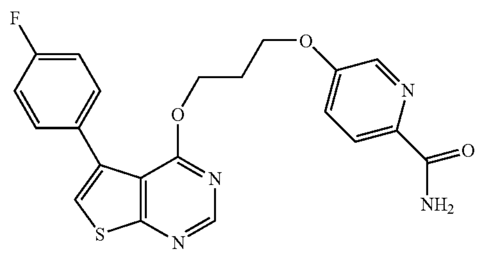 | 5-(3-{[5-(4-fluorophenyl)thieno[2,3-d]pyrimidin-4-yl]oxy}propoxy)pyridine-2-carboxamide |
| 59 | 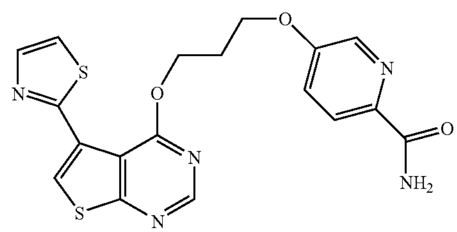 | 5-(3-{[5-(1,3-thiazol-2-yl)thieno[2,3-d]pyrimidin-4-yl]oxy}propoxy)-pyridine-2-carboxamid |
| 60 | 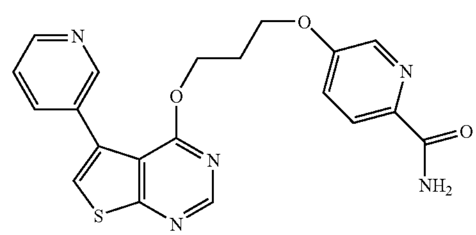 | 5-{3-[(5-pyridin-3-ylthieno[2,3-d]pyrimidin-4-yl)oxy]propoxy}pyridine-2-carboxamide |
| 61 | 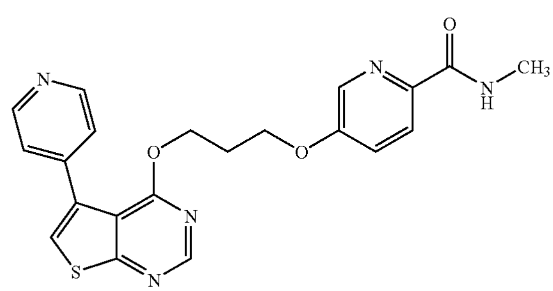 | N-methyl-5-{3-[(5-pyridin-4-ylthieno[2,3-d]pyrimidin-4-yl)oxy]-propoxy}pyridine-2-carboxamide |
| 62 | 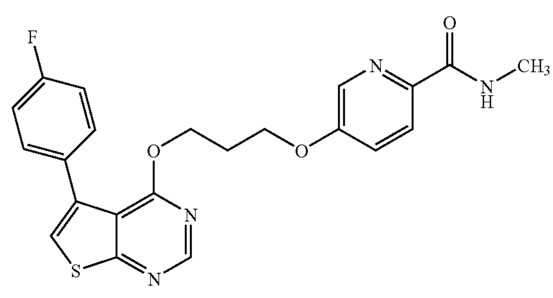 | 5-(3-{[5-(4-fluorophenyl)thieno[2,3-d]pyrimidin-4-yl]oxy}propoxy)-N-methylpyridine-2-carboxamide |

TABLE 1-continued

| Cpd # | Structure | Name |
|---|---|---|
| 63 | 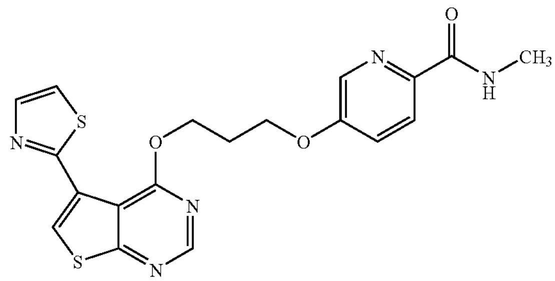 | N-methyl-5-(3-{[5-(1,3-thiazol-2-yl)thieno[2,3-d]pyrimidin-4-yl]oxy}-propoxy)pyridine-2-carboxamide |
| 64 | 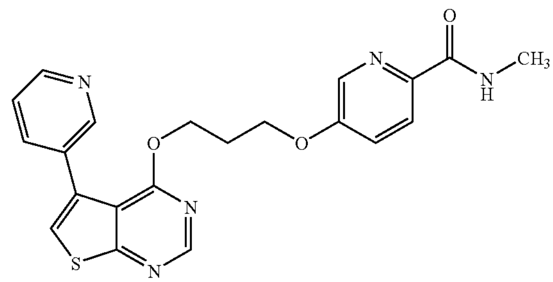 | N-methyl-5-{3-[(5-pyridin-3-ylthieno[2,3-d]pyrimidin-4-yl)oxy]-propoxy}pyridine-2-carboxamide |
| 65 | 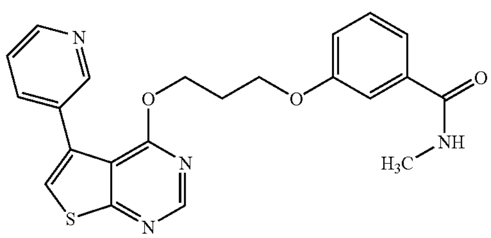 | N-methyl-3-{3-[(5-pyridin-3-ylthieno[2,3-d]pyrimidin-4-yl)oxy]propoxy}benzamide |
| 66 | 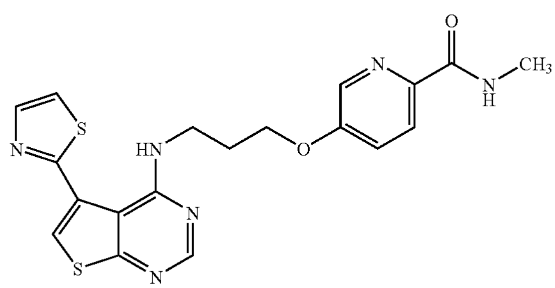 | N-methyl-5-(3-{[5-(1,3-thiazol-2-yl)-thieno[2,3-d]pyrimidin-4-yl]amino}-propoxy)pyridine-2-carboxamide |
| 67 | 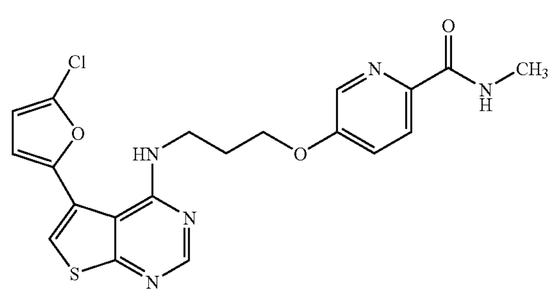 | 5-(3-{[5-(5-chloro-2-furyl)thieno[2,3-d]pyrimidin-4-yl]amino}propoxy)-N-methylpyridine-2-carboxamide |

TABLE 1-continued

| Cpd # | Structure | Name |
|---|---|---|
| 68 | 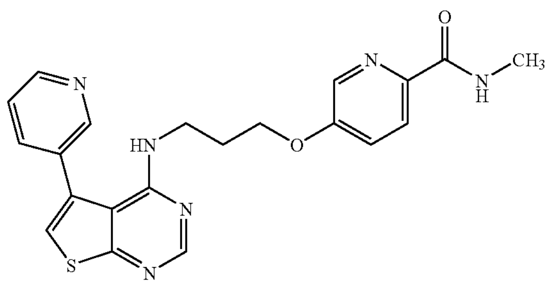 | N-methyl-5-{3-[(5-pyridin-3-ylthieno[2,3-d]pyrimidin-4-yl)amino]propoxy}pyridine-2-carboxamide |
| 69 | 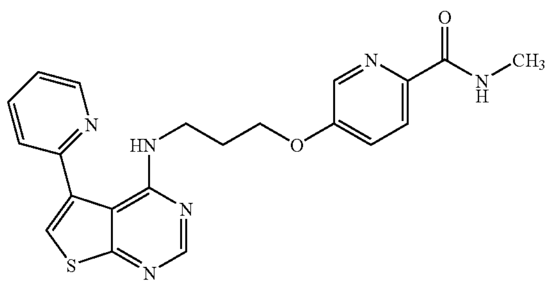 | N-methyl-5-{3-[(5-pyridin-2-ylthieno[2,3-d]pyrimidin-4-yl)amino]propoxy}pyridine-2-carboxamide |
| 70 | 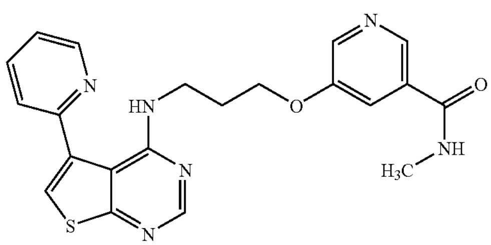 | N-methyl-5-{3-[(5-pyridin-2-ylthieno[2,3-d]pyrimidin-4-yl)amino]propoxy}-nicotinamide |
| 71 | 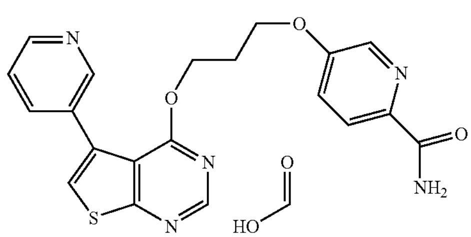 | 5-{3-[(5-pyridin-3-ylthieno[2,3-d]-pyrimidin-4-yl)oxy]propoxy}pyridine-2-carboxamide hydroformate |
| 72 | 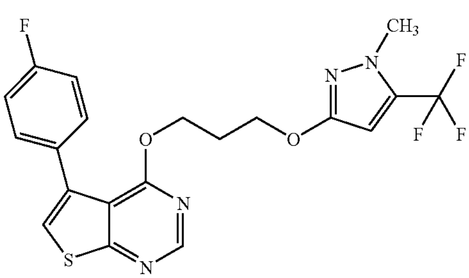 | 5-(4-fluorophenyl)-4-(3-{[1-methyl-5-(trifluoromethyl)-1H-pyrazol-3-yl]oxy}propoxy)thieno[2,3-d]pyrimidine |

TABLE 1-continued

| Cpd # | Structure | Name |
|---|---|---|
| 73 | 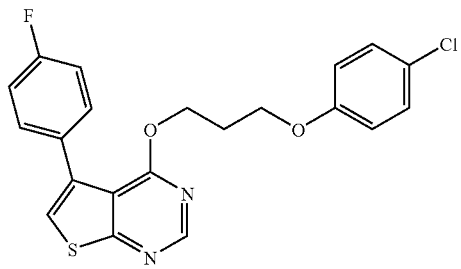 | 4-[3-(4-chlorophenoxy)propoxy]-5-(4-fluorophenyl)thieno[2,3-d]pyrimidine |
| 74 | 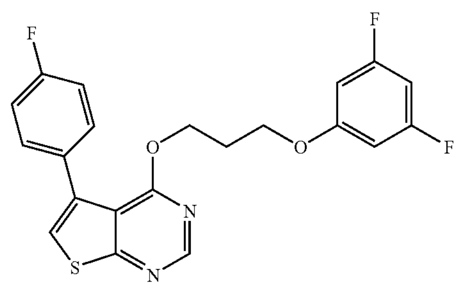 | 4-[3-(3,5-difluorophenoxy)propoxy]-5-(4-fluorophenyl)thieno[2,3-d]pyrimidine |
| 75 | 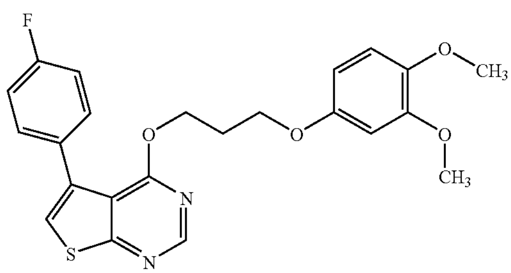 | 4-[3-(3,4-dimethoxyphenoxy)propoxy]-5-(4-fluorophenyl)thieno[2,3-d]pyrimidine |
| 76 | 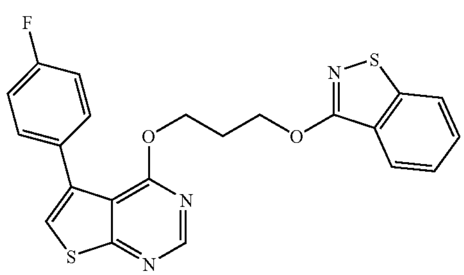 | 4-[3-(1,2-benzisothiazol-3-yloxy)propoxy]-5-(4-fluorophenyl)thieno[2,3-d]pyrimidine |
| 77 | 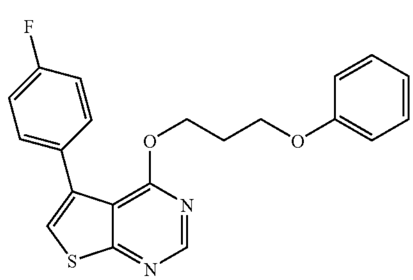 | 5-(4-fluorophenyl)-4-(3-phenoxypropoxy)-thieno[2,3-d]pyrimidine |

TABLE 1-continued

| Cpd # | Structure | Name |
|---|---|---|
| 78 | 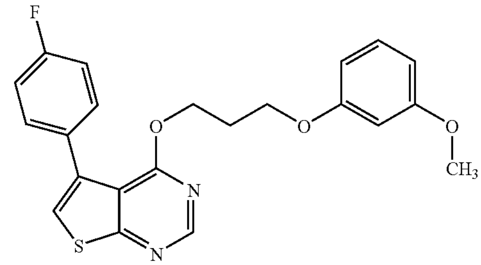 | 5-(4-fluorophenyl)-4-[3-(3-methoxy-phenoxy)propoxy]thieno[2,3-d]pyrimidine |
| 79 | 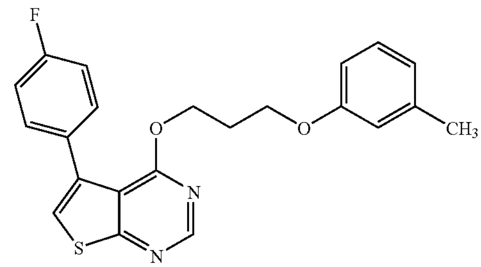 | 5-(4-fluorophenyl)-4-[3-(3-methyl-phenoxy)propoxy]thieno[2,3-d]pyrimidine |
| 80 | 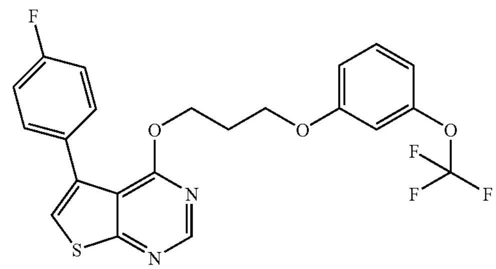 | 5-(4-fluorophenyl)-4-{3-[3-(trifluoro-methoxy)phenoxy]propoxy}thieno[2,3-d]pyrimidine |
| 81 | 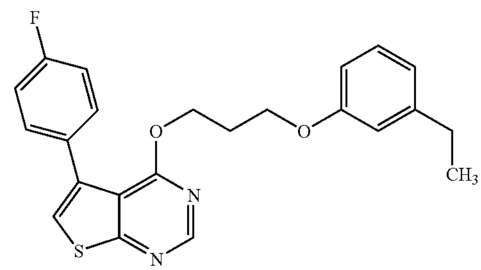 | 4-[3-(3-ethylphenoxy)propoxy]-5-(4-fluorophenyl)thieno[2,3-d]pyrimidine |
| 82 | 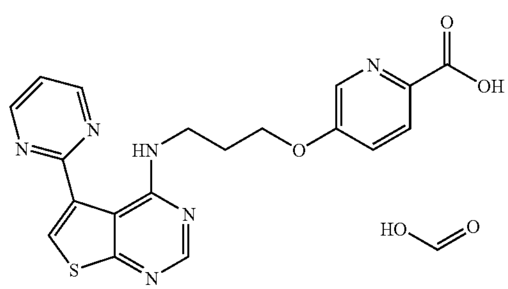 | 5-{3-[(5-pyrimidin-2-ylthieno[2,3-d]pyrimidin-4-yl)amino]propoxy}pyridine-2-carboxylic acid hydroformate |

TABLE 1-continued

| Cpd # | Structure | Name |
| --- | --- | --- |
| 83 | 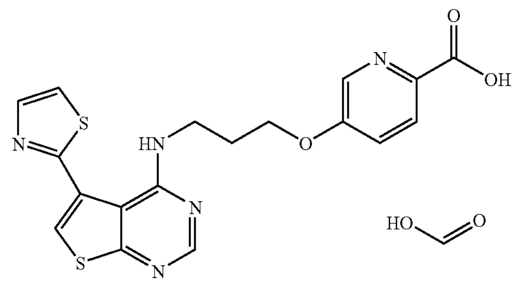 | 5-(3-{[5-(1,3-thiazol-2-yl)thieno[2,3-d]pyrimidin-4-yl]amino}propoxy)pyridine-2-carboxylic acid hydroformate |
| 84 | 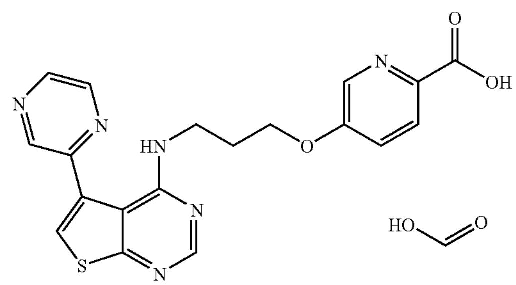 | 5-{3-[(5-pyrazin-2-ylthieno[2,3-d]pyrimidin-4-yl)amino]propoxy}pyridine-2-carboxylic acid hydroformate |
| 85 | 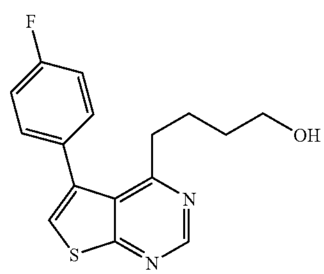 | 4-[5-(4-fluorophenyl)thieno[2,3-d]pyrimidin-4-yl]butan-1-ol |
| 86 | 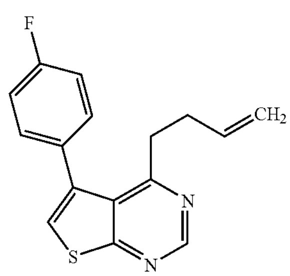 | 4-but-3-en-1-yl-5-(4-fluorophenyl)-thieno[2,3-d]pyrimidine |
| 87 | 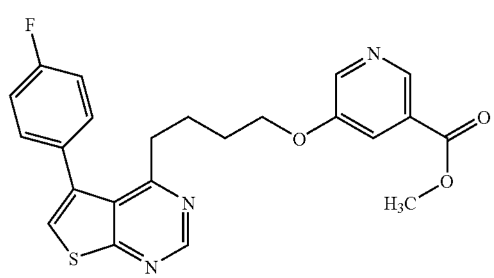 | methyl 5-{4-[5-(4-fluorophenyl)-thieno[2,3-d]pyrimidin-4-yl]butoxy}-nicotinate |

TABLE 1-continued

| Cpd # | Structure | Name |
|---|---|---|
| 88 | 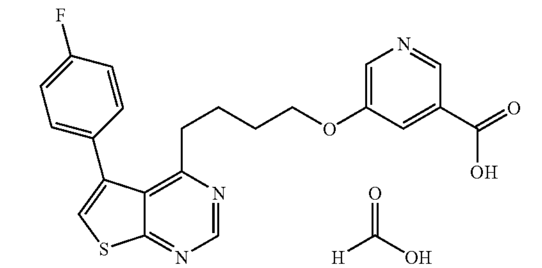 | 5-{4-[5-(4-fluorophenyl)thieno[2,3-d]pyrimidin-4-yl]butoxy}nicotinic acid hydroformate |
| 89 | 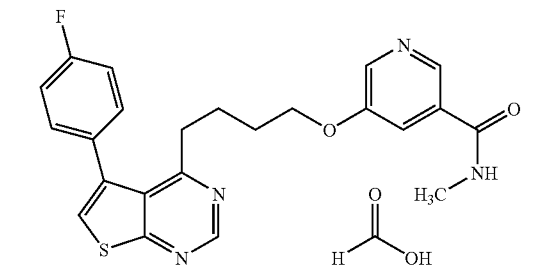 | 5-{4-[5-(4-fluorophenyl)thieno[2,3-d]pyrimidin-4-yl]butoxy}-N-methylnicotinamide hydroformate |
| 90 | 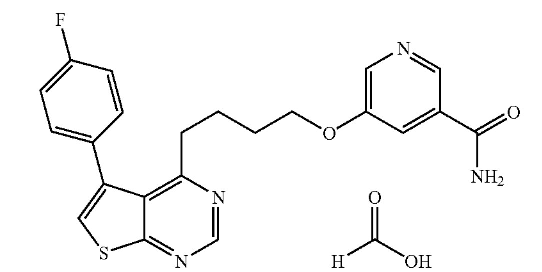 | 5-{4-[5-(4-fluorophenyl)thieno[2,3-d]pyrimidin-4-yl]butoxy}nicotinamide hydroformate |
| 91 | 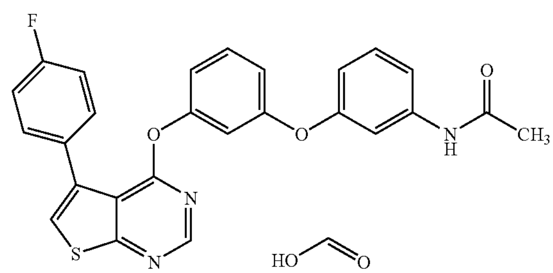 | N-[3-(3-{[5-(4-fluorophenyl)thieno[2,3-d]pyrimidin-4-yl]oxy}phenoxy)-phenyl]acetamide hydroformate |
| 92 | 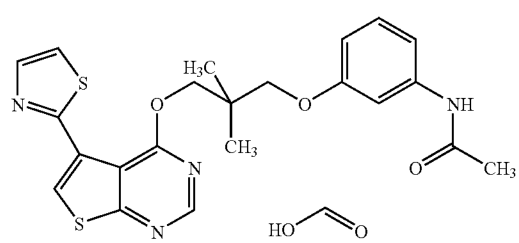 | N-[3-(2,2-dimethyl-3-{[5-(1,3-thiazol-2-yl)thieno[2,3-d]pyrimidin-4-yl]oxy}propoxy)phenyl]acetamide hydroformate |
| 93 | 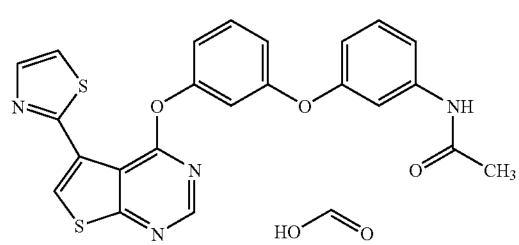 | N-[3-(3-{[5-(1,3-thiazol-2-yl)thieno[2,3-d]pyrimidin-4-yl]oxy}phenoxy)phenyl]-acetamide hydroformate |

TABLE 1-continued

| Cpd # | Structure | Name |
|---|---|---|
| 94 | 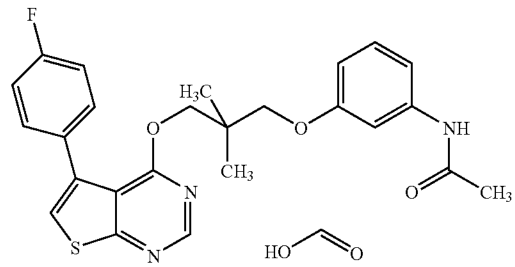 | N-[3-(3-{[5-(4-fluorophenyl)thieno[2,3-d]pyrimidin-4-yl]oxy}-2,2-dimethyl-propoxy)phenyl]acetamide hydroformate |
| 95 | 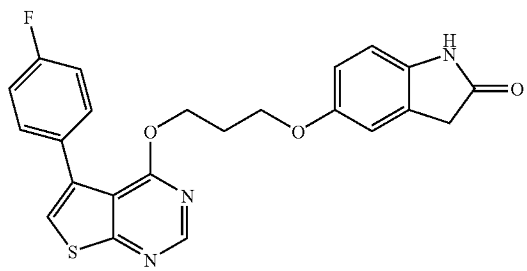 | 5-(3-{[5-(4-fluorophenyl)thieno[2,3-d]pyrimidin-4-yl]oxy}propoxy)-1,3-dihydro-2H-indol-2-one |
| 96 | 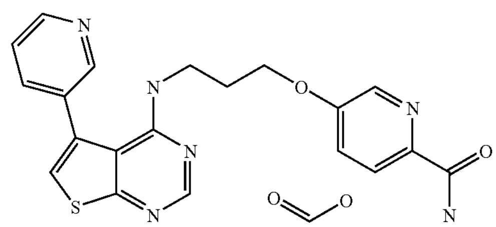 | 5-{3-[(5-pyridin-3-ylthieno[2,3-d]pyrimidin-4-yl)amino]propoxy}pyridine-2-carboxamide hydroformate |
| 97 | 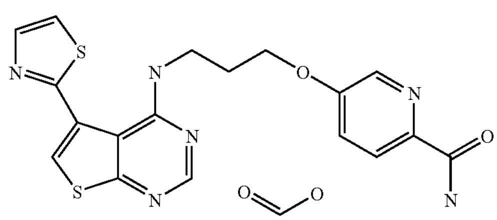 | 5-(3-{[5-(1,3-thiazol-2-yl)thieno[2,3-d]pyrimidin-4-yl]amino}propoxy)pyridine-2-carboxamide hydroformate |
| 98 | 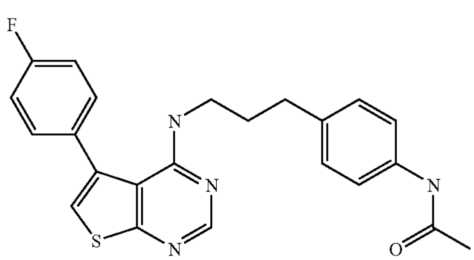 | N-[4-(3-{[5-(4-fluorophenyl)thieno[2,3-d]pyrimidin-4-yl]amino}propyl)phenyl]-acetamide |
| 99 | 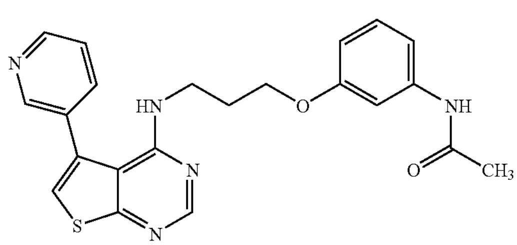 | N-(3-{3-[(5-pyridin-3-ylthieno[2,3-d]pyrimidin-4-yl)amino]propoxy}phenyl)acetamide |

TABLE 1-continued

| Cpd # | Structure | Name |
|---|---|---|
| 100 | 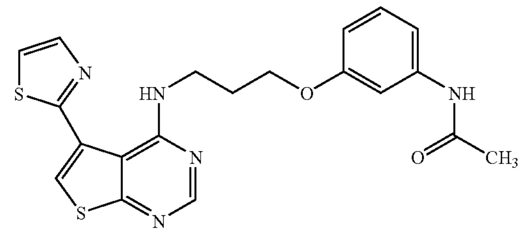 | N-[3-(3-{[5-(1,3-thiazol-2-yl)thieno[2,3-d]pyrimidin-4-yl]amino}propoxy)phenyl]acetamide |
| 101 | 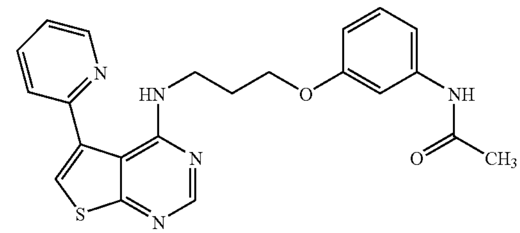 | N-(3-{3-[(5-pyridin-2-ylthieno[2,3-d]pyrimidin-4-yl)amino]propoxy}phenyl)acetamide |
| 102 | 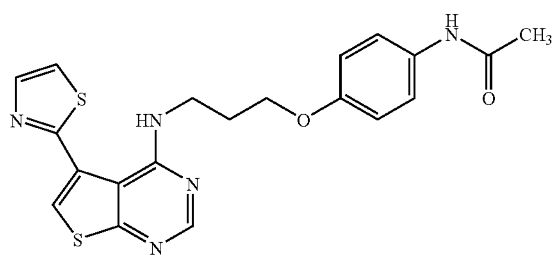 | N-[4-(3-{[5-(1,3-thiazol-2-yl)thieno[2,3-d]pyrimidin-4-yl]amino}propoxy)phenyl]acetamide |
| 103 | 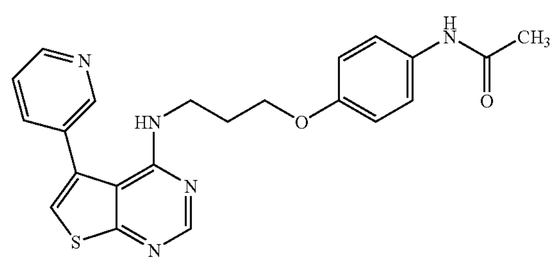 | N-(4-{3-[(5-pyridin-3-ylthieno[2,3-d]pyrimidin-4-yl)amino]propoxy}phenyl)acetamide |
| 104 | 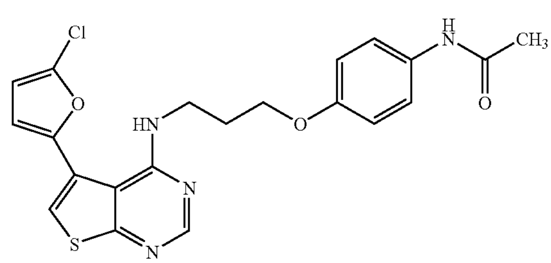 | N-[4-(3-{[5-(5-chloro-2-furyl)thieno[2,3-d]pyrimidin-4-yl]amino}propoxy)phenyl]acetamide |
| 105 | 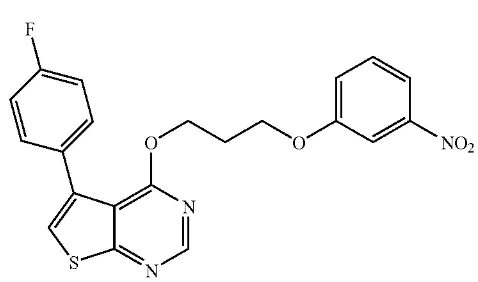 | 5-(4-fluorophenyl)-4-[3-(3-nitrophenoxy)propoxy]thieno[2,3-d]pyrimidine |

TABLE 1-continued

| Cpd # | Structure | Name |
|---|---|---|
| 106 | 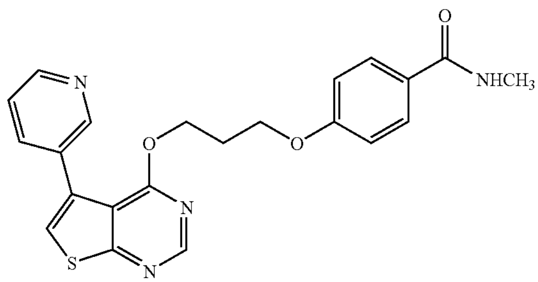 | N-methyl-4-{3-[(5-pyridin-3-ylthieno[2,3-d]pyrimidin-4-yl)oxy]propoxy}-benzamide |
| 107 | 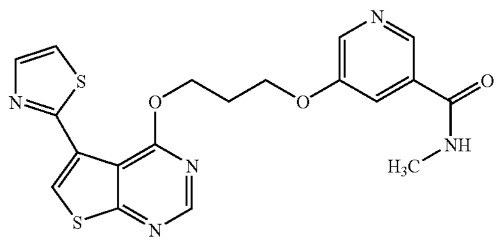 | N-methyl-5-(3-{[5-(1,3-thiazol-2-yl)thieno[2,3-d]pyrimidin-4-yl]oxy}propoxy)nicotinamide |
| 108 | 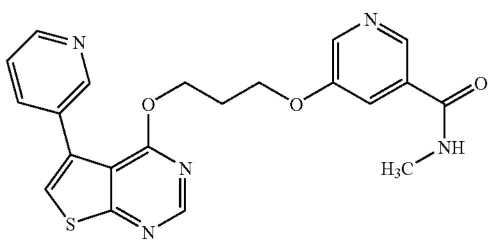 | N-methyl-5-{3-[(5-pyridin-3-ylthieno[2,3-d]pyrimidin-4-yl)oxy]propoxy}nicotinamide |
| 109 | 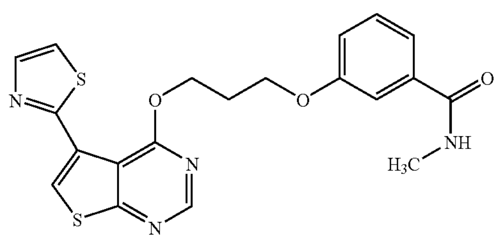 | N-methyl-3-(3-{[5-(1,3-thiazol-2-yl)thieno[2,3-d]pyrimidin-4-yl]oxy}propoxy)benzamide |
| 110 | 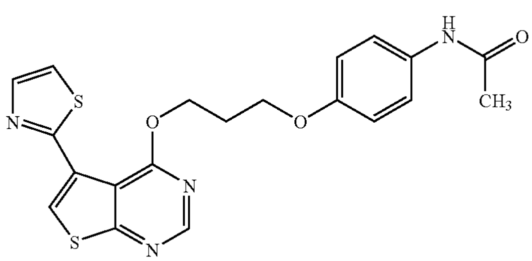 | N-[4-(3-{[5-(1,3-thiazol-2-yl)thieno[2,3-d]pyrimidin-4-yl]oxy}propoxy)phenyl]acetamide |
| 111 | 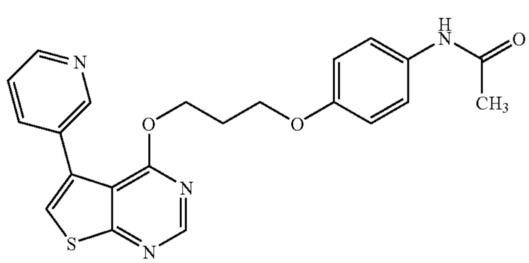 | N-(4-{3-[(5-pyridin-3-ylthieno[2,3-d]pyrimidin-4-yl)oxy]propoxy}phenyl)acetamide |

Also provided are s pharmaceutical compositions comprising at least one chemical entity described herein and a pharmaceutically acceptable carrier and, optionally, another active agent as discussed below. Also provided is a method of inhibiting a PDE10 enzyme, e.g., as determined by a conventional assay or one described herein, either in vitro or in vivo (in an animal, e.g., in an animal model, or in a mammal or in a human); a method of treating a psychiatric or neurological syndrome, e.g., pyschoses, obsessive-compulsive disorder and/or Parkinson's disease; a method of treating a disease state modulated by PDE10 activity, in a mammal, e.g., a human, e.g., those disease states mentioned herein.

Methods include, but are not limited to, methods of enhancing cognition in a patient in whom such enhancement is desired, methods of treating a patient suffering from cognition impairment or decline, methods of treating a patient having a disease involving decreased cAMP and/or cGMP levels, methods of inhibiting PDE10 enzyme activity in a patient, methods of treating a patient suffering psychoses, in particular schizophrenia or bipolar disorder, methods of treating a patient suffering from obsessive-compulsive disorder, methods of treating a patient suffering from Parkinson's disease. In certain embodiments, the disease state is one that involves elevated intracellular PDE10 levels or decreased cAMP and/or cGMP levels, e.g., involving neurological or psychiatric syndromes, especially those states associated with psychoses, most especially schizophrenia or bipolar disorder, obsessive-compulsive disorder, and/or Parkinson's disease. All methods comprise administering to the patient an effective amount of at least one chemical entity described herein. In certain embodiments, the patient is human.

Chemical entities described herein can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1994); Rodd's Chemistry of Carbon Compounds, Volumes 1-5 and Supplementals (Elsevier Science Publishers, 1989); Organic Reactions, Volumes 1-40 (John Wiley and Sons, 2003), March's Advanced Organic Chemistry, (John Wiley and Sons, 4th Edition) and Larock's Comprehensive Organic Transformations (VCH Publishers Inc., 1989). Those schemes are merely illustrative of some methods by which the chemical entities described herein can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., such as from about 0° C. to about 125° C., for example, at about room (or ambient) temperature, e.g., about 20° C.

Compounds of Formula I can be prepared as shown in Scheme 1 below.

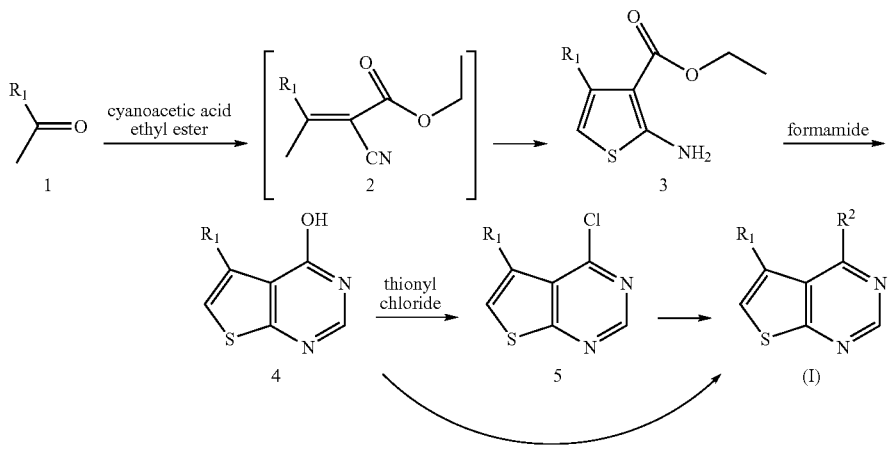

Scheme 1

Treatment of a mixture of a methyl ketone compound of formula I with cyanoacetic acid ethyl ester and sulfur with morpholine in a suitable alcoholic solvent such as ethanol provides a 2-amino-thiophene ethyl ester compound of formula 3. Reation of 3 with formamide provides a 4-hydroxythieneo[2,3-d]pyrimidine compound of formula 4. Compound 4 can then be converted to a compound of Formula I where $R^2$ is $-O(CR^3R^4)_n YR^5$ by reacting 4 with $LG(CR^3R^4)_n YR^5$ where LG is a suitable leaving group such as halo under conditions well known in the art.

Alternatively, compound 4 can be first converted to a compound of formula 5 by treating with a chlorinating agent such as thionyl chloride and the. Compound 5 is then converted to a compound of Formula I by treating it with is $HO(CR^3R^4)_n YR^5$, is $HS(CR^3R^4)_n YR^5$, or is $NH^2(CR^3R^4)_n YR^5$ under conditions well known in the art. Detailed descriptions of such procedures are provided in the Working examples below.

Compounds of Formula I wherein $R^2$ is $-(CR^3R^4)_n YR^5$ can be prepared by reaction of compound 5 with the Grignard $BrMg-(CR^3R^4)_n YR^5$ under anhydrous conditions in a polar aprotic solvent (such as THF) using CuI and/or $FeBr_2$ as catalysts.

The optical isomers of compounds of Formula I can be obtained by resolution of the racemic mixtures according to conventional processes, for example, by the formation of diastereomeric salts using an optically active acid or base or formation of covalent diastereomers. Examples of appropriate acids are tartaric, diacetyltartaric, dibenzoyltartaric, ditoluoyltartaric and camphorsulfonic acid. Mixtures of diastereomers can be separated into their individual diastereomers on the basis of their physical and/or chemical differences by methods known to those skilled in the art, for example, by chromatography or fractional crystallization. The optically active bases or acids are then liberated from the separated diastereomeric salts.

A different process for separation of optical isomers involves the use of chiral chromatography (e.g., chiral HPLC columns), with or without conventional derivation, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivitization, are also useful. The optically active compounds of Formula I can likewise be obtained by utilizing optically active starting materials in chiral syntheses processes under reaction conditions which do not cause racemization.

The compounds can be used in different enriched isotopic forms, e.g., enriched in the content of $^2H$, $^3H$, $^{11}C$, $^{13}C$ and/or $^{14}C$. In certain embodiments, the compounds are deuterated. Such deuterated forms can be made by the procedure described in U.S. Pat. Nos. 5,846,514 and 6,334,997. As described in U.S. Pat. Nos. 5,846,514 and 6,334,997, deuteration can improve the efficacy and increase the duration of action of drugs.

Deuterium substituted compounds can be synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] (2000), 110 pp. CAN 133:68895 AN 2000:473538 CAPLUS; Kabalka, George W.; Varma, Rajender S. The Synthesis of Radiolabeled Compounds via Organometallic Intermediates. Tetrahedron (1989), 45(21), 6601-21, CODEN: TETRAB ISSN: 0040-4020. CAN 112:20527 AN 1990:20527 CAPLUS; and Evans, E. Anthony. Synthesis of radiolabeled compounds, J. Radioanal. Chem. (1981), 64(1-2), 9-32. CODEN: JRACBN ISSN:0022-4081, CAN 95:76229 AN 1981:476229 CAPLUS.

The acid addition salts of the claimed compounds may be prepared by reaction of the compounds with the appropriate inorganic or organic acid via any of a number of known methods. Alternatively, alkali and alkaline earth metal salts are prepared by reacting the chemical entities described herein with the appropriate base via a variety of known methods. In certain embodiments, the salts formed are pharmaceutically acceptable for administration to mammals. However, pharmaceutically unacceptable salts of the compounds are suitable as intermediates, for example, for isolating the compound as a salt and then converting the salt back to the free base compound by treatment with an alkaline reagent. The free base can then, if desired, be converted to a pharmaceutically acceptable acid addition salt.

The chemical entities described herein can be administered alone or as an active ingredient of a formulation. Thus, also provided are pharmaceutical compositions comprising at least one chemical entity described herein and one or more pharmaceutically acceptable carriers.

The chemical entities described herein can be administered to anyone requiring PDE10 inhibition. Administration may be accomplished according to patient needs, for example, orally, nasally, parenterally (subcutaneously, intravenously, intramuscularly, intrasternally and by infusion) by inhalation, rectally, vaginally, topically and by ocular administration.

Various solid oral dosage forms can be used for administering chemical entities described herein including such solid forms as tablets, gelcaps, capsules, caplets, granules, lozenges and bulk powders. The chemical entities described herein can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the chemical entities described herein.

Various liquid oral dosage forms can also be used for administering chemical entities described herein, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the chemical entities described herein. The chemical entities described herein may be injected, for example, intravenously, in the form of an isotonic sterile solution. Other preparations are also possible.

Suppositories for rectal administration of the chemical entities described herein can be prepared by mixing the compound with a suitable excipient such as cocoa butter, salicylates and polyethylene glycols. Formulations for vaginal administration can be in the form of a pessary, tampon, cream, gel, paste, foam, or spray formula containing, in addition to the active ingredient, such suitable carriers as are known in the art.

For topical administration, the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, for treatment of disorders of the respiratory tract, the chemical entities described herein can be administered by inhalation in the form of a powder (e.g., micronized) or in the form of atomized solutions or suspensions. The aerosol formulation can be placed into a pressurized acceptable propellant.

Numerous standard references are available that describe procedures for preparing various formulations suitable for administering the chemical entities described herein. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

The chemical entities described herein can be administered as the sole active agent or in combination with other pharmaceutical agents such as other agents used in the treatment of psychoses, such as schizophrenia and bipolar disorder, obsessive-compulsive disorder, Parkinson's disease, cognitive impairment and/or memory loss, e.g., nicotinic α-7 agonists, PDE4 inhibitors, other PDE10 inhibitors, calcium channel blockers, muscarinic m1 and m2 modulators, adenosine receptor modulators, ampakines, NMDA-R modulators, mGluR modulators, dopamine modulators, serotonin modulators, canabinoid modulators, and cholinesterase inhibitors (e.g., donepezil, rivastigimine, and galanthanamine). In such combinations, each active ingredient can be administered either in accordance with their usual dosage range or a dose below their usual dosage range.

The chemical entities described herein can be administered in combination with other pharmaceutical agents used in the treatment of schizophrenia, e.g., Clozaril, Zyprexa, Risperidone, and Seroquel. Thus, also provided are methods for treating schizophrenia, including memory impairment associated with schizophrenia, comprising administering to a patient, simultaneously or sequentially, at least one chemical entities described herein and another agent used in the treatment of schizophrenia such as Clozaril, Zyprexa, Risperidone, and Seroquel. In methods using simultaneous administration, the agents can be present in a combined composition or can be administered separately. As a result, also provided are compositions comprising at least one chemical entity described herein and another pharmaceutical agent used in the treatment of schizophrenia, e.g., Clozaril, Zyprexa, Risperidone, and Seroquel. Similarly, also provided are kits containing a composition comprising at least one chemical entity described herein and another composition comprising another pharmaceutical agent used in the treatment of schizophrenia, e.g., Clozaril, Zyprexa, Risperidone, and Seroquel.

In addition, the chemical entities described herein can be administered in combination with other pharmaceutical agents used in the treatment bipolar disorder such as Lithium, Zyprexa, or Depakote. Thus, also provided are methods for treating bipolar disorder, including treating memory and/or cognitive impairment associated with the disease, comprising administering to a patient, simultaneously or sequentially, at least one chemical entity described herein and another agent used in the treatment of bipolar disorder such as Lithium, Zyprexa, or Depakote. In methods using simultaneous administration, the agents can be present in a combined composition or can be administered separately. As a result, also provided are compositions comprising a at least one chemical entity described herein and another pharmaceutical agent used in the treatment of bipolar disorder such as Lithium, Zyprexa, or Depakote. Similarly, also provided are kits containing a composition comprising at least one chemical entity described herein and another composition comprising another pharmaceutical agent used in the treatment of bipolar disorder such as Lithium, Zyprexa, or Depakote.

Also provided are methods for treating Parkinson's disease, including treating memory and/or cognitive impairment associated with Parkinson's disease, comprising administering to a patient, simultaneously or sequentially, at least one chemical entity described herein and another agent used in the treatment of Parkinson's disease such as Levodopa, Parlodel, Permax, Mirapex, Tasmar, Contan, Kemadin, Artane, and Cogentin. In methods using simultaneous administration, the agents can be present in a combined composition or can be administered separately. As a result, also provided are compositions comprising at least one chemical entity described herein and another pharmaceutical agent used in the treatment of Parkinson's disease such as Levodopa, Parlodel, Permax, Mirapex, Tasmar, Contan, Kemadin, Artane, and Cogentin. Similarly, also provided are kits comprising a composition comprising at least one chemical entity described herein and another composition comprising another pharmaceutical agent used in the treatment of Parkinson's disease such as Levodopa, Parlodel, Permax, Mirapex, Tasmar, Contan, Kemadin, Artane, and Cogentin.

In addition, also provided are methods for treating memory and/or cognitive impairment associated with Alzheimer's disease comprising administering to a patient, simultaneously or sequentially, at least one chemical entity described herein and another agent used in the treatment of Alzheimer's disease such as Reminyl, Cognex, Aricept, Exelon, Akatinol, Neotropin, Eldepryl, Estrogen and Cliquinol. In methods using simultaneous administration, the agents can be present in a combined composition or can be administered separately. As a result, also provided are compositions comprising at least one chemical entity described herein and another pharmaceutical agent used in the treatment of Alzheimer's disease such as Levodopa, Parlodel, Permax, Mirapex, Tasmar, Contan, Kemadin, Artane, and Cogentin. Similarly, also provided are kits containing a composition comprising at least one chemical entity described herein and another composition comprising another pharmaceutical agent used in the treatment of Alzheimer's disease such as Levodopa, Parlodel, Permax, Mirapex, Tasmar, Contan, Kemadin, Artane, and Cogentin.

Also provided are methods for treating Huntington's disease, including treating memory and/or cognitive impairment associated with Huntington's disease, comprising administering to a patient, simultaneously or sequentially, at least one chemical entity described herein and another agent used in the treatment of Huntington's disease such as Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone. In methods using simultaneous administration, the agents can be present in a combined composition or can be administered separately. As a result, also provided are compositions comprising at least one chemical entity described herein and another pharmaceutical agent used in the treatment of Huntington's disease such as Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone. Similarly, also provided are kits containing a composition comprising at least one chemical entity described herein and another composition comprising another pharmaceutical agent used in the treatment of Huntington's disease such as Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone.

Also provided are methods for treating memory and/or cognitive impairment associated with dementia comprising administering to a patient, simultaneously or sequentially, at least one chemical entity described herein and another agent used in the treatment of dementia such as Thioridazine, Haloperidol, Risperidone, Cognex, Aricept, and Exelon. In methods using simultaneous administration, the agents can be present in a combined composition or can be administered separately. As a result, also provided are compositions comprising at least one chemical entity described herein and another pharmaceutical agent used in the treatment of dementia such as Thioridazine, Haloperidol, Risperidone, Cognex, Aricept, and Exelon. Similarly, also provided are kits containing a composition comprising at least one chemical entity described herein and another composition comprising another pharmaceutical agent used in the treatment of dementia such as Thioridazine, Haloperidol, Risperidone, Cognex, Aricept, and Exelon.

Also provided are methods for treating memory and/or cognitive impairment associated with epilepsy comprising administering to a patient, simultaneously or sequentially, at least one chemical entity described herein and another agent used in the treatment of epilepsy such as Dilantin, Luminol, Tegretol, Depakote, Depakene, Zarontin, Neurontin, Barbita, Solfeton, and Felbatol. In methods using simultaneous administration, the agents can be present in a combined composition or can be administered separately. As a result, also provided are ompositions comprising at least one chemical entity described herein and another pharmaceutical agent used in the treatment of epilepsy such as Dilantin, Luminol, Tegretol, Depakote, Depakene, Zarontin, Neurontin, Barbita, Solfeton, and Felbatol. Similarly, also provided are kits containing a composition comprising at least one chemical entity described herein and another composition comprising another pharmaceutical agent used in the treatment of epilepsy such as Dilantin, Luminol, Tegretol, Depakote, Depakene, Zarontin, Neurontin, Barbita, Solfeton, and Felbatol.

Also provided are methods for treating memory and/or cognitive impairment associated with multiple sclerosis comprising administering to a patient, simultaneously or sequentially, at least one chemical entity described herein and another agent used in the treatment of multiple sclerosis such as Detrol, Ditropan XL, OxyContin, Betaseron, Avonex, Azothioprine, Methotrexate, and Copaxone. In methods using simultaneous administration, the agents can be present in a combined composition or can be administered separately. As a result, also provided are compositions comprising at least one chemical entity described herein and another pharmaceutical agent used in the treatment of multiple sclerosis such as Detrol, Ditropan XL, OxyContin, Betaseron, Avonex, Azothioprine, Methotrexate, and Copaxone. Similarly, also provided are kits containing a composition comprising at least one chemical entity described herein and another composition comprising another pharmaceutical agent used in the treatment of multiple sclerosis such as Detrol, Ditropan XL, OxyContin, Betaseron, Avonex, Azothioprine, Methotrexate, and Copaxone.

Also provided are chemical entities that inhibit PDE10 enzyme activity. PDE10 inhibitors will raise the levels of cAMP or cGMP within cells that express PDE10. Inhibition of PDE10 enzyme activity may be of relevance to diseases caused by deficient amounts of cAMP or cGMP in cells. Alternatively, PDE10 inhibitors may be of benefit in cases wherein raising the amount of cAMP or cGMP above normal levels results in a therapeutic effect. Inhibitors of PDE10 may be used to treat disorders of the peripheral and central nervous system, cardiovascular diseases, cancer, gastro-enterological diseases, endocrinological diseases and urological diseases. Thus, also provided are methods of selective inhibition of PDE10 enzymes in animals, e.g., mammals, for example, humans, wherein such inhibition has a therapeutic effect, such as where such inhibition may relieve conditions involving neurological or psychiatric syndromes, such as the loss of memory or psychoses. Such methods comprise administering to an animal in need thereof, such as a mammal, for example, a human, an inhibitory amount of at least one chemical entity described herein, alone or as part of a formulation.

Indications that may be treated with PDE10 inhibitors, either alone or in combination with other drugs, include, but are not limited to, those diseases thought to be mediated in part by the basal ganglia, prefrontal cortex and hippocampus. These indications include psychoses, Parkinson's disease, dementias, obsessive compulsion disorder, tardive dyskinesia, choreas, depression, mood disorders, impulsivity, drug addiction, attention deficit/hyperactivity disorder (ADHD), depression with parkinsonian states, personality changes with caudate or putamen disease, dementia and mania with caudate and pallidal diseases, and compulsions with pallidal disease.

Psychoses are disorders that affect an individual's perception of reality. Psychoses are characterized by delusions and hallucinations. Also provided are methods for treating patients suffering from all forms of psychoses, including but not limited to schizophrenia, late-onset schizophrenia, schizoaffective disorders, prodromal schizophrenia, and bipolar disorders. Treatment may be for the positive symptoms of schizophrenia as well as for the cognitive deficits and negative symptoms. Other indications for PDE10 inhibitors are psychoses resulting from drug abuse (including amphetamines and PCP), encephalitis, alcoholism, epilepsy, Lupus, sarcoidosis, brain tumors, multiple sclerosis, dementia with Lewy bodies, or hypoglycemia. Other psychiatric disorders, like posttraumatic stress disorder (PTSD), and schizoid personality may also be treated with PDE10 inhibitors.

Obsessive-compulsive disorder (OCD) has been linked to deficits in the frontal-striatal neuronal pathways. (Saxena S. et al., Br J Psychiatry Suppl. 1998;(35):26-37.) Neurons in these pathways project to striatal neurons that express PDE10. PDE10 inhibitors cause cAMP to be elevated in these neurons; elevations in cAMP result in an increase in CREB phosphorylation and thereby improve the functional state of these neurons. PDE10 inhibitors should be useful for the indication of OCD. OCD may result, in some cases, from streptococcal infections that cause autoimmune reactions in the basal ganglia (Giedd J. N. et al., Am. J. Psychiatry. 2000 February; 157(2):281-3). Because PDE10 inhibitors may serve a neuroprotective role, administration of PDE10 inhibitors may prevent the damage to the basal ganglia after repeated streptococcal infections and thereby prevent the development of OCD.

In the brain, the level of cAMP or cGMP within neurons is believed to be related to the quality of memory, such as long term memory. Without wishing to be bound to any particular mechanism, it is proposed that since PDE10 degrades cAMP or cGMP, the level of this enzyme affects memory in animals, for example, in humans. For example, a compound that inhibits cAMP phosphodiesterase (PDE) can thereby increase intracellular levels of cAMP, which in turn activate a protein kinase that phosphorylates a transcription factor (cAMP response binding protein), which transcription factor then binds to a DNA promoter sequence to activate genes that are important in long term memory. The more active such genes are, the better is long-term memory. Thus, by inhibiting a phosphodiesterase, long term memory can be enhanced.

Dementias are diseases that include memory loss and additional intellectual impairment separate from memory. Also provided are methods for treating patients suffering from memory impairment in all forms of dementia. Dementias are classified according to their cause and include: neurodegenerative dementias (e.g., Alzheimer's, Parkinson's disease, Huntington's disease, Pick's disease), vascular (e.g., infarcts, hemorrhage, cardiac disorders), mixed vascular and Alzheimer's, bacterial meningitis, Creutzfeld-Jacob Disease, multiple sclerosis, traumatic (e.g., subdural hematoma or traumatic brain injury), infectious (e.g., HIV), genetic (down syndrome), toxic (e.g., heavy metals, alcohol, some medications), metabolic (e.g., vitamin B12 or folate deficiency), CNS hypoxia, Cushing's disease, psychiatric (e.g., depression and schizophrenia), and hydrocephalus.

The condition of memory impairment is manifested by impairment of the ability to learn new information and/or the inability to recall previously learned information. Also provided are methods for dealing with memory loss separate from dementia, including mild cognitive impairment (MCI) and age-related cognitive decline. Also provided are methods of treatment for memory impairment as a result of disease. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, and head trauma as well as age-related cognitive decline. Also provided are methods for dealing with memory loss resulting from the use of general anesthetics, chemotherapy, radiation treatment, postsurgical trauma, and therapeutic intervention. Thus, in certain embodiments, also provided are methods of treating patients suffering from memory impairment due to, for example, Alzheimer's disease, multiple sclerosis, amylolaterosclerosis (ALS), multiple systems atrophy (MSA), schizophrenia, Parkinson's disease, Huntington's disease, Pick's disease, Creutzfeld-Jakob disease, depression, aging, head trauma, stroke, spinal cord injury, CNS hypoxia, cerebral senility, diabetes associated cognitive impairment, memory deficits from early exposure of anesthetic agents, multiinfarct dementia and other neurological conditions including acute neuronal diseases, as well as HIV and cardiovascular diseases. Also provided are agents and/or methods to stimulate the formation of memory in "normal" subjects (i.e., subjects who do not exhibit an abnormal or pathological decrease in a memory function), e.g., ageing middle-aged subjects. Lots of repetition, maybe you want to consolidate In certain embodiments, the chemical entities described herein are used in the treatment of a class of disorders known as polyglutamine-repeat diseases. These diseases share a common pathogenic mutation. The expansion of a CAG repeat, which encodes the amino acid glutamine, within the genome leads to production of a mutant protein having an expanded polyglutamine region. For example, Huntington's disease has been linked to a mutation of the protein huntingtin. In individuals who do not have Huntington's disease, huntingtin has a polyglutamine region containing about 8 to 31 glutamine residues. For individuals who have Huntington's disease, huntingtin has a polyglutamine region with over 37 glutamine residues. Aside from Huntington's disease (HD), other known polyglutamine-repeat diseases and the associated proteins are: dentatorubral-pallidoluysian atrophy, DRPLA (atrophin-1); spinocerebellar ataxia type-1 (ataxin-1); spinocerebellar ataxia type-2 (ataxin-2); spinocerebellar ataxia type-3 also called Machado-Joseph disease, MJD (ataxin-3); spinocerebellar ataxia type-6 (alpha 1a-voltage dependent calcium channel); spinocerebellar ataxia type-7 (ataxin-7); and spinal and bulbar muscular atrophy, SBMA, also know as Kennedy disease (androgen receptor). Thus, also provided are methods of treating a polyglutamine-repeat disease or CAG repeat expansion disease comprising administering to a patient, such as a human, a therapeutically effective amount of a compound. In certain embodiments, there is provided a method of treating Huntington's disease (HD), dentatorubral-pallidoluysian atrophy (DRPLA), spinocerebellar ataxia type-1, spinocerebellar ataxia type-2, spinocerebellar ataxia type-3 (Machado-Joseph disease), spinocerebellar ataxia type-6, spinocerebellar ataxia type-7, or spinal and bulbar muscular atrophy, comprising administering to a patient, such as a human, a therapeutically effective amount of a compound.

The basal ganglia are important for regulating the function of motor neurons; disorders of the basal ganglia result in movement disorders. Most prominent among the movement disorders related to basal ganglia function is Parkinson's disease (Obeso J A et al., Neurology, 2004 Jan. 13;62(1 Suppl 1):S17-30). Other movement disorders related to dysfunction of the basal ganglia include tardive dyskinesia, progressive supranuclear palsy and cerebral palsy, corticobasal degeneration, multiple system atrophy, Wilson disease, and dystonia, tics, and chorea. In certain embodiments, PDE10 inhibitors may be used to treat movement disorders related to dysfunction of basal ganglia neurons.

PDE10 inhibitors can be used to raise cAMP or cGMP levels and prevent neurons from undergoing apoptosis. PDE10 inhibitors may be anti-inflammatory by raising cAMP in glial cells. The combination of anti-apoptotic and anti-inflammatory properties, as well as positive effects on synaptic plasticity and neurogenesis, make these compounds useful to treat neurodegeneration resulting from any disease or injury, including stroke, spinal cord injury, Alzheimer's disease, multiple sclerosis, amylolaterosclerosis (ALS), and multiple systems atrophy (MSA).

Autoimmune diseases or infectious diseases that affect the basal ganglia may result in disorders of the basal ganglia including ADHD, OCD, tics, Tourette's disease, Sydenham chorea. In addition, any insult to the brain can potentially damage the basal ganglia including strokes, metabolic abnormalities, liver disease, multiple sclerosis, infections, tumors, drug overdoses or side effects, and head trauma. In certain embodiments, PDE10 inhibitors may be used to stop disease progression or restore damaged circuits in the brain by a combination of effects including increased synaptic plasticity, neurogenesis, anti-inflammatory, nerve cell regeneration and decreased apoptosis The growth of some cancer cells is inhibited by cAMP and cGMP. Upon transformation, cells may become cancerous by expressing PDE10 and reducing the amount of cAMP or cGMP within cells. In these types of cancer cells, inhibition of PDE10 activity will inhibit cell growth by raising cAMP (US20040138249, Pyrrolo (2.1a)dihydroisoquinolines and their use as phosphodiesterase 10a inhibitors). In some cases, PDE10 may be expressed in the transformed, cancerous cell but not in the parent cell line. In transformed renal carcinoma cells, PDE10 is expressed and PDE10 inhibitors reduce the growth rate of the cells in culture. Similarly, breast cancer cells are inhibited by administration of PDE10 inhibitors. Many other types of cancer cells may also be sensitive to growth arrest by inhibition of PDE10. Therefore, chemical entities described herein may be used to stop the growth of cancer cells that express PDE10.

The chemical entities described herein are also suitable for use in the treatment of diabetes and related disorders such as obesity, by focusing on regulation of the cAMP signaling system. By inhibiting PDE-10A activity, intracellular levels of cAMP and increased, thereby increasing the release of insulin-containing secretory granules and, therefore, increasing insulin secretion. See, e.g., WO 2005/012485.

Thus, in certain embodiments, there is provided a method of treating diabetes and related disorders comprising administering to a patient, such as a mammal, such as a human, a therapeutically effective amount of at least one chemical entity described herein. In certain embodiments, there is provided a method of treating type 1 diabetes, type 2 diabetes, Syndrome X, impaired glucose tolerance, impaired fasting glucose, gestational diabetes, maturity-onset diabetes of the young (MODY), latent autoimmune diabetes adult (LADA), associated diabetic dyslipidemia, hyperglycemia, hyperinsulinemia, dyslipidemia, hypertriglyceridemia, obesity and insulin resistance, comprising administering to a patient, such as a mammal, such as a human, a therapeutically effective amount of at least one chemical entity described herein.

The chemical entities described herein may also be administered in combination with other known therapies for the treatment of diabetes, including, but not limited to, PPAR ligands (e.g. agonists, antagonists, such as Rosiglitazone, Troglitazone and Pioglitazone), insulin secretagogues (for example, sulfonylurea drugs (such as Glyburide, Glimepiride, Chlorpropamide, Tolbutamide, and Glipizide) and non-sulfonyl secretagogues), □-glucosidase inhibitors (such as Acarbose, Miglitol, and Voglibose), insulin sensitizers (such as the PPAR-□ agonists, e.g., the glitazones; biguanides, PTP-1B inhibitors, DPP-IV inhibitors and 11beta-HSD inhibitors), hepatic glucose output lowering compounds (such as glucagon antagonists and metaformin, such as Glucophage and Glucophage XR), insulin and insulin derivatives (both long and short acting forms and formulations of insulin), and anti-obesity drugs (such as □-3 agonists, CB-1 agonists, neuropeptide Y5 inhibitors, Ciliary Neurotrophic Factor and derivatives (e.g., Axokine), appetite suppressants (e.g., Sibutramine), and lipase inhibitors (e.g., Orlistat)).

The dosages of the chemical entities described herein depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations.

The chemical entities described herein are typically administered at dosage levels and in a mammal customary for PDE10 inhibitors such as those known compounds mentioned above. For example, the compounds can be administered, in single or multiple doses, by oral administration at a dosage level of generally 0.001-100 mg/kg/day, for example, 0.01-100 mg/kg/day, such as 0.1-70 mg/kg/day, for example, 0.5-10 mg/kg/day. Unit dosage forms can contain generally 0.01-1000 mg of active compound, for example, 0.1-50 mg of active compound. For intravenous administration, the compounds can be administered, in single or multiple dosages, at a dosage level of, for example, 0.001-50 mg/kg/day, such as 0.001-10 mg/kg/day, for example, 0.01-1 mg/kg/day. Unit dosage forms can contain, for example, 0.1-10 mg of active compound.

In carrying out the procedures described herein, it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The present invention will now be further described by way of the following non-limiting examples. In applying the disclosure of these examples, it should be kept clearly in mind that other and different embodiments of the methods disclosed according to the present invention will no doubt suggest themselves to those of skill in the relevant art.

In the foregoing and in the following examples, all temperatures are set forth uncorrected in degrees Celsius; and, unless otherwise indicated, all parts and percentages are by weight.

EXAMPLES

In order that the invention described herein may be more readily understood, the following examples are set forth. It should be understood that these examples are for illustrative purposes only and are not to be construed as limiting this invention in any manner.

All NMR spectra were recorded at 300 MHz on a Bruker Instruments NMR unless otherwise stated. Coupling constants (J) are in Hertz (Hz) and peaks are listed relative to TMS (δ0.00 ppm). Microwave reactions were performed using a Personal Chemistry Optimizer™ microwave reactor in 10 mL Personal Chemistry microwave reactor vials. All reactions were performed with the fixed hold time ON unless otherwise stated. Sulfonic acid ion exchange resins (SCX) were purchased from Varian Technologies. Analytical HPLC was performed on 4.6 mm×100 mm Xterra $RPP_{18}$3.5µ columns using (i) a gradient of 20/80 to 80/20 water (0.1% formic acid)/acetonitrile (0.1% formic acid) over 6 min (Method A), (ii) a gradient of 20/80 to 80/20 water (0.1% formic acid)/acetonitrile (0.1% formic acid) over 8 min (Method B), (iii) a gradient of 40/80 to 80/40 water (0.1% formic acid)/acetonitrile (0.1% formic acid) over 6 min (Method C), (iv) a gradient of 40/80 to 80/40 water (0.1% formic acid)/acetonitrile (0.1% formic acid) over 8 min (Method D), or (v) an isocratic of 80/20 acetonitrile (0.1% formic acid)/water (0.1% formic acid) over 8 min (Method E). Preparative HPLC was performed on 30 mm×100 mm Xtera Prep $RP_{18}$5µ columns using an 8 min gradient of 95/5 to 20/80 water (0.1% formic acid)/acetonitrile (0.1% formic acid).

Example 1

4-(1-Acetyl-piperidin-4-yl)-2-aminothiophene-3-carboxylic acid ethyl ester

[See, e.g., Guetschow, Michael and Neumann, Ulf., *J. Med. Chem.*, 41, 10, 1729-1740, 1998].

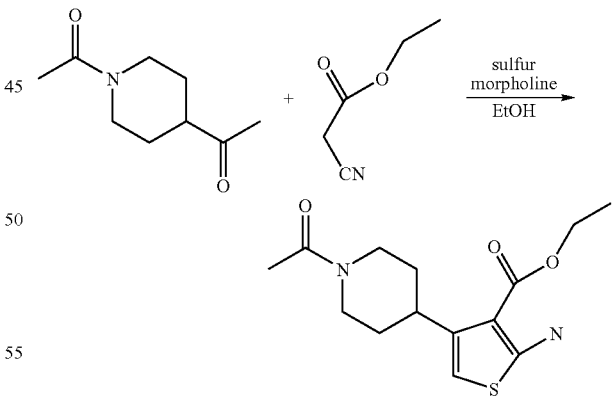

A mixture of 1-(4-acetylpiperidino)ethan-1-one (1.020 g, 6.028 mmol), sulfur (0.193 g, 6.03 mmol), cyanoacetic acid ethyl ester (0.682 g, 6.03 mol) and ethanol (2.00 mL) was treated with morpholine (0.525 g, 0.00603 mol) dropwise at 45° C. After 12 hours, the reaction mixture was diluted with ethyl acetate (60.0 mL), filtered and washed with of 5% aqueous sodium bicarbonate (2×40 mL). The organic layer was concentrated and purified by chromatography over silica gel using 2% methanol, 0.02% ammonia, 49% ethyl acetate, and 49% hexanes to give 700 mg (39%) of 4-(1-acetyl-piperidin-4-yl)-2-aminothiophene-3-carboxylic acid ethyl ester as a light brown solid.

MS [M+H] 297.1, $^1$H NMR (CDCl$_3$) δ (ppm) 6.10 (b, 2H), 5.85 (s, 1H), 4.85 (d, J=13.5 Hz, 1H), 4.32 (q, J=7.2 Hz, 2H), 3.88 (m, 1H), 3.31 (m, 1H), 3.12 (m, 1H), 2.61 (m, 1H), 2.12 (s, 3H), 2.00 (m, 2H), 1.62-1.35 (m, 5H).

The following compounds were synthesized in a similar manner using different starting materials:
4-(Pyridine-4-yl)-2-aminothiophene-3-carboxylic acid ethyl ester,
4-(Pyridine-3-yl)-2-aminothiophene-3-carboxylic acid ethyl ester,
4-(Pyridine-2-yl)-2-aminothiophene-3-carboxylic acid ethyl ester,
4-(Thiazol-2-yl)-2-aminothiophene-3-carboxylic acid ethyl ester,
4-(2-Furyl)-2-aminothiophene-3-carboxylic acid ethyl ester.

Example 2

4-Hydroxy-5-(2-furyl)thieno[2,3-d]pyrimidine

[See, e.g., Perrissin, Monique; Favre, Marylene; Luu-Duc, Cuong et al; *Eur. J. Med. Chem. Chim. Ther.*, 19, 5, 420-424, 1984].

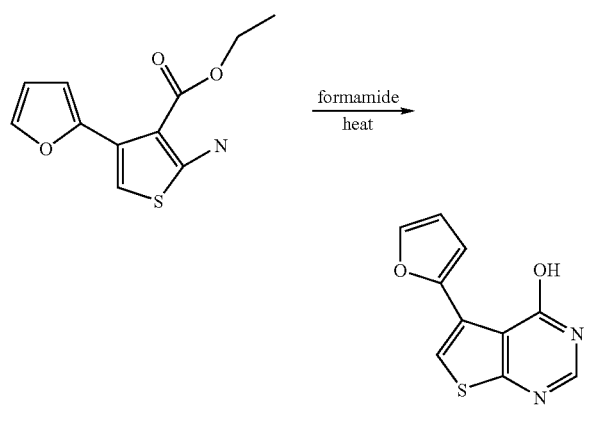

A mixture of ethyl 2-amino-4-(2-furyl)thiophene-3-carboxylate (1.00 g, 4.21 mmol) and formamide (10.0 g, 0.2 mol) was warmed by microwave at 200° C. for 10 minutes. The mixture was concentrated in vacuo at 90° C., diluted with 40 mL of 10% methanol/dichloromethane, and filtered through a 40 gram silica gel column using 5% methanol/dichloromethane to wash the material through the column. The filtrate was again concentrated and the remaining residue was purified by column chromatography over silica gel using a gradient elution from 5 to 10% methanol in dichloromethane to give 0.482 g (52.4%) of 4-hydroxy-5-(2-furyl)thieno[2,3-d]pyrimidine as a brown solid.

MS [M+H] 219.1, $^1$H NMR (10% CD$_3$OD/CDCl$_3$) δ (ppm) 7.90 (s, 1H), 7.50 (s, 1H), 7.45 (d, J=3.3 Hz, 1H), 7.40 (d, J=1.8 Hz, 1H), 5.43 (dd, J=3.3, 1.8 Hz, 1H).

The following compounds were synthesized in a similar manner using different starting materials:
4-Hydroxy-5-(pyridin-4-yl)thieno[2,3-d]pyrimidine,
4-Hydroxy-5-(pyridin-3-yl)thieno[2,3-d]pyrimidine,
4-Hydroxy-5-(pyridin-2-yl)thieno[2,3-d]pyrimidine,
4-Hydroxy-5-(thiazol-2-yl)thieno[2,3-d]pyrimidine,
4-Hydroxy-5-(1-acetylpiperidin-4-yl)thieno[2,3-d]pyrimidine.

Example 3

4-Chloro-5-(thiazol-2-yl)thieno[2,3-d]pyrimidine

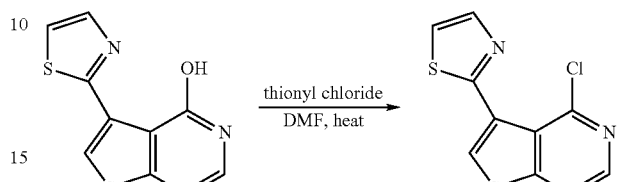

A mixture of thionyl chloride (15 ml, 200 mmol), 4-hydroxy-5-(thiazol-2-yl)thieno[2,3-d]pyrimidine (1.44 g, 12 mmol) and N,N-dimethylformamide (3 mL) was heated at 73° C. for 3 hours and then carefully poured into 200 mL of ice/water. The pH was adjusted to between 7 and 8 with sodium bicarbonate and then the product was extracted with ethyl acetate (2×450 mL). The organic fractions were combined, dried (MgSO$_4$) and concentrated. The resulting residue was purified by column chromatography over silica gel using a gradient elution from 10 to 20% ethyl acetate in hexanes to give 0.825 g (53%) of 4-chloro-5-(thiazol-2-yl)thieno[2,3-d]pyrimidine as a brown solid. MS [M+H] 254.0, $^1$H NMR (400 MHz, 10% CD$_3$OD/CDCl$_3$) δ (ppm) 8.92 (s, 1H), 8.00 (d, J=3.2 Hz, 1H), 7.85 (s, 1H), 7.55 (d, J=3.2 Hz, 1H).

The following compounds were synthesized in a similar manner using different starting materials:
4-Chloro-5-(pyridin-4-yl)thieno[2,3-d]pyrimidine,
4-Chloro-5-(pyridin-3-yl)thieno[2,3-d]pyrimidine,
4-Chloro-5-(pyridin-2-yl)thieno[2,3-d]pyrimidine,
4-Chloro-5-(2-furyl)thieno[2,3-d]pyrimidine.

Example 4

2) N-[3-(3-{[5-(4-Fluorophenyl)thieno[2,3-d]pyrimidin-4-yl]amino}-propoxy)phenyl]acetamide

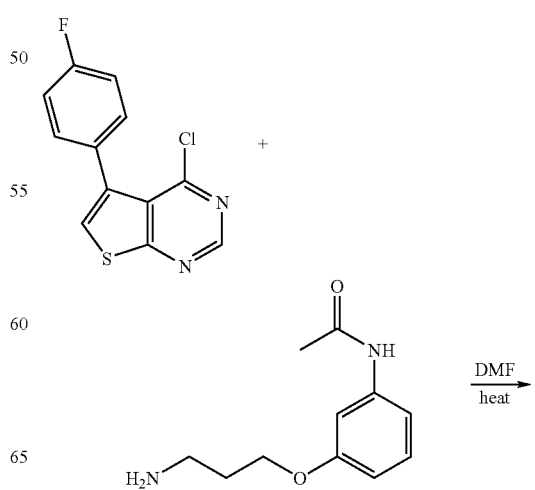

-continued

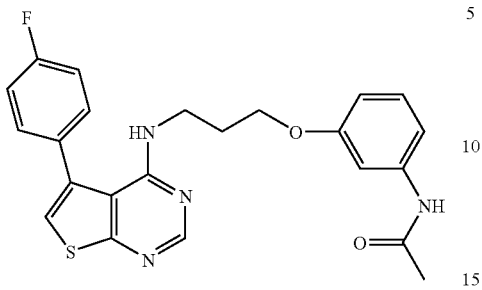

A mixture of 4-chloro-5-(4-fluorophenyl)thieno[2,3-d]pyrimidine (100 mg, 0.378 mmol), N-[3-(3-amino-propoxy)-phenyl]-acetamide (94 mg, 0.45 mmol), diisopropylethylamine (147 mg, 1.14 mmol) and N,N-dimethylformamide (3.0 mL) was warmed to 120° C. for 20 minutes by microwave irradiation. The solvent was then concentrated in vacuo and the residue was dissolved in ethyl acetate (50 mL) and washed with of aqueous sodium bicarbonate (2×30 mL). The organic layer was concentrated in vacuo and purified by column chromatography over silica gel using 1% methanol in dichloromethane as eluant to give 125 mg (73%) of N-[3-(3-{[5-(4-fluorophenyl)thieno[2,3-d]pyrimidin-4-yl]amino}propoxy)phenyl]acetamide as a white solid. MS [M+H] 437.1, $^1$H NMR (CDCl$_3$) 6 (ppm) 8.50 (s, 1H), 7.41-7.36 (m, 2H), 7.25 (s, 1H), 7.21 (t, J=8.1 Hz, 1H), 7.07-6.95 (m, 3H), 6.94 (d, J=8.1 Hz, 1H), 6.55 (d, J=8.4 Hz, 1H), 5.01 (b, 1H), 3.89 (t, J=6.0 Hz, 2H), 3.64 (m, 2H), 2.19 (s, 3H), 1.98 (m, 2H).

The following compounds were synthesized in a similar manner using different starting materials:

9) 3-[({2-[(5-phenylthieno[2,3-d]pyrimidin-4-yl)amino]ethyl}amino)methyl]-benzonitrile, MS[M+H] 386.2
10) Methyl 3-[({2-[(5-phenylthieno[2,3-d]pyrimidin-4-yl)amino]ethyl}amino)-methyl]benzoate, MS[M+H] 419.2
11) N-(5-phenylthieno[2,3-d]pyrimidin-4-yl)-N'-[3-(trifluoromethoxy)benzyl]ethane-1,2-diamine, MS[M+H] 445.2
99) N-(3-{3-[(5-pyridin-3-ylthieno[2,3-d]pyrimidin-4-yl)amino]propoxy}phenyl)-acetamide, MS[M+H] 420.1
100) N-[3-(3-{[5-(1,3-thiazol-2-yl)thieno[2,3-d]pyrimidin-4-yl]amino }propoxy)-phenyl]acetamide, MS[M+H] 426.0
101) N-(3-{3-[(5-pyridin-2-ylthieno[2,3-d]pyrimidin-4-yl)amino]propoxy}phenyl)-acetamide, MS[M+H] 420.1
102) N-[4-(3-{[5-(1,3-thiazol-2-yl)thieno[2,3-d]pyrimidin-4-yl]amino}propoxy)-phenyl]acetamide, MS[M+H] 426.0
103) N-(4-{3-[(5-pyridin-3-ylthieno[2,3-d]pyrimidin-4-yl)amino]propoxy}phenyl)-acetamide, MS [M+H] 420.0
104) N-[4-(3-{[5-(5-chloro-2-furyl)thieno[2,3-d]pyrimidin-4-yl]amino}propoxy)-phenyl]acetamide, MS[M+H] 443.1

Example 5

3) N-(3-Nitrobenzyl)-N'-(5-phenylthieno[2,3-d]pyrimidin-4-yl)ethane-1,2-diamine

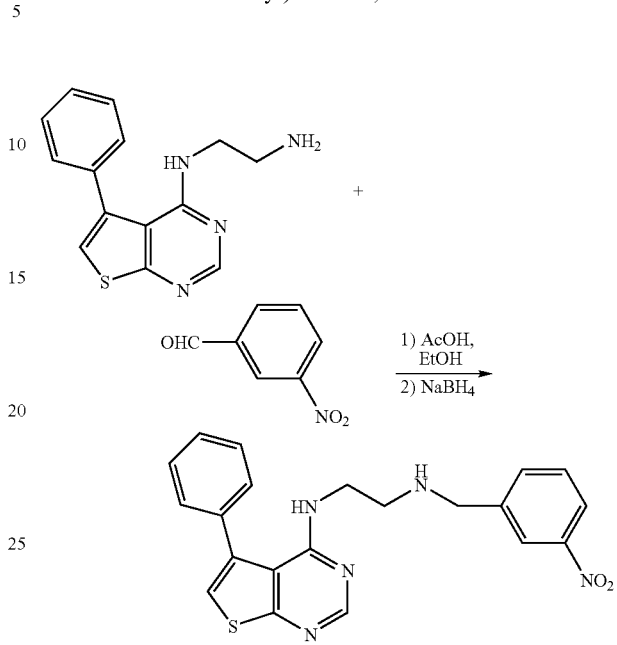

A mixture of N-(5-phenylthieno[2,3-d]pyrimidin-4-yl)ethane-1,2-diamine (Maybridge) (30 mg, 0.11 mmol), 3-nitrobenzaldehyde (18 mg, 0.12 mmol), acetic acid (6 mg, 0.10 mmol) and ethanol (3.0 mL) was stirred at room temperature for 30 minutes, followed by the addition of 7.6 mg (0.20 mmol) of sodium borohydride (7.6 mg, 0.20 mmol). The reaction was stirred for an additional 30 minutes and then water (0.2 mL) and ethyl acetate (20 mL) were added. The mixture was washed with aqueous sodium bicarbonate solution (2×20 mL) and the organic layer was separated, concentrated, and purified by column chromatography over silica gel using a gradient elution from 2.5% to 5% methanol in dichloromethane as eluant to give 34.2 mg (77%) N-(3-nitrobenzyl)-N'-(5-phenylthieno[2,3-d]pyrimidin-4-yl)ethane-1,2-diamine as a colorless gum. MS [M+H] 406.2, $^1$H NMR (CDCl$_3$) δ (ppm) 8.49 (s, 1H), 8.11 (d, J=6.6 Hz, 1H), 8.06 (s, 1H), 7.50-7.32 (m, 7H), 7.08 (s, 1H), 5.48 (b, 1H), 3.75 (s, 2H), 3.55 (m, 2H), 2.75 (m, 2H).

The following compounds were synthesized in a similar manner using different starting materials:

4) N-(3,4-dimethoxybenzyl)-N'-(5-phenylthieno[2,3-d]pyrimidin-4-yl)ethane-1,2-diamine, MS[M+H] 421.2
5) N-(2,1,3-benzothiadiazol-5-ylmethyl)-N'-(5-phenylthieno[2,3-d]pyrimidin-4-yl)ethane-1,2-diamine, MS[M+H] 419.1
6) N-{3-[({2-[(5-phenylthieno[2,3-d]pyrimidin-4-yl)amino]ethyl}amino)methyl]-phenyl}acetamide, MS{M+H] 418.2
7) N-{4-[({2-[(5-phenylthieno[2,3-d]pyrimidin-4-yl)amino]ethyl}amino)methyl]-phenyl}acetamide, MS[M+H] 418.2

Example 6

N-(3-formylphenyl)acetamide

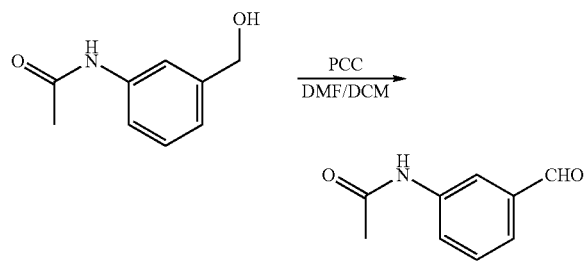

A mixture of N-(3-hydroxymethylphenyl)acetamide (165 mg, 1.0 mmol), celite (165 mg), pyridinium chlorochromate (645 mg, 3.0 mmol), N,N-dimethylformamide (1.0 mL) and dichloromethane (25 mL) was stirred at room temperature for 24 h. The reaction mixture was filtered and concentrated in vacuo. The resulting residue was dissolved in dichloromethane (40 mL) and washed with aqueous sodium bicarbonate solution (2×30 mL). The organic layer was concentrated and the product purified by chromatography over silica gel using ethyl acetate/hexanes (1:1) as eluant to give 130 mg (81%) of N-(3-formylphenyl)acetamide as a brown solid. MS [M+H] 164.2, $^1$H NMR (CDCl$_3$) δ (ppm) 9.96 (s, 1H), 8.22 (b, 1H), 8.03 (s, 1H), 7.89 (d, J=7.8 Hz, 1H), 7.61 (d, J=6.6 Hz, 1H), 7.47 (t, J=7.8 Hz, 1H), 2.22 (s, 1H).

Example 7

19) 3-(3-{[5-(4-Fluorophenyl)thieno[2,3-d]pyrimidin-4-yl]oxy}-propoxy)aniline

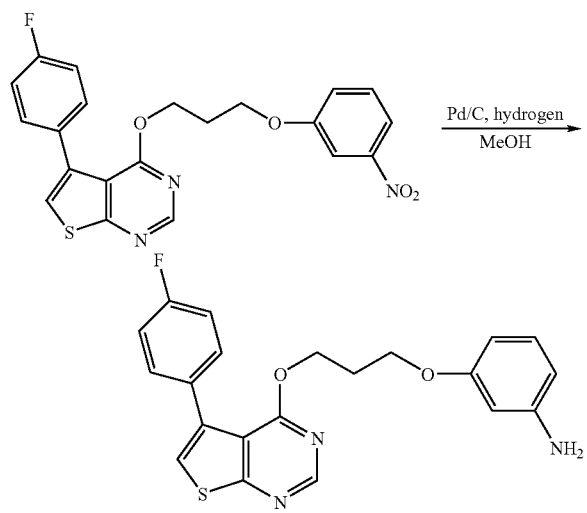

5-(4-Fluorophenyl)-4-[3-(3-nitrophenoxy)propoxy]thieno[2,3-d]pyrimidine (250 mg, 0.588 mmol) was dissolved in tetrahydrofuran (15 mL) and added (under an atmosphere of argon) to a suspension of 25 mg of 10% palladium/carbon in methanol (30 mL) and acetic acid (5 mL). The mixture was then shaken under 40 psi of hydrogen overnight. The palladium/carbon was removed by filtration and the filtrate was concentrated in vacuo. The residue was dissolved in ethyl acetate (50 mL) and washed with aqueous sodium bicarbonate solution (2×30 mL). The organic layer was separated, concentrated, and purified by column chromatography over silica gel using 33% ethyl acetate in hexanes as eluant to give 180 mg (76%) of 3-(3-{[5-(4-fluorophenyl)thieno[2,3-d]pyrimidin-4-yl]oxy}propoxy)aniline as a colorless gum. MS [M+H] 396.1, $^1$H NMR (CDCl$_3$) δ (ppm) 8.65 (s, 1H), 7.45-7.40 (m, 2H), 7.21 (s, 1H), 7.09-7.00 (m, 3H), 6.30 (d, J=2.1 Hz, 1H), 6.20 (d, J=2.8 Hz, 1H), 6.11 (s, 1H), 4.58 (t, J=6.0 Hz, 2H), 3.69 (t, J=6.0 Hz, 3H), 3.68 (b, 2H), 2.05 (m, 2H).

The following compounds were synthesized in a similar manner using different starting materials:

4-(3-{[5-(4-fluorophenyl)thieno[2,3-d]pyrimidin-4-yl]oxy}propoxy)aniline

Example 8

21) N-[3-(3-{[5-(4-Fluorophenyl)thieno[2,3-d]pyrimidin-4-yl]oxy}propoxy)phenyl]cyclopropanecarboxamide

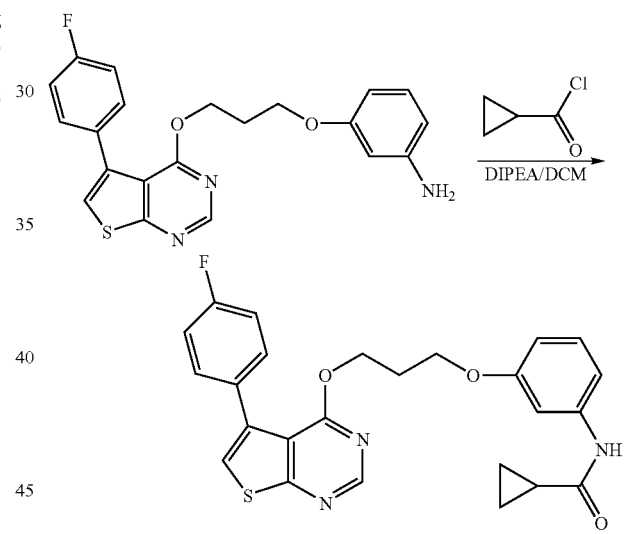

A mixture of 3-(3-{[5-(4-fluorophenyl)thieno[2,3-d]pyrimidin-4-yl]oxy}propoxy)aniline (10 mg, 0.025 mmol), diisopropylethylamine (13 mg, 0.10 mmol), and dichloromethane (2 mL) was treated with cyclopropanecarbonyl chloride (30 mg, 0.028 mmol) and stirred at room temperature for 6 hours. The solvent was removed in vacuo and the remaining residue was dissolved in ethyl acetate (25 mL), washed with aqueous sodium bicarbonate solution (2×20 mL), and the organic fraction was separated and concentrated. The product was purified by column chromatography over silica gel using 1% methanol and 0.01% ammonia in 1:1 ethyl acetate/hexanes to give 12 mg (quantitative yield) of N-[3-(3-{[5-(4-fluorophenyl)thieno[2,3-d]pyrimidin-4-yl]oxy}propoxy)phenyl]cyclopropanecarboxamide as a yellow gum. MS [M+H] 464.0, $^1$H NMR (CDCl$_3$) δ (ppm) 8.65 (s, 1H), 7.48 (s, 1H), 7.50-7.36 (m, 2H), 7.21 (s, 1H), 7.16 (d, J=8.1 Hz, 1H), 7.10-7.00 (m, 2H), 6.95 (d, J=7.5 Hz, 1H), 6.52 (d, J=8.1 Hz, 1H), 4.58 (t, J=6.0 Hz, 2H), 3.74 (t, J=6.0 Hz, 2H), 2.05 (m, 2H), 1.67 (m, 1H), 1.20-0.80 (m, 4H).

Example 9

27) N-(2-Amino-2-oxoethyl)-3-(3-{[5-(4-fluorophenyl)thieno[2,3-d]pyrimidin-4-yl]oxy}propoxy)benzamide

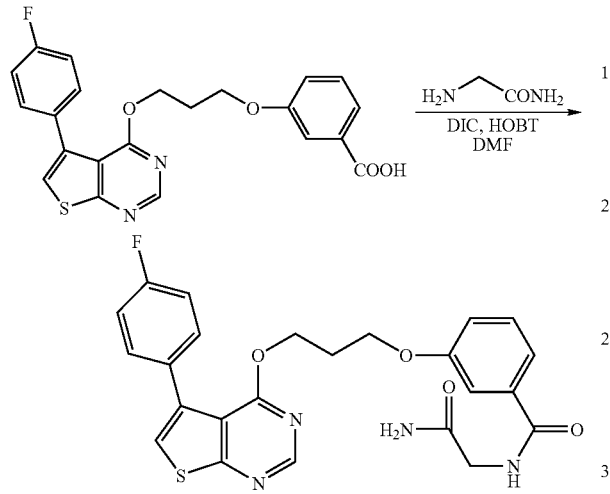

1,3-Diisopropylcarbodiimide (13.0 mg, 0.10 mmol) was added to a stirred mixture of 3-(3-{[5-(4-fluorophenyl)thieno[2,3-d]pyrimidin-4-yl]oxy}propoxy)benzoic acid (21 mg, 0.050 mmol), 2-amino-acetamide hydrochloride (11 mg, 0.10 mmol), 1-hydroxybenzotriazole (6.7 mg, 0.05 mmol), diisopropylethylamine (40 mg, 0.30 mmol) and 4-dimethylaminopyridine (13 mg, 0.10 mmol) in N,N-dimethylformamide (1.0 mL). The mixture was stirred at room temperature for 6 hours and then concentrated in vacuo. The resultant residue was dissolved in ethyl acetate (30 mL), washed with aqueous sodium bicarbonate solution (2×25 mL) and the organic layer was separated and concentrated. The product was purified by column chromatography over silica gel using 5% methanol in 1:1 of ethyl acetate/hexanes to give 9.6 mg (40%) of N-(2-amino-2-oxoethyl)-3-(3-{[5-(4-fluorophenyl)thieno[2,3-d]pyrimidin-4-yl]oxy}propoxy)benzamide as a white solid. MS [M+H] 481.1, $^1$H NMR (CDCl$_3$) δ (ppm) 8.68 (s, 1H), 7.60-7.24 (m, 4H), 7.21 (s, 1H), 7.18-6.95 (m, 3H), 6.90 (d, J=7.8 Hz, 1H), 6.31 (b, 1H), 5.62 (b, 1H), 4.59 (t, J=6.0 Hz, 2H), 4.19, (d, J=5.1 Hz, 2H), 3.74 (t, J=6.0 Hz, 2H), 2.10 (m, 2H).

The following compounds were synthesized in a similar manner using different starting materials:

8) 3-(Acetylamino)-N-{2-[(5-phenylthieno[2,3-d]pyrimidin-4-yl)amino]ethyl}-benzamide. MS[M+H] 432.2

22) 5-(4-Fluorophenyl)-4-(3-{3-[(4-methylpiperazin-1-yl)carbonyl]phenoxy}-propoxy)thieno[2,3-d]pyrimidine. MS[M+H] 507.1

23) 5-(4-Fluorophenyl)-4-{3-[3-(morpholin-4-ylcarbonyl)phenoxy]propoxy}-thieno[2,3-d]pyrimidine. MS[M+H] 494.1

24) N-Ethyl-3-(3-{[5-(4-fluorophenyl)thieno[2,3-d]pyrimidin-4-yl]oxy}propoxy)-benzamide. MS[M+H] 452.1

25) 3-(3-{[5-(4-Fluorophenyl)thieno[2,3-d]pyrimidin-4-yl]oxy}propoxy)-N,N-dimethylbenzamide MS [M+H] 452.1

26) N-[2-(Dimethylamino)ethyl]-3-(3-{[5-(4-fluorophenyl)thieno[2,3-d]pyrimidin-4-yl]oxy}propoxy)benzamide. MS[M+H] 495.1

28) 3-(3-{[5-(4-Fluorophenyl)thieno[2,3-d]pyrimidin-4-yl]oxy}propoxy)-N'-formylbenzohydrazide. MS[M+H] 467.0

Example 10

35) 3-(3-{[5-(4-Fluorophenyl)thieno[2,3-d]pyrimidin-4-yl]oxy}propoxy)benzohydrazide

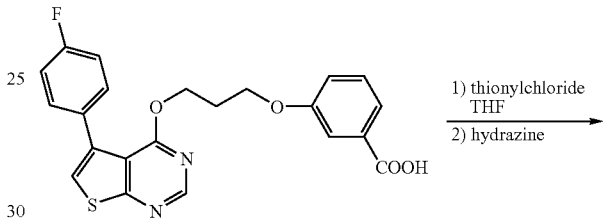

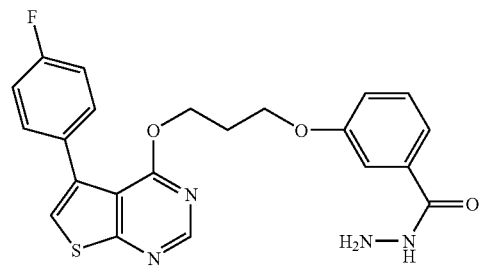

Thionyl chloride (13 mg, 0.11 mmol) was added to a solution of 3-(3-{[5-(4-fluorophenyl)thieno[2,3-d]pyrimidin-4-yl]oxy}propoxy)benzoic acid (43 mg, 0.10 mmol) in tetrahydrofuran (2.0 mL) with stirring at 70° C. Stirring continued for one hour at 70° C. and then the mixture was cooled to 25° C. and added to a solution of hydrazine (32 mg, 1.0 mmol) in tetrahydrofuran (2.0 mL). The reaction was stirred at room temperature for one hour and the solvent was then removed in vacuo. The residue was dissolved in ethyl acetate (30 mL), washed with of aqueous sodium bicarbonate solution (20 mL), concentrated, and purified by column chromatography over silica gel using 2% methanol in ethyl acetate as eluant to give 22 mg (50%) of 3-(3-{[5-(4-fluorophenyl)thieno[2,3-d]pyrimidin-4-yl]oxy}propoxy)benzohydrazide as a white solid. MS [M+H] 439.2, $^1$H NMR (CDCl$_3$) δ (ppm) 8.65 (s, 1H), 7.50-7.35 (m, 2H), 7.32-7.21 (m, 3H), 7.18 (s, 1H), 7.10-6.97 (m, 2H), 6.94 (d, J=2.7 Hz, 1H), 4.59 (t, J=6.9 Hz, 2H), 4.11 (s, 2H), 3.74 (t, J=6.0 Hz, 2H), 2.09 (m, 2H).

The following compound was synthesized in a similar manner using different starting materials:

36) 3-(3-{[5-(4-fluorophenyl)thieno[2,3-d]pyrimidin-4-yl]oxy}propoxy)-N-hydroxybenzamide. MS[M+H] 440.2

Example 11

3-Hydroxy-N-methylbenzamide

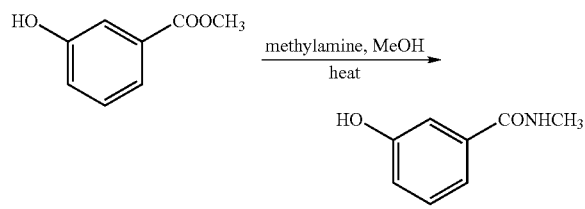

A solution of 3-hydroxybenzoic acid methyl ester (2.00 g, 0.0131 mol), methylamine (0.06 mol) and methanol (30 mL) was heated to 155° C. for 12 hours in a sealed tube. The solvent was removed in vacuo and the product was purified by column chromatography over silica gel using a gradient elution from 5 to 8% methanol in dichloromethane to give 1.20 g (60.4%) of 3-hydroxy-N-methylbenzamide as a yellow solid. MS [M+H] 152.2, $^1$H NMR (CDCl$_3$) δ (ppm) 7.55 (s, 1H), 7.30 (d, J=7.8 Hz, 1H), 7.18 (d, J=7.5 Hz, 1H), 7.01 (m, 1H), 6.65 (b, 1H), 6.20 (b, 1H), 3.03 (d, J=4.8 Hz, 3H).

The following compounds were synthesized in a similar manner using different starting materials:
3-hydroxybenzamide. MS[M+H] 138.1
5-hydroxynicotinamide. MS[M+H] 139.1
5-hydroxy-N-methylnicotinamide. MS[M+H] 153.2
5-hydroxy-N-methylpyridine-2-carboxamide. MS[M+S] 153.1
5-hydroxypyridine-2-carboxamide. MS[M+S] 139.1

Example 12a 54) 5-{3-[5-(4-Fluorophenyl)-thieno[2,3-d]pyrimidin-4-yloxy]-propoxy}-nicotinic acid

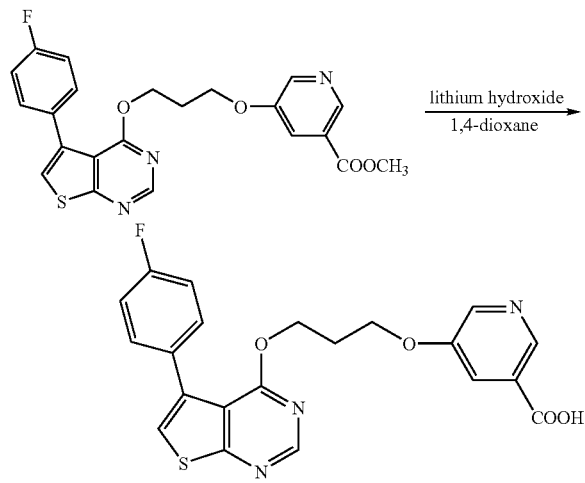

To a solution of 5-{3-[5-(4-fluorophenyl)-thieno[2,3-d]pyrimidin-4-yloxy]-propoxy}-nicotinic acid methyl ester (100 mg) in dioxane (10 mL) was added 0.80 M lithium hydroxide in water (2.0 mL). The reaction was stirred at ambient temperature for 16 hours, then acidified with 1M hydrochloric acid to pH 3, and the solvent removed under reduced pressure. The residue was dissolved in 20% methanol/dichloromethane (40 mL), filtered, and the filtrate was concentrated. The product was purified by column chromatography over silica gel using 10% methanol in dichloromethane as eluant to give 90 mg (93%) of 5-{3-[5-(4-fluorophenyl)-thieno[2,3-d]pyrimidin-4-yloxy]-propoxy}-nicotinic acid as a white solid. MS [M+H] 425.9, $^1$H NMR (CD$_3$OD) δ (ppm) 8.91 (s, 1H), 8.63 (s, 1H), 8.62 (s, 1H), 8.27 (s, 1H), 7.60-7.45 (m, 3H), 7.10 (t, J=8.7 Hz, 2H), 4.67 (t, J=9.0 Hz, 2H), 3.94 (t, J=9.3 Hz, 2H), 2.22 (t, J=9.0 Hz, 2H).

The following compound was synthesized in a similar manner using different starting materials:
20) 3-(3-{[5-(4-fluorophenyl)thieno[2,3-d]pyrimidin-4-yl]oxy}propoxy)benzoic acid. MS[M+H] 425.0

Example 12b 88) 5-{4-[5-(4-Fluorophenyl)thieno[2,3-d]pyrimidin-4-yl]butoxy}nicotinic acid hydroformate

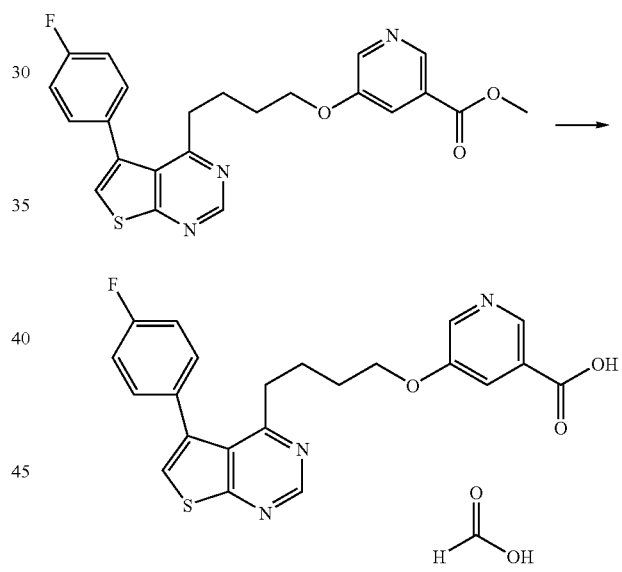

A mixture of methyl-5-{4-[5-(4-fluorophenyl)thieno[2,3-d]pyrimidin-4-yl]butoxy}nicotinate (0.010 g, 0.023 mmol) and potassium hydroxide (0.0112 g, 0.200 mmol) in methanol (0.5 mL) was stirred at room temperature for 12 h. Acetic acid (200 mg, 3.33 mmol) was then added, and the reaction solvent was removed by evaporation. The product was purified by column chromatography over silica gel using 5% methanol in dichloromethane as eluant to afford 8 g (83%) 5-{4-[5-(4-fluorophenyl)thieno[2,3-d]pyrimidin-4-yl]butoxy}nicotinic acid hydroformate as white solid. MS [M+H]=424.1, LC/MS (EI) t$_R$ 3.89 min (Method D), $^1$H NMR (10% MeOD/CDCl$_3$) δ (ppm) 8.94 (s, 1H), 8.73 (s, 1H), 8.28 (s, 1H), 7.68 (s, 1H), 7.40-7.30 (m, 3H), 7.10 (t, J=8.4 Hz, 2H), 3.84 (t, J=6.3 Hz, 2H), 2.68 (t, J=7.2 Hz, 2H), 1.75-1.59 (m, 2H), 1.59-1.45 (m, 2H)

Example 13

5-(3-Hydroxypropoxy)-N-methylpyridine-2-carboxamide

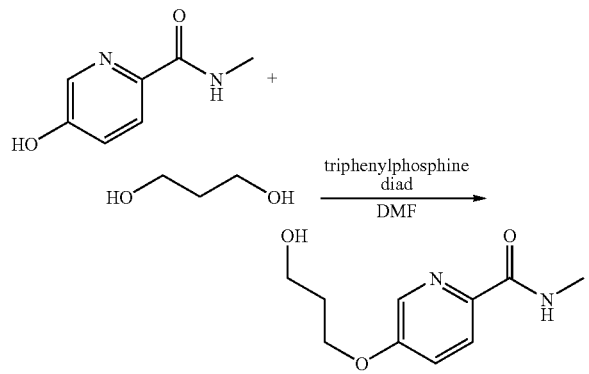

To a mixture of 5-hydroxy-N-methylpyridine-2-carboxamide (400 mg, 3.0 mmol), 1,3-propanediol (230 mg, 3.0 mmol), triphenylphosphine (786 mg, 3.0 mmol) and N,N-dimethylformamide (4.5 ml, 60 mmol) was added diisopropyl azodicarboxylate (606 mg, 3.0 mmol) while stirring at ambient temperature. After 18 hours, the solvent was removed under reduced pressure and the resulting residue was taken up in ethyl acetate (40 mL) and filtered. The filtrate was concentrated and purified by column chromatography over silica gel using methanol/ethyl acetate (3-4%) to give 488 mg (80%) of 5-(3-hydroxypropoxy)-N-methylpyridine-2-carboxamide as a colorless gum. MS [M+H] 211.2, $^1$H NMR (CDCl$_3$) δ (ppm) 8.19 (d, J=3.0 Hz, 1H), 8.13 (d, J=8.7 Hz, 1H), 7.83 (b, 1H), 7.28 (m, 1H), 4.21 (t, J=6.3 Hz, 2H), 3.88 (m, 2H), 3.02 (d, J=5.1 Hz), 2.08 (m, 2H).

The following compounds were synthesized in a similar manner using different starting materials:

N-[3-(3-hydroxy-propoxy)-phenyl]-acetamide. MS[M+H] 210.3

5-(3-hydroxypropoxy)pyridine-2-carboxamide. MS [M+H] 197.2

15) N-[4-(3-{[5-(4-fluorophenyl)thieno[2,3-d]pyrimidin-4-yl]oxy}propoxy)phenyl]-acetamide. MS[M+H] 438.2

16) 5-(4-fluorophenyl)-4-{3-[4-(1H-1,2,4-triazol-1-yl)phenoxy]propoxy}thieno[2,3-d]pyrimidine. MS[M+H] 448.1

17) 4-[3-(4-fluorophenoxy)propoxy]-5-(4-fluorophenyl)thieno[2,3-d]pyrimidine. MS[M+H] 399.1

18) methyl 3-(3-{[5-(4-fluorophenyl)thieno[2,3-d]pyrimidin-4-yl]oxy}propoxy)-benzoate. MS[M+H] 439.1

12) 5-(4-fluorophenyl)-4-[3-(3-nitrophenoxy)propoxy]thieno[2,3-d]pyrimidine. MS[M+H] 426.0

29) 3-(3-{[5-(4-fluorophenyl)thieno[2,3-d]pyrimidin-4-yl]oxy}propoxy)-N-methylbenzamide. MS[M+H] 438.2

30) 3-(3-{[5-(4-fluorophenyl)thieno[2,3-d]pyrimidin-4-yl]oxy}propoxy)benzamide. MS[M+H] 424.2

31) 3-(2-{[5-(4-fluorophenyl)thieno[2,3-d]pyrimidin-4-yl]oxy}ethoxy)-N-methylbenzamide. MS[M+H] 424.2

32) N-[3-(2-{[5-(4-fluorophenyl)thieno[2,3-d]pyrimidin-4-yl]oxy}ethoxy)phenyl]-urea. MS[M+H] 425.2

33) N-[3-(3-{[5-(4-fluorophenyl)thieno[2,3-d]pyrimidin-4-yl]oxy}propoxy)phenyl]-urea. MS[M+H] 439.2

34) 3-(2-{[5-(4-fluorophenyl)thieno[2,3-d]pyrimidin-4-yl]oxy}ethoxy)benzamide. MS[M+H] 410.2

50) 4-{3-[5-(4-fluorophenyl)-thieno[2,3d]pyrimidin-4-yloxy]-propoxy}-benzamide. MS[M+H] 424.0

37) 4-(2-{[5-(4-fluorophenyl)thieno[2,3-d]pyrimidin-4-yl]oxy}ethoxy)benzamide. MS[M+H] 410.1

53) 2-(3-{[5-(4-fluorophenyl)thieno[2,3-d]pyrimidin-4-yl]oxy}propoxy)benzamide. MS [M+H] 424.1

51) 5-{3-[5-(4-fluorophenyl)-thieno[2,3-d]pyrimidin-4-yloxy]-propoxy}-nicotinic acid methyl ester. MS[M+H] 440.0

Example 14

61) N-Methyl-5-{3-[(5-pyridin-4-ylthieno[2,3-d]pyrimidin-4-yl)oxy]propoxy}pyridine-2-carboxamide

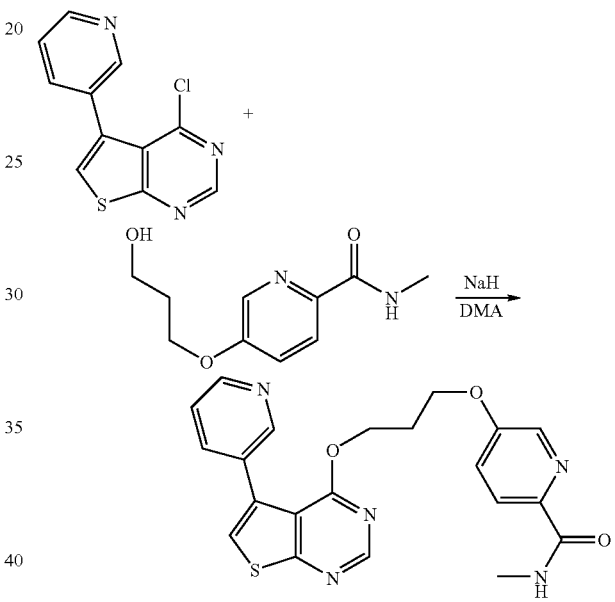

5-(3-Hydroxypropoxy)-N-methylpyridine-2-carboxamide (52 mg, 0.25 mmol) in N,N-dimethylacetamide (2.0 mL, 22 mmol) was treated with sodium hydride (11 mg, 60%, 0.27 mmol) at ambient temperature. After 1.5 hours, the mixture was added to a solution of 4-chloro-5-pyridin-4-ylthieno[2,3-d]pyrimidine (62 mg, 0.025 mmol) in N,N-dimethylacetamide (1.0 mL) and the resulting mixture was stirred at room temperature for 12 hours. The reaction mixture was then quenched by the addition of acetic acid (0.12 mL, 2.0 mmol) and the solvent was removed under reduced pressure. The residue was dissolved in ethyl acetate (50 mL), washed with 5% aqueous sodium bicarbonate (2×30 mL) and the organic layer was concentrated. The product was purified by silica gel chromatography using 3 to 5% methanol in ethyl acetate to give 72 mg (68%) of N-methyl-5-{3-[(5-pyridin-4-ylthieno[2,3-d]pyrimidin-4-yl)oxy]propoxy}pyridine-2-carboxamide as a white solid. MS [M+H] 422.0, $^1$H NMR (CDCl$_3$) δ (ppm) 8.74 (s, 1H), 8.66 (s, 1H), 8.54 (d, J=3.9 Hz, 1H), 8.11 (d, J=8.4 Hz, 1H), 8.05 (d, J=2.7 Hz, 1H), 7.90-7.73 (m, 2H), 7.33 (s, 1H), 7.28 (dd, J=7.8, 4.8 Hz, 1H), 7.11 (dd, J=8.7, 2.7 Hz, 1H), 4.62 (t, J=6.0 Hz, 2H), 3.76 (t, J=6.0 Hz, 2H), 3.01 (d, J=4.8 Hz, 3H), 2.13 (t, J=6.0 Hz, 2H).

The following compounds were synthesized in a similar manner using different starting materials:

3-[5-(4-fluorophenyl)-thieno[2,3-d]pyrimidin-4-yloxy]-propan-1-ol. MS[M+H] 305.2

5-(4-fluorophenyl)-4-isopropoxythieno[2,3-d]pyrimidine. MS[M+H] 289.2

105) 5-(4-fluorophenyl)-4-[3-(3-nitrophenoxy)propoxy] thieno[2,3-d]pyrimidine. MS[M+H] 426.1

14) N-[3-(3-{[5-(4-fluorophenyl)thieno[2,3-d]pyrimidin-4-yl]oxy}propoxy)phenyl]-acetamide. MS[M+H] 438.4

2-{[5-(4-fluorophenyl)thieno[2,3-d]pyrimidin-4-yl]oxy}ethanol. MS[M+H] 291.2

52) N-{3-[3-(5-furan-2-yl-thieno[2,3-d]pyrimidin-4-yloxy)-propoxy]-phenyl}-acetamide. MS[M+H] 410.0

N-{3-[3-(4-oxo-5-furan-2-yl-4-oxo-4H-thieno[2,3-d]pyrimidin-1-yl)propoxy]-phenyl}acetamide. MS[M+H] 410.1

N-{3-[3-(4-oxo-5-phenylthieno[2,3-d]pyrimidin-1(4H)-yl)propoxy]phenyl}-acetamide. MS[M+H] 420.0

Benzyl 4-(2-{[5-(4-fluorophenyl)thieno[2,3-d]pyrimidin-4-yl]oxy}ethyl)-piperazine-1-carboxylate. MS[M+H] 493.1

57) 5-{3-[(5-pyridin-4-ylthieno[2,3-d]pyrimidin-4-yl)oxy] propoxy}pyridine-2-carboxamide. MS[M+H] 408.1

58) 5-(3-{[5-(4-fluorophenyl)thieno[2,3-d]pyrimidin-4-yl]oxy}propoxy)pyridine-2-carboxamide. MS[M+H] 425.1

59) 5-(3-{[5-(1,3-thiazol-2-yl)thieno[2,3-d]pyrimidin-4-yl]oxy}propoxy)pyridine-2-carboxamide. MS[M+H] 414.1

60) 5-{3-[(5-pyridin-3-ylthieno[2,3-d]pyrimidin-4-yl)oxy] propoxy}pyridine-2-carboxamide. MS[M+H] 408.0

62) 5-(3-{[5-(4-fluorophenyl)thieno[2,3-d]pyrimidin-4-yl]oxy}propoxy)-N-methylpyridine-2-carboxamide. MS[M+H] 439.1

63) N-methyl-5-(3-{[5-(1,3-thiazol-2-yl)thieno[2,3-d]pyrimidin-4-yl]oxy}propoxy)-pyridine-2-carboxamide. MS[M+H] 428.0 Diethyl [5-(4-fluorophenyl)thieno[2,3-d]pyrimidin-4-yl]malonate. MS[M+H] 389.1

64) N-methyl-5{-3-[(5-pyridin-2-ylthieno[2,3-d]pyrimidin-4-yl)oxy]propoxy}-pyridine-2-carboxamide. MS[M+H] 422.1

106) N-methyl-4-{3-[(5-pyridin-3-ylthieno[2,3-d]pyrimidin-4-yl)oxy]propoxy}-benzamide. MS[M+H] 421.1

107) N-methyl-5-(3-{[5-(1,3-thiazol-2-yl)thieno[2,3-d]pyrimidin-4-yl]oxy}propoxy)-nicotinamide. MS[M+H] 428.0

108) N-methyl-5-{3-[(5-pyridin-3-ylthieno[2,3-d]pyrimidin-4-yl)oxy]propoxy}-nicotinamide. MS[M+H] 422.1

109) N-methyl-3-(3-{[5-(1,3-thiazol-2-yl)thieno[2,3-d]pyrimidin-4-yl]oxy}propoxy)-benzamide. MS[M+H] 427.0

110) N-[4-(3-{[5-(1,3-thiazol-2-yl)thieno[2,3-d]pyrimidin-4-yl]oxy}propoxy)phenyl]-acetamide. MS[M+H] 427.0

111) N-(4-{3-[(5-pyridin-3-ylthieno[2,3-d]pyrimidin-4-yl)oxy]propoxy}phenyl)-acetamide. MS[M+H] 421.0

65) N-methyl-3-{3-[(5-pyridin-3-ylthieno[2,3-d]pyrimidin-4-yl)oxy]propoxy}benzamide, MS [M+H]=421.1, LC/MS (EI) t$_R$ 5.42 min (Method B)

71) 5-{3-[(5-pyridin-3-ylthieno[2,3-d]pyrimidin-4-yl)oxy] propoxy}pyridine-2-carboxamide hydroformate, MS [M+H]=408.1, LC/MS (EI) t$_R$ 4.14 min (Method B)

72) 5-(4-fluorophenyl)-4-(3-{[1-methyl-5-(trifluoromethyl)-1H-pyrazol-3-yl]oxy}propoxy)thieno[2,3-d]pyrimidine, MS [M+H]=453.1, LC/MS (EI) t$_R$ 4.32 min (Method E)

73) 4-[3-(4-chlorophenoxy)propoxy]-5-(4-fluorophenyl) thieno[2,3-d]pyrimidine, MS [M+H]=415.1, LC/MS (EI) t$_R$ 5.65 min (Method E)

74) 4-[3-(3,5-difluorophenoxy)propoxy]-5-(4-fluorophenyl) thieno[2,3-d]pyrimidine, MS [M+H]=417.1, LC/MS (EI) t$_R$ 4.82 min (Method E)

75) 4-[3-(3,4-dimethoxyphenoxy)propoxy]-5-(4-fluorophenyl)thieno[2,3-d]pyrimidine, MS [M+H]=441.2, LC/MS (EI) t$_R$ 3.53 min (Method E)

76) 4-[3-(1,2-benzisothiazol-3-yloxy)propoxy]-5-(4-fluorophenyl)thieno[2,3-d]pyrimidine, MS [M+H]=438.1, LC/MS (EI) t$_R$ 5.89 min (Method E)

77) 5-(4-fluorophenyl)-4-(3-phenoxypropoxy)thieno[2,3-d] pyrimidine, MS [M+H]=356.1, LC/MS (EI) t$_R$ 5.24 min (Method E)

78) 5-(4-fluorophenyl)-4-[3-(3-methoxyphenoxy)propoxy] thieno[2,3-d]pyrimidine, MS [M+H]/=411.1, LC/MS (EI) t$_R$ 4.25 min (Method E)

79) 5-(4-fluorophenyl)-4-[3-(3-methylphenoxy)propoxy] thieno[2,3-d]pyrimidine, MS [M+H]=395.1, LC/MS (EI) t$_R$ 5.36 min (Method E)

80) 5-(4-fluorophenyl)-4-{3-[3-(trifluoromethoxy)phenoxy] propoxy}thieno [2,3-d]pyrimidine, MS [M+H]=465.1, LC/MS (EI) t$_R$ 5.61 min (Method E)

81) 4-[3-(3-ethylphenoxy)propoxy]-5-(4-fluorophenyl) thieno[2,3-d]pyrimidine, MS [M+H]=409.1, LC/MS (EI) t$_R$ 6.06 min (Method E)

92) N-[3-(2,2-dimethyl-3-{[5-(1,3-thiazol-2-yl)thieno[2,3-d]pyrimidin-4-yl]oxy}propoxy)phenyl]acetamide hydroformate, MS [M+H]=455.1, LC/MS (EI) t$_R$ 6.13 min (Method D)

94) N-[3-(3-{[5-(4-fluorophenyl)thieno[2,3-d]pyrimidin-4-yl]oxy}-2,2-dimethyl propoxy)phenyl]acetamide hydroformate, MS [M+H]=466.1, LC/MS (EI) t$_R$ 7.66 min (Method D).

Example 15

39) N-[3-(3-{[5-(4-Fluorophenyl)thieno[2,3-d]pyrimidin-4-yl]oxy}propoxy)-phenyl]methanesulfonamide

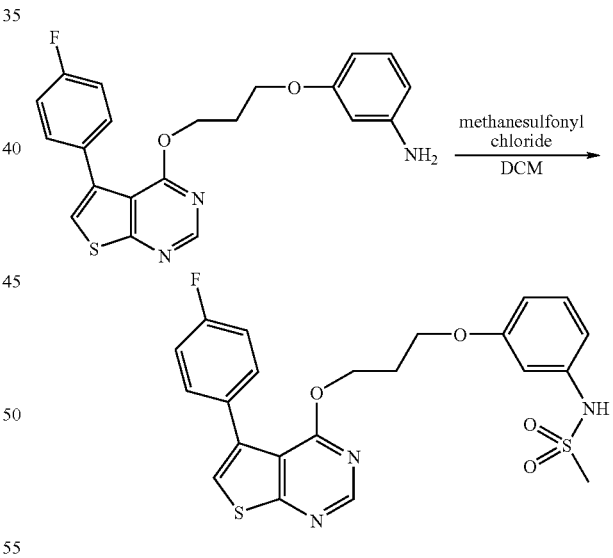

A solution of 3-(3-{[5-(4-fluorophenyl)thieno[2,3-d]pyrimidin-4-yl]oxy}propoxy)aniline (50 mg, 0.126 mmol) in dichloromethane (1.5 mL) was added to methanesulfonyl chloride (58 mg, 0.51 mmol) while stirring, followed by the addition of a solution of diisopropylethylamine (18 mg, 0.14 mmol) in dichloromethane (0.5 mL). Stirring was continued for 12 hours at room temperature and then the solvent was evaporated in vacuo. The residue was dissolved in ethyl acetate (30 mL), washed with sodium bicarbonate (2×25 mL) and the organic layer was isolated and concentrated. The product was purified by silica gel chromatography using 40% ethyl acetate in hexanes to give 23 mg (40%) of N-[3-(3-{[5-

(4-fluorophenyl)thieno[2,3-d]pyrimidin-4-yl]oxy}propoxy)phenyl]methanesulfonamide as a yellow solid. MS [M+H] 474.7. $^1$H NMR (400 MHz, CDCl$_3$) δ (ppm) 8.65 (s, 1H), 7.42 (m, 2H), 7.23 (t, J=68.0 Hz, 1H), 7.22 (s, 1H), 7.06-7.01 (m, 2H), 6.76 (dd, J=8.0, 2.0 Hz, 1H), 6.68 (t, J=2.4 Hz, 1H), 6.58 (dd, J=8.0, 2.4 Hz, 1H), 6.32 (b, 1H), 4.58 (t, J=6.0 Hz, 2H), 3.01 (s, 3H), 2.07 (m, 2H).

The following compounds were synthesized in a similar manner using different starting materials:

40) N-[4-(3-{[5-(4-fluorophenyl)thieno[2,3-d]pyrimidin-4-yl]oxy}propoxy)phenyl]-methanesulfonamide. MS[M+H] 474.7

41) N-[4-(3-{[5-(4-fluorophenyl)thieno[2,3-d]pyrimidin-4-yl]oxy}propoxy)phenyl]-N-(methylsulfonyl)methanesulfonamide. MS [M+H] 552.8

42) N-(ethylsulfonyl)-N-[4-(3-{[5-(4-fluorophenyl)thieno[2,3-d]pyrimidin-4-yl]oxy}propoxy)phenyl]ethanesulfonamide. MS [M+H] 580.9

46) N-[3-(3-{[5-(4-fluorophenyl)thieno[2,3-d]pyrimidin-4-yl]oxy}propoxy)phenyl]-ethanesulfonamide. MS[M+H] 488.2

43) N-[4-(3-{[5-(4-fluorophenyl)thieno[2,3-d]pyrimidin-4-yl]oxy}propoxy)phenyl]-ethanesulfonamide. MS[M−H] 486.7

Example 16

38) N-Ethyl-N'-[3-(3-{[5-(4-fluorophenyl)thieno[2,3-d]pyrimidin-4-yl]oxy}propoxy)phenyl]urea

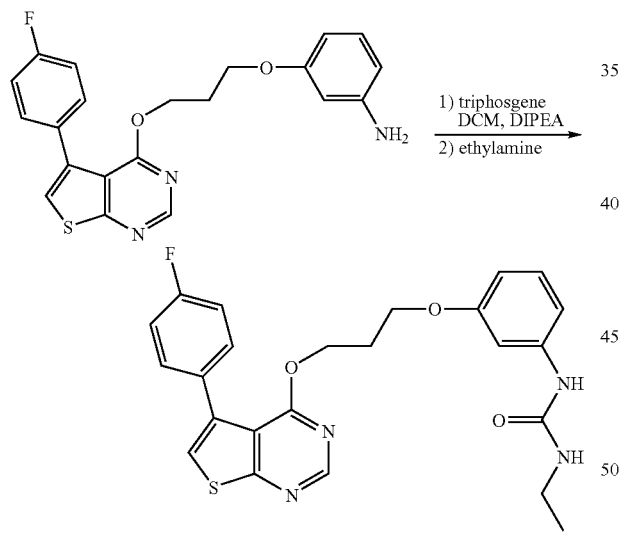

A mixture of 3-(3-{[5-(4-fluorophenyl)thieno[2,3-d]pyrimidin-4-yl]oxy}propoxy)aniline (25 mg, 0.063 mmol) and diisopropylethylamine (9.0 mg, 0.069 mmol) in dichloromethane (1.5 mL) was added in three portions over a period of 30 minutes to a solution of triphosgene (7.0 mg, 0.023 mmol) in dichloromethane (0.5 mL) while stirring at ambient temperature. Stirring continued for 15 minutes followed by the addition of ethylamine (0.075 mL, 2M in tetrahydrofuran). The reaction was stirred for 2 hours, then diluted with dichloromethane (30 mL) and washed with sodium bicarbonate (2×20 mL). The organic layer was dried (Na$_2$SO$_4$), concentrated, and purified by column chromatography over silica gel using 40% ethyl acetate in hexanes as eluant to give 15 mg (51%) of N-ethyl-N'-[3-(3-{[5-(4-fluorophenyl)thieno[2,3-d]pyrimidin-4-yl]oxy}propoxy)phenyl]urea as a white solid. MS [M+H] 467.3. $^1$H NMR (400 MHz, CDCl$_3$) δ (ppm) 8.64 (s, 1H), 7.45-7.38 (m, 2H), 7.21 (s, 1H), 7.18 (t, J=8.0 Hz, 1H), 7.06-7.01 (m, 2H), 6.82 (t, J=2.4 Hz, 1H), 6.79 (m, 1H), 6.50 (m, 1H), 4.58 (t, J=6.0 Hz, 2H), 3.72 (t, J=6.0 Hz, 2H), 3.30 (q, J=7.2 Hz, 2H), 2.06 (m, 2H), 1.16 (t, J=7.2 Hz, 3H).

The following compounds were synthesized in a similar manner using different starting materials:

44) N-[4-(3-{[5-(4-fluorophenyl)thieno[2,3-d]pyrimidin-4-yl]oxy}propoxy)phenyl]-N'-methylurea. MS [M+H] 453.5

45) N-ethyl-N'-[4-(3-{[5-(4-fluorophenyl)thieno[2,3-d]pyrimidin-4-yl]oxy}propoxy)-phenyl]urea. MS [M+H] 467.9

47) N-[3-(3-{[5-(4-fluorophenyl)thieno[2,3-d]pyrimidin-4-yl]oxy}propoxy)phenyl]-N'-methylurea. MS [M+H] 453.3

56) N-[4-(3-{[5-(4-fluorophenyl)thieno[2,3-d]pyrimidin-4-yl]oxy}propoxy)-phenyl]hydrazinecarboxamide. MS [M+H] 454.6

49) N-[3-(3-{[5-(4-fluorophenyl)thieno[2,3-d]pyrimidin-4-yl]oxy}propoxy)-phenyl]-N'-hydroxyurea. MS [M−H] 453.3

48) N-[3-(3-{[5-(4-fluorophenyl)thieno[2,3-d]pyrimidin-4-yl]oxy}propoxy)-phenyl]hydrazinecarboxamide. MS [M−H] 452.2

Example 17

66) N-Methyl-5-(3-[5-(1,3-thiazol-2-yl)thieno[2,3-d]pyrimidin-4-yl]aminopropoxy)pyridine-2-carboxamide

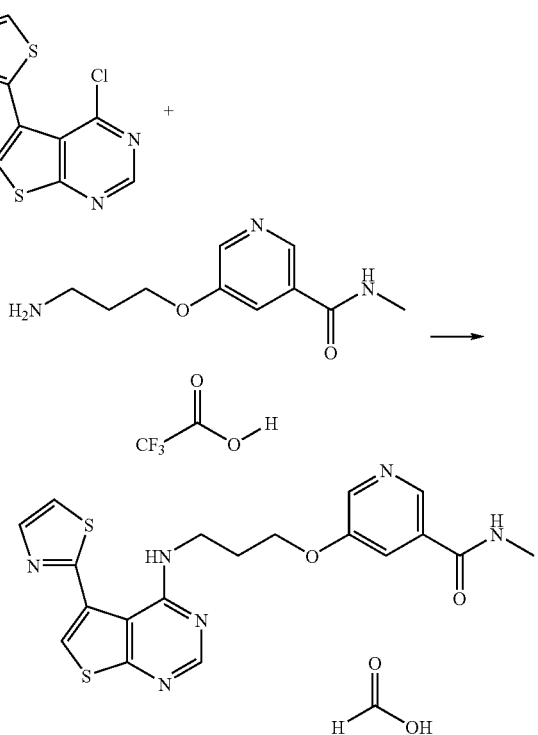

A mixture of 4-chloro-5-(1,3-thiazol-2-yl)thieno[2,3-d]pyrimidine (0.050 g, 0.20 mmol), 5-(3-aminopropoxy)-N-methylpyridine-2-carboxamide trifluoroacetate (0.070 g, 0.22 mmol), potassium carbonate (0.272 g, 1.97 mmol) and N,N-dimethylacetamide (2.4 mL) was heated at 120° C. for 13 h. The solvent was evaporated in vacuo, and the residue was treated with 5% sodium bicarbonate (20 mL) and ethyl acetate (20 mL). The precipitate was filtered and washed with water and ethyl ether. The resulting white solid was purified by column chromatography over silica gel to give 70 mg (81%) N-methyl-5-(3-[5-(1,3-thiazol-2-yl)thieno[2,3-d]pyrimidin-4-yl]aminopropoxy)pyridine-2-carboxamide. MS [M+H]=427, LC/MS (EI) $t_R$ 3.54 min (Method D), $^1$H NMR (10% MeOD/CDCl$_3$) δ (ppm) 10.85 (s, 1H), 8.30 (s, 1H), 8.12 (d, J=2.4 Hz, 1H), 8.00 (d, J=8.7 Hz, 1H), 7.94 (b, 1H), 7.71 (s, 1H), 7.50 (d, J=3.6 Hz, 1H), 7.28 (s, 1H), 7.21 (dd, J=8.7, 3.0 Hz, 1H), 4.15 (t, J=0.6 Hz, 2H), 3.80-3.74 (m, 2H), 2.94 (d, J=0.6 Hz, 3H), 2.24-2.18 (m, 2H).

The following compounds were synthesized in a similar manner using different starting materials:

13) N-[4-(3-{[5-(4-fluorophenyl)thieno[2,3-d]pyrimidin-4-yl]amino}propoxy)-phenyl]acetamide. MS[M+H] 437.2
67) 5-(3-{[5-(5-chloro-2-furyl)thieno[2,3-d]pyrimidin-4-yl])amino}propoxy)-N-methylpyridine-2-carboxamide, MS [M+H]=444, LC/MS (EI) $t_R$ 3.91 min (Method D)
68) N-methyl-5-{3-[(5-pyridin-3-ylthieno[2,3-d]pyrimidin-4-yl)amino]propoxy}pyridine-2-carboxamide, MS [M+H]=421, LC/MS (EI) $t_R$ 5.2 min (Method B)
69) N-methyl-5-{3-[(5-pyridin-2-ylthieno[2,3-d]pyrimidin-4-yl)amino]propoxy}pyridine-2-carboxamide, MS [M+H]=421, LC/MS (EI) $t_R$ 5.11 min (Method B)
70) N-methyl-5-{3-[(5-pyridin-2-ylthieno[2,3-d]pyrimidin-4-yl)amino]propoxy}nicotinamide, MS [M+H]=421.1, LC/MS (EI) $t_R$ 2.89 min (Method D)
82) 5-{3-[(5-pyrimidin-2-ylthieno[2,3-d]pyrimidin-4-yl)amino]propoxy}pyridine-2-carboxylic acid hydroformate, MS [M+H]=409.1, LC/MS (EI) $t_R$ 4.27 min (Method B)
83) 5-(3-{[5-(1,3-thiazol-2-yl)thieno[2,3-d]pyrimidin-4-yl]amino}propoxy)pyridine-2-carboxylic acid hydroformate, MS [M+H]=414.1, LC/MS (EI) $t_R$ 4.95 min (Method B)
84) 5-{3-[(5-pyrazin-2-ylthieno[2,3-d]pyrimidin-4-yl)amino]propoxy}pyridine-2-carboxylic acid hydroformate, MS [M+H]=409.1, LC/MS (EI) $t_R$ 4.11 min (Method B)
96) 5-{3-[(5-pyridin-3-ylthieno[2,3-d]pyrimidin-4-yl)amino]propoxy}pyridine-2-carboxamide hydroformate, MS [M+H]=407.1, LC/MS (EI) $t_R$ 4.12 min (Method B)
97) 5-(3-{[5-(1,3-thiazol-2-yl)thieno[2,3-d]pyrimidin-4-yl]amino}propoxy)pyridine-2-carboxamide hydroformate, MS [M+H]=413.1, LC/MS (EI) $t_R$ 5.49 min (Method B)

Example 18

87) Methyl 5-{4-[5-(4-fluorophenyl)thieno[2,3-d]pyrimidin-4-yl]butoxy}nicotinate

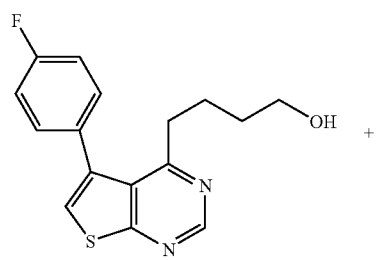

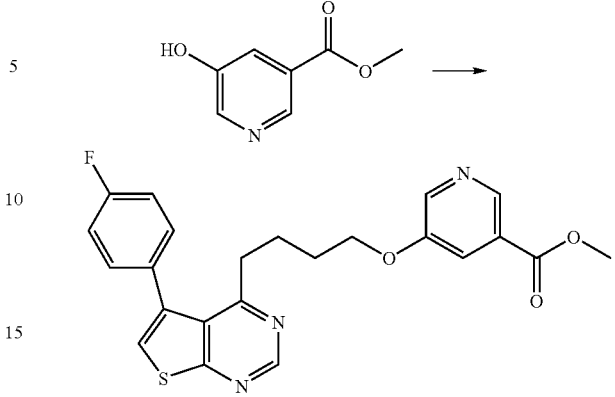

Diisopropyl azodicarboxylate (0.040 g, 0.20 mmol) was added to a mixture of 5-hydroxynicotinic acid methyl ester (0.038 g, 0.25 mmol), 4-[5-(4-fluorophenyl)thieno[2,3-d]pyrimidin-4-yl]butan-1-ol (0.060 g, 0.20 mmol), triphenylphosphine (0.052 g, 0.20 mol) and tetrahydrofuran (3.0 mL) at room temperature with stirring. After 16 h, the solvent was removed in vacuo. The residue was diluted with ethyl acetate (50 mL) and washed with sodium bicarbonate (1×40 mL). The organic solution was concentrated and purified by column chromatography (1.5-5% methanol/dichloromethane) to give 7 mg (8%) methyl 5-4-[5-(4-fluorophenyl)thieno[2,3-d]pyrimidin-4-yl]butoxynicotinate as white solid. MS [M+H]=438.1, LC/MS (EI) $t_R$ 4.63 min (Method D), $^1$H NMR (CDCl$_3$) δ (ppm) 9.02 (s, 1H), 8.82 (s, 1H), 8.38 (s, 1H), 7.68 (s, 1H), 7.42-7.35 (m, 2H), 7.34 (s, 1H), 7.20-7.10 (m, 2H), 3.97 (s, 3H), 3.88 (t, J=6.3 Hz, 2H), 2.72 (t, J=7.2 Hz, 2H), 1.81-1.66 (m, 2H), 1.66-1.53 (m, 2H).

The following compound was synthesized in a similar manner using different starting materials:
95) 5-(3-{[5-(4-fluorophenyl)thieno[2,3-d]pyrimidin-4-yl]oxy}propoxy)-1,3-dihydro-2H-indol-2-one, MS [M+H]=436.1, LC/MS (EI) $t_R$ 6.98 min (Method D)

Example 19

89) 5-{4-[5-(4-Fluorophenyl)thieno[2,3-d]pyrimidin-4-yl]butoxy}-N-methyl nicotinamide hydroformate

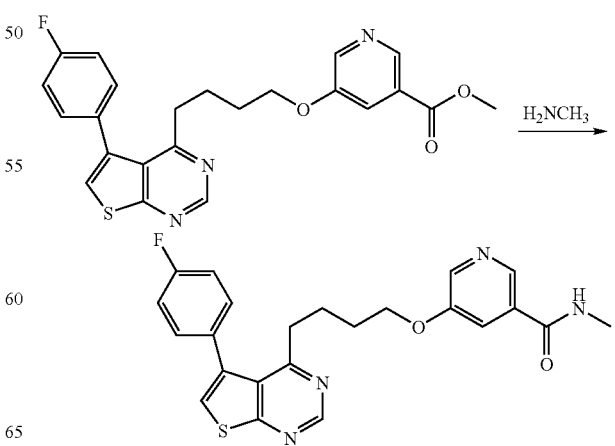

Methyl 5-{4-[5-(4-fluorophenyl)thieno[2,3-d]pyrimidin-4-yl]butoxy}nicotinate (0.010 g, 0.023 mmol) and methylamine (0.124 g, 0.004 mol) were mixed in 1-butanol (2.00 mL) and the resulting mixture subjected to microwave radiation for 2000 seconds at 170° C., followed by irradiation for 4000 seconds at 180° C. The solvent was removed by evaporation, and the product purified by preparative HPLC to give 2 mg (20%) 5-{4-[5-(4-fluorophenyl)thieno[2,3-d]pyrimidin-4-yl]butoxy}-N-methylnicotinamide hydroformate as a white solid. MS [M+H]=437.1, LC/MS (EI) $t_R$ 3.55 min (Method D), $^1$H NMR (10% MeOD/CDCl$_3$) δ (ppm) 8.93 (s, 1H), 8.43 (s, 1H), 8.20 (s, 1H), 7.70 (s, 1H), 7.60 (s, 1H), 7.40-7.28 (m, 4H), 7.11 (t, J=8.7 Hz, 2H), 3.84 (t, J=6.0 Hz, 2H), 2.95 (d, J=3.6 Hz, 3H), 2.67 (t, J=7.2 Hz, 2H), 1.75-1.59 (m, 2H), 1.59-1.45 (m, 2H)

Example 20

90) 5-{4-[5-(4-Fluorophenyl)thieno[2,3-d]pyrimidin-4-yl]butoxy}nicotinamide hydroformate

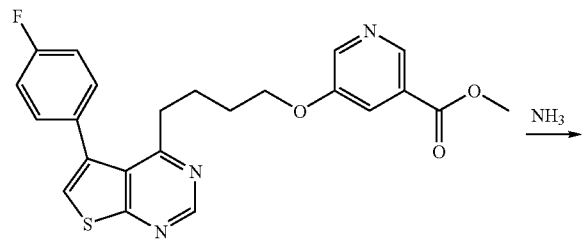

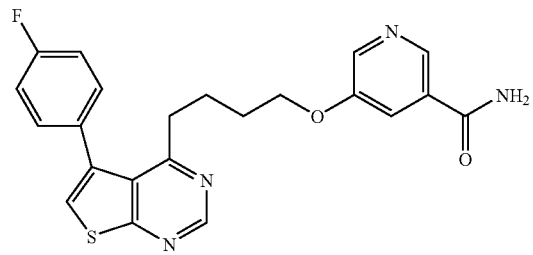

Methyl 5-{4-[5-(4-fluorophenyl)thieno[2,3-d]pyrimidin-4-yl]butoxy}nicotinate (0.015 g, 0.034 mmol) and ammonia (3.00 mL, 20%, 0.02 mol) were mixed in 1-butanol (1.00 mL) and the resulting mixture was heated at 180° C. for 20 h. The solvent was removed by evaporation, and the product was purified by preparative HPLC to give 5 mg (36%) 5-{4-[5-(4-fluorophenyl)thieno[2,3-d]pyrimidin-4-yl]butoxy}nicotinamide hydroformate as a white solid. MS [M+H]=423.1, LC/MS (EI) $t_R$ 3.45 min (Method D), $^1$H NMR (7% MeOD/CDCl$_3$) δ (ppm) 8.92 (s, 1H), 8.50 (s, 1H), 8.25 (s, 1H), 7.62 (s, 1H), 7.40-7.30 (m, 3H), 7.10 (t, J=8.4 Hz, 2H), 3.84 (t, J=6.0 Hz, 2H), 2.66 (t, J=7.5 Hz, 2H), 1.75-1.58 (m, 2H), 1.59-1.45 (m, 2H).

Example 21

91) N-[3-(3-[5-(4-Fluorophenyl)thieno[2,3-d]pyrimidin-4-yl]oxyphenoxy)phenyl]acetamide

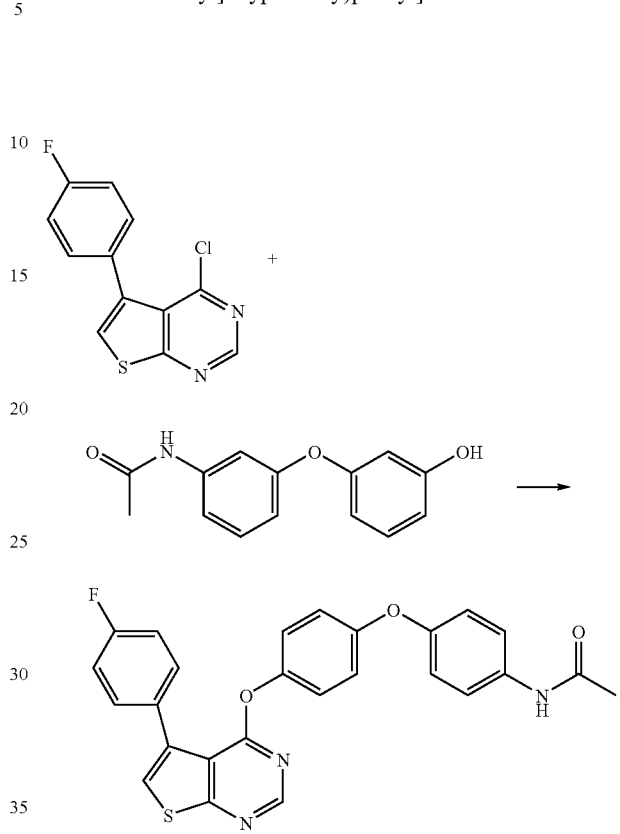

N-[3-(3-hydroxyphenoxy)phenyl]acetamide (0.032 g, 0.13 mmol) in N,N-dimethylacetamide (2.5 mL) was treated with sodium hydride (0.0063 g, 0.16 mol) at room temperature over a period of 1.5 h. 4-chloro-4-(4-fluorophenyl)thieno[2,3-d]pyrimidine (0.052 g, 0.20 mmol) was added, and the mixture was stirred at room temperature for 2 h. The reaction mixture was then treated with acetic acid (0.2 mL) for 5 min, and the solvent was evaporated in vacuo. The residue was dissolved in ethylacetate (50 mL) and washed with 5% solium bicarbonate (2×30 mL). The organic layer was concentrated and the product purified by silica gel chromatography (15% ethyl acetate/hexane) to afford 20 mg (32%) N-[3-(3-[5-(4-fluorophenyl)thieno[2,3-d]pyrimidin-4-yl]oxyphenoxy)phenyl]acetamide as colorless gum. MS [M+H]=472, LC/MS (EI) $t_R$ 7.57 min (Method D), $^1$H NMR (CDCl$_3$) δ (ppm) 8.65 (s, 1H), 8.50 (s, 1H), 7.58-7.48 (m, 2H), 7.35 (m, 2H), 7.33-7.27 (m, 3H), 7.25 (s, 1H), 7.21 (s, 1H), 7.09 (t, J=8.7 Hz, 2H), 6.93-6.84 (m, 3H), 6.84-6.74 (m, 2H), 2.17 (s, 3H)

The following compound was synthesized in a similar manner using different starting materials:

93) N-[3-(3-{[5-(1,3-thiazol-2-yl)thieno[2,3-d]pyrimidin-4-yl]oxy}phenoxy)phenyl]acetamide hydroformate, MS [M+H]=461, LC/MS (EI) $t_R$ 6.19 min (Method D)

Example 22

86) 4-But-3-en-1-yl-5-(4-fluorophenyl)thieno[2,3-d]pyrimidine

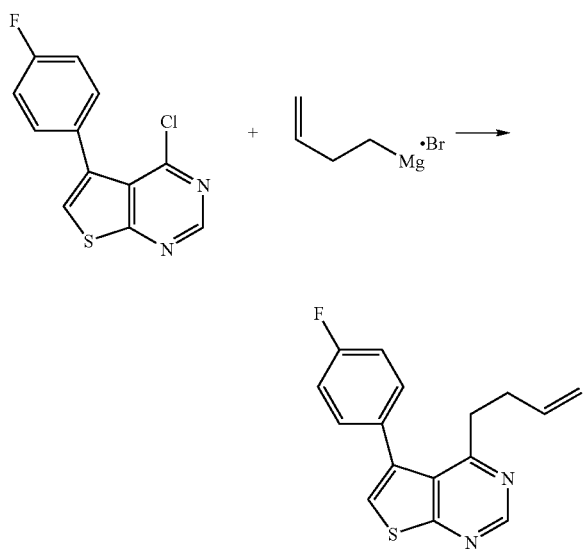

3-Butenylmagnesium bromide (0.0040 mol) was added to a solution of 4-chloro-5-(4-fluorophenyl)thieno[2,3-d]pyrimidine (0.529 g, 0.00200 mol), copper (I) iodide (0.038 g, 0.00020 mol) and ferrous bromide (0.043 g, 0.00020 mol) in tetrahydrofuran (10 mL) and the resulting mixture was maintained at room temperature for 5 h, then quenched by the addition of water (10 mL). Ethyl acetate (50 mL) was added and the mixture was filtered. The filtrate was washed with a saturated solution of sodium bicarbonate (40 mL) and the organics were concentrated and purified by silica gel column chromatography (using 15% ethyl acetate/hexane as eluent) to afford 4-But-3-en-1-yl-5-(4-fluorophenyl)thieno[2,3-d]pyrimidine as a white solid in 67% yield.

Example 23

85) 4-[5-(4-fluorophenyl)thieno[2,3-d]pyrimidin-4-yl]butan-1-ol

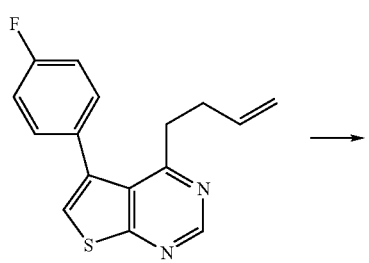

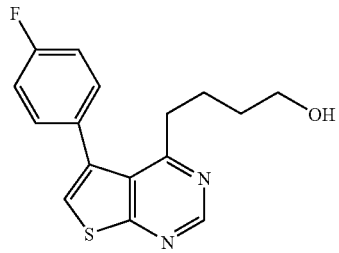

9-BBN (0.236 g, 0.00193 mol) in tetrahydrofuran (5.00 mL) was treated with 4-but-3-en-1-yl-5-(4-fluorophenyl)thieno[2,3-d]pyrimidine (0.500 g, 0.00176 mol) in tetrahydrofuran (3.0 mL) at 50° C. for 1 h. Ethanol (1.0 mL), 6 N sodium hydroxide (0.33 mL) and 30% hydrogen peroxide (0.67 mL) were then added successively and the resulting mixture was maintained at 50° C. for 1 h. The reaction was then cooled to room temperature, diluted with ethyl acetate (50 mL) and washed with sodium bicarbonate (2×30 mL). The organic layers were combined, concentrated and purified by column chromatography over silica gel (using ethyl acetate/hexane 1:5-1:1 as an eluent) to afford 4-[5-(4-fluorophenyl)thieno[2,3-d]pyrimidin-4-yl]butan-1-ol as a white solid in 47% yield.

Example 24

98) N-[4-(3-{[5-(4-fluorophenyl)thieno[2,3-d]pyrimidin-4yl]amino}propyl)phenyl]acetamide

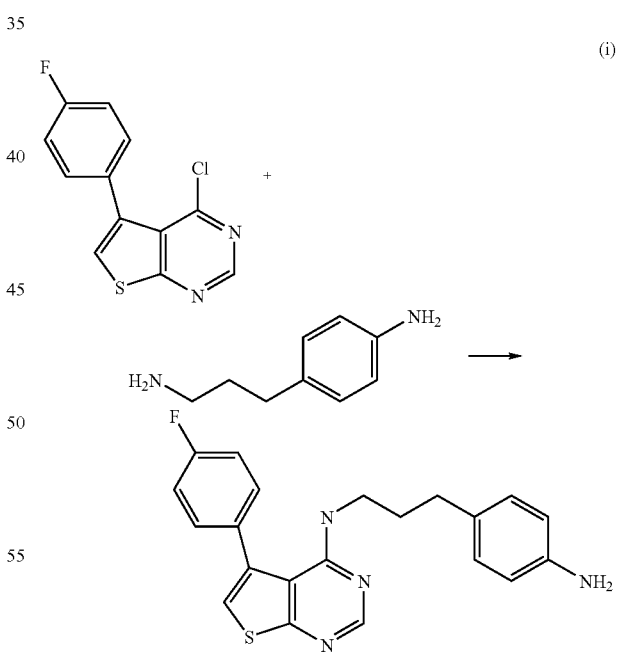

(i)

4-(3-aminopropyl)aniline (0.034 g, 0.23 mmol) was added to a solution of 4-chloro-5-(4-fluorophenyl)thieno[2,3-d]pyrimidine (0.04 g, 0.15 mmol), copper(I) iodide (0.009 g, 0.04 mmol) and potassium carbonate (0.0626 g, 0.453 mmol) in N,N-dimethylacetamide (3 mL) and the resulting mixture was subjected to microwave radiation at 140° C. for 4 hours. The solvent was then removed by evaporation, and the residue was dissolved in ethyl acetate (50 mL), filtered, and the organics were washed with a saturated solution of sodium bicarbonate (30 mL). Concentration and purification by silica gel column chromatography (using 1-3% methanol, 0.06% ammonia in 1:1 ethyl acetate/hexane) afforded N-[3-(4-aminophenyl)propyl]-5-(4-fluorophenyl)thieno[2,3-d]pyrimidin-4-amine as a white solid in 30% yield.

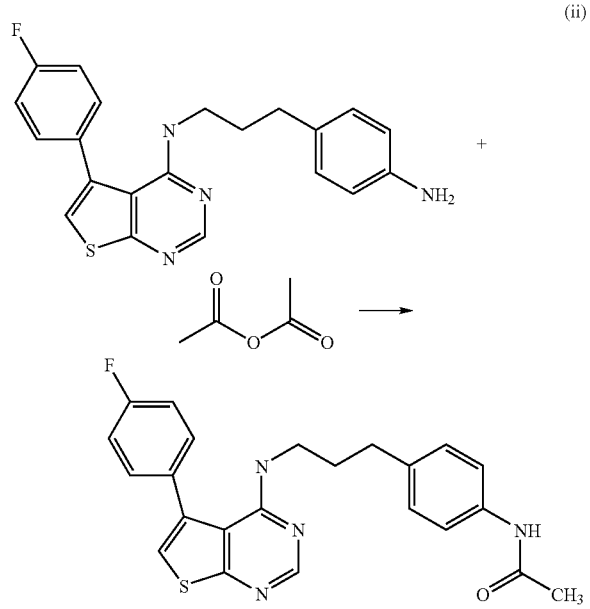

A mixture of N-[3-(4-aminophenyl)propyl]-5-(4-fluorophenyl)thieno[2,3-d]pyrimidin-4-amine (0.014 g, 0.037 mmol) and acetic anhydride (0.01 mL) in methylene chloride (2.0 mL) was heated to 60° C. for 6 h. The reaction was allowed to cool to room temperature and concentrated in vacuo. The residue was then dissolved in ethyl acetate (30 mL) and the organic layer was washed with sodium bicarbonate (2×25 mL). Concentration, followed by followed by silica gel column chromatography purification (using 3% methanol in 1:1 ethyl acetate/hexane and ammonia (0.03%) as eluent) afforded N-[4-(3-{[5-(4-fluorophenyl)thieno[2,3-d]pyrimidin-4-yl]amino}propyl)phenyl]acetamide in 90% yield.

Example 25

55) N-(3-{3-[(5-phenylthieno[2,3-d]pyrimidin-4-yl)oxy]propoxy}phenyl)acetamide

A mixture of 5-phenylthieno[2,3-d]pyrimidin-4(1H)-one (0.023 g, 0.10 mmol), N-[3-(3-bromopropoxy)phenyl]acetamide (0.0274 g, 0.10 mmol), potassium carbonate (0.0418 g, 0.30 mmol) and N,N-dimethylformamide (1.0 mL) was heated to 90° C. for 6 h. The reaction was then allowed to cool to room temperature and concentrated in vacuo. The residue was dissolved in ethyl acetate (30 mL), water (30 mL) was added, and the organic layer was separated, Concentration, followed by followed by silica gel column chromatography purification (using 1.50% methanol in 1:1 ethyl acetate/hexane and ammonia (0.03%) as eluent) afforded N-(3-{3-[(5-phenylthieno[2,3-d]pyrimidin-4-yl)oxy]propoxy}phenyl)acetamide in 66% yield. N-{4-[3-(4-oxo-5-phenylthieno[2,3-d]pyrimidin-1(4H)-yl)propoxy]phenyl}acetamide was also formed in 12% yield during the reaction.

Example 26 mPDE10A7 Enzyme Activity and Inhibition

To analyze the enzyme activity, 5 µl of serial diluted mPDE10A7 (PDE10A7 isoform enzyme) containing lysate were incubated with equal volumes of diluted (100-fold) fluorescein labeled cAMP or cGMP for 30 minutes in MDC HE 96-well assay plates at room temperature. Both the enzyme and the substrates were diluted in the following assay buffer: Tris/HCl (pH 8.0) 50 mM, $MgCl_2$ 5 mM, 2-mercaptoethanol 4 mM, BSA 0.33 mg/ml. After incubation, the reaction was stopped by adding 20 µl of diluted (400-fold) binding reagents and was incubated for an hour at room temperature. The plates were counted in an Analyst GT (Molecular Devices) for fluorescence polarization. An IMAP Assay kit (Molecular Device) was used to assess enzyme properties of mPDE10A7. Data were analyzed with SoftMax Pro.

To check the inhibition profile, 10 µl of serial diluted compounds were incubated with 30-µl of diluted PDE enzymes in a 96-well polystyrene assay plate for 30 minutes at room temperature. After incubation, 5 µl of the compound-enzyme mixture were aliquoted into a MDC HE black plate, mixed with 5 µl of 100-fold diluted fluorescein labeled substrates (cAMP or cGMP), and incubated for 30 minutes at room temperature. The reaction was stopped by adding 20 µl of diluted binding reagents and counted in an Analyst GT for fluorescence polarization. The data were analyzed with SoftMax Pro.

Certain chemical entities described herein show activity with $IC_{50}$ values of generally less than 5 µM, and in certain embodiments, less than 0.5 µM.

Example 27

Apomorphine Induced Deficits in Prepulse Inhibition of the Startle Response in Rats, an in vivo Test for Antipsychotic Activity The thought disorders that are characteristic of schizophrenia may result from an inability to filter, or gate, sensorimotor information. The ability to gate sensorimotor information can be tested in many animals as well as in humans. A test that is commonly used is the reversal of apomorphine-induced deficits in the prepulse inhibition of the startle response. The startle response is a reflex to a sudden intense stimulus such as a burst of noise. In this example, rats are exposed to a sudden burst of noise, at a level of 120 db for 40 msec, e.g. the reflex activity of the rats is measured. The reflex of the rats to the burst of noise may be attenuated by preceding the startle stimulus with a stimulus of lower intensity, at 3 to 12 db above background (65 db), which will attenuate the startle reflex by 20 to 80% (Geyer, M. A. and Swerdlow, N. R., Measurement of Startle Response, Prepulse Inhibition and Habituation, Unit 8.7 in Current Protocols in Neuroscience, 2003, John Wiley & Sons).

The prepulse inhibition of the startle reflex, described above, may be attenuated by drugs that affect receptor signaling pathways in the CNS. One commonly used drug is the dopamine receptor agonist apomorphine. Administration of apomorphine will reduce the inhibition of the startle reflex produced by the prepulse. Antipsychotic drugs such as haloperidol will prevent apomorphine from reducing the prepulse inhibition of the startle reflex. This assay may be used to test the antipsychotic efficacy of PDE10 inhibitors, as they reduce the apomorphine-induced deficit in the prepulse inhibition of startle. Therefore, PDE 10 inhibitors may be useful in restoring the deficits in sensorimotor gating that contribute to the thought disorders that characterize schizophrenia.

The preceding examples can be repeated with similar success by substituting the generically or specifically described reactants and/or operating conditions of this invention for those used in the preceding examples.

While the invention has been illustrated with respect to the production and of particular compounds, it is apparent that variations and modifications of the invention can be made without departing from the spirit or scope of the invention. Upon further study of the specification, further aspects, objects and advantages of this invention will become apparent to those skilled in the art.

We claim

1. A compound of Formula I:

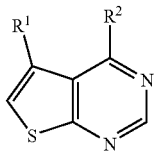

(Formula I)

or a pharmaceutically acceptable salt thereof, wherein
$R^1$ is chosen from:
  (i) $C_{6-10}$ aryl;
  (ii) substituted $C_{6-10}$ aryl chosen from mono-, di-, and tri-substituted aryl wherein the substituents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —$COR^9$, —$CSR^9$, —$SR^9$, cyano, hydroxyl, nitro, and thio;
  (iii) heterocyclyl;
  (iv) substituted heterocyclyl chosen from mono-, di-, and tri-substituted heterocyclyl wherein the substitutents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —$COR^9$, —$CSR^9$, —$SR^9$, cyano, hydroxyl, nitro, oxo, and thio;
  (v) heteroaryl; and
  (vi) substituted heteroaryl chosen from mono-, di-, and tri-substituted heteroaryl wherein the substitutents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —$COR^9$, —$CSR^9$, —$SR^9$, cyano, hydroxyl, nitro, oxo, and thio;
$R^2$ is chosen from $C_{2-4}$ hydroxyalkyl, $C_{2-4}$ alkenyl, $C_{2-4}$ alkenylene-$R^5$, $C_{2-4}$ alkynyl, $C_{2-4}$ alkynylene-$R^5$, —O-arylene-Y—$R^5$, —X(CR$^3$R$^4$)$_n$YR$^5$ and —(CR$^6$R$^7$)$_m$YR$^5$ where:
X is chosen from —O—, —S— and —NR$^9$—;
Y is chosen from —O—, —S— and —NR$^9$—;
n is chosen from 2, 3, 4, and 5;
m is chosen from 2, 3, 4, and 5;
$R^3$ and $R^4$ are each independently chosen from:
  (i) H;
  (ii) halo;
  (iii) $C_{1-12}$ alkyl;
  (iv) $C_{2-12}$ alkenyl;
  (v) $C_{2-12}$ alkynyl;
  (vi) $C_{3-12}$ cycloalkyl;
  (vii) substituted $C_{1-12}$ alkyl chosen from mono-, di-, and tri-substituted $C_{1-12}$ alkyl and wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl;
  (viii) substituted $C_{2-12}$ alkenyl chosen from mono-, di-, and tri-substituted $C_{2-12}$ alkenyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl;
  (ix) substituted $C_{2-12}$ alkynyl chosen from mono-, di-, and tri-substituted $C_{2-12}$ alkynyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl; and
  (x) substituted $C_{3-12}$ cycloalkyl chosen from mono-, di-, and tri-substituted $C_{3-12}$ cycloalkyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl;
$R^6$ and $R^7$ are independently chosen from
  (xi) H;
  (xii) halo;
  (xiii) $C_{1-12}$ alkyl;
  (xiv) $C_{2-12}$ alkenyl;
  (xv) $C_{2-12}$ alkynyl;
  (xvi) $C_{3-12}$ cycloalkyl;
  (xvii) substituted $C_{1-12}$ alkyl chosen from mono-, di-, and tri-substituted $C_{1-12}$ alkyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl;
  (xviii) substituted $C_{2-12}$ alkenyl chosen from mono-, di-, and tri-substituted $C_{2-12}$ alkenyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl;
  (xix) substituted $C_{2-12}$ alkynyl chosen from mono-, di-, and tri-substituted $C_{2-12}$ alkynyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl; and (xx) substituted $C_{3-12}$ cycloalkyl chosen from mono-, di-, and tri-substituted $C_{3-12}$ cycloalkyl wherein the substituents are independently chosen from halo, hydroxy, $C_{1-4}$-alkoxy, halogenated $C_{1-4}$ alkoxy, nitro, cyano, carboxy, amino, $C_{1-4}$ alkylamino, di-$C_{1-4}$-alkylamino, $C_{1-4}$-hydroxyalkyl, $C_{2-4}$-hydroxyalkoxy, $C_{1-4}$-alkylthio, $C_{1-4}$-alkylsulphinyl, and $C_{1-4}$-alkylsulphonyl; and $R^5$ is chosen from $C_{6-10}$ aryl, substituted $C_{6-10}$ aryl, Het, substituted Het, $C_{6-10}$ aryl-$C_{1-8}$ alkyl, substituted $C_{1-10}$ aryl-$C_{1-8}$ alkyl, Het-$C_{1-8}$ alkyl, and substituted Het-$C_{1-8}$ alkyl, wherein the alkyl portions of $C_{6-10}$ aryl-$C_{1-8}$ alkyl and Het-$C_{1-8}$ alkyl are optionally substituted by oxo and wherein:

substituted $C_{6-10}$ aryl is chosen from mono-, di-, and tri-substituted $C_{6-10}$ aryl wherein the substituents are independently chosen from
(1) $C_{1-8}$ alkyl,
(2) $C_{3-8}$ cycloalkyl,
(3) $C_{4-8}$ cycloalkylalkyl,
(4) $C_{1-8}$ alkoxy,
(5) $C_{3-8}$ cycloalkoxy,
(6) $C_{4-8}$ cycloalkylalkoxy,
(7) halo,
(8) amino,
(9) cyano,
(10) hydroxyl,
(11) nitro,
(12) $C_{1-8}$ halogenated alkyl,
(13) $C_{1-8}$ halogenated alkoxy,
(14) $C_{1-8}$ hydroxyalkyl,
(15) $C_{2-8}$ hydroxyalkoxy,
(16) $C_{3-8}$ alkenyloxy,
(17) $C_{1-8}$ alkylamino,
(18) di-$C_{1-8}$ alkylamino,
(19) carboxy,
(20) alkoxycarbonyl,
(21) carboxamido,
(22) aminocarbonyl,
(23) hydroxyaminocarbonyl,
(24) alkylaminocarbonyl,
(25) dialkylaminocarbonyl,
(26) urea,
(27) hydroxyurea,
(28) alkylurea,
(29) dialkylaminoalkylcarbonyl,
(30) aminocarbonylalkylaminocarbonyl,
(31) acylamido,
(32) HCO—NH—NH—CO—,
(33) $NH_2NHCO$—,
(34) $NH_2NHCONH$—,
(35) acyloxy,
(36) $C_{1-8}$ alkylthio,
(37) $C_{1-8}$ alkylsulphinyl,
(38) $C_{1-8}$ alkylsulphonyl,
(39) $C_{1-8}$ alkylsulphonamido,
(40) (alkylsuphonyl)$_2$amino-,
(41) thiol group,
(42) aminosulfonyl,
(43) alkylaminosulfonyl,
(44) $C_{6-10}$ aryl,
(45) substituted $C_{6-10}$ aryl chosen from mono-, di-, and trisubstituted $C_{6-10}$ aryl wherein the substituents are independently chosen from $C_{1-8}$ alkyl, halogenated $C_{1-8}$ alkyl, $C_{1-4}$ alkoxy, halogenated $C_{1-4}$ alkoxy, $C_{1-8}$ hydroxyalkyl, $C_{2-8}$ hydroxyalkoxy, amino, $C_{1-8}$alkylamino, di-$C_{1-8}$ alkylamino, $C_{1-8}$ alkylsulphinyl, $C_{1-8}$ alkylsulphonyl, $C_{1-8}$ alkylsulphonamido, —$COR^9$, —$CSR^9$, —$SR^9$, cyano, hydroxyl, nitro, and thio;
(46) heterocyclyl;
(47) substituted heterocyclyl chosen from mono-, di-, and trisubstituted heterocyclyl wherein the substitutents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —$COR^9$, —$CSR^9$, —$SR^9$, cyano, hydroxyl, nitro, oxo, and thio;
(48) heterocyclyl-carbonyl; and
(49) substituted heterocyclyl-carbonyl chosen from mono-, di-, and trisubstituted heterocyclyl-carbonyl wherein the substituents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —$COR^9$, —$CSR^9$, —$SR^9$, cyano, hydroxyl, nitro, oxo, and thio; and Het is chosen from heterocyclyl, substituted heterocyclyl chosen from mono-, di-, and tri-substituted heterocyclyl, heteroaryl, and substituted heteroaryl chosen from mono-, di-, and tri-substituted heteroaryl, wherein the substituents are independently chosen from
(1) $C_{1-8}$ alkyl,
(2) $C_{3-8}$ cycloalkyl,
(3) $C_{4-8}$ cycloalkylalkyl,
(4) $C_{1-8}$ alkoxy,
(5) $C_{3-8}$ cycloalkoxy,
(6) $C_{4-8}$ cycloalkylalkoxy,
(7) halo,
(8) amino,
(9) cyano,
(10) hydroxyl,
(11) nitro,
(12) $C_{1-8}$ halogenated alkyl,
(13) $C_{1-8}$ halogenated alkoxy,
(14) $C_{1-8}$ hydroxyalkyl,
(15) $C_{2-8}$ hydroxyalkoxy
(16) $C_{3-8}$ alkenyloxy,
(17) $C_{1-8}$ alkylamino,
(18) di-$C_{1-8}$ alkylamino,
(19) carboxy,
(20) alkoxycarbonyl,
(21) carboxamido,
(22) aminocarbonyl,
(23) hydroxyaminocarbonyl,
(24) alkylaminocarbonyl,
(25) dialkylaminocarbonyl,
(26) urea,
(27) hydroxyurea,
(28) alkylurea,
(29) dialkylaminoalkylcarbonyl,
(30) aminocarbonylalkylaminocarbonyl,
(31) acylamido,

(32) HCO—NH—NH—CO—,
(33) NH$_2$NHCO—,
(34) NH$_2$NHCONH—,
(35) acyloxy,
(36) C$_{1-8}$ alkylthio,
(37) C$_{1-8}$ alkylsulphinyl,
(38) C$_{1-8}$ alkylsulphonyl,
(39) C$_{1-8}$ alkylsulphonamido,
(40) (alkylsuphonyl)$_2$amino-,
(41) thiol group,
(42) aminosulfonyl,
(43) alkylaminosulfonyl,
(44) oxo,
(45) C$_{6-20}$ aryl,
(46) substituted C$_{6-20}$ aryl chosen from mono-, di-, and tri-substituted C$_{6-20}$ aryl wherein the substituents are independently chosen from halo, C$_{1-8}$ alkyl, halogenated C$_{1-8}$ alkyl, C$_{1-4}$ alkoxy, halogenated C$_{1-4}$ alkoxy, C$_{1-8}$ hydroxyalkyl, C$_{2-8}$ hydroxyalkoxy, amino, C$_{1-8}$ alkylamino, di-C$_{1-8}$ alkylamino, C$_{1-8}$ alkylsulphinyl, C$_{1-8}$ alkylsulphonyl, C$_{1-8}$ alkylsulphonamido, —COR$^9$, —CSR$^9$, —SR$^9$, cyano, hydroxyl, nitro, and thio,
(47) heterocyclyl,
(48) substituted heterocyclyl chosen from mono-, di-, and trisubstituted heterocyclyl wherein the substituents are independently chosen from halo, C$_{1-8}$ alkyl, halogenated C$_{1-8}$ alkyl, C$_{1-4}$ alkoxy, halogenated C$_{1-4}$ alkoxy, hydroxy C$_{1-8}$ alkyl, hydroxy C$_{2-8}$ alkoxy, amino, C$_{1-8}$ alkylamino, di-C$_{1-8}$ alkylamino, C$_{1-8}$ alkylsulphinyl, C$_{1-8}$ alkylsulphonyl, C$_{1-8}$ alkylsulphonamido, —COR$^9$, —CSR$^9$, —SR$^9$, cyano, hydroxyl, nitro, oxo, and thio,
(49) heteroaryl,
(50) substituted heteroaryl chosen from mono-, di-, and trisubstituted heteroaryl wherein the substituents are independently chosen from halo, C$_{1-8}$ alkyl, halogenated C$_{1-8}$ alkyl, C$_{1-4}$ alkoxy, halogenated C$_{1-4}$ alkoxy, hydroxy C$_{1-8}$ alkyl, hydroxy C$_{2-8}$ alkoxy, amino, C$_{1-8}$ alkylamino, di-C$_{1-8}$ alkylamino, C$_{1-8}$ alkylsulphinyl, C$_{1-8}$ alkylsulphonyl, C$_{1-8}$ alkylsulphonamido, —COR$^9$, —CSR$^9$, —SR$^9$, cyano, hydroxyl, nitro, oxo, and thio,
(51) heterocyclyl-carbonyl,
(52) substituted heterocyclyl-carbonyl chosen from mono-, di-, and trisubstituted heterocyclyl-carbonyl wherein the substituents are independently chosen from halo, C$_{1-8}$alkyl, halogenated C$_{1-8}$ alkyl, C$_{1-4}$alkoxy, halogenated C$_{1-4}$ alkoxy, hydroxy C$_{1-8}$ alkyl, hydroxy C$_{2-8}$ alkoxy, amino, C$_{1-8}$ alkylamino, di-C$_{1-8}$ alkylamino, C$_{1-8}$ alkylsulphinyl, C$_{1-8}$ alkylsulphonyl, C$_{1-8}$ alkylsulphonamido, —COR$^9$, —CSR$^9$, —SR$^9$, cyano, hydroxyl, nitro, oxo, and thio,
(53) heteroaryl-carbonyl, and
(54) substituted heteroaryl-carbonyl chosen from mono-, di-, and trisubstituted heteroaryl-carbonyl wherein the substituents are independently chosen from halo, C$_{1-8}$ alkyl, halogenated C$_{1-8}$ alkyl, C$_{1-4}$ alkoxy, halogenated C$_{1-4}$ alkoxy, hydroxy C$_{1-8}$ alkyl, hydroxy C$_{2-8}$ alkoxy, amino, C$_{1-8}$ alkylamino, di-C$_{1-8}$alkylamino, C$_{1-8}$ alkylsulphinyl, C$_{1-8}$ alkylsulphonyl, C$_{1-8}$ alkylsulphonamido, —COR$^9$, —CSR$^9$, —SR$^9$, cyano, hydroxyl, nitro, oxo, and thio, and R$^9$ is chosen from H, C$_{1-8}$ alkyl, C$_{3-8}$ cycloalkyl, substituted C$_{1-8}$ alkyl chosen from mono-, di-, and trisubstituted C$_{1-8}$ alkyl, and substituted C$_{3-8}$ cycloalkyl chosen from mono-, di-, and trisubstituted C$_{3-8}$ cycloalkyl wherein the substituents are independently chosen from halo, C$_{1-4}$-alkyl, C$_{1-4}$-alkoxy, and oxo; and provided that the compound of Formula I is not chosen from:
(i) when R$^1$ is 4-methylphenyl, then R$^2$ is not —O-p-phenylene-O—(CH$_2$)phenyl, —O-p-phenylene-NH—C(O)-thiophen-2-yl, or —O—(CH$_2$)$_2$—O-(phenyl);
(ii) when R$^1$ is phenyl, then R$^2$ is not —O-p-phenylene-NH—C(O)-3, -4-dimethoxyphenyl, —O—(CH$_2$)$_2$—O-(4-methylphenyl),
—O—(CH$_2$)$_2$—O-phenyl, —O 13 (CH$_2$)$_2$—O-(3-bromophenyl),
—NH—(CH$_2$)$_2$—NH(3-CF$_3$-pyridin-2-yl),
—S—(CH$_2$)$_2$—O-(3-methylphenyl),
—S—(CH$_2$)$_2$—O-(4-F-phenyl), —S—(CH$_2$)$_2$—O-(2,4-dichlorophenyl),
—NH—(CH$_2$)$_2$—NH(4-CF$_3$-pyrimidin-2-yl), or —NH—(CH$_2$)$_2$—O-(3-acetylaminophenyl);
(iii) when R$^1$ is 4-fluorophenyl, then R$^2$ is not chosen from
—O—(CH$_2$)$_2$—O-(2-chlorophenyl) and —O—(CH$_2$)$_2$—O-(4-fluorophenyl);
(iv) when R$^1$ is 4-chlorophenyl, then R$^2$ is not chosen from —O-p-phenylene-O—CH$_2$-phenyl and —O—(CH$_2$)$_2$—O-(4-methylphenyl);
(v) when R$^1$ is 3-methylphenyl, then R$^2$ is not —O—(CH$_2$)$_2$—O-(phenyl);
(vi) when R$^1$ is 3,4-dimethylphenyl, then R$^2$ is not chosen from —O-p-phenylene-O—CH$_2$-phenyl; and
(vii) 5-(2-chlorophenyl)-4-[4-(phenylmethoxy)phenoxy]-thieno[2,3-d]pyrimidine.

2. A compound according to claim 1 wherein R$^5$ is chosen from pyridin-3-yl and pyridin-4-yl, each of which is optionally substituted with one or two groups chosen from
(1) C$_{1-8}$ alkyl,
(2) C$_{3-8}$ cycloalkyl,
(3) C$_{4-8}$ cycloalkylalkyl,
(4) C$_{1-8}$ alkoxy,
(5) C$_{3-8}$ cycloalkoxy,
(6) C$_{4-8}$ cycloalkylalkoxy,
(7) halo,
(8) amino,
(9) cyano,
(10) hydroxyl,
(11) nitro,
(12) C$_{1-8}$ halogenated alkyl,
(13) C$_{1-8}$ halogenated alkoxy,
(14) C$_{1-8}$ hydroxyalkyl,
(15) C$_{2-8}$ hydroxyalkoxy
(16) C$_{3-8}$ alkenyloxy,
(17) C$_{1-8}$ alkylamino,
(18) di-C$_{1-8}$ alkylamino,
(19) carboxy,
(20) alkoxycarbonyl,
(21) carboxamido,
(22) aminocarbonyl,
(23) hydroxyaminocarbonyl,
(24) alkylaminocarbonyl,
(25) dialkylaminocarbonyl,
(26) urea,
(27) hydroxyurea,
(28) alkylurea,
(29) dialkylaminoalkylcarbonyl,
(30) aminocarbonylalkylaminocarbonyl,
(31) acylamido,
(32) HCO—NH—NH—CO—,
(33) NH$_2$NHCO—,

(34) NH$_2$NHCONH—,
(35) acyloxy,
(36) C$_{1-8}$ alkylthio,
(37) C$_{1-8}$ alkylsulphinyl,
(38) C$_{1-8}$ alkylsulphonyl,
(39) C$_{1-8}$ alkylsulphonamido,
(40) (alkylsuphonyl)$_2$amino-,
(41) thiol group,
(42) aminosulfonyl,
(43) alkylaminosulfonyl,
(44) oxo,
(45) C$_{6-20}$ aryl,
(46) substituted C$_{6-20}$ aryl chosen from mono-, di-, and tri-substituted C$_{6-20}$ aryl wherein the substituents are independently chosen from halo, C$_{1-8}$ alkyl, halogenated C$_{1-8}$ alkyl, C$_{1-4}$ alkoxy, halogenated C$_{1-4}$ alkoxy, C$_{1-8}$ hydroxyalkyl, C$_{2-8}$ hydroxyalkoxy, amino, C$_{1-8}$ alkylamino, di-C$_{1-8}$ alkylamino, C$_{1-8}$ alkylsulphinyl, C$_{1-8}$ alkylsulphonyl, C$_{1-8}$alkylsulphonamido, —COR$^9$, —CSR$^9$, —SR$^9$, cyano, hydroxyl, nitro, and thio,
(47) heterocyclyl,
(48) substituted heterocyclyl chosen from mono-, di-, and trisubstituted heterocyclyl wherein the substituents are independently chosen from halo, C$_{1-8}$alkyl, halogenated C$_{1-8}$ alkyl, C$_{1-4}$ alkoxy, halogenated C$_{1-4}$ alkoxy, hydroxy C$_{1-8}$ alkyl, hydroxy C$_{2-8}$ alkoxy, amino, C$_{1-8}$ alkylamino, di-C$_{1-8}$ alkylamino, C$_{1-8}$ alkylsulphinyl, C$_{1-8}$ alkylsulphonyl, C$_{1-8}$ alkylsulphonamido, —COR$^9$, —CSR$^9$, —SR$^9$, cyano, hydroxyl, nitro, oxo, and thio,
(49) heteroaryl,
(50) substituted heteroaryl chosen from mono-, di-, and trisubstituted heteroaryl wherein the substituents are independently chosen from halo, C$_{1-8}$alkyl, halogenated C$_{1-8}$ alkyl, C$_{1-4}$alkoxy, halogenated C$_{1-4}$ alkoxy, hydroxy C$_{1-8}$ alkyl, hydroxy C$_{2-8}$ alkoxy, amino, C$_{1-8}$ alkylamino, di-C$_{1-8}$ alkylamino, C$_{1-8}$ alkylsulphinyl, C$_{1-8}$ alkylsulphonyl, C$_{1-8}$ alkylsulphonamido, —COR$^9$, —CSR$^9$, —SR$^9$, cyano, hydroxyl, nitro, oxo, and thio,
(51) heterocyclyl-carbonyl,
(52) substituted heterocyclyl-carbonyl chosen from mono-, di-, and trisubstituted heterocyclyl-carbonyl wherein the substituents are independently chosen from halo, C$_{1-8}$ alkyl, halogenated C$_{1-8}$ alkyl, C$_{1-4}$ alkoxy, halogenated C$_{1-4}$ alkoxy, hydroxy C$_{1-8}$ alkyl, hydroxy C$_{2-8}$alkoxy, amino, C$_{1-8}$ alkylamino, di-C$_{1-8}$ alkylamino, C$_{1-8}$ alkylsulphinyl, C$_{1-8}$ alkylsulphonyl, C$_{1-8}$ alkylsulphonamido, —COR$^9$, —CSR$^9$, —SR$^9$, cyano, hydroxyl, nitro, oxo, and thio,
(53) heteroaryl-carbonyl, and
(54) substituted heteroaryl-carbonyl chosen from mono-, di-, and trisubstituted heteroaryl-carbonyl wherein the substituents are independently chosen from halo, C$_{1-8}$ alkyl, halogenated C$_{1-8}$ alkyl, C$_{1-4}$ alkoxy, halogenated C$_{1-4}$ alkoxy, hydroxy C$_{1-8}$ alkyl, hydroxy C$_{2-8}$alkoxy, amino, C$_{1-8}$ alkylamino, di-C$_{1-8}$ alkylamino, C$_{1-8}$ alkylsulphinyl, C$_{1-8}$ alkylsulphonyl, C$_{1-8}$ alkylsulphonamido, —COR$^9$, —CSR$^9$, —SR$^9$, cyano, hydroxyl, nitro, oxo, and thio.

3. A compound according to claim 1 wherein R$^5$ is chosen from pyridin-2-yl and pyridin-4-yl, each of which is optionally substituted with one or two groups chosen from
(1) C$_{1-8}$ alkyl,
(2) C$_{3-8}$ cycloalkyl,
(3) C$_{4-8}$ cycloalkylalkyl,
(4) C$_{1-8}$ alkoxy,
(5) C$_{3-8}$ cycloalkoxy,
(6) C$_{4-8}$ cycloalkylalkoxy,
(7) halo,
(8) amino,
(9) cyano,
(10) hydroxyl,
(11) nitro,
(12) C$_{2-8}$ halogenated alkyl,
(13) C$_{1-8}$ halogenated alkoxy,
(14) C$_{1-8}$ hydroxyalkyl,
(15) C$_{2-8}$ hydroxyalkoxy,
(16) C$_{3-8}$ alkenyloxy,
(17) C$_{1-8}$ alkylamino,
(18) di-C$_{1-8}$ alkylamino,
(19) carboxy,
(20) alkoxycarbonyl,
(21) carboxamido,
(22) aminocarbonyl,
(23) hydroxyaminocarbonyl,
(24) alkylaminocarbonyl,
(25) dialkylaminocarbonyl,
(26) urea,
(27) hydroxyurea,
(28) alkylurea,
(29) dialkylaminoalkylcarbonyl,
(30) aminocarbonylalkylaminocarbonyl,
(31) acylamido,
(32) HCO—NH—NH—CO—,
(33) NH$_2$NHCO—,
(34) NH$_2$NHCONH—,
(35) acyloxy,
(36) C$_{1-8}$ alkylthio,
(37) C$_{1-8}$ alkylsulphinyl,
(38) C$_{1-8}$ alkylsulphonyl,
(39) C$_{1-8}$ alkylsulphonamido,
(40) (alkylsuphonyl)$_2$amino-,
(41) thiol group,
(42) aminosulfonyl,
(43) alkylaminosulfonyl,
(44) oxo,
(45) C$_{6-20}$ aryl,
(46) substituted C$_{6-20}$ aryl chosen from mono-, di-, and tri-substituted C$_{6-20}$ aryl wherein the substituents are independently chosen from halo, C$_{1-8}$alkyl, halogenated C$_{1-8}$ alkyl, C$_{1-4}$alkoxy, halogenated C$_{1-4}$ alkoxy, hydroxy C$_{1-8}$ alkyl, hydroxy C$_{2-8}$ alkoxy, amino, C$_{1-8}$ alkylamino, di-C$_{1-8}$ alkylamino, C$_{1-8}$ alkylsulphinyl, C$_{1-8}$ alkylsulphonyl, C$_{1-8}$ alkylsulphonamido, —COR$^9$, —CSR$^9$, —SR$^9$, cyano, hydroxyl, nitro, and thio,
(47) heterocyclyl,
(48) substituted heterocyclyl chosen from mono-, di-, and trisubstituted heterocyclyl wherein the substituents are independently chosen from halo, C$_{1-8}$ alkyl, halogenated C$_{1-8}$ alkyl, C$_{1-4}$ alkoxy, halogenated C$_{1-4}$ alkoxy, hydroxy C$_{1-8}$ alkyl, hydroxy C$_{2-8}$ alkoxy, amino, C$_{1-8}$ alkylamino, di-C$_{1-8}$ alkylamino, C$_{1-8}$ alkylsulphinyl, C$_{1-8}$ alkylsulphonyl, C$_{1-8}$ alkylsulphonamido, —COR$^9$, —CSR$^9$, —SR$^9$, cyano, hydroxyl, nitro, oxo, and thio,
(49) heteroaryl,
(50) substituted heteroaryl chosen from mono-, di-, and trisubstituted heteroaryl wherein the substituents are independently chosen from halo, C$_{1-8}$ alkyl, halogenated C$_{1-8}$ alkyl, C$_{1-4}$ alkoxy, halogenated C$_{1-4}$ alkoxy, hydroxy C$_{1-8}$ alkyl, hydroxy C$_{2-8}$ alkoxy, amino, C$_{1-8}$ alkylamino, di-C$_{1-8}$ alkylamino, C$_{1-8}$ alkylsulphinyl, C$_{1-8}$ alkylsulphonyl, C$_{1-8}$ alkylsulphonamido, —COR$^9$, —CSR$^9$, —SR$^9$, cyano, hydroxyl, nitro, oxo, and thio,

(51) heterocyclyl-carbonyl,
(52) substituted heterocyclyl-carbonyl chosen from mono-, di-, and trisubstituted heterocyclyl-carbonyl wherein the substituents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$ alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —$COR^9$, —$CSR^9$, —$SR^9$, cyano, hydroxyl, nitro, oxo, and thio,
(53) heteroaryl-carbonyl, and
(54) substituted heteroaryl-carbonyl chosen from mono-, di-, and trisubstituted heteroaryl-carbonyl wherein the substituents are independently chosen from halo, $C_{1-8}$ alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$alkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —$COR^9$, —$CSR^9$, —$SR^9$, cyano, hydroxyl, nitro, oxo, and thio.

4. A compound according to claim 1 wherein the compound of Formula I is chosen from compounds of Formula II:

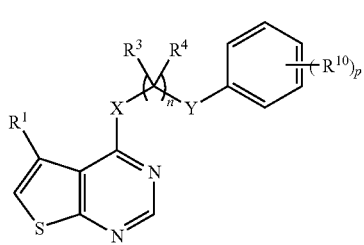

(Formula II)

wherein
p is chosen from 1, 2, and 3; and
for each occurrence, $R^{10}$ is independently chosen from
(1) $C_{1-8}$ alkyl,
(2) $C_{3-8}$ cycloalkyl,
(3) $C_{4-8}$ cycloalkylalkyl,
(4) $C_{3-8}$ cycloalkoxy,
(5) $C_{4-8}$ cycloalkylalkoxy,
(6) amino,
(7) cyano,
(8) nitro,
(9) $C_{1-8}$ halogenated alkyl,
(10) $C_{1-8}$ halogenated alkoxy,
(11) $C_{1-8}$ hydroxyalkyl,
(12) $C_{2-8}$ hydroxyalkoxy,
(13) $C_{1-8}$ alkylamino,
(14) di-$C_{1-8}$alkylamino,
(15) carboxy,
(16) alkoxycarbonyl,
(17) aminocarbonyl,
(18) hydroxyaminocarbonyl,
(19) alkylaminocarbonyl,
(20) dialkylaminocarbonyl,
(21) urea,
(22) hydroxyurea,
(23) alkylurea,
(24) dialkylaminoalkylcarbonyl,
(25) aminocarbonylalkylaminocarbonyl,
(26) acylamido,
(27) HCO—NH—NH—CO—,
(28) $NH_2NHCO$—,
(29) $NH_2NHCONH$—,
(30) acyloxy,
(31) $C_{1-8}$ alkylthio,
(32) $C_{1-8}$ alkylsulphinyl,
(33) $C_{1-8}$ alkylsulphonyl,
(34) $C_{1-8}$ alkylsulphonamido,
(35) (alkylsuphonyl)$_2$amino,
(36) thiol,
(37) aminosulfonyl,
(38) alkylaminosulfonyl,
(39) $C_{6-20}$ aryl,
(40) substituted $C_{6-20}$ aryl chosen from mono-, di-, and tri-substituted $C_{6-20}$ aryl wherein the substituents are independently chosen from halo, $C_{1-8}$ alkyl, halogenated $C_{1-8}$ alkyl, $C_{1-4}$ alkoxy, halogenated $C_{1-4}$ alkoxy, $C_{1-8}$ hydroxyalkyl, $C_{2-8}$ hydroxyalkoxy, amino, $C_{1-8}$ alkylamino, di-$C_{1-8}$ alkylamino, $C_{1-8}$ alkylsulphinyl, $C_{1-8}$ alkylsulphonyl, $C_{1-8}$ alkylsulphonamido, —$COR^9$, —$CSR^9$, —$SR^9$, cyano, hydroxyl, nitro, and thio,
(41) heterocyclyl-carbonyl and,
(42) substituted heterocyclyl-carbonyl chosen from mono-, di-, and trisubstituted heterocyclyl-carbonyl wherein the substituents are independently chosen from halo, $C_{1-8}$alkyl, halogenated $C_{1-8}$ alkyl, $C_{1-4}$ alkoxy, halogenated $C_{1-4}$ alkoxy, hydroxy $C_{1-8}$ alkyl, hydroxy $C_{2-8}$alkoxy, amino, $C_{1-8}$alkylamino, di-$C_{1-8}$ alkylamino, $C_{1-8}$ alkylsulphinyl, $C_{1-8}$alkylsulphonyl, $C_{1-8}$alkylsulphonamido, —$COR^9$, —$CSR^9$, —$SR^9$, cyano, hydroxyl, nitro, oxo, and thio.

5. A compound according to claim 1 wherein $R^2$ is chosen from —O-arylene-Y—$R^5$, —$X(CR^3R^4)_nYR^5$ and —$(CR^6R^7)_mYR^5$.

6. A compound according to claim 5 wherein $R^2$ is —$X(CR^3R^4)_nY$—$R^5$.

7. A compound according to claim 5 wherein $R^2$ is —O-arylene-Y—$R^5$.

8. A compound according to claim 7 wherein $R^2$ is —O-phenylene-Y—$R^5$.

9. A compound according to claim 8 wherein the —O and —$YR^5$ substituents attached the phenylene group are meta-substituted.

10. A compound according to claim 5 wherein $R^2$ is —$(CR^6R^7)_mYR^5$.

11. A compound according to claim 1 wherein X is —NH—.

12. A compound according to claim 1 wherein X is —O—.

13. A compound according to claim 1 wherein Y is —O—.

14. A compound according to claim 1 wherein Y is —NH—.

15. A compound according to claim 1 wherein n is chosen from 3, 4, and 5.

16. A compound according to claim 1 wherein m is chosen from 3, 4, and 5.

17. A compound according to claim 1 wherein $R^3$ and $R^4$ are independently chosen from H, $CH_3$, and F.

18. A compound according to claim 1 wherein $R^6$ and $R^7$ are independently chosen from H, $CH_3$, and F.

19. A compound according to claim 1 wherein —$(CR^6R^7)_mY$—$R^5$ is —$(CH_2)_4$—O—$R^5$.

20. A compound according to claim 1 wherein —$X(CR^3R^4)_nY$—$R^5$ is chosen from —NH—$(CH_2)_3$—O—$R^5$, —NH—$(CH_2)_2$—NH—$R^5$, —O—$(CH_2)_2$—O—$R^5$, —O—$(CH_2)_3$—O—$R^5$, —O—$CH_2$—$C(CH_3)_2$—$CH_2$—O—$R^5$, and —NH—$(CH_2)_2$—O—$R^5$.

21. A compound according to claim 20 wherein —$X(CR^3R^4)_nY$—$R^5$ is chosen from —NH—$(CH_2)_3$—O—$R^5$ and —O—$(CH_2)_3$—O—$R^5$.

22. A compound according to claim 1 wherein the compound of Formula I is chosen from compounds of Formula (Ia):

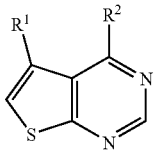

(Formula Ia)

wherein:
R² is chosen from X(CR³R⁴)$_n$YR⁵ and —(CR⁶R⁷)$_m$YR⁵; and Y is chosen from O, S, and NR⁹.

23. A compound according to claim 1 wherein R¹ is chosen from C$_{6-10}$ aryl and substituted C$_{6-10}$ aryl wherein substituted C$_{6-10}$ aryl is chosen from mono-, di-, and tri-substituted C$_{6-10}$ aryl.

24. A compound according to claim 23 wherein R¹ is chosen from phenyl and phenyl substituted with one, two or three halo.

25. A compound according to claim 1 wherein R¹ is chosen from heterocyclyl, substituted heterocyclyl, heteroaryl, and substituted heteroaryl.

26. A compound according to claim 25 wherein R¹ is chosen from 5-chloro-furan-2-yl, furan-2-yl, pyridin-4-yl, pyridin-3-yl, pyridin-2-yl, 1,3-thiazol-2-yl, 5-pyrimidin-2-yl and 5-pyrazin-2-yl.

27. A compound according to claim 1 wherein R⁹ is chosen from H, C$_{1-4}$ alkyl; C$_{3-8}$ cycloalkyl, substituted C$_{1-4}$ alkyl chosen from mono-, di-, and tri-substituted C$_{1-4}$ alkyl; and substituted C$_{3-8}$ cycloalkyl chosen from mono-, di-, and tri-substituted C$_{3-8}$ cycloalkyl, wherein the substituents on the alkyl and cycloalkyl groups are independently chosen from halo, C$_{1-4}$-alkyl, C$_{1-4}$-alkoxy, and oxo.

28. A compound according to claim 1 wherein
R¹ is chosen from
  C$_{6-10}$ aryl,
  substituted C$_{6-10}$ aryl chosen from mono-, di-, and trisubstituted aryl wherein the substitutent is halo,
  heterocyclyl, and
  substituted heterocyclyl;
R² is —X(CR³R⁴)$_n$Y—R⁵;
—X(CR³R⁴)$_n$Y— is chosen from —NH—(CH$_2$)$_3$—O—, —NH—(CH$_2$)$_2$—NH—, —O—(CH$_2$)$_2$—O—, —O—(CH$_2$)$_3$—O—, —O—CH$_2$—C(CH$_3$)$_2$—CH$_2$—O—, and —NH—(CH$_2$)$_2$—O—; and
R⁵ is chosen from
  phenyl,
  benzyl,
  benzoyl,
  benzothiadiazolyl,
  pyrazolyl,
  benzisothiazolyl,
  dihydroindolyl,
  pyridinyl,
  substituted phenyl chosen from mono-, di-, and tri-substituted phenyl wherein the substituents are independently chosen from alkyl-CO—NH—, NH$_2$—CO—NH—, alkyl-NH—CO—NH—, NH$_2$—NH—CO—NH—, OH—NH—CO—NH—, NH$_2$—CO—, NH$_2$—NH—CO—, HO—NH—CO—, alkyl-NH—CO—, (alkyl)$_2$N—CO—, HCO—NH—NH—CO—, alkyl-SO$_2$—NH—, (alkyl-SO$_2$)$_2$N-nitro, C$_{1-8}$ alkyl, C$_{1-8}$ halogenated alkoxy, cyano, alkoxycarbonyl, halo, amino, carboxy, and morpholinylcarbonyl,
  substituted benzyl chosen from mono-, di-, and tri-substituted benzyl wherein the substituents are independently chosen from alkyl-CO—NH—, NH$_2$—CO—NH—, alkyl-NH—CO—NH—, NH$_2$—NH—CO—NH—, OH—NH—CO—NH—, NH$_2$—CO—, NH$_2$—NH—CO—, HO—NH—CO—, alkyl-NH—CO—, (alkyl)$_2$N—CO—, HCO—NH—NH—CO—, alkyl-SO$_2$—NH—, (alkyl-SO$_2$)$_2$N-nitro, C$_{1-8}$ alkyl, C$_{1-8}$ halogenated alkoxy, cyano, alkoxycarbonyl, halo, amino, carboxy, and morpholinylcarbonyl,
  substituted benzoyl chosen from mono-, di-, and tri-substituted benzoyl wherein the substituents are independently chosen from alkyl-CO—NH—, NH$_2$—CO—NH—, alkyl-NH—CO—NH—, NH$_2$—NH—CO—NH—, OH—NH—CO—NH—, NH$_2$—CO—, NH$_2$—NH—CO—, HO—NH—CO—, alkyl-NH—CO—, (alkyl)$_2$N—CO—, HCO—NH—NH—CO—, alkyl-SO$_2$—NH—, (alkyl-SO$_2$)$_2$N-nitro, C$_{1-8}$ alkyl, C$_{1-8}$ halogenated alkoxy, cyano, alkoxycarbonyl, halo, amino, carboxy, and morpholinylcarbonyl,
  substituted benzothiadiazolyl chosen from mono-, di-, and tri-substituted benzothiadiazolyl wherein the substituents are independently chosen from alkyl-CO—NH—, NH$_2$—CO—NH—, alkyl-NH—CO—NH—, NH$_2$—NH—CO—NH—, OH—NH—CO—NH—, NH$_2$—CO—, NH$_2$—NH—CO—, HO—NH—CO—, alkyl-NH—CO—, (alkyl)$_2$N—CO—, HCO—NH—NH—CO—, (alkyl)-SO$_2$—NH—, (alkyl-SO$_2$)$_2$N—, nitro, C$_{1-8}$ alkyl, C$_{1-8}$ alkoxy, C$_{1-8}$ halogenated alkoxy, cyano, alkoxycarbonyl, triazolyl, halo, amino, carboxy, and morpholinylcarbonyl,
  substituted pyrazolyl chosen from mono-, di-, and tri-substituted pyrazolyl wherein the substituents are independently chosen from alkyl-CO—NH—, NH$_2$—CO—NH—, alkyl-NH—CO—NH—, NH$_2$—NH—CO—NH—, OH—NH—CO—NH—, NH$_2$—CO—, NH$_2$—NH—CO—, HO—NH—CO—, alkyl-NH—CO—, (alkyl)$_2$N—CO—, HCO—NH—NH—CO—, alkyl-SO$_2$—NH—, (alkyl-SO$_2$)$_2$N—, nitro, C$_{1-8}$ alkyl, C$_{1-8}$ alkoxy, C$_{1-8}$ halogenated alkoxy, cyano, alkoxycarbonyl, triazolyl, halo, amino, carboxy, and morpholinylcarbonyl,
  substituted benzisothiazolyl chosen from mono-, di-, and tri-substituted benzisothiazolyl wherein the substituents are independently chosen from alkyl-CO—NH—, NH$_2$—CO—NH—, alkyl-NH—CO—NH—, NH$_2$—NH—CO—NH—, OH—NH—CO—NH—, NH$_2$—CO—, NH$_2$—NH—CO—, HO—NH—CO—, alkyl-NH—CO—, (alkyl)$_2$N—CO—, HCO—NH—NH—CO—, alkyl-SO$_2$—NH—, (alkyl-SO$_2$)$_2$N—, nitro, C$_{1-8}$ alkyl, C$_{1-8}$ alkoxy, C$_{1-8}$ halogenated alkoxy, cyano, alkoxycarbonyl, triazolyl, halo, amino, carboxy, and morpholinylcarbonyl,
  substituted dihydroindolyl chosen from mono-, di-, and tri-substituted dihydroindolyl wherein the substituents are independently chosen from alkyl-CO—NH—, NH$_2$—CO—NH—, alkyl-NH—CO—NH—, NH$_2$—NH—CO—NH—, OH—NH—CO—NH—, NH$_2$—CO—, NH$_2$—NH—CO—, HO—NH—CO—, alkyl-NH—CO—, (alkyl)$_2$N—CO—, HCO—NH—NH—CO—, alkyl-SO$_2$—NH—, (alkyl-SO$_2$)$_2$N—, nitro, C$_{1-8}$ alkyl, C$_{1-8}$ alkoxy, C$_{1-8}$ halogenated alkoxy, cyano, alkoxycarbonyl, triazolyl, halo, amino, carboxy, and morpholinylcarbonyl, and substituted pyridinyl chosen from mono-, di-, and tri-substituted pyridinyl wherein the substituents are independently chosen from alkyl-CO—NH—, NH$_2$—CO—NH—, alkyl-NH—CO—NH—, NH$_2$—NH—CO—NH—, OH—NH—CO—NH—, NH$_2$—CO—, NH$_2$—NH—CO—, HO—NH—CO—, alkyl-NH—CO—, (alkyl)$_2$N—CO—, HCO—NH—NH—CO—, alkyl-SO$_2$—NH—, (alkyl-SO$_2$)$_2$N—, nitro, C$_{1-8}$ alkyl, C$_{1-8}$ alkoxy, C$_{1-8}$ halogenated alkoxy, cyano, alkoxycarbonyl, triazolyl, halo, amino, carboxy, and morpholinylcarbonyl.

29. A compound according to claim 1 wherein
R$^1$ is chosen from
  C$_{6-10}$ aryl,
  substituted C$_{6-10}$ aryl,
  heterocyclyl, and
  substituted heterocyclyl;
R$^2$ is —X(CR$^3$R$^4$)$_n$Y—R$^5$;
—X(CR$^3$R$^4$)$_n$Y— is chosen from —NH—(CH$_2$)$_3$—O—, —NH—(CH$_2$)$_2$—NH—, —O—(CH$_2$)$_3$—O—, and —NH—(CH$_2$)$_2$—O—;
R$^5$ is chosen from
  phenyl,
  benzyl,
  benzoyl,
  benzothiadiazolyl,
  pyrazolyl,
  benzisothiazolyl,
  dihydroindolyl,
  pyridinyl,
  substituted phenyl chosen from mono-, di-, and tri-substituted phenyl wherein the substituents are independently chosen from alkyl-CO—NH—, NH$_2$—CO—NH—, alkyl-NH—CO—NH—, NH$_2$—NH—CO—NH—, OH—NH—CO—NH—, NH$_2$—CO—, NH$_2$—NH—CO—, HO—NH—CO—, alkyl-NH—CO—, (alkyl)$_2$N—CO—, HCO—NH—NH—CO—, alkyl-SO$_2$—NH—, (alkyl-SO$_2$)$_2$N—, nitro, C$_{1-8}$ alkyl, C$_{1-8}$ alkoxy, C$_{1-8}$ halogenated alkoxy, cyano, alkoxycarbonyl, halo, amino, carboxy, and morpholinylcarbonyl,
  substituted benzyl chosen from mono-, di-, and tri-substituted benzyl wherein the substituents are independently chosen from alkyl-CO—NH—, NH$_2$—CO—NH—, alkyl-NH—CO—NH—, NH$_2$—NH—CO—NH—, OH—NH—CO—NH—, NH$_2$—CO—, NH$_2$—NH—CO—, HO—NH—CO—, alkyl-NH—CO—, (alkyl)$_2$N—CO—, HCO—NH—NH—CO—, alkyl-SO$_2$—NH—, (alkyl-SO$_2$)$_2$N—, nitro, C$_{1-8}$ alkyl, C$_{1-8}$ alkoxy, C$_{1-8}$ halogenated alkoxy, cyano, alkoxycarbonyl, halo, amino, carboxy, and morpholinylcarbonyl,
  substituted benzoyl chosen from mono-, di-, and tri-substituted benzoyl wherein the substituents are independently chosen from alkyl-CO—NH—, NH$_2$—CO—NH—, alkyl-NH—CO—NH—, NH$_2$—NH—CO—NH—, OH—NH—CO—NH—, NH$_2$—CO—, NH$_2$—NH—CO—, HO—NH—CO—, alkyl-NH—CO—, (alkyl)$_2$N—CO—, HCO—NH—NH—CO—, alkyl-SO$_2$—NH—, (alkyl-SO$_2$)$_2$N—, nitro, C$_{1-8}$ alkyl, C$_{1-8}$ alkoxy, C$_{1-8}$ halogenated alkoxy, cyano, alkoxycarbonyl, halo, amino, carboxy, and morpholinylcarbonyl,
  substituted benzothiadiazolyl chosen from mono-, di-, and tri-substituted benzothiadiazolyl wherein the substituents are independently chosen from alkyl-CO—NH—, NH$_2$—CO—NH—, alkyl-NH—CO—NH—, NH$_2$—NH—CO—NH—, OH—NH—CO—NH—, NH$_2$—CO—, NH$_2$—NH—CO—, HO—NH—CO—, alkyl-NH—CO—, (alkyl)$_2$N—CO—, HCO—NH—NH—CO—, alkyl-SO$_2$—NH—, (alkyl-SO$_2$)$_2$N—, nitro, C$_{1-8}$ alkyl, C$_{1-8}$ alkoxy, C$_{1-8}$ halogenated alkoxy, cyano, alkoxycarbonyl, halo, amino, carboxy, and morpholinylcarbonyl,
  substituted pyrazolyl chosen from mono-, di-, and tri-substituted pyrazolyl wherein the substituents are independently chosen from alkyl-CO—NH—, NH$_2$—CO—NH—, alkyl-NH—CO—NH—, NH$_2$—NH—CO—NH—, OH—NH—CO—NH—, NH$_2$—CO—, NH$_2$—NH—CO—, HO—NH—CO—, alkyl-NH—CO—, (alkyl)$_2$N—CO—, HCO—NH—NH—CO—, alkyl-SO$_2$—NH—, (alkyl-SO$_2$)$_2$N—, nitro, C$_{1-8}$ alkyl, C$_{1-8}$ alkoxy, C$_{1-8}$ halogenated alkoxy, cyano, alkoxycarbonyl, halo, amino, carboxy, and morpholinylcarbonyl,
  substituted benzisothiazolyl chosen from mono-, di-, and tri-substituted benzisothiazolyl wherein the substituents are independently chosen from alkyl-CO—NH—, NH$_2$—CO—NH—, alkyl-NH—CO—NH—, NH$_2$—NH—CO—NH—, OH—NH—CO—NH—, NH$_2$—CO—, NH$_2$—NH—CO—, HO—NH—CO—, alkyl-NH—CO—, (alkyl)$_2$N—CO—, HCO—NH—NH—CO—, alkyl-SO$_2$—NH—, (alkyl-SO$_2$)$_2$N—, nitro, C$_{1-8}$ alkyl, C$_{1-8}$ alkoxy, C$_{1-8}$ halogenated alkoxy, cyano, alkoxycarbonyl, halo, amino, carboxy, and morpholinylcarbonyl,
  substituted dihydroindolyl chosen from mono-, di-, and tri-substituted dihydroindolyl wherein the substituents are independently chosen from alkyl-CO—NH—, NH$_2$—CO—NH—, alkyl-NH—CO—NH—, NH$_2$—NH—CO—NH—, OH—NH—CO—NH—, NH$_2$—CO—, NH$_2$—NH—CO—, HO—NH—CO—, alkyl-NH—CO—, (alkyl)$_2$N—CO—, HCO—NH—NH—CO—, alkyl-SO$_2$—NH—, (alkyl-SO$_2$)$_2$N—, nitro, C$_{1-8}$ alkyl, C$_{1-8}$ alkoxy, C$_{1-8}$ halogenated alkoxy, cyano, alkoxycarbonyl, halo, amino, carboxy, and morpholinylcarbonyl, and
  substituted pyridinyl chosen from mono-, di-, and tri-substituted pyridinyl wherein the substituents are independently chosen from alkyl-CO—NH—, NH$_2$—CO—NH—, alkyl-NH—CO—NH—, NH$_2$—NH—CO—NH—, OH—NH—CO—NH—, NH$_2$—CO—, NH$_2$—NH—CO—, HO—NH—CO—, alkyl-NH—CO—, (alkyl)$_2$N—CO—, HCO—NH—NH—CO—, alkyl-SO$_2$—NH—, (alkyl-SO$_2$)$_2$N—, nitro, C$_{1-8}$ alkyl, C$_{1-8}$ alkoxy, C$_{1-8}$ halogenated alkoxy, cyano, alkoxycarbonyl, halo, amino, carboxy, and morpholinylcarbonyl 30. A compound according to claim 1 wherein R$^1$ is chosen from phenyl, furanyl, pyridinyl, pyrimidinyl, thiazolyl, substituted phenyl, substituted furanyl, substituted pyridinyl, substituted pyrimidinyl, and substituted thiazolyl, and R$^2$ is —X(CR$^3$R$^4$)$_n$YR$^5$.

31. A compound according to claim 1 wherein R$^1$ is chosen from phenyl and phenyl substituted by halo, and R$^2$ is —X(CR$^3$R$^4$)$_n$YR$^5$.

32. A compound according to claim 1 wherein R$^1$ is chosen from phenyl, furanyl, pyridinyl, thiazolyl, substituted phenyl, substituted furanyl, substituted pyridinyl, and substituted thiazolyl, and R$^2$ is chosen from —NH—(CH$_2$)$_3$—O—R$^5$, —NH—(CH$_2$)$_2$—NH—R$^5$, —O—(CH$_2$)$_3$—O—R$^5$, and —NH—(CH$_2$)$_2$—O—R$^5$.

33. A compound according to claim 1 wherein R$^1$ is chosen from phenyl and phenyl substituted by halo, and R$^2$ is chosen from —NH—(CH$_2$)$_3$—O—R$^5$, —NH—(CH$_2$)$_2$—NH—R$^5$, —O—(CH$_2$)$_3$—O—R$^5$, and —NH—(CH$_2$)$_2$—O—R$^5$.

34. A compound according to claim 1 wherein R$^1$ is chosen from phenyl, furanyl, pyridinyl, and thiazolyl, substituted phenyl, substituted furanyl, substituted pyridinyl, and substituted thiazolyl; R$^2$ is chosen from NH—(CH$_2$)$_3$—O—R$^5$ and —O—(CH$_2$)$_3$—O—R$^5$; and R$^5$ is chosen from phenyl, benzyl, benzoyl, benzothiadiazolyl, pyridinyl, substituted phenyl, substituted benzyl, substituted benzoyl, substituted benzothiadiazolyl, and substituted pyridinyl.

35. A compound according to claim 1 wherein R$^1$ is chosen from phenyl, furanyl, pyridinyl, and thiazolyl, substituted phenyl, substituted furanyl, substituted pyridinyl, and substituted thiazolyl; R$^2$ is chosen from NH—(CH$_2$)$_3$—O—R$^5$ and —O—(CH$_2$)$_3$—O—R$^5$, and R$^5$ is chosen from phenyl and pyridinyl, which in each case is substituted by one, two or three of alkyl-CO—NH—, NH$_2$—CO—NH—, alkyl-NH—CO—NH—, NH$_2$—NH—CO—NH—, OH—NH—CO—NH—, NH$_2$—CO—, NH$_2$—NH—CO—, HO—NH—CO—, alkyl-NH—CO—, (alkyl)$_2$N—CO—, HCO—NH—NH—CO—, alkyl-SO$_2$—NH—, (alkyl-SO$_2$)$_2$N—, nitro, C$_{1-8}$ alkyl, C$_{1-8}$ alkoxy, C$_{1-8}$ halogenated alkoxy, cyano, alkoxycarbonyl, halo, amino, carboxy, and morpholinylcarbonyl.

36. A compound according to claim 1 wherein R$^1$ is chosen from phenyl, furanyl, pyridinyl, thiazolyl, substituted phenyl, substituted furanyl, substituted pyridinyl, and substituted thiazolyl; R$^2$ is —O—(CH$_2$)$_3$—O—R$^5$, and R$^5$ is chosen from phenyl and pyridinyl, which in each case is substituted by alkyl-CO—NH—, NH$_2$—CO—NH—, alkyl-NH—CO—NH—, NH$_2$—NH—CO—NH—, OH—NH—CO—NH—, NH$_2$—CO—, NH$_2$—NH—CO—, HO—NH—CO—, alkyl-NH—CO—, HCO—NH—NH—CO—, alkyl-SO$_2$—NH—, (alkyl-SO$_2$)$_2$N—, nitro, C$_{1-8}$ alkyl, C$_{1-8}$ alkoxy, C$_{1-8}$ halogenated alkoxy, cyano, alkoxycarbonyl, halo, amino, carboxy, or morpholinylcarbonyl.

37. A compound according to claim 1 wherein the compound of Formula I is chosen from
- N-[3-(3-{[5-(4-fluorophenyl)thieno[2,3-d]pyrimidin-4-yl]amino}propoxy)-phenyl]-acetamide,
- N-(3-nitrobenzyl)-N'-(5-phenylthieno[2,3-d]pyrimidin-4-yl)ethane-1,2-diamine,
- N-(3,4-dimethoxybenzyl)-N'-(5-phenylthieno[2,3-d]pyrimidin-4-yl)ethane-1,2-diamine,
- N-(2,1,3-benzothiadiazol-5-ylmethyl)-N'-(5-phenylthieno[2,3-d]pyrimidin-4-yl)ethane-1,2-diamine,
- N-{3-[({2-[(5-phenylthieno[2,3-d]pyrimidin-4-yl)amino]ethyl}amino)methyl]-phenyl}-acetamide,
- N-{4-[({2-[(5-phenylthieno[2,3-d]pyrimidin-4-yl)amino]ethyl}amino)methyl]-phenyl}-acetamide,
- 3-(acetylamino)-N-{2-[(5-phenylthieno[2,3-d]pyrimidin-4-yl)amino]-ethyl}benzamide,
- 3-[({2-[(5-phenylthieno[2,3-d]pyrimidin-4-yl)amino]ethyl}amino)methyl]-benzonitrile,
- methyl 3-[({2-[(5-phenylthieno[2,3-d]pyrimidin-4-yl)amino]ethyl}amino)-methyl]-benzoate,
- N-(5-phenylthieno[2,3-d]pyrimidin-4-yl)-N'-[3-(trifluoromethoxy)benzyl]ethane-1,2-diamine,
- 5-(4-fluorophenyl)-4-[3-(3-nitrophenoxy)propoxy]thieno[2,3-d]pyrimidine,
- N-[4-(3-{[5-(4-fluorophenyl)thieno[2,3-d]pyrimidin-4-yl]amino}propoxy)-phenyl]-acetamide,
- N-[3-(3-{[5-(4-fluorophenyl)thieno[2,3-d]pyrimidin-4-yl]oxy}propoxy)phenyl]-acetamide,
- N-[4-(3-{[5-(4-fluorophenyl)thieno[2,3-d]pyrimidin-4-yl]oxy}propoxy)phenyl]-acetamide,
- 4-[3-(4-fluorophenoxy)propoxy]-5-(4-fluorophenyl)thieno[2,3-d]pyrimidine, methyl 3-(3-{[5-(4-fluorophenyl)thieno[2,3-d]pyrimidin-4-yl]oxy}propoxy)benzoate,
- 3-(3-{[5-(4-fluorophenyl)thieno[2,3-d]pyrimidin-4-yl]oxy}propoxy)aniline,
- 3-(3-{[5-(4-fluorophenyl)thieno[2,3-d]pyrimidin-4-yl]oxy}propoxy)benzoic acid,
- 5-(4-fluorophenyl)-4-(3-{3-[(4-methylpiperazin-1-yl)carbonyl]phenoxy}-propoxy)-thieno[2,3-d]pyrimidine,
- 5-(4-fluorophenyl)-4-{3-[3-(morpholin-4-ylcarbonyl)phenoxy]propoxy}-thieno[2,3-d]pyrimidine,
- N-ethyl-3-(3-{[5-(4-fluorophenyl)thieno[2,3-d]pyrimidin-4-yl]oxy}propoxy)-benzamide,
- 3-(3-{[5-(4-fluorophenyl)thieno[2,3-d]pyrimidin-4-yl]oxy}propoxy)-N,N-dimethylbenzamide,
- 3-(3-{[5-(4-fluorophenyl)thieno[2,3-d]pyrimidin-4-yl]oxy}propoxy)-N'-formylbenzohydrazide,
- 3-(3-{[5-(4-fluorophenyl)thieno[2,3-d]pyrimidin-4-yl]oxy}propoxy)-N-methylbenzamide,
- N-[3-(2-{[5-(4-fluorophenyl)thieno[2,3-d]pyrimidin-4-yl]oxy}ethoxy)-benzohydrazide phenyl]-urea,
- N-[3-(3-{[5-(4-fluorophenyl)thieno[2,3-d]pyrimidin-4-yl]oxy}propoxy)-phenyl]urea,
- 3-(2-{[5-(4-fluorophenyl)thieno[2,3-d]pyrimidin-4-yl]oxy}ethoxy)benzamide,
- 3-(3-{[5-(4-fluorophenyl)thieno[2,3-d]pyrimidin-4-yl]oxy}propoxy)-benzohydrazide,
- 3-(3-{[5-(4-fluorophenyl)thieno[2,3-d]pyrimidin-4-yl]oxy}propoxy)-N-hydroxybenzamide,
- 4-(2-{[5-(4-fluorophenyl)thieno[2,3-d]pyrimidin-4-yl]oxy}ethoxy)benzamide
- N-ethyl-N'-[3-(3-{[5-(4-fluorophenyl)thieno[2,3-d]pyrimidin-4-yl]oxy}propoxy)phenyl]urea,
- N-[3-(3-{[5-(4-fluorophenyl)thieno[2,3-d]pyrimidin-4-yl]oxy}propoxy)phenyl]-methanesulfonamide,
- N-[4-(3-{[5-(4-fluorophenyl)thieno[2,3-d]pyrimidin-4-yl]oxy}propoxy)phenyl]-methanesulfonamide,
- N-[4-(3-{[5-(4-fluorophenyl)thieno[2,3-d]pyrimidin-4-yl]oxy}propoxy)phenyl]-N-(methylsulfonyl)methansulfonamide,
- N-(ethylsulfonyl)-N-[4-(3-{[5-(4-fluorophenyl)thieno[2,3-d]pyrimidin-4-yl]oxy}-propoxy)phenyl]ethanesulfonamide,
- N-[4-(3-{[5-(4-fluorophenyl)thieno[2,3-d]pyrimidin-4-yl]oxy}propoxy)phenyl]-ethanesulfonamide,
- N-[4-(3-{[5-(4-fluorophenyl)thieno[2,3-d]pyrimidin-4-yl]oxy}propoxy)phenyl]-N'-methylurea,
- N-ethyl-N'-[4-(3-{[5-(4-fluorophenyl)thieno[2,3-d]pyrimidin-4-yl]oxy}propoxy)-phenyl]-urea,
- N-[3-(3-{[5-(4-fluorophenyl)thieno[2,3-d]pyrimidin-4-yl]oxy}propoxy)phenyl]-ethanesulfonamide,
- N-[3-(3-{[5-(4-fluorophenyl)thieno[2,3-d]pyrimidin-4-yl]oxy}propoxy)phenyl]-N'-methylurea,
- N-[3-(3-{[5-(4-fluorophenyl)thieno[2,3-d]pyrimidin-4-yl]oxy}propoxy)phenyl]-hydrazinecarboxamide,
- N-[3-(3-{[5-(4-fluorophenyl)thieno[2,3-d]pyrimidin-4-yl]oxy}propoxy)phenyl]-N'-hydroxyurea,
- 4-{3-[5-(4-fluorophenyl)-thieno[2,3d]pyrimidin-4-yloxy]-propoxy}-benzamide,
- 5-{3-[5-(4-fluorophenyl)-thieno[2,3-d]pyrimidin-4-yloxy]-propoxy}-nicotinic acid, methyl ester,
- N-{3-[3-(5-furan-2-yl-thieno[2,3d]pyrimidin-4-yloxy)-propoxy]-phenyl}acetamide,
- 2-(3-{[5-(4-fluorophenyl)thieno[2,3-d]pyrimidin-4-yl]oxy}propoxy)benzamide, 5-{3-[5-(4-fluorophenyl)-thieno[2,3-d]pyrimidin-4-yloxy]-propoxy}-nicotinic acid,
N-(3-{3-[(5-phenylthieno[2,3-d]pyrimidin-4-yl)oxy]propoxy}phenyl)acetamide,
N-[4-(3-{[5-(4-fluorophenyl)thieno[2,3-d]pyrimidin-4-yl]oxy}propoxy)phenyl]-hydrazinecarboxamide,
5-{3-[(5-pyridin-4-ylthieno[2,3-d]pyrimidin-4-yl)oxy]propoxy}pyridine-2-carboxamide,
5-(3-{[5-(4-fluorophenyl)thieno[2,3-d]pyrimidin-4-yl]oxy}propoxy)pyridine-2-carboxamide,
5-(3-{[5-(1,3-thiazol-2-yl)thieno[2,3-d]pyrimidin-4-yl]oxy}propoxy)pyridine-2-carboxamide,
5-{3-[(5-pyridin-3-ylthieno[2,3-d]pyrimidin-4-yl)oxy]propoxy}pyridine-2-carboxamide
N-methyl-5-{3-[(5-pyridin-4-ylthieno[2,3-d]pyrimidin-4-yl)oxy]propoxy}-pyridine-2-carboxamide,
5-(3-{[5-(4-fluorophenyl)thieno[2,3-d]pyrimidin-4-yl]oxy}propoxy)-N-methylpyridine-2-carboxamide,
N-methyl-5-(3-{[5-(1,3-thiazol-2-yl)thieno[2,3-d]pyrimidin-4-yl]oxy}propoxy)-pyridine-2-carboxamide, and
N-methyl-5-{3-[(5-pyridin-3-ylthieno[2,3-d]pyrimidin-4-yl)oxy]propoxy}-pyridine-2-carboxamide.

38. A compound according to claim 1 wherein the compound of Formula I is chosen from
N-methyl-3-{3-[(5-pyridin-3-ylthieno[2,3-d]pyrimidin-4-yl)oxy]propoxy}benzamide,
N-methyl-5-(3-{[5-(1,3-thiazol-2-yl)-thieno[2,3-d]pyrimidin-4-yl]amino}-propoxy)pyridine-2-carboxamide,
5-(3-{[5-(5-chloro-2-furyl)thieno[2,3-d]pyrimidin-4-yl]amino}propoxy)-N-methylpyridine-2-carboxamide,
N-methyl-5-{3-[(5-pyridin-3-ylthieno[2,3-d]pyrimidin-4-yl)amino]propoxy}pyridine-2-carboxamide,
N-methyl-5-{3-[(5-pyridin-2-ylthieno[2,3-d]pyrimidin-4-yl)amino]propoxy}pyridine-2-carboxamide,
N-methyl-5-{3-[(5-pyridin-2-ylthieno[2,3-d]pyrimidin-4-yl)amino]propoxy}-nicotinamide,
5-{3-[(5-pyridin-3-ylthieno[2,3-d]-pyrimidin-4-yl)oxy]propoxy}pyridine-2-carboxamide hydroformate,
5-(4-fluorophenyl)-4-(3-{[1-methyl-5-(trifluoromethyl)-1H-pyrazol-3-yl]oxy}propoxy)thieno[2,3-d]pyrimidine,
4-[3-(4-chlorophenoxy)propoxy]-5-(4-fluorophenyl)thieno[2,3-d]pyrimidine,
4-[3-(3,5-difluorophenoxy)propoxy]-5-(4-fluorophenyl)thieno[2,3-d]pyrimidine,
4-[3-(3,4-dimethoxyphenoxy)propoxy]-5-(4-fluorophenyl)thieno[2,3-d]pyrimidine,
4-[3-(1,2-benzisothiazol-3-yloxy)propoxy]-5-(4-fluorophenyl)thieno[2,3-d]pyrimidine,
5-(4-fluorophenyl)-4-(3-phenoxypropoxy)-thieno[2,3-d]pyrimidine,
5-(4-fluorophenyl)-4-[3-(3-methoxy-phenoxy)propoxy]thieno[2,3-d]pyrimidine,
5-(4-fluorophenyl)-4-[3-(3-methyl-phenoxy)propoxy]thieno[2,3-d]pyrimidine,
5-(4-fluorophenyl)-4-{3-[3-(trifluoro-methoxy)phenoxy]propoxy}thieno[2,3-d]pyrimidine,
4-[3-(3-ethylphenoxy)propoxy]-5-(4-fluorophenyl)thieno[2,3-d]pyrimidine,
5-{3-[(5-pyrimidin-2-ylthieno[2,3-d]pyrimidin-4-yl)amino]propoxy}pyridine-2-carboxylic acid hydroformate,
5-(3-{[5-(1,3-thiazol-2-yl)thieno[2,3-d]pyrimidin-4-yl]amino}propoxy)pyridine-2-carboxylic acid hydroformate,
5-{3-[(5-pyrazin-2-ylthieno[2,3-d]pyrimidin-4-yl)amino]propoxy}pyridine-2-carboxylic acid hydroformate,
4-[5-(4-fluorophenyl)thieno[2,3-d]pyrimidin-4-yl]butan-1-ol,
4-but-3-en-1-yl-5-(4-fluorophenyl)-thieno[2,3-d]pyrimidine,
Methyl 5-{4-[5-(4-fluorophenyl)-thieno[2,3-d]pyrimidin-4-yl]butoxy}-nicotinate,
5-{4-[5-(4-fluorophenyl)thieno[2,3-d]pyrimidin-4-yl]butoxy}nicotinic acid hydroformate,
5-{4-[5-(4-fluorophenyl)thieno[2,3-d]pyrimidin-4-yl]butoxy}-N-methylnicotinamide hydroformate,
5-{4-[5-(4-fluorophenyl)thieno[2,3-d]pyrimidin-4-yl]butoxy}nicotinamide hydroformate,
N-[3-(3-{[5-(4-fluorophenyl)thieno[2,3-d]pyrimidin-4-yl]oxy}phenoxy)-phenyl]acetamide hydroformate,
N-[3-(2,2-dimethyl-3-{[5-(1,3-thiazol-2-yl)thieno[2,3-d]pyrimidin-4-yl]oxy}propoxy)phenyl]acetamide hydroformate,
N-[3-(3-{[5-(1,3-thiazol-2-yl)thieno[2,3-d]pyrimidin-4-yl]oxy}phenoxy)phenyl]-acetamide hydroformate,
N-[3-(3-{[5-(4-fluorophenyl)thieno[2,3-d]pyrimidin-4-yl]oxy}-2,2-dimethyl-propoxy)phenyl]acetamide hydroformate,
5-(3-{[5-(4-fluorophenyl)thieno[2,3-d]pyrimidin-4-yl]oxy}propoxy)-1,3-dihydro-2H-indol-2-one,
5-{3-[(5-pyridin-3-ylthieno[2,3-d]pyrimidin-4-yl)amino]propoxy}pyridine-2-carboxamide hydroformate,
5-(3-{[5-(2,3-thiazol-2-yl)thieno[2,3-d]pyrimidin-4-yl]amino}propoxy)pyridine-2-carboxamide hydroformate,
N-(3-{3-[(5-pyridin-2-ylthieno[2,3-d]pyrimidin-4-yl)amino]propoxy}phenyl)-acetamide,
N-[3-(3-{[5-(1,3-thiazol-2-yl)thieno[2,3-d]pyrimidin-4-yl]amino}propoxy)-phenyl]acetamide,
N-[4-(3-{[5-(1,3-thiazol-2-yl)thieno[2,3-d]pyrimidin-4-yl]amino)propoxy}-phenyl]acetamide,
N-(4-{3-[(5-pyridin-3-ylthieno[2,3-d]pyrimidin-4-yl)amino]propoxy}phenyl)-acetamide,
N-[4-(3-{[5-(5-chloro-2-furyl)thieno[2,3-d]pyrimidin-4-yl]amino}propoxy)-phenyl]acetamide,
N-methyl-4-{3-[(5-pyridin-3-ylthieno[2,3-d]pyrimidin-4-yl)oxy]propoxy}-benzamide,
N-methyl-5-(3-{[5-(1,3-thiazol-2-yl)thieno[2,3-d]pyrimidin-4-yl]oxy}propoxy)-nicotinamide,
N-methyl-5-{3-[(5-pyridin-3-ylthieno[2,3-d]pyrimidin-4-yl)oxy]propoxy}-nicotinamide,
N-methyl-3-(3-{[5-(1,3-thiazol-2-yl)thieno[2,3-d]pyrimidin-4-yl]oxy}propoxy)-benzamide,
N-[4-(3-{[5-(1,3-thiazol-2-yl)thieno[2,3-d]pyrimidin-4-yl]oxy}propoxy)phenyl]-acetamide, and
N-(4-{3-[(5-pyridin-3-ylthieno[2,3-d]pyrimidin-4-yl)oxy]propoxy}phenyl)-acetamide.

39. A pharmaceutical composition comprising a compound according to claim 1 and a pharmaceutically acceptable carrier.

40. A compound according to claim 1 wherein n is chosen from 2 and 3.

41. A compound according to claim 37, wherein the compound is N-[3-(3-{[5-(4-fluorophenyl)thieno[2,3-d]pyrimidin-4-yl]oxy}propoxy)phenyl]-acetamide.

42. A compound according to claim 37, wherein the compound is 5-(4-fluorophenyl)-4- [3-(3 -nitrophenoxy)propoxy]thieno[2,3-d]pyrimidine.

43. A compound according to claim 38, wherein the compound is N-[3 -(3- {[5-(1,3 -thiazol-2-yl)thieno[2,3-d]pyrimidin-4-yl]amino }propoxy)-phenyl]acetamide.

* * * * *